(12) United States Patent
Watnick et al.

(10) Patent No.: US 8,771,946 B2
(45) Date of Patent: Jul. 8, 2014

(54) PKD MUTATIONS AND EVALUATION OF SAME

(75) Inventors: Terry J. Watnick, Chevy Chase, MD (US); Miguel Garcia-Gonzales, Brion (ES); Gregory G. Germino, Chevy Chase, MD (US); Jeffrey G. Jones, Wilbraham, MA (US)

(73) Assignees: Athena Diagnostics, Inc., Worcester, MA (US); The Johns Hopkins University, Baltimore, MD (US)

( * ) Notice: Subject to any disclaimer, the term of this patent is extended or adjusted under 35 U.S.C. 154(b) by 685 days.

(21) Appl. No.: 12/309,337

(22) PCT Filed: Jul. 24, 2007

(86) PCT No.: PCT/US2007/016705
§ 371 (c)(1),
(2), (4) Date: Sep. 2, 2009

(87) PCT Pub. No.: WO2008/094194
PCT Pub. Date: Aug. 7, 2008

(65) Prior Publication Data
US 2010/0047785 A1    Feb. 25, 2010

Related U.S. Application Data

(60) Provisional application No. 60/832,780, filed on Jul. 24, 2006.

(51) Int. Cl.
*C12Q 1/68* (2006.01)
*C12P 19/34* (2006.01)
*C07H 21/02* (2006.01)

(52) U.S. Cl.
USPC .................. 435/6.11; 435/91.1; 536/23.1

(58) Field of Classification Search
None
See application file for complete search history.

(56) References Cited

U.S. PATENT DOCUMENTS

| | | | |
|---|---|---|---|
| 6,485,960 B1 | 11/2002 | Harris et al. | |
| 6,656,681 B1 | 12/2003 | Harris et al. | |
| 6,916,619 B2 | 7/2005 | Jones et al. | |
| 7,083,915 B2 | 8/2006 | Somlo et al. | |
| 7,273,701 B2 | 9/2007 | Jones et al. | |
| 7,294,465 B2 | 11/2007 | Somlo et al. | |
| 7,553,644 B2 | 6/2009 | Germino et al. | |
| 2003/0008288 A1 | 1/2003 | Germino et al. | |
| 2006/0246504 A1 | 11/2006 | Germino et al. | |

FOREIGN PATENT DOCUMENTS

| | | | |
|---|---|---|---|
| CA | 2 461 106 A1 | 10/2004 | |
| JP | 2004-313194 | 11/2004 | |
| WO | WO 95/18225 | 7/1995 | |
| WO | WO 96/12033 A | 4/1996 | |
| WO | WO 02/06529 A | 1/2002 | |
| WO | WO 2008/094194 | 8/2008 | |

OTHER PUBLICATIONS

Thomas, Ruth et al. Identification of mutations in the repeated part of the autosomal dominant polycystic kidney disease type 1 gene, PKD1, by long range PCR. AM J Hum Genet 1999 vol. 65 pp. 39-49.*
Juppner Functional properties of the PTH/PTHrP receptor. Bone 1995 vol. 17 No. 2 Supplement 39S-42S.*
Garcia-Gonzales, Miguel et al. Polycystic kidney disease (PKD): from the clinical genetic test, through in vitro and in vivo analysis, and back to humans found online at http://hdl.handle.net/10347/9599 available date Jan. 7, 2014.*
Turco, A.E., et al., "A Novel Nonsense Mutation in the PKD1 Gene (C3817T) is Associated with Autosomal Dominant Polycystic Kidney Disease (ADPKD) in a Large Three-Generation Italian Family," *Human Molecular Genetics*, 4:1331-1335 (Jan. 1995).
Bresin, E., et al., "A Common Polymorphism in Exon 46 of the Human Autosomal Dominant Polycystic Kidney Disease 1 Gene (PKD1)," *Molecular and Cellular Probes*, 10:463-465 (Dec. 1996).
Peral, B., et al., "Screening 3' Region of the Polycystic Kidney Disease 1 (PKD1) Gene Reveals Six Novel Mutations," *Am. Journ. Hum. Genetics*, 58:86-96 (Jan. 1996).
Peral, B., et al., "A Stable, Nonsense Mutation Associated With a Case of Infantile Onset Polycystic Kidney Disease 1 (PKD1)," *Human Molecular Genetics*, 5:539-542 (1996, mo. not available).
Neophytou, P., et al., "Detection of a Novel Nonsense Mutation and an Intragenic Polymorphism in the PKD1 Gene of a Cypriot Family with Autosomal Dominant Polycystic Kidney Disease," *Human Genetics*, 98:437-442 (Jan. 1996).
Turco, A.E., et al., "Three Novel Mutations of the PKD1 Gene in Italian Families with Autosomal Dominant Polycystic Kidney Disease," *Human Mutation*, 10:164-167 (1997, mo. not available).
Roelfsma, J.H., et al., "Mutation Detection in the Repeated Part of the PKD1 Gene," *Am. Journ. Hum. Genetics*, 61:1044-1052 (Nov. 1997).
Rossetti, S., et al., "Detection of Mutations in Human Genes by a New Rapid Method: Cleavage Fragment Length Polymorphism Analysis (CFLPA)," *Molecular and Cellular Probes*, 11:155-160 (Apr. 1997).
Perrichot, R.A., et al., "DGGE Screening of PKD1 Gene Reveals Novel Mutations in a Large Cohort of 146 Unrelated Patients," *Human Genetics*, 105:231-239 (Jan. 1999).
Watnick, T., et al., "Mutation Detection of PKD1 Identifies a Novel Mutation Common to Three Families with Aneurysms and/or Very-Early-Onset Disease," *Am. Journ. Hum. Genetics*, 65:1561-1571 (Dec. 1999).
Thongnoppakhun, A., et al., "A Novel Splice-Acceptor Site Mutation (IVS13-2A>T) of Polycystic Kidney Disease 1 (PKD1) Gene Resulting in an RNA Processing Defect with a 74-Nucleotide Deletion in Exon 14 of the mRNA Transcript," *Human Mutation*, 15:115 (Jan. 2000).

(Continued)

*Primary Examiner* — Amanda Haney
(74) *Attorney, Agent, or Firm* — Foley & Lardner LLP

(57) ABSTRACT

The present invention relates to methods of detecting novel mutations in a PKD1 and/or PKD2 gene that have been determined to be associated with autosomal dominant polycystic kidney disease (ADPKD) in order to detect or predict the occurrence of ADPKD in an individual.

5 Claims, 37 Drawing Sheets

(56) References Cited

OTHER PUBLICATIONS

Thomas, R., et al., "Identification of Mutations in the Repeated Part of the Autosomal Dominant Polycystic Kidney Disease Type 1 Gene, PKD1, by Long-Range PCR," *Am. Journ. Hum. Genetics*, 65:39-49 (Jul. 1999).

Bouba, I., et al., "Novel PKD1 Deletions and Missense Variants in a Cohort of Hellenic Polycystic Kidney Disease Families," *Eur. Journ. Hum. Genetics*, 9:677-684 (Sep. 2001).

Garcia-Gonzalez, M.A., et al., "Evaluating the Clinical Utility of a Molecular Genetic Test for Polycystic Kidney Disease," *Mol. Genetics and Metabolism*, 92:160-167 (May 2007).

Reiterová, J., et al., "Four Novel Mutations of the PKD2 Gene in Czech Families With Autosomal Dominant Polycystic Kidney Disease," *Human Mutation*, Online (Feb. 2002).

Reynolds, D.M., et al., "Aberrant Splicing in the PKD2 Gene as a Cause for Polycystic Kidney Disease," *J. Am. Soc. Nephrol.*, 10:2342-2351 (May 1999).

Rossetti, S., et al., "A Complete Mutation Screen of the ADPKD Genes by DHPLC," *Kidney International*, 61:1588-1599 (2002, mo. not available).

Invitation to Pay Additional Fees, PCT/US2007/016705, mailed Sep. 24, 2008.

International Preliminary Report on Patentability, PCT/US2007/016705, issued Jan. 27, 2009.

Rossetti et al., "Mutation Analysis of the Entire PKD1 Gene: Genetic and Diagnostic Implications," *Am. J. Hum. Genet.*, vol. 68, pp. 46-63 (2001).

* cited by examiner

Figure 1

```
gcactgcagc gccagcgtcc gagcgggcgg ccgagctccc ggagcggcct ggccccgagc 60
cccgagcggg cgtcgctcag cagcaggtcg cggccgcgca gccccatcca gccccgcgcc 120
cgccatgccg tccgcgggcc ccgcctgagc tgcggtctcc gcgcgcgggc gggcctgggg 180
acggcggggc catgcgcgcg ctgcctaac gatgccgccc gccgcgcccg cccgcctggc 240
gctggccctg ggcctgggcc tgtggctcgg ggcgctggcg gggggccccg ggcgcggctg 300
cgggccctgc gagccccct gcctctgcgg cccagcgccc ggcgccgcct gccgcgtcaa 360
ctgctcgggc cgcgggctgc ggacgctcgg tcccgcgctg cgcatcccg cggacgccac 420
agcgctagac gtctcccaca acctgctccg ggcgctggac gttgggctcc tggcgaacct 480
ctcggcgctg gcagagctgg atataagcaa caacaagatt tctacgttag aagaaggaat 540
atttgctaat ttatttaatt taagtgaaat aaacctgagt gggaacccgt ttgagtgtga 600
ctgtggcctg gcgtggctgc cgcgatgggc ggaggagcag caggtgcggg tggtgcagcc 660
cgaggcagcc acgtgtgctg ggcctggctc cctggctggc cagcctctgc ttggcatccc 720
cttgctggac agtggctgtg gtgaggagta tgtcgcctgc ctccctgaca acagctcagg 780
caccgtggca gcagtgtcct tttcagctgc ccacgaaggc ctgcttcagc cagaggcctg 840
cagcgccttc tgcttctcca ccggccaggg cctcgcagcc ctctcggagc agggctggtg 900
cctgtgtggg gcggcccagc cctccagtgc ctcctttgcc tgcctgtccc tctgctccgg 960
ccccccgcca cctcctgccc ccacctgtag gggccccacc ctcctccagc acgtcttccc 1020
tgcctcccca ggggccaccc tggtggggcc ccacggacct ctggcctctg gccagctagc 1080
agccttccac atcgctgccc cgctccctgt cactgccaca cgctgggact tcggagacgg 1140
ctccgccgag gtggatgccg ctgggccggc tgcctcgcat cgctatgtgc tgcctgggcg 1200
ctatcacgtg acggccgtgc tggccctggg ggccggctca gccctgctgg ggacagacgt 1260
gcaggtggaa gcggcacctg ccgccctgga gctcgtgtgc cgtcctcgg tgcagagtga 1320
cgagagcctt gacctcagca tccagaaccg cggtggttca ggcctggagg ccgcctacag 1380
catcgtggcc ctgggcgagg agccggcccg agcggtgcac ccgctctgcc ctcggacac 1440
ggagatcttc cctggcaacg ggcactgcta ccgcctggtg gtggagaagg cggcctggct 1500
gcaggcgcag gagcagtgtc aggcctgggc cggggccgcc ctggcaatgg tggacagtcc 1560
cgccgtgcag cgcttcctgg tctcccgggt caccaggagc ctagacgtgt ggatcggctt 1620
ctcgactgtg caggggggtgg aggtgggccc agcgccgcag ggcgaggcct tcagcctgga 1680
gagctgccag aactggctgc ccggggagcc acacccagcc acagccgagc actgcgtccg 1740
gctcgggccc accgggtggt gtaacaccga cctgtgctca gcgccgcaca gctacgtctg 1800
cgagctgcag cccggaggcc cagtgcagga tgccgagaac ctcctcgtgg gagcgccag 1860
tggggacctg cagggacccc tgacgcctct ggcacagcag gacggcctct cagccccgca 1920
cgagcccgtg gaggtcatgg tattcccggg cctgcgtctg agccgtgaag ccttcctcac 1980
cacggccgaa tttgggaccc aggagctccg gcggccccgcc cagctgcggc tgcaggtgta 2040
ccggctcctc agcacagcag ggaccccgga gaacggcagc gagcctgaga gcaggtcccc 2100
ggacaacagg acccagctgg ccccccgcgtg catgccaggg ggacgctggt gccctggagc 2160
caacatctgc ttgccgctgg acgcctcttg ccaccccag gcctgcgcca atggctgcac 2220
gtcagggcca gggctacccg ggccccta tgcgctatgg agagagttcc tcttctccgt 2280
tgccgcgggg cccccgcgc agtactcggt caccctccac ggccaggatg tcctcatgct 2340
ccctggtgac ctcgttggct tgcagcacga cgctggccct ggcgcctcc tgcactgctc 2400
gccggctccc ggccaccctg gtccccaggc ccgtacctc tccgccaacg cctcgtcatg 2460
gctgccccac ttgccagccc agctggaggg cacttgggcc tgccctgcct gtgccctgcg 2520
gctgcttgca gccacggaac agctcaccgt gctgctgggc ttgaggccca accctggact 2580
gcggatgcct gggcgctatg aggtccgggc agaggtgggc aatggcgtgt ccaggcacaa 2640
cctctcctgc agctttgacg tggtctcccc agtggctggg ctgcgggtca tctaccctgc 2700
ccccgcgac ggccgcctct acgtgcccac caacggctca gccttggtgc tccaggtgga 2760
ctctggtgcc aacgccacgg ccacggctcg ctggcctggg ggcagtgtca gcgcccgctt 2820
tgagaatgtc tgccctgccc tggtggccac cttcgtgccc ggctgcccct gggagaccaa 2880
cgatacccctg ttctcagtgg tagcactgcc gtggctcagt gagggggagc acgtggtgga 2940
cgtggtggtg gaaacagcgc cagccgggc caacctcagc ctgcgggtga cggcggagga 3000
gcccatctgt ggcctccgcg ccacgcccag ccccgaggcc cgtgtactgc agggagtcct 3060
agtgaggtac agcccgtgg tggaggccgg ctcggacatg gtcttccggt ggaccatcaa 3120
cgacaagcag tccctgacct tccagaacgt ggtcttcaat gtcatttatc agagcgcggc 3180
ggtcttcaag ctctcactga cggcctccaa ccacgtgagc aacgtcaccg tgaactacaa 3240
cgtaaccgtg gagcggatga acaggatgca gggtctgcag gtctccacag tgccggccgt 3300
gctgtccccc aatgccacgc tagcactgac ggcgggcgtg ctggtggact cggccgtgga 3360
ggtggccttc ctgtggaact tggggatggg ggagcaggcc ctccaccagt tccagcctcc 3420
```

FIG. 1A

Figure 1 con.

```
gtacaacgag tccttcccgg ttccagaccc ctcggtggcc caggtgctgg tggagcacaa 3480
tgtcatgcac acctacgctg ccccaggtga gtacctcctg accgtgctgg catctaatgc 3540
cttcgagaac ctgacgcagc aggtgcctgt gagcgtgcgc gcctccctgc cctccgtggc 3600
tgtgggtgtg agtgacggcg tcctggtggc cggccggccc gtcaccttct acccgcaccc 3660
gctgccctcg cctggggtg ttctttacac gtgggacttc ggggacggct cccctgtcct 3720
gacccagagc cagccggctg ccaaccacac ctatgcctcg aggggcacct accacgtgcg 3780
cctggaggtc aacaacacgg tgagcggtgc ggcggcccag gcggatgtgc gcgtctttga 3840
ggagctccgc ggactcagcg tggacatgag cctgccgtg gagcagggcg ccccgtggt 3900
ggtcagcgcc gcggtgcaga cgggcgacaa catcacgtgg accttcgaca tgggggacgg 3960
caccgtgctg tcgggcccgg aggcaacagt ggagcatgtg tacctgcggg cacagaactg 4020
cacagtgacc gtgggtgcgg ccagccccgc cggccacctg gcccggagcc tgcacgtgct 4080
ggtcttcgtc ctggaggtgc tgcgcgttga acccgccgcc tgcatcccca cgcagcctga 4140
cgcgcggctc acggcctacg tcaccgggaa cccggcccac tacctcttcg actggacctt 4200
cggggatggc tcctccaaca cgaccgtgcg ggggtgcccg acggtgacac acaacttcac 4260
gcggagcggc acgttccccc tggcgctggt gctgtccagc cgcgtgaaca gggcgcatta 4320
cttcaccagc atctgcgtgg agccagaggt gggcaacgtc accctgcagc cagagaggca 4380
gtttgtgcag ctcggggacg aggcctggct ggtggcatgt gcctggccca cgttcccta 4440
ccgctacacc tgggactttg gcaccgagga agccgccccc accgtgcca ggggccctga 4500
ggtgacgttc atctaccgag acccaggctc ctatcttgtg acagtcaccg cgtccaacaa 4560
catctctgct gccaatgact cagccctggt ggaggtgcag gagcccgtgc tggtcaccag 4620
catcaaggtc aatggctccc ttgggctgga gctgcagcag ccgtacctgt tctctgctgt 4680
gggccgtggg cgccccgcca gctacctgtg ggatctgggg gacggtgggt ggctcgaggg 4740
tccggaggtc acccacgctt acaacagcac aggtgacttc accgttaggg tggccggctg 4800
gaatgaggtg agccgcagcg aggcctggct caatgtgacg gtgaagcggc gcgtgcgggg 4860
gctcgtcgtc aatgcaagcc gcacggtggt gcccctgaat gggagcgtga gcttcagcac 4920
gtcgctggag gccggcagtg atgtgcgcta ttcctgggtg ctctgtgacc gctgcacgcc 4980
catccctggg ggtcctacca tctcttacac cttccgctcc gtgggcacct tcaatatcat 5040
cgtcacgggct gagaacgagg tgggctccgc ccaggacagc atcttcgtct atgtcctgca 5100
gctcatagag gggctgcagg tggtgggcgg tggccgctac ttccccacca accacgggt 5160
acagctgcag gccgtggtta gggatggcac caacgtctcc tacagctgga ctgcctggag 5220
ggacaggggc ccggccctgg ccggcagcgg caaaggcttc tcgctcaccg tgctcgaggc 5280
cggcacctac catgtgcagc tgcgggccac caacatgctg ggcagcgcct gggcgactg 5340
caccatggac ttcgtggagc ctgtggggtg gctgatggtg accgcctccc cgaacccagc 5400
tgccgtcaac acaagcgtca ccctcagtgc cgagctggct ggtggcagtg gtgtcgtata 5460
cacttggtcc ttggaggagg ggctgagctg ggagacctcc gagccattta ccacccatag 5520
cttccccaca cccggcctgc acttggtcac catgacggca gggaacccgc tgggctcagc 5580
caacgccacc gtggaagtgg atgtgcaggt gcctgtgagt ggcctcagca tcagggccag 5640
cgagcccgga ggcagcttcg tggcggccgg gtcctctgtg ccctttggg ggcagctggc 5700
cacgggcacc aatgtgagct ggtgctgggc tgtgcccggc ggcagcagca agcgtggccc 5760
tcatgtcacc atggtcttcc cggatgctgg caccttctcc atccggctca atgcctccaa 5820
cgcagtcagc tgggtctcag ccacgtacaa cctcacggcg gaggagccca tcgtgggcct 5880
ggtgctgtgg gccagcagca aggtggtggc gcccgggcag ctggtccatt tcagatcct 5940
gctggctgcc ggctcagctg tcaccttccg cctgcaggtc ggcggggcca ccccgaggt 6000
gctccccggg ccccgtttct cccacagctt ccccgcgtc ggagaccacg tggtgagcgt 6060
gcggggcaaa aaccacgtga gctgggccca ggcgcaggtg cgcatcgtgg tgctggaggc 6120
cgtgagtggg ctgcagatgc ccaactgctg cgagcctggc atcgccacgg cactgagag 6180
gaacttcaca gcccgcgtgc agcgcggctc tcggtcgcc tacgcctggt acttctcgct 6240
gcagaaggtc cagggcgact cgctggtcat cctgtcgggc cgcgacgtca cctacacgcc 6300
cgtggccgcg gggctgttgg agatccaggt gcgcgccttc aacgccctgg gcagtgagaa 6360
ccgcacgctg gtgctggagg ttcaggacgc cgtccagtat gtggccctgc agagcggccc 6420
ctgcttcacc aaccgctcgg cgcagtttga ggccgccacc agcccagcc ccggcgtgt 6480
ggcctaccac tgggactttg gggatgggtc gccagggcag gacacagatg agcccagggc 6540
cgagcactcc tacctgaggc ctggggacta ccgcgtgcag gtgaacgcct ccaacctggt 6600
gagcttcttc gtgcgcagg ccacggtgac cgtccaggtg ctggcctgcc gggagccgga 6660
ggtggacgtg gtcctgcccc tgcaggtgct gatgcggcga tcacagcgca actacttgga 6720
ggcccacgtt gacctgcgcg actgcgtcac ctaccagact gagtaccgct gggaggtgta 6780
tcgcaccgcc agctgccagc ggccggggcg cccagcgcgt gtggccctgc ccggcgtgga 6840
```

FIG. 1B

Figure 1 con.

```
cgtgagccgg cctcggctgg tgctgccgcg gctggcgctg cctgtggggc actactgctt 6900
tgtgtttgtc gtgtcatttg gggacacgcc actgacacag agcatccagg ccaatgtgac 6960
ggtggccccc gagcgcctgg tgcccatcat tgagggtggc tcataccgcg tgtggtcaga 7020
cacacgggac ctggtgctgg atgggagcga gtcctacgac cccaacctgg aggacggcga 7080
ccagacgccg ctcagtttcc actgggcctg tgtggcttcg acacagaggg aggctggcgg 7140
gtgtgcgctg aactttgggc cccgcgggag cagcacggtc accattccac gggagcggct 7200
ggcggctggc gtggagtaca ccttcagcct gaccgtgtgg aaggccggcc gcaaggagga 7260
ggccaccaac cagacggtgc tgatccggag tggccgggtg cccattgtgt ccttggagtg 7320
tgtgtcctgc aaggcacagg ccgtgtacga agtgagccgc agctcctacg tgtacttgga 7380
gggccgctgc tcaattgca gcagcggctc caagcgaggg cggtgggctg cacgtacgtt 7440
cagcaacaag acgctggtgc tggatgagac caccacatcc acgggcagtg caggcatgcg 7500
actggtgctg cggcggggcg tgctgcggga cggcgaggga tacaccttca cgctcacggt 7560
gctgggccgc tctggcgagg aggagggctg cgcctccatc cgcctgtccc caaccgccc 7620
gccgctgggg ggctcttgcc gcctcttccc actgggcgct gtgcacgccc tcaccaccaa 7680
ggtgcacttc gaatgcacgg gctggcatga cgcggaggat gctggcgccc gctggtgta 7740
cgccctgctg ctgcggcgct gtcgccaggg ccactgcgag gagttctgtg tctacaaggg 7800
cagcctctcc agctacggag ccgtgctgcc cccgggtttc aggccacact tcgaggtggg 7860
cctggccgtg gtggtgcagg accagctggg agccgctgtg gtcgccctca acaggtcttt 7920
ggccatcacc ctcccagagc ccaacggcag cgcaacgggg ctcacagtct ggctgcacgg 7980
gctcaccgct agtgtgctcc cagggctgct gcggcaggcc gatccccagc acgtcatcga 8040
gtactcgttg gccctggtca ccgtgctgaa cgagtacgag cgggccctgg acgtggcggc 8100
agagcccaag cacgagcggc agcaccgagc ccagatacgc aagaacatca cggagactct 8160
ggtgtccctg agggtccaca ctgtggatga catccagcag atcgctgctg cgctggccca 8220
gtgcatgggg cccagcaggg agctcgtatg ccgctcgtgc ctgaagcaga cgctgcacaa 8280
gctggaggcc atgatgctca tcctgcaggc agagaccctc gcgggcaccg tgacgcccac 8340
cgccatcgga gacagcatcc tcaacatcac aggagacctc atccacctgg ccagctcgga 8400
cgtgcgggca ccacagccct cagagctggg agccgagtca ccatccagga tggtggcgtc 8460
ccaggcctac aacctgacct ctgccctcat gcgcatcctc atgcgctccc gcgtgctcaa 8520
cgaggagccc ctgacgctgg cgggcgagga gatcgtggcc cagggcaagc gctcggaccc 8580
gcggagcctg ctgtgctatg gcggcgcccc agggcctggc tgccacttct ccatcccga 8640
ggctttcagc ggggccctgg ccaacctcag tgacgtggtg cagctcatct ttctggtgga 8700
ctccaatccc tttccctttg gctatatcag caactacacc gtctccacca aggtggcctc 8760
gatggcattc cagacacagg ccggcgccca gatccccatc gagcggctgg cctcagagcg 8820
cgccatcacc gtgaaggtgc ccaacaactc ggactgggct gcccggggcc accgcagctc 8880
cgccaactcc gccaactccg ttgtggtcca gccccaggcc tccgtcggtg ctgtggtcac 8940
cctggacagc agcaaccctg cggccgggct gcatctgcag ctcaactata cgctgctgga 9000
cggccactac ctgtctgagg aacctgagcc ctacctggca gtctacctac actcggagcc 9060
ccggcccaat gagcacaact gctcggctag caggaggatc cgcccagagt cactccaggg 9120
tgctgaccac cggccctaca ccttcttcat ttccccgggg agcagagacc cagcggggag 9180
ttaccatctg aacctctcca gccacttccg ctggtcggcg ctgcaggtgt ccgtgggcct 9240
gtacacgtcc ctgtgccagt acttcagcga ggaggacatg tgtggcgga cagagggct 9300
gctgcccctg gaggagacct cgccccgcca ggccgtctgc ctcacccgcc acctcaccgc 9360
cttcggcgcc agcctcttcg tgccccaag ccatgtccgc tttgtgttc ctgagccgac 9420
agcggatgta aactacatcg tcatgctgac atgtgctgtg tgcctggtga cctacatggt 9480
catggccgcc atcctgcaca agctggacca gttggatgcc agccggggcc gcgccatccc 9540
tttctgtggg cagcggggcc gcttcaagta cgagatcctc gtcaagacag gctggggccg 9600
gggctcaggt accacggccc acgtgggcat catgctgtat ggggtggaca gccggagcgg 9660
ccaccggcac ctggacggcg acagagcctt ccaccgcaac agcctggaca tcttccggat 9720
cgccaccccg cacagcctgg gtagcgtgtg gaagatccga gtgtggcacg acaacaaagg 9780
gctcagccct gcctggttcc tgcagcacgt catcgtcagg gacctgcaga cggcacgcag 9840
cgccttcttc ctggtcaatg actggctttc ggtggagacg gaggccaacg ggggcctggt 9900
ggagaaggag gtgctggccg cgagcgacgc agccctttg cgcttccggc gcctgctggt 9960
ggctgagctg cagcgtggct cttttgacaa gcacatctgg ctctccatat gggaccggcc 10020
gcctcgtagc cgtttcactc gcatccagag ggccacctgc tgcgttctcc tcatctgcct 10080
cttcctgggc gccaacgccg tgtggtacgg ggctgttggc gactctgcct acagcacggg 10140
gcatgtgtcc aggctgagcc cgctgagcgt cgacacagtc gctgttggcc tggtgtccag 10200
cgtggttgtc tatcccgtct acctggccat cctttttctc ttccggatgt cccggagcaa 10260
```

FIG. 1C

Figure 1 con.

```
ggtggctggg agcccgagcc ccacacctgc cgggcagcag gtgctggaca tcgacagctg 10320
cctggactcg tccgtgctgg acagctcctt cctcacgttc tcaggcctcc acgctgaggc 10380
ctttgttgga cagatgaaga gtgacttgtt tctggatgat tctaagagtc tggtgtgctg 10440
gccctccggc gagggaacgc tcagttggcc ggacctgctc agtgacccgt ccattgtggg 10500
tagcaatctg cggcagctgg cacggggcca ggcgggccat gggctggggcc cagaggagga 10560
cggcttctcc ctggccagcc cctactcgcc tgccaaatcc ttctcagcat cagatgaaga 10620
cctgatccag caggtccttg ccgaggggggt cagcagccca gcccctaccc aagacaccca 10680
catggaaacg gacctgctca gcagcctgtc cagcactcct ggggagaaga cagagacgct 10740
ggcgctgcag aggctggggg agctggggcc acccagccca ggcctgaact gggaacagcc 10800
ccaggcagcg aggctgtcca ggacaggact ggtggagggt ctgcggaagc gcctgctgcc 10860
ggcctggtgt gcctccctgg cccacgggct cagcctgctc ctggtggctg tggctgtggc 10920
tgtctcaggg tgggtgggtg cgagcttccc cccggggcgtg agtgttgcgt ggctcctgtc 10980
cagcagcgcc agcttcctgg cctcattcct cggctgggag ccactgaagg tcttgctgga 11040
agccctgtac ttctcactgg tggccaagcg gctgcacccg gatgaagatg acaccctggt 11100
agagagcccg gctgtgacgc ctgtgagcgc acgtgtgccc cgcgtacggc caccccacgg 11160
ctttgcactc ttcctggcca aggaagaagc ccgcaaggtc aagaggctac atggcatgct 11220
gcggagcctc ctggtgtaca tgctttttct gctggtgacc ctgctggcca gctatgggga 11280
tgcctcatgc catgggcacg cctaccgtct gcaaagcgcc atcaagcagg agctgcacag 11340
ccgggccttc ctggccatca cgcggtctga ggagctctgg ccatggatgg cccacgtgct 11400
gctgccctac gtccacggga accagtccag cccagagctg ggcccccac ggctgcggca 11460
ggtgcggctg caggaagcac tctacccaga ccctcccggc cccagggtcc acacgtgctc 11520
ggccgcagga ggcttcagca ccagcgatta cgacgttggc tgggagagtc ctcacaatgg 11580
ctcggggacg tgggcctatt cagcgccgga tctgctgggg gcatggtcct ggggctcctg 11640
tgccgtgtat gacagcgggg gctacgtgca ggagctgggc ctgagcctgg aggagagccg 11700
cgaccggctg cgcttcctgc agctgcacaa ctggctggac aacaggagcc gcgctgtgtt 11760
cctggagctc acgcgctaca gcccggccgt ggggctgcac gccgccgtca cgctgcgcct 11820
cgagttcccg gcggccggcc gcgccctcag cgtccgccct ttgcgctgcg 11880
ccgcctcagc gcgggcctct cgctgcctct gctcaccctcg gtgtgcctgc tgctgttcgc 11940
cgtgcacttc gccgtggccg aggcccgtac ttggcacagg gaagggcgct ggcgcgtgct 12000
gcggctcgga gcctgggcgc ggtggctgct ggtggcgctg acgcggcca cggcactggt 12060
acgcctcgcc cagctgggtg ccgctgaccg ccagtggacc cgtttcgtgc gcggccgccc 12120
gcgccgcttc actagcttcg accaggtggc gcagctgagc tccgcagccc gtggcctggc 12180
ggcctcgctg ctcttcctgc ttttggtcaa ggctgcccag cagctacgct tcgtgcgcca 12240
gtggtccgtc tttggcaaga cattatgccg agctctgcca gagctcctgg gggtcacctt 12300
gggcctggtg gtgctcgggg tagcctacgc ccagctggcc atcctgctcg tgtcttcctg 12360
tgtggactcc ctctggagcg tggcccaggc cctgttggtg ctgtgccctg ggactgggct 12420
ctctaccctg tgtcctgccg agtcctggca cctgtcaccc ctgctgtgtg tggggctctg 12480
ggcactgcgg ctgtggggcg ccctacggct gggggctgtt attctccgct ggcgctacca 12540
cgccttgcgt ggagagctgt accggccggc ctgggagccc caggactacg agatggtgga 12600
gttgttcctg cgcaggctgc gcctctggat gggcctcagc aaggtcaagg agttccgcca 12660
caaagtccgc tttgaaggga tggagccgct gccctctcgc tcctccaggg gctccaaggt 12720
atcccccggat gtgcccccac ccagcgctgg ctcgatgcc tcgcacccct ccacctcctc 12780
cagccagctg gatgggctga gcgtgagcct gggccggctg gggacaaggt gtgagcctga 12840
gccctcccgc ctccaagccg tgttcgaggc cctgctcacc cagtttgacc gactcaacca 12900
ggccacagag gacgtctacc agctggagca gcagctgcac agcctgcaag ccgcaggag 12960
cagccgggcg cccgccggat cttcccgtgg cccatccccg ggcctgcggc cagcactgcc 13020
cagccgcctt gcccgggcca gtcggggtgt ggacctggcc actggcccca gcaggacacc 13080
ccttcgggcc aagaacaagg tccaccccag cagcacttag tcctccttcc tggcggggggt 13140
gggccgtgga gtcggagtgg acaccgctca gtattacttt ctgccgctgt caaggccgag 13200
ggccaggcag aatggctgca cgtaggttcc ccagagagca ggcagggcca tctgtctgtc 13260
tgtgggcttc agcactttaa agaggctgtg tggccaacca ggacccaggg tccctcccc 13320
agctcccttg gaaggacac agcagtattg gacggtttct agcctctgag atgctaattt 13380
atttccccga gtcctcaggt acagcgggct gtgccggcc ccacccctg ggcagatgtc 13440
ccccactgct aaggctgctg gcttcaggga gggttagcct gcaccgccgc caccctgccc 13500
ctaagttatt acctctccag ttcctaccgt actccctgca ccgtctcact gtgtgtctcg 13560
tgtcagtaat ttatatggtg ttaaaatgtg tatattttg tatgtcacta ttttcactag 13620
ggctgagggg cctgcgccca gagctggcct cccccaacac ctgctgcgct tggtaggtgt 13680
```

FIG. 1D

Figure 1 con.

```
ggtggcgtta tggcagcccg gctgctgctt ggatgcgagc ttggccttgg gccggtgctg 13740
ggggcacagc tgtctgccag gcactctcat cacccccagag gccttgtcat cctcccttgc 13800
cccaggccag gtagcaagag agcagcgccc aggcctgctg gcatcaggtc tgggcaagta 13860
gcaggactag gcatgtcaga ggaccccagg gtggttagag gaaaagactc ctcctggggg 13920
ctggctccca gggtggagga aggtgactgt gtgtgtgtgt gtgtgcgcgc gcgacgcgcg 13980
agtgtgctgt atggcccagg cagcctcaag gccctcggag ctggctgtgc ctgcttctgt 14040
gtaccacttc tgtgggcatg gccgcttcta gagcctcgac acccccccaa ccccgcacc 14100
aagcagacaa agtcaataaa agagctgtct gactgc                          14136
```

```
ggctcctgag gcgcacagcg ccgagcgcgg cgccgcgcac ccgcgcgccg gacgccagtg   60
accgcgatgg tgaactccag tcgcgtgcag cctcagcagc ccggggacgc caagcggccg  120
cccgcgcccc gcgcgccgga cccgggccgg ctgatggctg gctgcgcggc cgtgggcgcc  180
agcctcgccg ccccgggccg cctctgcgag cagcggggcc tggagatcga gatgcagcgc  240
atccggcagg cggccgcgcg ggaccccccg gccggagccg cggcctcccc ttctcctccg  300
ctctcgtcgt gctcccggca ggcgtggagc cgcgataacc ccggcttcga ggccgaggag  360
gaggaggagg aggtggaagg ggaagaaggc ggaatggtgg tggagatgga cgtagagtgg  420
cgcccgggca gccggaggtc ggccgcctcc tcggccgtga gctccgtggg cgcgcggagc  480
cggggcttg ggggctacca cggcgcgggc caccgagcg ggaggcggcg ccggcgagag  540
gaccagggcc cgccgtgccc cagcccagtc ggcggcgggg accgctgca tcgccacctc  600
ccctggaag ggcagccgcc ccgagtggcc tgggcggaga ggctggttcg cgggctgcga  660
ggtgtaagag cgcgcgaccc gcagcggcag atgcacgaac cagaacggcc ggcgccggng  720
gcttcttaaa taaaatgata tctttcttt tcttcattat tatttaaag gtctctgggg  780
aacaagactc atggaggaaa gcagcactaa ccgagagaaa taccttaaaa gtgttttacg  840
ggaactggtc acatacctcc ttttctcat agtcttgtgc atctgtaagt agaatatttc  900
cttgcactaa tgggaaagtt ttgaaacgat gtgaatttgt ccaaaatgtt tatccacagg  960
aacaatccct tgtgaaggc tgctggtatg tggatgtgtg ccggttccct tggggcgttc 1020
atttggatct ttctgtgttc cagtgaccta cggcatgatg agctccaatg tgtactacta 1080
cacccggatg atgtcacagc tcttcctaga caccccgtg tccaaaacgg agaaaactaa 1140
ctttaaaact ctgtcttcca tggaagactt ctggaaggta tttggaaata actttgaaag 1200
tacctctcta tcacaagcca atgcttggtt atgcaacgat gcaggcaggg caaagcagcg 1260
gcatgagctt gaacttnnnn agatgttnnc tttcttttag ttcacagaag gctccttatt 1320
ggatgggctg tactggaaga tgcagcccag caaccagact gaagctgaca accgaagttt 1380
catcttctat gagaacctgc tgttaggggt tccacgaata cggcaactcc gagtcagaaa 1440
tggatcctgc tctatccccc aggacttgag agatgaaatt aaagagtgct atgatgtcta 1500
ctctgtcagt agtgaagata gggctccctt tgggccccga atggaaccg cgtaagtgtc 1560
tgtgactcat tggcactcgg tgatattcat ccttgtaatt gcctcaagtg ttccactgat 1620
tgtaactgtt tgttttngg ttttgttttt aatcagttgg atctacacaa gtgaaaaga 1680
cttgaatggt agtagccact ggggaatcat tgcaacttat agtggagctg ctattatct 1740
ggatttgtca agaacaagag aggaaacagc tgcacaagtt gctagcctca agaaaaatgt 1800
ctggctggac cgaggaacca gggcaacttt tattgacttc tcagtgtaca cgccaacat 1860
taacctgttc tgtgtggtca ggtgtgtgac tgaggacatg catccctcct atttctgtgt 1920
ggttgtacat acatcctatt ctagggttac ccagaaaaac cttttntgc aggttgttat 1980
tgttttaatt gttcttattt acatgcaggt tattggttga attcccagca acaggtggtg 2040
tgattccatc ttggcaattt cagcctttaa agctgatccg atatgtcaca actttgatt 2100
tcttcctggc agcctgtgag attatcttt gtttctttat cttttactat gtggtggaag 2160
agatattgga aattcgcatt cacaaactac actatttcag gagtttctgg aattgtctgg 2220
atgttgtgat cgttgtggta ggtccganca ncancaccaa atttcctatt ctattctaca 2280
agnatgttaa caattaatac attggtgaag aaaaatatac tagtcatatt aaggtaagtt 2340
tcatatttct aaaacactgt aataaaatat aaatatttg cttttcagct gtcagtggta 2400
gctataggaa ttaacatata cagaacatca aatgtggagg tgctactaca gtttctggaa 2460
gatcaaaata cttttcccca ctttgagcat ctggcatatt ggcagataca gttcaacaat 2520
atagctgctg tcacagtatt ttttgtctgg attaaggtaa tttataaatt tcatgttcta 2580
cattnnaaat aatattttct ttaaaaaaaa tgagttccac aaaancatgc gaaacaatgt 2640
tttattatac acagtcacac catttggttt atccattcat ctattgatgt cttctctctc 2700
ttacagctct tcaaattcat caattttaac aggaccatga gccagctctc gacaaccatg 2760
tctcgatgtg ccaaagacct gtttggcttt gctattatgt tcttcattat tttcctagcg 2820
tatgctcagt tggcatacct tgtctttggc actcaggtcg atgacttcag tactttccaa 2880
gagtgtatgt aagtatatat gaattaaga agaaaattt agtcagagta gncactgttg 2940
cgtggacant ctttggtttt gtattgtggt gntttgtntt attttttatag cttcactcaa 3000
ttccgtatca ttttgggcga tatcaacttt gcagagattg aggaagctaa tcgagttttg 3060
ggaccaattt atttcactac atttgtgttc tttatgttct tcattctttt ggtatgtaca 3120
tttatattta tagtggaggt tcaatttaaa cttcgtaaat ccttgtcttc tcttttttga 3180
ttgataattc caaattatgt ttcttccttt aattttgcc ctcctttcat ttacaaacag 3240
aatatgtttt tggctatcat caatgatact tactctgaag tgaaatctga cttggcacag 3300
cagaaagctg aaatggaact ctcagatctt atcagaaagg taggaaaaac cttaattctc 3360
aaaaattctt ctgtttctga cataaaatga gcattgtttc acccanattt tagaatacnc 3420
```

FIG. 2A

Figure 2 con.

```
taaaccaagt cttttatttt ttctctctct gatagggcta ccataaagct ttggtcaaac 3480
taaaactgaa aaaaaatacc gtggatgaca tttcagagag tctgcggcaa ggaggaggca 3540
agttaaactt tgacgaactt cgacaagatc tcaaagggtg agaatcatgc ttcctgaggt 3600
tctnaaaaat tcctgcttct aaagataaat tcctggtgat aagagtattt ctagcccaag 3660
ggctcatggg aacanaggat gaatgttatc tgtatcctct ctctaatttc aggaagggcc 3720
atactgatgc agagattgag gcaatattca caaagtacga ccaagatgga gaccaagaac 3780
tgaccgaaca tgaacatcag cagatgagag acgacttgga gaaagagagg gtgggtctgg 3840
tttaggagna accggatttg atttggtacc tacaacacca cacttctgtg gggtctcagt 3900
gttctgctcc tcactcagtg accccttgtt cttcaggagg acctggattt ggatcacagt 3960
tctttaccac gtcccatgag cagccgaagt ttccctcgaa gcctggatga ctctgaggag 4020
gatgacgatg aagatagcgg acatagctcc agaaggaggg gaagcatttc tagtggcgtt 4080
tcttacgaag agtttcaagt gtaagtataa aggaattggc agaatttgcg tngacaattt 4140
gtccctctgt actgtgtttt ccttgcagcc tggtgagacg agtggaccgg atggagcatt 4200
ccatcggcag catagtgtcc aagattgacg ccgtgatcgt gaagctagag attatggagc 4260
gagccaaact gaagaggagg gaggtgctgg gaaggctgtt ggatggggtg gccgaggtca 4320
gtagtcatga gctgaanaca ccgctgctga gcatggtgtt attaatnnna atatatgttg 4380
ctgacagttg tatttnaagt attnactgac ccccaacacc agtttctttt tccttttta 4440
ggatgaaagg ctgggtcgtg acagtgaaat ccatagggaa cagatggaac ggctagtacg 4500
tgaagagttg gaacgctggg aatccgatga tgcagcttcc cagatcagtc atggtttagg 4560
cacgccagtg ggactaaatg gtcaacctcg ccccagaagc tcccgcccat cttcctccca 4620
atctacagaa ggcatggaag gtgcaggtgg aaatgggagt tctaatgtcc acgtatgata 4680
tgtgtgtttc agtatgtgtg tttctaataa gtgaggaagt ggctgtcctg aattgctgta 4740
acaagcacac tatttatatg ccctgaccac cataggatgc tagtctttgt gaccgattgc 4800
taatcttctg cactttaatt tattttatat aaactttacc catggttcaa agatttttt 4860
ttctttttct catataagaa atctaggtgt aaatattgag tacagaaaaa aaatcttcat 4920
gatgtgtatt gagcggtacg cccagttgcc accatgactg agtcttctca gttgacaatg 4980
aagtagcctt ttaaagctag aaaactgtca aagggcttct gagtttcatt tccagtcaca 5040
aaaatcagta ttgttatttt tttccaagag tgtgaaggaa aatgggcaa ttcctttcca 5100
ctctgcata gttcatgagc ttaatacata gctttctttt aagaaggag ccttttttt 5160
caactagctt cctggggtaa acttttctaa aagataaaat gggaaggaac tccaaactat 5220
gatagaatct gtgtgaatgg ttaagatgaa tgttaaatac tatgcttttt tgtaagttga 5280
tcgtatctga tgtctgtggg actaactgta tcacttaatt tttaccttat tttggctcta 5340
atttgaataa gctgagtaaa accaccaaag atcagttata ggataaaatg gcatctctaa 5400
ccataacaca ggagaattgg aaggagccct aagttgtcac tcagtttaat ttcttttaat 5460
ggttagttta gcctaaagat ttatctgcat attcttttc ccatgtggct ctactcattt 5520
gcaactgaat ttaatgttat aactcatcta gtgagaccaa cttactaaat ttttagtatg 5580
cactgaaagt ttttatccaa caattatgtt catttaagc aaaattttaa gaaagttttg 5640
aaattcataa agcatttggt tttaaactat tttaagaata tagtactcgg tcaggtatgn 5700
nncacgcctg taatcccagc actttgggag gccgaaacag gcgaatcact tgagcccagg 5760
agttcaagac caacatggc aatgtggcga aactccatct ctacaaaaaa tgcaaaaata 5820
aaaatatag tactcaagta ttcttgatcc tgtgtttcaa aactagaatt tgtaatgcaa 5880
atggagctca gtctaataaa aaagagggttt tggtattaaa agttcataca ttagacagta 5940
tcagccaaaa tttgagttag caacactgtt ttctt'acga gagggtctca cccaaattta 6000
tggggagaaa tctatttctc aaaaaaaaaa aatcttcttt tacagaaatg ttgagtaagg 6060
tgacattttg agcgctaata agcaaaagag catgcagtgc tgttgaataa ccctcacttg 6120
gagaaccaag agaatcctgt cgtttaatgc tatattttaa tttcacaagt tgttcattta 6180
actggtagaa tgtcagtcca atctccaatg agaacatgag caaatagacc tttccaggtt 6240
gaaagtgaaa catactgggt ttctgtaagt ttttcctcat ggcttcatct ctatctttac 6300
tttctcttga atatgctaca caaagttctt tattactaca tactaaagtt tgcattccag 6360
ggatattgac tgtacatatt tatgtatatg taccatgttg ttacatgtaa acaaacttca 6420
atttgaagtg cagctattat gtggtatcca tgtgatcga ccatgtgcca tatatcaatt 6480
atggtcacta gaaagtctct ttatgatact ttttattgta ctgtttttca tttcacttgc 6540
aaaattttgc agaattcctc ctttctaccc ataaattaca tataattttt cttctttagt 6600
catggagaac nccccccat catctcancc ctattancttt tcccatgtgt actggtatta 6660
ttaaaaagac atttacatac gcaagttttt cactgacaan caagaatgtt attaatgtgt 6720
aatactgagc acntttactt cttaataaa                                    6749
```

| Codon Number | | |
|---|---|---|
| | | Exon 1 |
| | 212 | atgccgcccgccgcgcccgcccgcctggcgctggccctgggcctg |
| 1 | | M P P A A P A R L A L A L G L |
| | 257 | ggcctgtggctcggggcgctggcggggggccccggcgcgcgactgc |
| 16 | | G L W L G A L A G G F G R G C |
| | 302 | gggccctgcgagccccctgcctctgcggcccagcgcccggcgcc |
| 31 | | G P C E P P C L C G P A P G A |
| | 347 | gcctgccgcgtcaactgctcgggccgcggactgcggacgctcggt |
| 46 | | A C R V N C S G R G L R T L G |
| | | Exon 2 |
| | 392 | cccgccctgcgcatcccgcggacgccacagcgct |
| 61 | | P A L R I P A D A T A L |
| | 437 | |
| 76 | | |
| | | Exon 3 |
| | 482 | ggatataagcaacaacaagatttctacg |
| 91 | | D I S N N K I S T |
| | | Exon 4 |
| | 527 | ttagaagaaggaatatttgctaatttatttaatttaagtgaaat |
| 106 | | L E E G I F A N L F N L S E I |
| | 572 | |
| 121 | | |
| | 617 | |
| 136 | | |
| | 662 | |
| 151 | | |
| | | Exon 5-A |
| | 707 | gtgaggagtat |
| 166 | | G E E Y |
| | 752 | gtcgcctgcctccctgacaacagctcaggcaccgtggcagcagtg |
| 181 | | V A C L P D N S S G T V A A V |

FIG. 3A

Figure 3 con.

```
797 tccttttcagctgcccacgaaggcctgcttcagccagaggcctgc
196  S  F  S  A  A  H  E  G  L  L  Q  P  E  A  C 842 agcgccttctgcttctccaccggccagggcctcacagccctctcg
211  S  A  F  C  F  S  T  G  Q  G  L  A  A  L  S
                                → 5-B
887 gagcagggctggtgcctgtgtgggcggcccagccctccagtgcc
226  E  Q  G  W  C  L  C  G  A  A  Q  P  S  S  A
              ←       5-A
932 tcctttgcctgcctgtccctctgctccggccccccgccacctcct
241  S  F  A  C  L  S  L  C  S  G  P  P  P  P 977 gcccccacctgtaggggcccaccctcctccagcacgtcttccct
256  A  P  T  C  R  G  P  T  L  L  Q  H  V  F  P 1022 gcctcccagggggccaccctggtggggccccacggacctctggcc
271  A  S  P  G  A  T  L  V  G  P  H  G  P  L  A 1067 tctggccagctagcagccttccacatcgctgccccgctccctgtc
286  S  G  Q  L  A  A  F  H  I  A  A  P  L  P  V
                                    → 5-C
1112 actgccacacgctgggacttcggagacggctccgccgaggtggat
301  T  A  T  R  W  D  F  G  D  G  S  A  E  V  D
                                  ←       5-B
1157 gccgctgggccggctgcctcgcatcgctatgtgctgcctgggcgc
316  A  A  G  P  A  A  S  H  R  Y  V  L  P  G  R 1202 tatcacgtgacggccgtgctggccctgggggccggctcagccctg
331  Y  H  V  T  A  V  L  A  L  G  A  G  S  A  L 1247 ctggggacagacgtgcaggtggaagcggcacctgccgccctggag
346  L  G  T  D  V  Q  V  E  A  A  P  A  A  L  E 1292 ctcgtgtgcccgtcctcggtgcagagtgacgagagccttgacctc
361  L  V  C  P  S  S  V  Q  S  D  E  S  L  D  L 1337 agcatccagaaccgcggtggttcaggcctggaggccgcctacagc
376  S  I  Q  N  R  G  G  S  G  L  E  A  A  Y  S
                                        Exon 6
1382 atcgtggccctgggcgaggagccggcccgag...
391  I  V  A  L  G  E  E  P  A  R ...
```

FIG. 3B

Figure 3 con.

```
1427 ...
406  ...

1472 ...
421  ...

1517 ...
436  ...                                          Exon 7

1562 ...gagcctagac
451  ...            S L D 1607 gtgtggatcggcttctcgactgtgcaggggtggaggtgggccca
466   V  W  I  G  F  S  T  V  Q  G  V  E  V  G  P 1652 gcgccgcagggcgaggccttcagctggagagctgccagaactgg
481   A  P  Q  G  E  A  F  S  L  E  S  C  Q  N  W 1697 ctgcccggggagccacacccagccacagccgagcactgcgtccgg
496   L  P  G  E  P  H  P  A  T  A  E  H  C  V  R 1742 ctcgggcccaccgggtggtgtaacaccgacctgtgctcagcgccg
511   L  G  P  T  G  W  C  N  T  D  L  C  S  A  P
                                          Exon 8
1787 cacagctacgtctgcgagctgcagcccggag...
526   H  S  Y  V  C  E  L  Q  P  G

1832 ...
541  ...

1877 ...
556  ...
             Exon 9
1922 ...gtcatggtattcccgggcctgcgtctgagccgt
571  ...    V  M  V  F  P  G  L  R  L  S  R 1967 gaagccttcctcaccacggccgaatttgggacccaggagctccgc
586   E  A  F  L  T  T  A  E  F  G  T  Q  E  L  R 2012 cggcccgcccagctgcggctgcaggtgtaccggctcctcagcaca
601   R  P  A  Q  L  R  L  Q  V  Y  R  L  L  S  T
      Exon 10
2057 gcag...
616   A
```

FIG. 3C

Figure 3 con.

```
      2102 ...
631        ...

2147 ...
646        ...

2192 ...
661        ...

2237 ...
676        ...                                    Exon 11-A

2282 ......................gtcaccctccacggccag
691                              V  T  L  H  G  Q 2327 gatgtcctcatgctccctggtgacctcgttggcttgcagcacgac
706        D  V  L  M  L  P  G  D  L  V  G  L  Q  H  D 2372 gctggccctggcgcctcctgcactgctcgccggctcccggccac
721        A  G  P  G  A  L  L  H  C  S  P  A  P  G  H 2417 cctggtccccagggccccgtacctctccgccaacgcctcgtcatgg
736        P  G  P  Q  A  P  Y  L  S  A  N  A  S  S  W
                                                  → 11-B 2462 ctgccccacttgccagcccagctggagggcacttgggcctgccct
751        L  P  H  L  P  A  Q  L  E  G  T  W  A  C  P 2507 gcctgtgccctgcggctgcttgcagccacggaacagctcaccgtg
766        A  C  A  L  R  L  L  A  A  T  E  Q  L  T  V
           ←         11-A 2552 ctgctgggcttgaggcccaaccctggactgcggatgcctgggcgc
781        L  L  G  L  R  P  N  P  G  L  R  M  P  G  R 2597 tatgaggtccggggcagaggtgggcaatggcgtgtctccaggcacaac
796        Y  E  V  R  A  E  V  G  N  G  V  S  R  H  N 2642 ctctcctgcagctttgacgtggtctccccagtggctgggctgcgg
811        L  S  C  S  F  D  V  V  S  P  V  A  G  L  R 2687 gtcatctaccctgcccccccgcgacggccgcctctacgtgcccacc
826        V  I  Y  P  A  P  R  D  G  R  L  Y  V  P  T 2732 aacggctcagccttggtgctccaggtggactctggtgccaacgcc
841        N  G  S  A  L  V  L  Q  V  D  S  G  A  N  A
```

FIG. 3D

Figure 3 con.

```
2777 acggccacggctcgctggcctggggcagtgtcagcgcccgcttt
856       T  A  T  A  R  W  P  G  G  S  V  S  A  R  F
                                              → 11-C
2822 gagaatgtctgccctgcccggtggccaccttcgtgcccggctgc
871       E  N  V  C  P  A  L  V  A  T  F  V  P  G  C 2867 ccctgggagaccaacgatacccctgttctcagtggtagcactgccg
886       P  W  E  T  N  D  T  L  F  S  V  V  A  L  P
                                              ← 11-B
2912 tggctcagtgagcgggagcacgtggtggacgtggtggtggaaaac
901       W  L  S  E  G  E  H  V  V  D  V  V  V  E  N 2957 agcgccagccgggccaacctcagcctgcgggtgacggcggaggag
916       S  A  S  R  A  N  L  S  L  R  V  T  A  E  E 3002 cccatctgtggcctccgcgccacgcccagccccgaggccgtgta
931       P  I  C  G  L  R  A  T  P  S  P  E  A  R  V
                                     Exon 12
3047 ctgcagggagtcctagtg...
946       L  Q  G  V  L  V

3092 ...
961

3137 ...
976                              Exon 13

3182 ...ctgacggcctccaaccacgtgagcaacgtc
991       L  T  A  S  N  H  V  S  N  V 3227 accgtgaactacaacgtaaccgtggagcggatgaacaggatgcag
1006      T  V  N  Y  N  V  T  V  E  R  M  N  R  M  Q 3272 ggtctgcaggtctccacagtgccggccgtgctgtcccccaatgcc
1021      G  L  Q  V  S  T  V  P  A  V  L  S  P  N  A 3317 acgctagcactgacggcgggcgtgctggtggactcggccgtggag
1036      T  L  A  L  T  A  G  V  L  V  D  S  A  V  E
                              Exon 14
3362 gtggccttcct...
1051      V  A  F  L

Figure 3 con.

```
     3452 ...
1081      ...
               Exon 15-A
     3497 ......gtgagtacctcctgaccgtgctggcatctaatgcc
1096       ...  G  E  Y  L  L  T  V  L  A  S  N  A 3542 ttcgagaacctgacgcagcaggtgcctgtgagcgtgcgcgcctcc
1111       F  E  N  L  T  Q  Q  V  P  V  S  V  R  A  S 3587 ctgccctccgtggctgtgggtgtgagtgacggcgtcctggtggcc
1126       L  P  S  V  A  V  G  V  S  D  G  V  L  V  A
                                              →15-B 3632 ggccggcccgtcaccttctacccgcacccgctgccctcgcctggg
1141       G  R  P  V  T  F  Y  P  H  P  L  P  S  P  G 3677 ggtgttctttacacgtgggacttcggggacggctcccctgtcctg
1156       G  V  L  Y  T  W  D  F  G  D  G  S  P  V  L
          ←      15-A 3722 acccagagccagccggctgccaaccacacctatgcctcgaggggc
1171       T  Q  S  Q  P  A  A  N  H  T  Y  A  S  R  G 3767 acctaccacgtgcgcctggaggtcaacaacacggtgagcgtgcc
1186       T  Y  H  V  R  L  E  V  N  N  T  V  S  G  A 3812 gcggcccaggcggatgtgcgcgtctttgaggagctccgcggactc
1201       A  A  Q  A  D  V  R  V  F  E  E  L  R  G  L
                                           →15-C 3857 agcgtggacatgagcctggccgtggagcagggcgcccccgtggtg
1216       S  V  D  M  S  L  A  V  E  Q  G  A  P  V  V
                                   ←        15-B 3902 gtcagcgccgcggtgcagacgggcgacaacatcacgtggaccttc
1231       V  S  A  A  V  Q  T  G  D  N  I  T  W  T  F 3947 gacatgggggacggcaccgtgctgtcgggcccggaggcaacagtg
1246       D  M  G  D  G  T  V  L  S  G  P  E  A  T  V 3992 gagcatgtgtacctgcgggcacagaactgcacagtgaccgtgggt
1261       E  H  V  Y  L  R  A  Q  N  C  T  V  T  V  G 4037 gcggccagccccgccggccacctggcccggagcctgcacgtgctg
1276       A  A  S  P  A  G  H  L  A  R  S  L  H  V  L
               →15-D 4082 gtcttcgtcctggaggtgctgcgcgttgaacccgccgcctgcatc
1291       V  F  V  L  E  V  L  R  V  E  P  A  A  C  I
          ←      15-C
```

FIG. 3F

Figure 3 con.

```
     4127 cccacgcagcctgacgcgcggctcacggcctacgtcaccgggaac
1306      P  T  Q  P  D  A  R  L  T  A  Y  V  T  G  N 4172 ccggcccactacctcttcgactggaccttcggggatggctcctcc
1321      P  A  H  Y  L  F  D  W  T  F  G  D  G  S  S 4217 aacacgaccgtgcggggtgcccgacggtgacacacaacttcacg
1336      N  T  T  V  R  G  C  P  T  V  T  H  N  F  T
                                              →15-E 4262 cggagcggcacgttccccctggcgctggtgctgtccagccgcgtg
1351      R  S  G  T  F  P  L  A  L  V  L  S  S  R  V
                                    ← 15-D 4307 aacagggcgcattacttcaccagcatctgcgtggagccagaggtg
1366      N  R  A  H  Y  F  T  S  I  C  V  E  P  E  V 4352 ggcaacgtcaccctgcagccagagaggcagtttgtgcagctcggg
1381      G  N  V  T  L  Q  P  E  R  Q  F  V  Q  L  G 4397 gacgaggcctggctggtcgcatgtgcctggccccgttccctac
1396      D  E  A  W  L  V  A  C  A  W  P  P  F  P  Y 4442 cgctacacctgggactttggcaccgaggaagccgcccccacccgt
1411      R  Y  T  W  D  F  G  T  E  E  A  A  P  T  R
                                        →15-F 4487 gccagggccctgaggtgacgttcatctaccgagacccaggctcc
1426      A  R  G  P  E  V  T  F  I  Y  R  D  P  G  S
                                    ← 15-E 4532 tatcttgtgacagtcaccgcgtccaacaacatctctgctgccaat
1441      Y  L  V  T  V  T  A  S  N  N  I  S  A  A  N 4577 gactcagccctggtggaggtgcaggagcccgtgctggtcaccagc
1456      D  S  A  L  V  E  V  Q  E  P  V  L  V  T  S 4622 atcaaggtcaatggctcccttgggctggagctgcagcagccgtac
1471      I  K  V  N  G  S  L  G  L  E  L  Q  Q  P  Y
                                        →15-G 4667 ctgttctctgctgtgggccgtgggcgccccgccagctacctgtgg
1486      L  F  S  A  V  G  R  G  R  P  A  S  Y  L  W 4712 gatctggggacggtgggtgactcgagggtccggaggtcacccac
1501      D  L  G  D  G  G  W  L  E  G  P  E  V  T  H
                    ← 15-F 4757 gcttacaacagcacaggtgacttcaccgttagggtggccggctgg
1516      A  Y  N  S  T  G  D  F  T  V  R  V  A  G  W
```

FIG. 3G

Figure 3 con.

```
4802 aatgaggtgagccgcagcgaggcctggctcaatgtgacggtgaag
1531      N  E  V  S  R  S  E  A  W  L  N  V  T  V  K
                    → 15-H 4847 cggcgcgtgcggggctcgtcgtcaatgcaagccgcacggtggtg
1546      R  R  V  R  G  L  V  V  N  A  S  R  T  V  V
              ←              15-G 4892 ccctgaatgggagcgtgagcttcagcacgtcgctggaggccggc
1561      P  L  N  G  S  V  S  F  S  T  S  L  E  A  G 4937 agtgatgtgcgctattcctgggtgctctgtgaccgctgcacgccc
1576      S  D  V  R  Y  S  W  V  L  C  D  R  C  T  P 4982 atccctggggtcctaccatctcttacaccttccgctccgtgggc
1591      I  P  G  G  P  T  I  S  Y  T  F  R  S  V  G
                                            → 15-I 5027 accttcaatatcatcgtcacggctgagaacgaggtgggctccgcc
1606      T  F  N  I  I  V  T  A  E  N  E  V  G  S  A 5072 caggacagcatcttcgtctatgtcctgcagctcatagaggggctg
1621      Q  D  S  I  F  V  Y  V  L  Q  L  I  E  G  L
     ←        15-H 5117 caggtggtgggcggtaaatacttccccaccaaccacacggta
1636      Q  V  V  G  G  K  Y  F  P  T  N  H  T  V 5162 cagctgcaggccgtggttagggatggcaccaacgtctcctacagc
1651      Q  L  Q  A  V  V  R  D  G  T  N  V  S  Y  S
                                            → 15-J 5207 tggactgcctggagggacagggggcccggccctggccggcagcggc
1666      W  T  A  W  R  D  R  G  P  A  L  A  G  S  G 5252 aaaggcttctcgctcaccgtgctcgaggccggcacctaccatgtc
1681      K  G  F  S  L  T  V  L  E  A  G  T  Y  H  V
                        ←         15-I 5297 cagctgcgggccaccaacatgctgggcagcgcctgggccgactgc
1696      Q  L  R  A  T  N  M  L  G  S  A  W  A  D  C 5342 accatggacttcgtggagcctgtggggtggctgatggtgaccgcc
1711      T  M  D  F  V  E  P  V  G  W  L  M  V  T  A 5387 tccccgaacccagctgccgtcaacacaagcgtcaccctcagtgcc
1726      S  P  N  P  A  A  V  N  T  S  V  T  L  S  A 5432 gagctggctggtggcagtggtgtcgtatacacttggtccttggag
1741      E  L  A  G  G  S  G  V  V  Y  T  W  S  L  E
```

FIG. 3H

Figure 3 con.

```
              →  15-K
       5477  gaggggctgagctgggagacctccgagccatttaccacccatagc
1756         E  G  L  S  W  E  T  S  E  P  F  T  T  H  S 5522  ttccccacacccggcctgcacttggtcaccatgacggcagggaac
1771         F  P  T  P  G  L  H  L  V  T  M  T  A  G  N 5567  ccgctgggctcagccaacgccaccgtggaagtggatgtgcaggtg
1786         P  L  G  S  A  N  A  T  V  E  V  D  V  Q  V 5612  cctgtgagtggcctcagcatcagggccagcgagcccggaggcagc
1801         P  V  S  G  L  S  I  R  A  S  E  P  G  G  S 5657  ttcgtggcggccgggtcctctgtgccctttggggggcagctggcc
1816         F  V  A  A  G  S  S  V  P  F  W  G  Q  L  A
                                       ←  15-J
       5702  acgggcaccaatgtgagctggtgctgggctgtgcccggcggcagc
1831         T  G  T  N  V  S  W  C  W  A  V  P  G  G  S 5747  agcaagcgtggccctcatgtcaccatggtcttcccggatgctggc
1846         S  K  R  G  P  H  V  T  M  V  F  P  D  A  G 5792  accttctccatccggctcaatgcctccaacgcagtcagctgggtc
1861         T  F  S  I  R  L  N  A  S  N  A  V  S  W  V 5837  tcagccacgtacaacctcacggcggaggagcccatcgtgggcctg
1876         S  A  T  Y  N  L  T  A  E  E  P  I  V  G  L
                 →  15-L
       5882  gtgctgtgggccagcagcaaggtggtggcgcccgggcagctggtc
1891         V  L  W  A  S  S  K  V  V  A  P  G  Q  L  V
                                    ←  15-K
       5927  catttcagatcctgctggctgccggctcagctgtcaccttccgc
1906         H  F  Q  I  L  L  A  A  G  S  A  V  T  F  R 5972  ctgcaggtcggcggggccaaccccgaggtgctccccgggccccgt
1921         L  Q  V  G  G  A  N  P  E  V  L  P  G  P  R 6017  ttctcccacagcttccccgcgtcggagaccacgtggtgagcgtg
1936         F  S  H  S  F  P  R  V  G  D  H  V  V  S  V 6062  cggggcaaaaaccacgtgagctgggcccaggcgcaggtgcgcatc
1951         R  G  K  N  H  V  S  W  A  Q  A  Q  V  R  I 6107  gtggtgctggaggccgtgagtgggctgcagatgcccaactgctgc
1966         V  V  L  E  A  V  S  G  L  Q  M  P  N  C  C
```

FIG. 3I

Figure 3 con.

```
      6152 gagcctggcatcgccacgggcactgagaggaacttcacagcccgc
1981       E  P  G  I  A  T  G  T  E  R  N  F  T  A  R 6197 gtgcagcgcggctctcgggtcgcctacgcctggtacttctcgctg
1996       V  Q  R  G  S  R  V  A  Y  A  W  Y  F  S  L
                → 15-M 6242 cagaaggtccagggcgactcgctggtcatcctgtcgggccgcgac
2011       Q  K  V  Q  G  D  S  L  V  I  L  S  G  R  D 6287 gtcacctacacgcccgtggccgcgggctgttggagatccaggtg
2026       V  T  Y  T  P  V  A  A  G  L  L  E  I  Q  V
                                    ←              15-L 6332 cgcgccttcaacgccctgggcagtgagaaccgcacgctggtgctg
2041       R  A  F  N  A  L  G  S  E  N  R  T  L  V  L 6377 gaggttcaggacgccgtccagtatgtggccctgcagagcggcccc
2056       E  V  Q  D  A  V  Q  Y  V  A  L  Q  S  G  P 6422 tgcttcaccaaccgctcggcgcagtttgaggccgccaccagcccc
2071       C  F  T  N  R  S  A  Q  F  E  A  A  T  S  P 6467 agcccccggcgtgtggcctaccactgggactttggggatggtcg
2086       S  P  R  R  V  A  Y  H  W  D  F  G  D  G  S 6512 ccagggcaggacacagatgagcccagggccgagcactcctacctg
2101       P  G  Q  D  T  D  E  P  R  A  E  H  S  Y  L 6557 aggcctggggactaccgcgtgcaggtgaacgcctccaacctggtg
2116       R  P  G  D  Y  R  V  Q  V  N  A  S  N  L  V 6602 agcttcttcgtggcgcaggccacggtgaccgtccaggtgctggcc
2131       S  F  F  V  A  Q  A  T  V  T  V  Q  V  L  A 6647 tgccgggagccggaggtggacgtggtcctgcccctgcaggtgctg
2146       C  R  E  P  E  V  D  V  V  L  P  L  Q  V  L
                                             → 15-N 6692 atgcggcgatcacagcgcaactacttggaggcccacgttgacctg
2161       M  R  R  S  Q  R  N  Y  L  E  A  H  V  D  L 6737 cgcgactgcgtcacctaccagactgagtaccgctgggaggtgtat
2176       R  D  C  V  T  Y  Q  T  E  Y  R  W  E  V  Y 6782 cgcaccgccagctgccagcggccggggcgcccagcgcgtgtggcc
2191       R  T  A  S  C  Q  R  P  G  R  P  A  R  V  A
```

FIG. 3J

Figure 3 con.

← 15-M

```
6827 ctgcccggcgtggacgtgagccggcctcggctggtgctgccgcgg
2206  L  P  G  V  D  V  S  R  P  R  L  V  L  P  R 6872 ctggcgctgcctgtggggcactactgctttgtgtttgtcgtgtca
2221  L  A  L  P  V  G  H  Y  C  F  V  F  V  V  S 6917 tttggggacacgccactgacacagagcatccaggccaatgtgacg
2236  F  G  D  T  P  L  T  Q  S  I  Q  A  N  V  T 6962 gtggcccccgagcgcctggtgcccatcattgagggtggctcatac
2251  V  A  P  E  R  L  V  P  I  I  E  G  G  S  Y 7007 cgcgtgtggtcagacacacgggacctggtgctggatgggagcgag
2266  R  V  W  S  D  T  R  D  L  V  L  D  G  S  E 7052 tcctacgaccccaacctggaggacggcgaccagacgccgctcagt
2281  S  Y  D  P  N  L  E  D  G  D  Q  T  P  L  S
```
Exon 16
```
7097 ttccactgggcctgtgtggcttcgacacag...
2296  F  H  W  A  C  V  A  S  T  Q ...

7142 ...
2311

7187 ...
2326

7232 ...
2341
```
Exon 17
```
7277 gtgctgatccggagtggccgggtgcccatcgtgtccttggagtgt
2356  V  L  I  R  S  G  R  V  P  I  V  S  L  E  C 7322 gtgtcctgcaaggcacaggccgtgtacgaagtgagccgcagctcc
2371  V  S  C  K  A  Q  A  V  Y  E  V  S  R  S  S 7367 tacgtgtacttggagggccgctgcctcaattgcagcagcggctcc
2386  Y  V  Y  L  E  G  R  C  L  N  C  S  S  G  S
```
Exon 18
```
7412 aagcgaggg...
2401  K  R  G ...

Figure 3 con.

```
      7502 [sequence]
2431       [sequence]

7547 [sequence]
2446       [sequence]

7592 [sequence]
2461       [sequence]

7637 [sequence]
2476       [sequence]
                                         Exon 19
      7682 [sequence]gctggcatgacgcggaggatgctggc
2491                                G  W  H  D  A  E  D  A  G 7727 gccccgctggtgtacgccctgctgctgcggcgctgtcgccagggc
2506     A  P  L  V  Y  A  L  L  L  R  R  C  R  Q  G 7772 cactgcgaggagttctgtgtctacaagggcagcctctccagctac
2521     H  C  E  E  F  C  V  Y  K  G  S  L  S  S  Y 7817 ggagccgtgctgccccccgggtttcaggccacacttcgaggtgggc
2536     G  A  V  L  P  P  G  F  R  P  H  F  E  V  G 7862 ctggccgtggtggtgcaggaccagctgggagccgctgtggtcgcc
2551     L  A  V  V  V  Q  D  Q  L  G  A  A  V  V  A
                 Exon 20
      7907 ctcaacag[sequence]
2566     L  N  R 7952 [sequence]
2581       [sequence]

7997 [sequence]
2596       [sequence]
                                              Exon 21
      8042 [sequence]tacgagcgggcc
2611       [sequence]         Y  E  R  A 8087 ctggacgtggcggcagagcccaagcacgagcggcagcaccgagcc
2626     L  D  V  A  A  E  P  K  H  E  R  Q  H  R  A 8132 cagatacgcaagaacatcacggagactctggtgtccctgagggtc
2641     Q  I  R  K  N  I  T  E  T  L  V  S  L  R  V
```

FIG. 3L

Figure 3 con.

```
      8177 cacactgtggatgacatccagcagatcgctgctgcgctggcccag
2656       H  T  V  D  D  I  Q  Q  I  A  A  A  L  A  Q
                        Exon 22
      8222 tgcatggaggagcggagcgcgctggagcggcgcgcgcaggcggag
2671       C  M  E  E  R  S  A  L  E  R  R  A  Q  A  E 8267 cagacgcgccaccaggcggagcgcgcgctggacgcctcagactcg
2686       Q  T  R  H  Q  A  E  R  A  L  D  A  S  D  S 8312 gcgcgcgcggcgctggaggacccgctggcccaggtggacctgctc
2701       A  R  A  A  L  E  D  P  L  A  Q  V  D  L  L
                                    Exon 23-A
      8357 atccagcagatcgagacctcatccacctggccagctcggac
2716       I  Q  Q  I  E  T  S  S  T  W  P  A  R  T 8402 gtgcggcaccacagccctcagagctgggagccgagtcaccatct
2731       V  R  A  P  Q  P  S  E  L  G  A  E  S  P  S 8447 cggatggtggcgtcccaggcctacaacctgacctctgccctcatg
2746       R  M  V  A  S  Q  A  Y  N  L  T  S  A  L  M 8492 cgcatcctcatgcgctcccgcgtgctcaacgaggagcccctgacg
2761       R  I  L  M  R  S  R  V  L  N  E  E  P  L  T
                                              → 23-B
      8537 ctggcgggcgaggagatcgtggcccagggcaagcgctcggacccg
2776       L  A  G  E  E  I  V  A  Q  G  K  R  S  D  P 8582 cggagcctgctgtgctatggcggcgccccagggcctggctgccac
2791       R  S  L  L  C  Y  G  G  A  P  G  P  G  C  H 8627 ttctccatccccgaggctttcagcggggccctggccaacctcagt
2806       F  S  I  P  E  A  F  S  G  A  L  A  N  L  S
                           → 23-C
      8672 gacgtggtgcagctcatctttctggtggactccaatcccttccc
2821       D  V  V  Q  L  I  F  L  V  D  S  N  P  F  P
       ←        23-A          ←       23-B
      8717 tttggctatatcagcaactacaccgtctccaccaaggtggcctcg
2836       F  G  Y  I  S  N  Y  T  V  S  T  K  V  A  S 8762 atggcattccagacacaggccggcgcccagatccccatcgagcgc
2851       M  A  F  Q  T  Q  A  G  A  Q  I  P  I  E  R 8807 ctggcctcagagcgcgccatcaccgtgaaggtgcccaacaactcg
2866       L  A  S  E  R  A  I  T  V  K  V  P  N  N  S
```

FIG. 3M

Figure 3 con.

```
      8852 gactgggctgcccggggccaccgcagctccgccaactccgccaac
2881       D  W  A  A  R  G  H  R  S  S  A  N  S  A  N 8897 tccgttgtggtccagccccaggcctccgtcggtgctgtggtcacc
2896       S  V  V  Q  P  Q  A  S  V  G  A  V  V  T 8942 ctggacagcagcaaccctgcggccgggctgcatctgcagctcaac
2911       L  D  S  S  N  P  A  A  G  L  H  L  Q  L  N
                                        Exon 24
      8987 tatacgctgctggacg
2926       Y  T  L  D 9032
2941

9077
2956
                                                    Exon 25
      9122                                      gagcaga
2971                                              S  R 9167 gacccagcggggagttaccatctgaacctctccagccacttccgc
2986       D  P  A  G  S  Y  H  L  N  L  S  S  H  F  R 9212 tggtcggcgctgcaggtgtccgtgggcctgtacacgtccctgtgc
3001       W  S  A  L  Q  V  S  V  G  L  Y  T  S  L  C 9257 cagtacttcagcgaggaggacatggtgtggcggacagaggggctg
3016       Q  Y  F  S  E  E  D  M  V  W  R  T  E  G  L 9302 ctgcccctggaggagacctcgccccgccaggccgtctgcctcacc
3031       L  P  L  E  E  T  S  P  R  Q  A  V  C  L  T 9347 cgccacctcaccgccttcggcgccagcctcttcgtgccccaagc
3046       R  H  L  T  A  F  G  A  S  L  F  V  P  P  S
                                  Exon 26
      9392 catgtccgctttgtgtttcct
3061       H  V  R  F  V  F  P 9437
3076

Figure 3 con.

```
9527 [............................................]
3106 [............................................]
                                          Exon 27
9572 [..................................]gtaccacg
3121 [..............................]  G  T  T 9617 gccacgtgggcatcatgctgtatggggtggacagccgagcggc
3136  A  H  V  G  I  M  L  Y  G  V  D  S  R  S  G 9662 caccggcacctggacggcgacagagccttccaccgcaacagcctg
3151  H  R  H  L  D  G  D  R  A  F  H  R  N  S  L 9707 gacatcttccggatcgccaccccgcacagcctgggtagcgtgtgg
3166  D  I  F  R  I  A  T  P  H  S  L  G  S  V  W
                                      Exon 28
9752 aagatccgagtgtggcacgacaacaaag[............]
3181  K  I  R  V  W  H  D  N  K  [............]

9797 [............................................]
3196 [............................................]

9842 [............................................]
3211 [............................................]
                                          Exon 29
9887 [.................................]gcgacgca
3226 [.............................]  S  D  A 9932 gccttttgcgcttccggcgcctgctggtggctgagctgcagcgt
3241  A  L  L  R  F  R  R  L  L  V  A  E  L  Q  R 9977 ggcttctttgacaagcacatctggctctccatatgggaccggccg
3256  G  F  F  D  K  H  I  W  L  S  I  W  D  R  P 10022 cctcgtagccgtttcactcgcatccagagggccacctgctgcgtt
3271   P  R  S  R  F  T  R  I  Q  R  A  T  C  C  V 10067 ctcctcatctgcctcttcctgggcgccaacgccgtgtggtacggg
3286   L  L  I  C  L  F  L  G  A  N  A  V  W  Y  G
                                       Exon 30
10112 gctgttggcgactctgcctacag[....................]
3301   A  V  G  D  S  A  Y  S[....................]

Figure 3 con.

```
10202 ................................................
3331  ................................................
           Exon 31
10247 ............gtggctgggagcccgagccccacacctgcc
3346  . . . . . . . V  A  G  S  P  S  P  T  P  A 10292 gggcagcaggtgctggacatcgacagctgcctggactcgtcc gtg
3361  G  Q  Q  V  L  D  I  D  S  C  L  D  S  S  V
                                                    Exon 32
10337 ctggacagctcctcctcacgttctcaggcctccacgctgagg..
3376  L  D  S  S  F  L  T  F  S  G  L  H  A  E  .

10382 ................................................
3391  ................................................
          Exon 33
10427 ag tctggtgtgctggccctccggcgagggaacgctcagttggccg
3406  S  L  V  C  W  P  S  G  E  G  T  L  S  W 10472 gacctgctcagtgacccgtccattgtgggtagcaatctgcggcag
3421  D  L  L  S  D  P  S  I  V  G  S  N  L  R  Q 10517 ctggcacggggccaggcgggccatgggctgggcccagaggaggac
3436  L  A  R  G  Q  A  G  H  G  L  G  P  E  E  D 10562 ggcttctccctggccagcccctactcgcctgccaaatccttctca
3451  G  F  S  L  A  S  P  Y  S  P  A  K  S  F  S
          Exon 34
10607 gcatcag...........................................
3466  A  S  . . . . . . . . . . . . . . . . . .

10652 ................................................
3481  ................................................
           Exon 35
10697 ..........gtccagcactcctggggagaagacagagacgctg
3496  . . . . .  S  S  T  P  G  E  K  T  E  T  L 10742 gcgctgcagaggctgggggagctggggccacccagcccaggcctg
3511  A  L  Q  R  L  G  E  L  G  P  P  S  P  G  L
                                                    Exon 36
10787 aactgggaacagccccaggcagcgaggctgtccaggacag....
3526  N  W  E  Q  P  Q  A  A  R  L  S  R  T  . .

Figure 3 con.

```
10877 ...
3556

10922 ...
3571

10967 ...
3586
                                              Exon 37
11012 ........gtcttgctggaagccctgtacttctca
3601                    V  L  L  E  A  L  Y  F  S 11057 ctggtggccaagcggctgcacccggatgaagatgacaccctgta
3616  L  V  A  K  R  L  H  P  D  E  D  D  T  L  V 11102 gagagcccggctgtgacgcctgtgagcgcacgtgtgccccgcgta
3631  E  S  P  A  V  T  P  V  S  A  R  V  P  R  V 11147 cggccagcccacggctttgcactcttcctggccaaggaagaagcc
3646  R  P  P  H  G  F  A  L  F  L  A  K  E  E  A
                                              Exon 38
11192 cgcaaggtcaagaggctacatggcatgctgcgg..........
3661  R  K  V  K  R  L  H  G  M  L  R ...

11237 ...
3676

11282 ...
3691
                                              Exon 39
11327 .......................................gtctgac
3706                                           S  E 11372 gagctctggccatggatggcccacgtgctgctgccctacgtccac
3721  E  L  W  P  W  M  A  H  V  L  L  P  Y  V  H 11417 gggaaccagtccagcccagagctggggcccccacggctgcggcag
3736  G  N  Q  S  S  P  E  L  G  P  P  R  L  R  Q
                                              Exon 40
11462 gtgccgctgcaggaa..............................
3751  V  R  L  Q  E ...

Figure 3 con.

```
        11552 ...................................................
3781          ...................................................
                                    Exon 41
        11597 ..........................ggcatggtcctggggctcctgt
3796          ..........................  A  W  S  W  G  S  C 11642 gccgtgtatgacagcggggctacgtgcaggagctgggcctgagc
3811           A  V  Y  D  S  G  G  Y  V  Q  E  L  G  L  S 11687 ctggaggagagccgcgaccggctgcgcttcctgcagctgcacaac
3826           L  E  E  S  R  D  R  L  R  F  L  Q  L  H  N
                                    Exon 42
        11732 tggctggacaacag...........................
3841           W  L  D  N  R...........................

11777 ...................................................
3856          ...................................................

11822 ...................................................
3871          ...................................................

11867 ...................................................
3886          ...................................................
                                    Exon 43
        11912 ..........gtgtgcctgctgctgttcgccgtgcacttcgccgtg
3901          ..........  V  C  L  L  L  F  A  V  H  F  A  V 11957 gccgaggcccgtacttggcacagggaagggcgctggcgcgtgctg
3916           A  E  A  R  T  W  H  R  E  G  R  W  R  V  L 12002 cggctcggagcctgggcgcggtggctgctggtggcgctgacggcg
3931           R  L  G  A  W  A  R  W  L  L  V  A  L  T  A 12047 gccacggcactggtacgcctcgcccagctgggtgccgctgaccgc
3946           A  T  A  L  V  R  L  A  Q  L  G  A  A  D  R 12092 cagtggacccgtttcgtgcgcggccgcccgcgccgcttcactagc
3961           Q  W  T  R  F  V  R  G  R  P  R  R  F  T  S 12137 ttcgaccaggtggcgcagctgagctccgcagcccgtggcctggcg
3976           F  D  Q  V  A  Q  L  S  S  A  A  R  G  L  A
                                                    Exon 44
        12182 gcctcgctgctcttcctgcttttggtcaag..................
3991           A  S  L  L  F  L  L  L  V  K..................
```

FIG. 3R

Figure 3 con.

```
12227 ...
4006

12272 ...
4021

Exon 45
12317 ...................ctcgtgtcttcctgt
4036                    L  V  S  S  C 12362 gtggactccctctggagcgtggcccaggccctgttggtgctgtgc
4051  V  D  S  L  W  S  V  A  Q  A  L  L  V  L  C 12407 cctgggactgggctctctaccctgtgtcctgccgagtcctggcac
4066  P  G  T  G  L  S  T  L  C  P  A  E  S  W  H 12452 ctgtcacccctgctgtgtgtggggctctgggcactgcggctgtgg
4081  L  S  P  L  L  C  V  G  L  W  A  L  R  L  W 12497 ggcgccctacggctggggctgttattctccgctggcgctaccac
4096  G  A  L  R  L  G  A  V  I  L  R  W  R  Y  H 12542 gccttgcgtggagagctgtaccggccggcctgggagccccagga c
4111  A  L  R  G  E  L  Y  R  P  A  W  E  P  Q  D 12587 tacgagatggtggagttgttcctgcgcaggctgcgcctctggatg
4126  Y  E  M  V  E  L  F  L  R  R  L  R  L  W  M
                                Exon 46
12632 ggcctcagcaaggtcaaggag........................
4141  G  L  S  K  V  E  .........................

Figure 3 con.

| Codon Number | | |
|---|---|---|
| 1 | 67 | Exon 1-A atggtgaactccagtcgcgtgcagcctcagcagcccggggacgcc<br>M V N S S R V Q F Q Q P G D A |
| 16 | 112 | aagcggccgccgcgcccgcgcgccggacccggccggctgatg<br>K R P P A P R A P D P G R L M |
| 31 | 157 | gctggctgcgcggccgtgggcgccagcctcgccgcccgggcggc<br>A G C A A V G A S L A A P G G |
| 46 | 202 | ctctgcgagcagcggggcctggagatcgagatgcagcgcatccgg<br>L C E Q R G L E I E M Q R I R |
| 61 | 247 | caggcggccgcccgggacccccggccggagccgcggcctcccct 1-B<br>Q A A A R D P P A G A A A S P |
| 76 | 292 | tctcctccgctctcgtcgtgctcccggcaggcgtggagccgcgat 1-A<br>S P P L S S C S R Q A W S R D |
| 91 | 337 | aaccccggcttcgaggccgaggaggaggaggaggaggtggaaggc<br>N P G F E A E E E E E V E G |
| 106 | 382 | gaagaagccggaatggtggtggagatggacgtagagtggcgcccg<br>E E G G M V V E M D V E W R P |
| 121 | 427 | ggcagccggaggtcggccgcctcctcggccgtgagctccgtgggc<br>G S R R S A A S S A V S S V G |
| 136 | 472 | gcgcggagccgagggcttggcggctaccacggcgcgggccaccccg 1-C<br>A R S R G L G G Y H G A G H P |
| 151 | 517 | agcggggaggcggcgccggcgagaggaccaggacccgccgtgcccc<br>S G R R R R R E D Q G P P C P |
| 166 | 562 | agcccagtcggcggcggcgacccgctgcatcgccacctccccctg 1-B<br>S P V G G G D P L H R H L P L |
| 181 | 607 | gaagggcagccgccccgagtggcctgggcggagaggctggttcgc<br>E G Q P P R V A W A E R L V R |
| 196 | 652 | gggctgcg... Exon 2<br>G L R |
| 211 | 697 | ... |
|  | 742 | ...Exon 3 tgacctacggc |

FIG. 4A

Figure 4 con.

```
226                                              L  T  Y  G
        787 atgatgagctccaatgtgtactactacacccggatgatgtcacag
241          M  M  S  S  N  V  Y  Y  Y  T  R  M  M  S  Q
        832 ctcttcctagacacccccgtgtccaaaacggagaaaactaacttt
256          L  F  L  D  T  P  V  S  K  T  E  K  T  N  F
                                                    Exon 4
        877 aaaactctgtcttccatggaagacttctggaag
271          K  T  L  S  S  M  E  D  F  W  K
        922
286
        967
301
       1012
316
       1057
331
       1102
346
                                 Exon 5
       1147                 ttggatctacacaagtgaaaagacttgaat
361                          W  I  Y  T  S  E  K  D  L  N
       1192 ggtagtagccactgggcaatcattgcaacttatagtggagctggc
376          G  S  S  H  W  G  I  I  A  T  Y  S  G  A  G
       1237 tattatctggatttgtcaagaacaagagaggaaacagctgcacaa
391          Y  Y  L  D  L  S  R  T  R  E  E  T  A  A  Q
       1282 gttgctagcctcaagaaaaatgtctggctggaccgaggaaccagg
406          V  A  S  L  K  K  N  V  W  L  D  R  G  T  R
       1327 gcaactttattgacttctcagtgtacaacgccaacattaacctc
421          A  T  F  I  D  F  S  V  Y  N  A  N  I  N  L
                            Exon 6
       1372 ttctgtgtggtcag
436          F  C  V  V  R
       1417
451
       1462
466
       1507
481
```

FIG. 4B

Figure 4 con.

```
      1552 [................................................]
496        [................................................]
                                          Exon 7
      1597 [..............]ctgtcagtggtagctataggaattaac
511        [.............] L  S  V  V  A  I  G  I  N 1642 atatacagaacatcaaatgtggaggtgctactacagtttctggaa
526        I  Y  R  T  S  N  V  E  V  L  L  Q  F  L  E 1687 gatcaaaatactttccccaactttgagcatctggcatattggcag
541        D  Q  N  T  F  P  N  F  E  H  L  A  Y  W  Q 1732 atacagttcaacaatatagctgctgtcacagtattttttgtctgc
556        I  Q  F  N  N  I  A  A  V  T  V  F  F  V  C
                Exon 8
      1777 attaag[.....................................]
571        I  K [.....................................]

1822 [................................................]
586        [................................................]

1867 [................................................]
601        [................................................]

1912 [................................................]
616        [................................................]
                      Exon 9
      1957 [......]cttcactcaattccgtatcattttgggcgatatcaac
631              F  T  Q  F  R  I  I  L  G  D  I  N 2002 tttgcagagattcaggaagctaatcgagttttgggaccaatttat
646        F  A  E  I  E  E  A  N  R  V  L  G  P  I  Y
                                                    Exon 10
      2047 ttcactacatttgtgttcttatgttcttcattctttc[......]
661        F  T  T  F  V  F  F  M  F  F  I  L  L [....]

2092 [................................................]
676        [................................................]

2137 [................................................]
691        [................................................]
                Exon 11
      2182 aa]ggctaccataaagctttggtcaaactaaaactgaaaaaaaat
706           G  Y  H  K  A  L  V  K  L  K  L  K  K  N 2227 accgtggatgacatttcagagagtctgcggcaaggaggaggcaag
721        T  V  D  D  I  S  E  S  L  R  Q  G  G  G  K Exon 12
      2272 ttaaactttg[..........]aagatctcaaagg[........]
```

FIG. 4C

Figure 4 con.

```
736             L N F D E L R Q D L K G ...
     2317  ...
751         ...

2362  ...
766         ...
                              Exon 13
     2407  ...gaggacctggatttggatcacagttct
781               ...  E D L D L D H S S 2452  ttaccacgtcccatgagcagccgaagtttccctcgaagcctggat
796         L P R P M S S R S F P R S L D 2497  gactctgaggaggatgacgatgaagatagcggacatagctccaga
811         D S E E D D D E D S G H S S R 2542  aggacgggaagcatttctagtggcgtttcttacgaagagtttcaa
826         R R G S I S S G V S Y E E F Q
                   Exon 14
     2587  gt...
841         V ...

2632  ...
856         ...

2677  ...
871         ...
                              Exon 15
     2722  ...gatgaaaggctgggtcgtgacagtgaaatc
886               ...  D E R L G R D S E I 2767  cataggggaacagatggaacggctagtacgtgaagagttggaacgc
901         H R E Q M E R L V R E E L E R 2812  tgggaatccgatgatgcagcttcccagatcagtcatggtttaggc
916         W E S D D A A S Q I S H G L G 2857  acgccagtgggactaaatggtcaacctcgccccagaagctcccgc
931         T P V G L N G Q P R P R S S R 2902  ccatcttcctcccaatctacagaaggcatggaaggtgcaggtgga
946         P S S S Q S T E G M E G A G G 2947  aatgggagttctaatgtccacgtatga 2973  (SEQ ID NO. 5)
961         N G S S N V H V *             (SEQ ID NO. 6)
```

FIG. 4D

… # PKD MUTATIONS AND EVALUATION OF SAME

RELATED APPLICATIONS

This application is the U.S. National Stage of International Application No. PCT/US2007/016705, filed Jul. 24, 2007, published in English, and claims priority under 35 U.S.C. §119 or 365 to U.S. Provisional Application No. 60/832,780, filed Jul. 24, 2006. The entire teachings of the above applications are incorporated herein by reference.

GOVERNMENT SUPPORT

The invention was supported in part by Becas FPI de investigacion from Ministerio de Ciencia y Technologia (Spain) and grants R01DK70617, P50-DK57325 and R37DK48006 from the National Institutes of Health. The Governments have certain rights in the invention.

SEQUENCE LISTING

The instant application contains a Sequence Listing which has been submitted electronically in ASCII format and is hereby incorporated by reference in its entirety. The ASCII copy, created on Jan. 28, 2014, is named 103779-0367_SL.txt and is 171,496 bytes in size.

BACKGROUND OF THE INVENTION

Autosomal dominant polycystic kidney disease (ADPKD) is an exceptionally common inherited disorder in humans, affecting approximately one in every 600 to 1000 individuals (Gabow P. A., *N Engl J Med* 329(5):332-342, 1993). The disease is characterized by age dependent growth of renal cysts such that end-stage renal disease (ESRD) typically ensues during mid-adulthood. ADPKD may alternatively, or in addition, involve cysts in other organs including liver and spleen, as well as gastrointestinal, cardiovascular, and musculoskeletal abnormalities (Gabow P. A., *N Engl J Med* 329 (5):332-342, 1993; Gabow P et al., *Adv Nephrol* 18:19-32, 1989). Both ADPKD type 1 and type 2 share the entire range of renal and extrarenal manifestations, but type 2 appears to have a delayed onset relative to type 1. The common phenotypic complications observed for ADPKD which include hypertension, hematuria and urinary tract infection, seem to be clinically milder in type 2 patients.

Approximately 85 percent of ADPKD cases are caused by mutations in the PKD1 gene [MIM 601313], which is located on chromosome 16, while the remainder are due to mutations in the PKD2 gene [MIM 173910] located on chromosome 4 (Peters et al., *Contrib Nephrol* 97:128-139, 1992; European Polycystic Kidney Disease Consortium, *Cell*, 77(6):8.81-894, 1994; International Polycystic Kidney Disease Consortium, *Cell* 81(2):289-298, 1995; Hughes J. et al, *Nat Genet.* 10(2):151-160, 1995; Mochizuki T. et al., *Science* 272(5266):1339-1342, 1996). However, genetic testing for ADPKD has posed a unique set of challenges in terms of DNA diagnostics. PKD1 analysis in particular has been complicated because the 5' portion of the gene (exons 1-34) is replicated in at least five highly homologous copies (with less than 2% divergence) elsewhere on chromosome 16 (Hughes J. et al, *Nat Genet.* 10(2):151-160, 1995). Further complicating PKD1 mutant analysis, PKD1 has a high rate of potentially non-pathogenic DNA variation; thus the nature of each change detected must be verified. Several techniques have been used to detect mutations in the PKD1 gene including using gene-specific primers to amplify large products screened via nested PCR techniques, denaturing high-performance liquid chromatography (DHPLC) to screen nested PCR products for mutations and direct sequencing of the entire PKD1 coding sequence (Watnick T J et al., *Hum Mol Genet.* 6(9):1473-1481, 1997; Watnick T J et al., *Mol Cell* 2(2):247-251, 1998; Watnick T. et al., *Am J Hum Genet.* 65(6):1561-1571, 1999; Phakdeekitcharoen B. et al., *Kidney Int* 58(4):1400-1412, 2000; Phakdeekitcharoen B. et al., *J Am Soc Nephrol* 12:955-963, 2001; Thomas R. et al., *Am J Hum Genet.* 65(1):39-49, 1999; Perichot R. A., *Hum Genet.* 105 (3):231-239, 1999; Perichot R. et al., *Eur J Hum Genet.* 8(5):353-359, 2000; Afzal A. R. et al., *Genet.* 4(4):365-370; Rossetti S. et al., *Lancet* 361(9376):2196-2201, 2003; Rossetti S. et al., *Kidney Int* 61:1588-1599, 2002; Rossetti S. et al, *Am J Hum Genet.* 68(1):46-63, 2001, Inoue S. et al., *Hum Mutat* 19(6):622-628, 2002; Burtey S. et al., *J Med Genet.* 39(6):422-429, 2002; Mizoguchi M. et al., *J Hum Genet.* 46(9):511-517, 2001; Zhang D. Y. et al., *Zhonghua Yi Xue Yi Chuan Xue Za Zhi* 21(3):211-214, 2004). However, some of these strategies may not be cost effective for routine clinical sample analysis and/or their mutation detection rate has not been established or is inadequate. For example, direct DNA sequencing of the entire coding regions of PKD1 and PKD2 is considered necessary because no mutational hot spots have been identified in either PKD1 or PKD2. Although several pathogenic mutations in PKD1 and PKD2 have been identified, the known mutations do not account for all those individuals with ADPKD. Thus, to accurately diagnose and treat the disease, there remains a need to identify other mutations of PKD1 or PKD2 which are linked to ADPKD.

SUMMARY OF THE INVENTION

Several novel nucledtide sequence alterations in the PKD1 and PKD2 genes have been identified that are associated with ADPKD. The mutations in PKD1 and PKD2 were found by direct sequencing of the genes and the pathogenicity of the mutations determined using a combination of various analyses and algorithms. The mutations in the PKD1 and PKD2 genes identified as pathogenic can be used to detect and/or predict the occurrence of ADPKD in an individual. This is important clinically in diagnostic and prognostic analysis of the genes for ADPKD.

Accordingly, the invention relates to methods of detecting or predicting the occurrence of ADPKD in an individual. In one aspect, the present invention relates to a method of detecting or predicting the occurrence of autosomal dominant polycystic kidney disease (ADPKD) in an individual comprising detecting the presence of one or more nucleotide sequence alterations in a PKD1 gene having the nucleotide sequence of SEQ ID NO:1 or SEQ ID NO:7 in a nucleic acid sample obtained from said individual, wherein said one or more alterations are selected from the group consisting of: a deletion of TTTAA at nucleotide positions 559 to 563 of SEQ ID NO:1, an insertion of CT at nucleotide position 1124 of SEQ ID NO:1, an insertion of an A, T, G, or C at nucleotide position 2291 of SEQ ID NO:1, an insertion of an A, T, G, or C at nucleotide position 2297 of SEQ ID NO:1, an insertion a T at nucleotide position 5365 of SEQ ID NO:1, an insertion of a G at nucleotide position 6666 of SEQ ID NO:1, an insertion of an A at nucleotide position 6881 of SEQ ID NO:1, a deletion of a T at nucleotide position 8713 of SEQ ID NO:1, an insertion of an A, T, G, or C at nucleotide position 9134 of SEQ ID NO:1, an insertion of 5 nucleotides at nucleotide position 9536 of SEQ ID NO:1, a deletion of a T at nucleotide position 10239 of SEQ ID NO:1, a change of a C to an A at nucleotide position 483 of SEQ ID NO:1, a change of a C to a T at nucleotide position 4517 of SEQ ID NO:1, a change of a C to an A at nucleotide position 7006 of SEQ ID NO:1, a change of a C to T at nucleotide position 8267 of SEQ ID NO:1, a change of a G to a T at nucleotide position 8639 of SEQ ID NO:1, a change of a G to an A at nucleotide position 20168 of SEQ ID NO:7, a change of a G to a T at nucleotide position 31025 of SEQ ID NO:7, a change of a G to a C at nucleotide position 33415 of SEQ ID NO:7, a deletion of CAA between nucleotide positions 508 to 516 of SEQ ID NO:1, a deletion of TGG at nucleotide positions 1848 to 1850 of SEQ ID NO:1, a deletion of CCAACTCCG at nucleotide positions 8892 to 8900 of SEQ ID NO:1, a deletion of AAG at nucleotide positions 9905 to 9907 of SEQ ID NO:1, a deletion of CTC at nucleotide positions 10070 to 10072 of SEQ ID NO:1, a deletion of TGG at nucleotide positions 12597 to 12599 of SEQ ID NO:1, a change of a C to an A at nucleotide position 1023 of SEQ ID NO:1, a change of a G to an A at nucleotide position 385 of SEQ ID NO:1, a change of an A to a G at nucleotide position 1470 of SEQ ID NO:1, a change of a C to a T at nucleotide position 4262 of SEQ ID NO:1, a change of a T to an A at nucleotide position 8855 of SEQ ID NO:1, a change of an A to a G at nucleotide position 1794 of SEQ ID NO:1, a change of a G to an A at nucleotide position 6036 of SEQ ID NO:1, a change of a C to a T at nucleotide position 2042 of SEQ ID NO:1, a change of a C to a T at nucleotide position 3351 of SEQ ID NO:1, a change of an A to a G at nucleotide position 6756 of SEQ ID NO:1, a change of a C to a T at nucleotide position 5793 of SEQ ID NO:1, a change of a C to a T at nucleotide position 6707 of SEQ ID NO:1, a change of a G to a C at nucleotide position 10187 of SEQ ID NO:1, a change of a C to a G at nucleotide position 7116 of SEQ ID NO:1, a change of an A to a G at nucleotide position 10311 of SEQ ID NO:1, a change of a T to a C at nucleotide position 7554 of SEQ ID NO:1, a change of a C to a T at nucleotide position 7757 of SEQ ID NO:1, a change of a T to a C at nucleotide position 8067 of SEQ ID NO:1, a change of a C to a T at nucleotide position 8138 of SEQ ID NO:1, a change of a C to a T at nucleotide position 8509 of SEQ ID NO:1, a change of a C to an A at nucleotide position 10096 of SEQ ID NO:1 and a change of a C to a T at nucleotide position 12658 of SEQ ID NO:1. The detection of one or more of the listed nucleotide sequence alterations indicates that the individual has ADPKD or will develop ADPKD. In one embodiment, at least one nucleotide sequence alteration other than the one or more nucleotide sequence alterations listed above is also detected in SEQ ID NO:1 and/or SEQ ID NO:4, wherein the at least one nucleotide sequence alteration which is also detected is associated with ADPKD. In another aspect, the one or more nucleotide sequence alterations are detected by sequencing, polymerase chain reaction (PCR), DHPLC or combinations of the foregoing.

The present invention also relates to a method of detecting or predicting the occurrence of autosomal dominant polycystic kidney disease (ADPKD) in an individual comprising detecting the presence of one or more nucleotide sequence alterations in a PKD2 gene having the nucleotide sequence of SEQ ID NO:4 in a nucleic acid sample obtained from said individual, wherein said one or more alterations are selected from the group consisting of: an insertion of an A at nucleotide position 2226 of SEQ ID NO:4, a deletion of AG at nucleotide positions 2422 to 2423 of SEQ ID NO:4, a change of a C to a T at nucleotide position 2680 of SEQ ID NO:4, IVS7−1G>A, IVS8+5G>A, a deletion of TGG at nucleotide positions 374-376 of SEQ ID NO:4 and a deletion of TTC between nucleotide positions 1876-1881 of SEQ ID NO:4, wherein detection of the one or more nucleotide sequence alterations indicates that the individual has ADPKD or will develop ADPKD. In one embodiment, at least one nucleotide sequence alteration other than the one or more nucleotide sequence alterations listed above is also detected in SEQ ID NO:1 and/or SEQ ID NO:4, wherein the at least one nucleotide sequence alteration also detected is associated with ADPKD. In yet another embodiment, the one or more nucleotide sequence alterations are detected by sequencing, PCR, DHPLC or combinations thereof.

The present invention further relates to a method for detecting in an individual the presence or absence of a mutant PKD gene comprising obtaining a nucleic acid sample from the individual and detecting the presence or absence of one or more nucleotide sequence alterations in a PKD1 or PKD2 gene of the individual, wherein the one or more alterations are selected from the group consisting of: a deletion of TTTAA at nucleotide positions 559 to 563 of SEQ ID NO:1, an insertion of CT at nucleotide position 1124 of SEQ ID NO:1, an insertion of an A, T, G, or C at nucleotide position 2291 of SEQ ID NO:1, an insertion of an A, T, G, or C at nucleotide position 2297 of SEQ ID NO:1, an insertion of a T at nucleotide position 5365 of SEQ ID NO:1, an insertion of a G at nucleotide position 6666 of SEQ ID NO:1, an insertion of an A at nucleotide position 6881 of SEQ ID NO:1, a deletion of a T at nucleotide position 8713 of SEQ ID NO:1, an insertion of an A, T, G, or C at nucleotide position 9134 of SEQ ID NO:1, an insertion of 5 nucleotides at nucleotide position 9536 of SEQ ID NO:1, a deletion of a T at nucleotide position 10239 of SEQ ID NO:1, a change of a C to an A at nucleotide position 483 of SEQ ID NO:1, a change of a C to a T at nucleotide position 4517 of SEQ ID NO:1, a change of a C to an A at nucleotide position 7006 of SEQ ID NO:1, a change of a C to T at nucleotide position 8267 of SEQ ID NO:1, a change of a G to a T at nucleotide position 8639 of SEQ ID NO:1, a change of a G to an A at nucleotide position 20168 of SEQ ID NO:7, a change of a G to a T at nucleotide position 31025 of SEQ ID NO:7, a change of a G to a C at nucleotide position 33415 of SEQ ID NO:7, a deletion of CAA between nucleotide positions 508 to 516 of SEQ ID NO:1, a deletion of TGG at nucleotide positions 1848 to 1850 of SEQ ID NO:1, a deletion of CCAACTCCG at nucleotide positions 8892 to 8900 of SEQ ID NO:1, a deletion of AAG at nucleotide positions 9905 to 9907 of SEQ ID NO:1, a deletion of CTC at nucleotide positions 10070 to 10072 of SEQ ID NO:1, a deletion of TGG at nucleotide positions 12597 to 12599 of SEQ ID NO:1, a change of a C to an A at nucleotide position 1023 of SEQ ID NO:1, a change of a G to an A at nucleotide position 385 of SEQ ID NO:1, a change of an A to a G at nucleotide position 1470 of SEQ ID NO:1, a change of a C to a T at nucleotide position 4262 of SEQ ID NO:1, a change of a T to an A at nucleotide position 8855 of SEQ ID NO:1, a change of an A to a G at nucleotide position 1794 of SEQ ID NO:1, a change of a G to an A at nucleotide position 6036 of SEQ ID NO:1, a change of a C to a T at nucleotide position 2042 of SEQ ID NO:1, a change of a C to a T at nucleotide position 3351 of SEQ ID NO:1, a change of an A to a G at nucleotide position 6756 of SEQ ID NO:1, a change of a C to a T at nucleotide position 5793 of SEQ ID NO:1, a change of a C to a T at nucleotide position 6707 of SEQ ID NO:1, a change of a G to a C at nucleotide position 10187 of SEQ ID NO:1, a change of a C to a G at nucleotide position 7116 of SEQ ID NO:1, a change of an A to a G at nucleotide position 10311 of SEQ ID NO:1, a change of a T to a C at nucleotide position 7554 of SEQ ID NO:1, a change of a C to a T at nucleotide position 7757 of SEQ ID NO:1, a change of a T to a C at nucleotide position 8067 of SEQ ID NO:1, a change of a C to a T at nucleotide position 8138 of SEQ ID NO:1, a change of a C to a T at nucleotide position 8509 of SEQ ID NO:1, a change of a C to an A at nucleotide position 10096 of SEQ ID NO:1, a change of a C to a T at nucleotide position 12658 of SEQ ID NO:1, a change of a C to an A at nucleotide position 7476 of SEQ ID NO:1, a change of a C to a G at nucleotide position 3527 of SEQ ID NO:1, a change of a C to an A at nucleotide position 1947 of SEQ ID NO:1, a change of an A to a G at nucleotide position 3312 of SEQ ID NO:1, a change of a C to a G at nucleotide position 4391 of SEQ ID NO:1, a change of a T to an A at nucleotide position 11040 of SEQ ID NO:1, a change of a G to a T at nucleotide position 840 of SEQ ID NO:1, a change of a G to an A at nucleotide position 7197 of SEQ ID NO:1, a change of a G to a C at nucleotide position 351 of SEQ ID NO:1, a change of a G to an A at nucleotide position 4757 of SEQ ID NO:1, a change of an A to a C at nucleotide position 1023 of SEQ ID NO:1, an insertion of: an A at nucleotide position 2226 of SEQ ID NO:4, a deletion of AG at nucleotide positions 2422 to 2423 of SEQ ID NO:4, a change of a C to a T at nucleotide position 2680 of SEQ ID NO:4, IVS7-1 G>A, IVS8+5G>A, a deletion of TGG at nucleotide positions 374-376 of SEQ ID NO:4, a deletion of TTC between nucleotide positions 1876-1881 of SEQ ID NO:4 and a change of a G to an A at nucleotide position 634 of SEQ ID NO:4, wherein detection of the one or more nucleotide sequence alterations is indicative of a mutant PKD gene. In one embodiment, the presence or absence of the one or more nucleotide sequence alterations in the PKD1 or PKD2 gene of the individual indicates that the individual has ADPKD. In another embodiment, the presence or absence of one or more nucleotide sequence alterations in the PKD1 or PKD2 nucleic acid sequence is detected by sequencing, PCR and/or DHPLC.

The identification of mutations associated with ADPKD provides conclusive diagnostic information, allows the blood relatives of an individual to be pre-symptomatically and inexpensively evaluated for counseling and planning using targeted PKD gene analysis and allows prospective living-related kidney donors to be tested and subsequently accepted or rejected for donation with greater certainty. Pre-symptomatic testing for ADPKD may be particularly relevant not only in the evaluation of living kidney donors from ADPKD families, but also in the early detection for treatment with new agents that may be indicated for use early in the course of the disease (e.g., before cystic disease is apparent), family planning, the detection of ADPKD in young individuals (e.g., those under 30) for whom ultrasound imaging may not be accurate and/or adequate or in those families with PKD2-associated ADPKD, a clinically milder disease. In addition, clinicians may encounter patients with atypical cystic disease in whom the diagnosis is not obvious. Thus, using the novel, pathogenic mutations identified in the PKD1 and PKD2 genes, the methods of the invention help to better assist in the diagnosis and management of existing ADPKD and/or predict the likelihood of the occurrence of ADPKD in an individual.

BRIEF DESCRIPTION OF THE DRAWINGS

FIGS. 1A-1E depict the PKD1 coding sequence (GenBank Accession No. L33243) (SEQ ID NO:1).

FIGS. 2A-2B depict the PKD2 coding sequence (GenBank Accession Nos. AF004859-AF004873) (SEQ ID NO:4).

FIGS. 3A-3T depict wild-type PKD1 cDNA coding sequence according to one embodiment of the invention. Exon and PCR product junctions are depicted above the nucleotide sequence and amino acids are positioned under the center of each codon.

FIGS. 4A-4D depict wild-type PKD2 cDNA coding sequence according to one embodiment of the invention. Exon and PCR product junctions are depicted above the nucleotide sequence and amino acids are positioned under the center of each codon.

FIG. 5A discloses SEQ ID NOS 8-23, respectively, in order of appearance.

DETAILED DESCRIPTION OF THE INVENTION

Figures 5A, 5B, 5C:
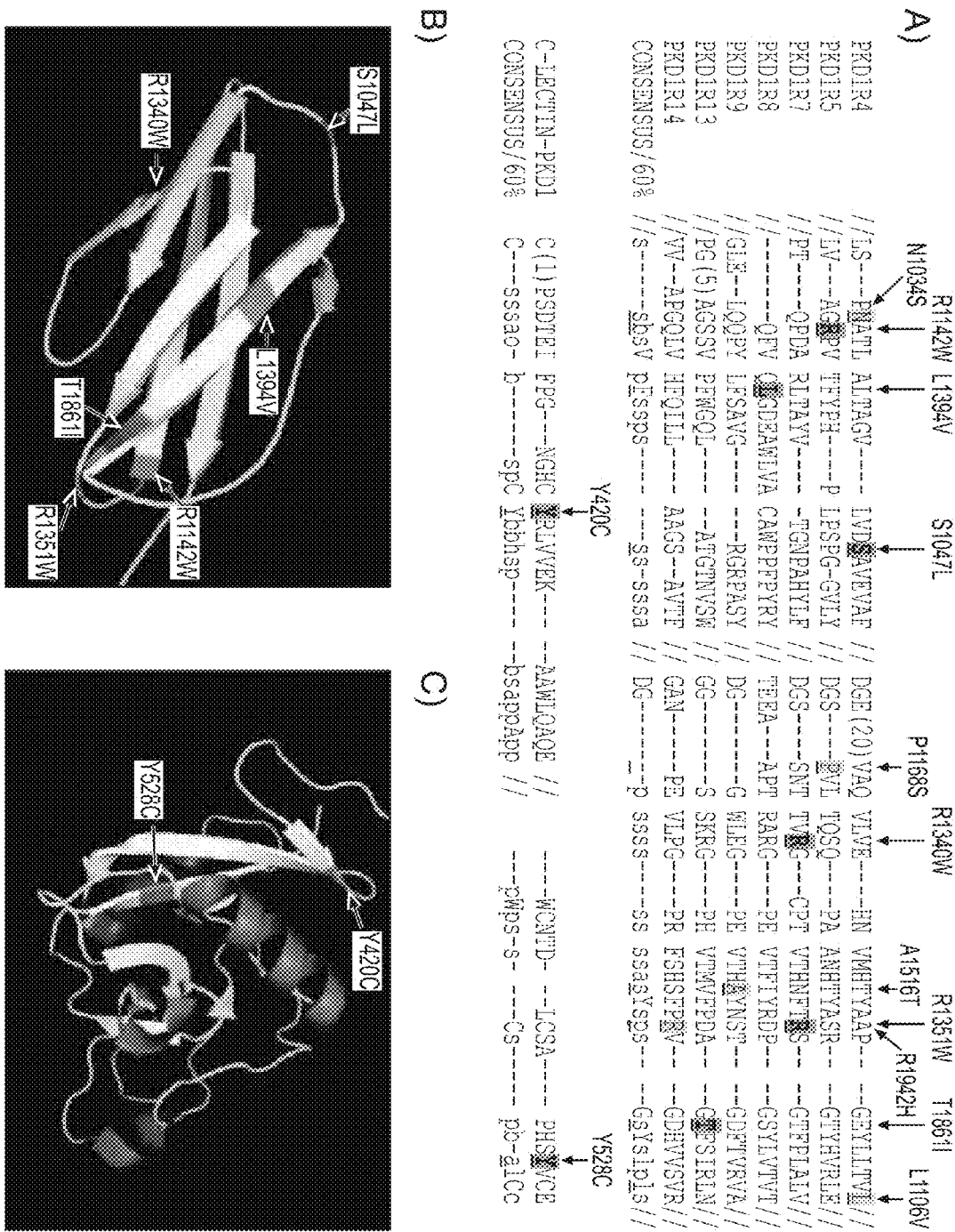
FIG. 5A illustrates missense mutations affecting the PKD1 repeats and C-lectin domain. Changes that disrupt the consensus sequence are red (dark-shaded) those that do not are yellow (light-shaded). Consensus sequence code: l (aliphatic), a (aromatic), c (charged), (small residue), p (polar residue), b (big residue), h (hydrophobic), capital letters represent the corresponding amino acid codon.
FIGS. 5B and 5C illustrate ribbon diagrams of the PKD repeat (5B) and C-lectin domain (5C) with potential pathogenic missense changes indicated.

The PKD genes are genomic DNA sequences that map to chromosomal position 16p13.3 (PKD1) or chromosomal position 4q21-23 (PKD2) and give rise to messenger RNA molecules encoding PKD1 and PKD2 proteins. The PKD1 and PKD2 genes comprise the sequences of SEQ ID NO:1 and SEQ ID NO:4, respectively, which include introns and putative regulatory sequences. Like many other genes, PKD1 and PKD2 gene sequences, when compared among individuals, show sequence variations that do not affect gene expression or expression and/or function of the gene product.

The PKD1 gene (e.g., GenBank Accession Number L39891, SEQ ID NO:7) spans about 54 kb of genomic DNA on chromosome 16 (16p13.3) and contains a 12,906 basepair coding sequence divided into 46 exons from which a 14 kb mRNA is transcribed. The protein product of PKD1, polycystin-1 (PC-1) (GeneBank Accession No. AAC37576, SEQ ID NO:3), is a 4303 amino acid protein with a predicted mass of 460 kDa which forms multiprotein complexes at the cell membrane and is thought to function in cell-cell and cell-matrix signal regulation. (Arnould T et al., *J. Biol. Chem.* 273:6013-6018, 1992; Parnell S. C. et al., *J Biol Chem*, 277: 19566-19572, 2002; Bhunia A. K. et al., *Cell,* 109:157-168, 2002; Nauli S. M. et al., *Nat Genet.* 33:129-137, 2003). Approximately 75% of the PKD1 gene is duplicated and shares about 97% identity with its homologous copies. The reiterated region encompasses a 50 kb (5') portion of the gene containing the first 34 exons. Only the most 3', 5.7 kb of the gene, containing exons 35-46, is unique to PKD1. Another notable feature of the PKD1 gene is a polypyrimidine tract in intron 21 that is 2.5 kb long, the longest described in the human genome.

The PKD2 gene (see e.g., GenBank Accession Numbers AF004859 (exon1)-AF004873 (exon 15), SEQ ID NO:4) (see also GenBank Accession Number V50928) spans 68 kb of genomic DNA and is located on chromosome 4 (4q21-23). PKD2 contains 15 exons and encodes a 5.4 kb transcript (see e.g., GenBank Accession Number NM000297) from which a 968-amino acid protein product, polycystin-2 (PC-2) of approximately 110 kDa is generated (SEQ ID NO:6) (see also GenBank Accession Number NP00288). Polycystin-2 has been shown to interact with the carboxy-terminus of PC-1 and functions as a cation channel in complex with PC-1. (Gonzalez-Perrett S. et al., *Proc Natl Acad Sci USA* 98:1182-1187, 2000; Vassilev P. M. et al, *Biochem Biophys Res Commun* 282:341-350, 2001; Koulen P. et al., *Nat Cell Biol* 4:191-197, 2002; Hanaoka K. et al., *Nature* 408:990-994, 2000). Unlike PKD1, PKD2 is a single copy gene, making its analysis much more straight-forward. See Table 1 for a summary of the PKD genes. Further discussion of PKD1 and PKD2 genes, gene and protein alterations and methods of detecting the same can be found in US 2006/0246504, US 2003/0008288, WO 2002/006529, US 2005/017399, U.S. Pat. No. 7,083,915, U.S. Pat. No. 6,031,088, U.S. Pat. No. 6,228,591, US 2007/0166755, US 2005/0100898, U.S. Pat. No. 6,916,619, U.S. Pat. No. 6,656,681, U.S. Pat. No. 6,485,960, U.S. Pat. No. 6,380,360 and WO 1995/018225, which are all herein incorporated by reference.

TABLE 1

PKD gene description

| Gene Description | PKD1 | PKD2 | |
|---|---|---|---|
| Chromosome | 16p13.3 | 4q21-23 | |
| Genomic length | 54 kb | 68 kb | |
| Exons | 46 | 15 | |
| Base pairs | 12,909 | 2,904 | |
| Codons | 4,303 | 968 | |
| Protein | Polycystin-1 | Polycystin-2 | |
| Analysis: | | | Total |
| Long Range PCRs | 8 | — | 8 |
| Amplicons | 54 | 17 | 71 |
| Base Pairs evaluated (including adjacent intronic sequence) | 13,830 | 3,204 | 17,034 |

PKD Gene Analysis

Genomic DNA obtained from a sample from a subject can be used as the template for generating one or more PKD-specific amplification products (e.g., long-range PKD amplification products). DNA testing is advantageous as it has the potential to provide genetic information to an isolated individual (e.g., when family members are unavailable for linkage studies. Both copies of the PKD genes in an individual should be analyzed/sequenced to identify bona fide gene mutations, as mutations have been detected on a normal haplotype and/or in combination with other amino acid truncating mutations.

A sample can be a biological material which is isolated from its natural environment containing target nucleic acid (e.g., a nucleic acid comprising a PKD gene), and may consist of purified or isolated nucleic acid, or may comprise a biological sample such as a tissue sample, a biological fluid sample, or a cell sample comprising the target nucleic acid. Collecting a tissue sample also includes in vitro harvest of cultured human cells derived from an individual's tissue or any means of in vivo sampling directly from a subject, for example, by blood draw, spinal tap, tissue smear or tissue biopsy. Optionally, tissue samples can be stored before analysis by well known storage means that preserve a sample's nucleic acid(s) in an analyzable condition, such as quick freezing, or a controlled freezing regime, in the presence of a cryoprotectant, for example, dimethyl sulfoxide (DMSO), glycerol, or propanediol-sucrose. Tissue samples can also be pooled before or after storage for purposes of amplifying them for analysis. In some embodiments, the sample contains DNA, tissue or cells from two or more different individuals. In another embodiment, the amount of sample necessary to analyze a PKD gene is dependent on the type of sample (e.g., more than 5 milliliters of blood) and this amount is best assessed by one of skill in the art. Preferably, aseptic techniques are used to obtain these samples to avoid their contamination.

Methods of isolating genomic DNA from a particular sample are well known and routine (see Sambrook et al., supra, 1989). In a particular embodiment, amplification of the genomic PKD DNA has advantages over the cDNA amplification process, including, for example, the allowance of the analysis of exons and introns of the PKD gene. As such, a target sequence of interest associated with either an intron or exon sequence of a PKD gene can be amplified and characterized.

A target sequence of interest is any sequence or locus of a PKD gene that contains or is thought to contain a nucleotide sequence alteration, including those alterations that correlate with a PKD-associated disorder or disease (e.g., ADPKD).

Mutations in a PKD gene can be detected by amplification, including, for example, by polymerase chain reaction (PCR), ligase chain reaction, self sustained sequence replication, a transcriptional amplification system, Q-Beta Replicase, or any other nucleic acid amplification method, followed by the detection of the amplification products. Accordingly, in one embodiment, genomic DNA extracted from whole blood serves as a template for highly specific PKD1 gene amplification by long-range amplification of 8 segments encompassing the entire PKD1 duplicated region. The specific long-range amplification prevents the spurious amplification of PKD1 homologs that would otherwise confound the analysis. These PKD1 homologs are sequences which are closely related to PKD1, but which do not encode an expressed PKD1 gene product. In fact, analysis of the PKD1 gene had not been amenable to genetic analysis largely because of the presence of at least three highly homologous copies of the gene that map proximal to PKD1 along chromosome 16 (16p13.1). The sequence of these PKD1 gene homologs are contained in GenBank Accession Nos. AC002039, AC010488, AC040158, AF320593 AND AF320594 (each of which is incorporated herein by reference). Several examples of such homologs that map to chromosomal location 16p 13.1 or 4q21-23 have been identified and sequenced. A PKD1 homologue may share more than 95% sequence identity to an authentic PKD gene.

In some embodiments of the invention, a nested amplification is performed using amplified products in a preceding amplification reaction as templates. Preferably, the nested amplification reaction is a nested PCR using PCR amplified products from a preceding PCR reaction as templates. In addition to optimizing the annealing temperature of the primers, "nested" amplification can be used to increase the specificity and sensitivity of the PKD-specific amplification assay. For example, a method comprising a nested PCR can involve two sequential PCR reactions. After multiple cycles of PCR (e.g., 10 to 40, or 10 to 30 or 10 to 20 cycles) with the first pair of primers comprising at least one PKD-specific primer (e.g., a PKD-specific primer and a control primer or two PKD-specific primers), a small amount aliquot of the first reaction (e.g., 1 µl of a 50 µl reaction) serves as the template for a second round comprising multiple cycles of PCR reaction (e.g., 10 to 40, or 10 to 30 or 10 to 20 cycles) with a new set of primers comprising at least one PKD-specific primer (e.g., a PKD-specific primer and a control primer or two PKD-specific primers) that anneal to sequences internal to, or nested between, the first pair.

In a particular embodiment, the 8 long range PCR products described above serve as template for 43 nested PCR reactions and cover exons 1-34 of the PKD1 gene. The unique region of the PKD1 gene (exons 35-46) and the entire PKD2 gene are amplified from genomic DNA as 28 additional gene segments. Using the nested PCR procedure, the template that is successfully amplified is selected twice for PKD-specificity. The use of nested PCR can also greatly enhance the yield of the species-specific product and, therefore, the sensitivity of the assay, when a single primer pair fails by itself.

Methods for designing primers and for performing PCR are known in the art (see Current Protocols in Molecular Biology, supra). The general criteria for selecting primers applies to primers for both the long-range PCR and nested PCR. With regard to primer for the nested PCR, both nested primers should anneal to sequences internal to (e.g., within) the first pair of primers and at least one of the nested primers. Some PKD1-specific primers which eliminate unintended amplification of PKD1 homologs have been developed (see, e.g., U.S. 2003/0008288, which is incorporated herein by reference). Other such primers can be designed, where a "PKD-specific" primer would be a nucleic acid sequence which anneals to a sequence within a PKD gene (including introns and exons) under specific stringent conditions. A PKD-specific primer, anneals to a unique site present in the authentic expressed PKD1 gene, and not to PKD1 homologs or other sequences under specific stringent conditions. Thus, PKD-specific primers can be designed using these unique PKD sites. The length of a unique site may vary from several nucleotides to thousands of nucleotides. Most of unique sites that have been identified comprises less than or equal to 100 nucleotides, e.g., less than or equal to 50 nucleotides, or less than or equal to 30 nucleotides. Amplification using PKD-specific primers increases the specificity of the amplification reaction and reduces the amount of by-products amplified from PKD homologs. The primers may be 10 to 60 nucleotides in length, for example, 18-52 nucleotides in length.

The 71 PCR products are bi-directionally sequenced to detect nucleotide sequence alterations. In a particular embodiment, all PCR primers comprise a tag (e.g., M13 forward and reverse primer sequences) to permit bi-directional sequencing of all fragments with the same primers. Methods of sequencing DNA are well-known in the art and are dependent on the primer position and/or fragment length. For example, in one embodiment, sequencing is performed using ABI Big Dye terminator chemistry followed by electrophoresis on an ABI 3730 capillary sequencer. Nucleotide alterations of the invention can be detected in a PKD sequence to assess existing or potential ADPKD. Novel alterations identified can be clinically interpreted as disease-associated mutations, for example, frameshift or nonsense mutations or invariant splice site changes. Benign polymorphisms would include silent or conservative missense mutations, intronic variants and synonymous codon changes.

Sequence alterations in a PKD gene can also be detected using denaturing high performance liquid chromatography (DHPLC). DHPLC has been used to detect sequence variants by separating a heteroduplex (resulting from the presence of a mutation) and a homoduplex having the same basepair length. This separation is based on the fact that a heteroduplex has a lower melting temperature ($T_m$) than a homoduplex. DHPLC can separate heteroduplexes that differ by as little as one base pair under certain conditions. The "heteroduplex site separation temperature" or "midpoint temperature" or "$T_m$" is defined herein to mean, the temperature at which one or more base pairs denature, i.e., separate, at the site of base pair mismatch in a heteroduplex DNA fragment. When DHPLC is carried out at a partially denaturing temperature, i.e., a temperature sufficient to denature a heteroduplex at the site of a base pair mismatch, homoduplexes can be separated from heteroduplexes having the same base pair length and detected by various methods (e.g., gel electrophoresis). DHPLC can also be used to separate duplexes having different basepairs in length.

Evaluation of Identified PKD Nucleotide Alterations

Numerous novel nucleotide alterations in PKD have been identified (see Tables 4-7). These sequence alterations were then evaluated to determine whether they were pathogenic, this is, resulted in an altered PKD gene product (e.g., protein, polypeptide). A "nucleotide sequence alteration" or "nucleotide alteration" or "mutation" refers to a nucleotide sequence modification including one or more substitutions (transitions or transversions), deletions (including loss of locus), insertions (including duplications), translocations, inversions and/or other modifications relative to a normal PKD gene (e.g., SEQ ID NO:1, SEQ ID NO:7 or SEQ ID NO:4). Thus, a nucleotide alteration/change in a PKD1 or PKD2 nucleotide sequence (e.g., DNA or mRNA) can be a deletion, insertion, substitution or inversion, or can be silent such that there is no change in the reading frame of a polypeptide encoded by the PKD polynucleotide. Pathogenic mutations are those nucleic acid alterations that result in an amino acid change (e.g., a non-silent or non-conservative change) and/or introduces a STOP codon into the nucleotide sequence, or changes nucleotide sequence involved in transcription or translation of the PKD1 or PKD2 nucleotide sequence; for example, a change that results in altered splicing of a PKD1 or PKD2 gene transcript into an mRNA (see FIGS. 7A and 7B). An "amino acid alteration" refers to an amino acid modification including a substitution, a frameshift, a deletion, a truncation and an insertion, and/or other modifications relative to the normal PKD amino acid sequence (e.g., SEQ ID NO:3 or SEQ ID NO:6). Thus, a mutation in a PKD gene sequence can result in the expression of a truncated PKD polypeptide, or even a complete loss of expression of the PKD polypeptide.

In contrast, polymorphic mutations or variants are those nucleic acid alterations that do not alter and/or are not expected to alter a PKD protein/polypeptide in the above-described manner and/or do not correlate with the signs or symptoms of a PKD-associated disorder such as ADPKD (see Tables 8 and 9). These mutations include, for example, nucleotide substitutions that do not result in a change in the encoded amino acid, i.e., silent mutations, in which the wild type (see, e.g., SEQ ID NOs:1, 7 or 4) and mutant codons both encode the same amino acid; those that do not segregate with the disease or those that are found in a panel of unaffected individuals. Nucleic acid alterations that cause conservative amino acid substitutions in which a wild-type amino acid (see, e.g., SEQ ID NOs:3 or 6) is substituted for another amino acid with similar properties, may also be non-pathogenic polymorphic mutations, as it would be expected that the secondary structure and hydropathic nature of the PKD polypeptide would be substantially unchanged by these mutations. In general, the following groups of amino acid substitutions are thought to be conservative: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. With respect to PKD mutations, polymorphisms are then defined as: (i) sequence variants not predicted to alter an amino acid; (ii) missense changes found in homozygosity in at least one individual; (iii) intronic sequences of unknown significance; or (iv) changes in the 3' UTR of unknown significance. Accordingly, polymorphic mutations would be expected to result in a PKD protein/polypeptide that is still properly expressed and/or fully functional; that is, these variants would not be expected to be associated with ADPKD.

Nucleotide sequence alterations identified in PKD1 and PKD2 genes can be evaluated for pathogenicity in a number of ways. Mutant PKD nucleotide sequence can be compared to wild-type PKD sequence (SEQ ID NOs:1 and 4) and the effect of the nucleic acid sequence alterations on amino acid codon(s) assessed. For example, a change in nucleotide sequence that produces a stop codon (e.g., UGA, UAA, UAG) or a frameshift, which generally results in a nonsensical polypeptide and/or also produces a stop codon, or that alters a consensus donor/acceptor splice site would result in a non-functional PKD protein, a truncated PKD protein, or obliterate its expression altogether. These mutations would be expected to be pathogenic and thus correlates with ADPKD.

PKD nucleic acid sequence alterations that do not result in the production of a stop codon, frameshift or splice site mutation can also be assessed by comparing the mutant PKD amino acid sequence to the wild-type PKD amino acid sequence from various species to determine if the alteration affects an amino acid residue that is conserved across several species. In particular, an amino acid change (i.e., a missense mutation) or a deletion of several adjacent nucleotide residues (e.g., a deletion of 3, 6 or 9 nucleotides) which would cause a complete deletion of one or more amino acid residues (i.e., an in-frame deletion; see also Table 5) would result in a PKD polypeptide that is still expressed. The change or loss of an amino acid residue conserved across several species (e.g., human, canine, mouse, fish, fruit fly, nematode, etc), where a "conserved" amino acid residue is one that is identical or has similar properties (e.g., ala, pro, gly, glu, asp, gin asn, ser, thr), would strongly indicate that the amino acid residue is important/critical to PKD protein function. Accordingly, such PKD mutations might also be expected to be associated with and/or predictive of ADPKD.

Furthermore, there are also several algorithms that can be used to predict/evaluate alterations to a PKD nucleic acid sequence, particularly those that result in a missense mutation. These algorithms include, for example, the Miller/Kumar matrix (Miller M. P. and Kumar S., *Hum Mol. Genet.* 10(21):2319-2328, 2001); Grantham's chemical difference matrix; Online Mendelian Inheritance in Man (OMIM), //www.ncbi.nlm.nih.gov/Omim/; Splice Site Prediction by Neural Network (SSPNN) (see also Reese M. G. et al., *J Comput Biol* 4(3):311-323, 1997), //fruitfly.org.seqtools/splice.html; Automated Splice Site Analyses (ASSA) (see also, Nalla V. K. et al., *Hum Mutat* 25(4):334-342, 2005 and Rogan P. K. et al., *Hum Mutat* 12 (3)153-171, 1998), //splice.cmh.edu/; Simple Modular Architecture Research Tool (SMART), //smart.embl.de; Pfam, //www.sanger.ac.uk/Software/Pfam/; MDRD equation: //nephron.com/cgi-bin/MDRDSI.cgi; Prediction of Protein Sorting Signals and Localization Sites in Amino Acid Sequences II (PSORT II) (see also Krogh A. et al., *J Mol Biol* 305:567-580, 2001), //psort.ims.u-tokyo.acjp/form2.html; and Transmembrane Helices Prediction (TMHMM), (see also Grimm D. H. et al, *J Biol Chem* 278:36786-36793, 2003), //www.cbs.dtu.dk.services/TMHMM/. By predicting mRNA and/or protein structure, function and motifs, these and other algorithms can help determine the likelihood that a mutation (e.g., a missense mutation) represents a pathogenic change as opposed to a polymorphism.

Further assessment of PKD mutations not clearly pathogenic could also be aided with a dataset comprising complete sequence information from a population of unaffected, ethnically diverse individuals. Normal or wild-type PKD1 and PKD2 sequence information from such a population would be a useful control for comparison to novel PKD mutations identified to both evaluate the presence or absence of a sequence variant in the control population and expand the spectrum of known non-pathogenic sequence variants. Having such a dataset to compare to PKD mutations that have been identified would be advantageous diagnostically and prognostically, especially in the analysis of individuals having less than a 50% probability of having ADPKD (e.g., individuals not the progeny and/or siblings of an individual with ADPKD).

The effect of mutations in a PKD gene on a PKD gene product can be assessed and/or confirmed by expressing a polynucleotide having or constructed (e.g., a recombinant polynucleotide) to have the identified mutation(s). The polynucleotide can comprise the mutant PKD polypeptide or a portion of a recombinant nucleic acid molecule, which, for example, can encode a fusion PKD protein (e.g., a tagged PKD protein). The mutant polynucleotide or recombinant nucleic acid molecule can be inserted into a vector, which can be an expression vector, and can be derived from a plasmid, a virus or the like. The expression vector generally contains an origin of replication, a promoter, and one or more genes that allow phenotypic selection of transformed cells containing the vector. Expression vectors suitable for use are well-known in the art e.g., a T7-based expression vector for expression in bacteria, a pMSXND expression vector for expression in mammalian cells or baculovirus-derived vectors for expression in insect cells and the like. The choice of a vector will depend on the size of the polynucleotide sequence and the host cell to be employed. Thus, the vector used in the methods of the invention can be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides. Cosmids and phagemids are particularly suited for the expression or manipulation of a PKD polynucleotide (e.g., SEQ ID NO:1) or a mutant PKD1 polynucleotide.

A variety of host-expression vector systems can be utilized to express wildtype PKD polynucleotide sequence (e.g., SEQ ID NO:1 or SEQ ID NO:4), the PKD coding sequence (e.g., SEQ ID NO:2 or SEQ ID NO:5) and a variant or mutant PKD1 or PKD2 polynucleotide. In a particular embodiment, the PKD polynucleotide(s) is tagged (e.g., FLAG, Myc, biotin, streptavadin, avadin and the like) to aid in purification and/or visualization of the PKD polypeptide after it has been exposed. Such host-expression systems represent vehicles by which the nucleotide sequences of interest can be produced and subsequently purified, and also represent cells that, when transformed or transfected with the appropriate nucleotide coding sequences, can express a PKD protein, including a PKD variant or mutant polypeptide or peptide portion thereof in situ. Such cells include, but are not limited to, microorganisms such as bacteria (e.g., *E. coli*, *B. subtilis*) transformed with recombinant bacteriophage DNA, plasmid DNA or cosmid DNA expression vectors containing a PKD1 polynucleotide, or oligonucleotide portion thereof (wild type, variant or other mutant); yeast (e.g., *Saccharomyces, Pichia*) transformed with recombinant yeast expression vectors containing a PKD polynucleotide, or oligonucleotide portions thereof (wild type, variant or other PKD mutant); insect cell systems infected with recombinant virus expression vectors (e.g., baculovirus) containing a PKD polynucleotide, or oligonucleotide portion thereof (wild type, PKD variant or other mutant); plant cell systems infected with recombinant virus expression vectors (e.g., cauliflower mosaic virus or tobacco mosaic virus) or transformed with recombinant plasmid expression vectors (e.g., Ti plasmid) containing a mutant PKD polynucleotide, or oligonucleotide portion thereof; or mammalian cell systems (e.g., HEK293, COS, CHO, BHK, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter). Further discussion of vectors and expressions systems for PKD polynucleotides can be found, for example, in US 2003/0008288.

Figure 8A:
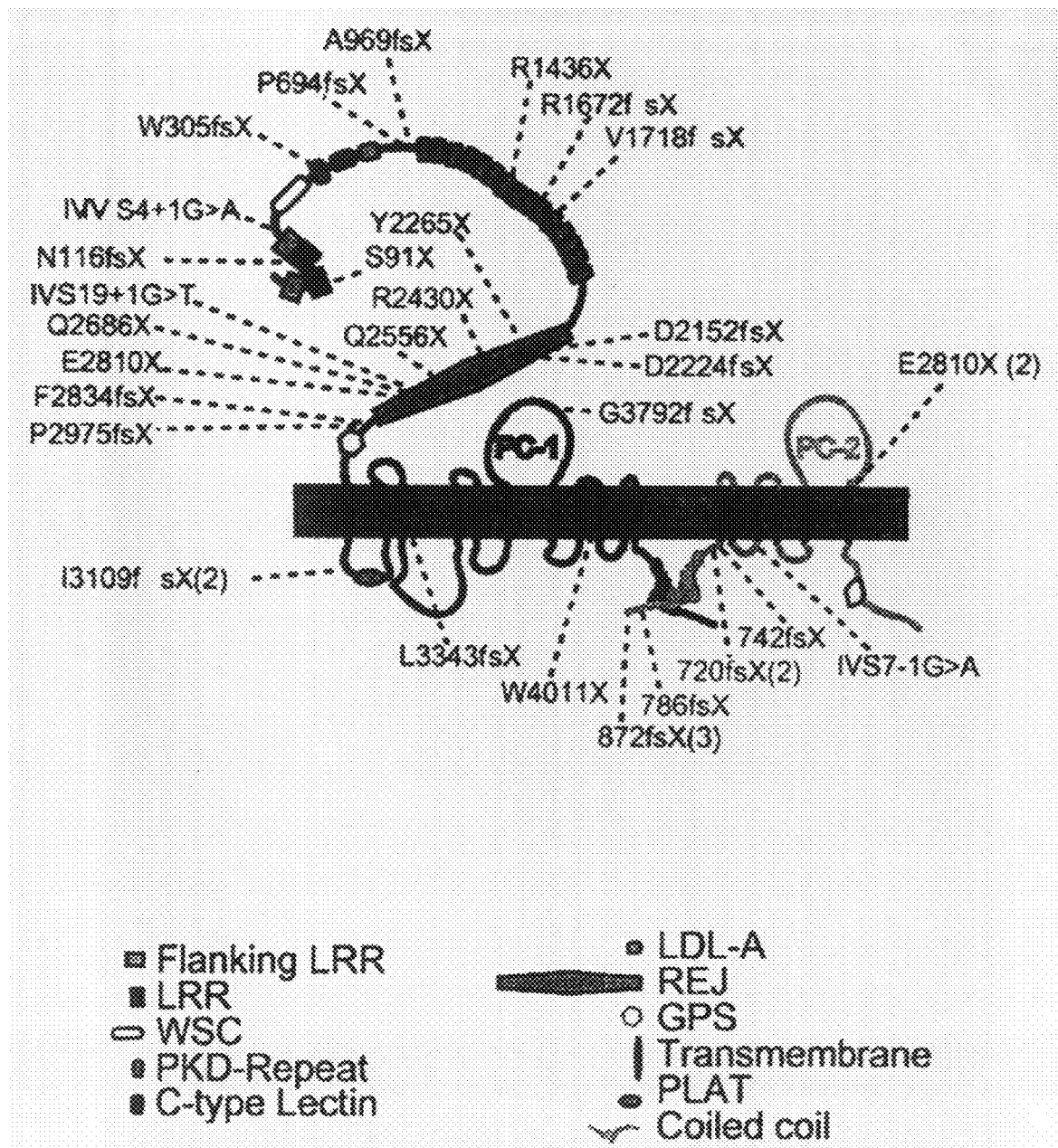
FIGS. 8A and 8B are schematic representations of polycystin-1 (PC-1) (8A) and polycystin-2 (PC-2) (8B). The location of pathogenic (Class I and Class II, see Example) mutations are indicated.

For instance, the PKD1 gene product, polycystin-1 (PC-1), which is believed to function as a cell surface signaling receptor at cell-cell and cell-matrix junctions and as a mechanosensor in renal cells, is an 11-transmembrane glycoprotein with a long N-terminal extracellular region and short cytoplasmic tail (Boletta A. and Germino G. G., *Trends Cell Biol* 13(9):484-492, 2003; Harris P. C. and Torres V. E., *Curr Opin Nephrol Hypentens* 15(4):456-463, 2006; Nauli S. M. et al., *Nat Genet.* 33(2):129-137, 2003; Hughes J. et al., *Nat Genet.* 10(2):151-160, 1995) (see also FIG. 8A). PC1 has several amino acid sequence motifs of interest (e.g., receptor for egg jelly (REJ) domain, G-protein coupled receptor proteolytic site (GPS), C-type lectin domain, leucine rich repeat (LRR), polycystic kidney disease repeat (PKD-R), transmembrane domain (TM), coiled-coil domain (CC)) (see also FIG. 4). A site useful for evaluation of PC-1 function/activity is the GPS domain, a site at which the PC-1 protein undergoes cleavage (Qian F. et al., *Proc Natl Acad Sci* USA 99(26):16981-16986, 2002). Cleavage of PC1 at this site produces an N-terminal fragment (NTF) and a C-terminal fragment (CTF) and this cleavage is critical for normal PC-1 function (Qian F. et al., *Proc Natl Acad Sci* USA 24:99(26):16981-16986). Thus, expression and cleavage of the PKD1 gene product can be used to assess the pathogenicity of identified PKD1 mutations, particularly missense mutations. PKD1 mutants can be constructed (e.g., in an expression vector) and expressed (as, e.g., a recombinantly tagged fusion protein) in the above-described manner and the cleavage of the PKD1 mutant gene products assayed (e.g., by immunoprecipitation and/or western blot, fluoresence of a tag, radioactivity or the like).

One or more of the above-described methods to assess/evaluate PKD mutations can be used to determine whether PKD1 or PKD2 gene mutations that have been identified are benign polymorphisms or pathogenic, such that the mutations can be associated with ADPKD and, subsequently used to diagnose or predict ADPKD in, for instance, the methods of the invention.

Methods of the Invention

The PKD mutations identified and determined to be pathogenic are listed in Tables 4-7. These mutations are used in the methods of the invention to detect or predict the occurrence of ADPKD in an individual or detect the presence or absence of a mutant PKD gene in an individual. Specifically, ADPKD is detected or the occurrence of ADPKD is predicted by detecting the presence of one or more of the identified nucleotide sequence alterations in a PKD1 gene having the nucleotide sequence of SEQ ID NO:1 or SEQ ID NO:7 in a nucleic acid sample obtained from an individual. Similarly, ADPKD can be detected or predicted in an individual using the methods of the invention by detecting the presence of one or more of the identified nucleotide sequence alterations in a PKD2 gene having the nucleotide sequence of SEQ ID NO:4 in a nucleic acid sample obtained from an individual. As several mutations in the PKD genes that are associated with ADPKD have been detected in just a single individual/family (see e.g., Table 7), these other nucleotide sequence alterations in a PKD1 gene (e.g., SEQ ID NO:1 or 7) and/or PKD2 gene (SEQ ID NO:4) not listed above (see Summary of Invention and Tables 4-7) can also be detected in the methods of the invention. The methods can be performed by obtaining a sample (e.g., biological fluid, tissue, cell) from an individual by one or more-procedures (e.g., DNA isolation method/kit) and/or one or more methods (e.g., sequencing, PCR, DHPLC) as described above.

In addition, the invention relates to methods of detecting the presence or absence of a mutant PKD gene in an individual by obtaining a nucleic acid sample from the individual (e.g., biological fluid, tissue or cell sample), by the above-described methods (e.g., DNA isolation method/kit) and detecting the presence or absence of one or more of the identified nucleotide sequence alterations in a PKD1 or PKD2 gene, by using one or more of the above-described processes (e.g., sequencing, PCR, DHPLC or the like). In a particular embodiment, detection of one or more of the identified PKD nucleotide sequence alterations indicates that the individual has ADPKD or may develop ADPKD.

EXEMPLIFICATION

Patient Recruitment and Clinical Evaluation

Eighty-two unrelated ADPKD patients were recruited from outpatient nephrology clinics. The Johns Hopkins Institutional Review board approved the study and informed consent was obtained from each patient. A diagnosis of ADPKD was based on established ultrasound criteria described (Ravine et al., *Lancet* 2:343(8901):824-7, 1994). A detailed medical history was obtained from each participant at the time of entry into the study. A coded blood sample was collected from each proband and sent to Athena Diagnostics, Inc. for mutation analysis. In most cases routine laboratory data were obtained as part of the standard medical evaluation.

Baseline characteristics of the study population are summarized in Table 2. The average age of the study participants was 46.5 years of age. Only 22% had reached ESRD at the time that mutation analysis was performed. The average glomerular filtration rate (GFR) for those that had not reached ESRD was 68 ml/min. Family history was either unknown or was negative for ADPKD in 34% of the patients.

Mutation Analysis

DNA sequence analysis of patient samples was performed using methods described in detail previously and optimized at Athena Diagnostics, Inc (Watnick T J et al., *Hum Mol Genet.* 6(9):1473-1481, 1997; Watnick T J et al., *Mol Cell* 2(2):247-251, 1998; Watnick T. et al., *Am J Hum Genet.* 65(6):1561-1571, 1999; Phakdeekitcharoen B. et al., *Kidney Int* 58(4):1400-1412, 2000; Phakdeekitcharoen B. et al., *J Am Soc Nephiol* 12:955-963, 2001), which references are incorporated in entirety herein. For example, genomic DNA is derived from whole blood using a Puregene® DNA extraction kit (Gentra Systems, Inc. Minneapolis, Minn.) or other suitable extraction method. Amplified DNA product served as a template for highly specific long-range PCR amplification of the 8 segments encompassing the entire PKD1 duplicated region, to prevent the amplification of PKD1 homologs that would confound the analysis. The 8 long range PCR products served as template for 43 nested PCR reactions while the unique region of the PKD1 gene and the entire PKD2 gene were amplified from genomic DNA as 28 additional gene segments. PCR primers were tagged with M13 forward and reverse primer sequences to permit bi-directional sequencing of all fragments with the same primers.

PCR products were then bi-directionally sequenced, for example, using ABI Big Dye™ terminator chemistry (versions 3.1 and 1.1 depending upon primer position and/or fragment length) followed by electrophoresis on an ABI 3730 capillary sequencer (Applera Corporation, Norwalk, Conn.). This process provides sequence data for the entire coding region of the PKD1 and PKD2 genes including the highly conserved exon-intron splice junctions.

Analysis of Normal Samples

A normal population was selected from anonymized samples, older than 65, submitted to Athena Diagnostics, Inc for ataxia testing. PCR products from a minimum of 171 individuals were sequenced to determine the frequency of certain common variants in either PKD1 or PKD2. Complete DNA analysis was not performed for these samples.

Generation of PC-1 Variant Constructs for Cleavage Testing

Missense variants were generated, for example using the QuickChange™ Site-Directed Mutagenesis Kit (Stratagene). The full-length wild type PKD1 cDNA construct and three of the constructs have been previously described (Q3016R, F3064L, F2853S) (Hanaoka K. et al., Nature 408:990-994, 2000; Qian F. et al., Proc Natl Acad Sci USA 24:99(26): 16981-16986, 2002), incorporated in entirety herein.

Cleavage Assay

Constructs were transfected into HEK293 cells using Lipofectamine Plus™ (Life Technologies, Rockville, Md.). After transfection, the cells were lysed in buffer [20 mM sodium phosphate, pH 7.2, 150 mM NaCl, 1 mM EDTA, 10% (vol/vol) glycerol, 0.5% Triton X-100] for 1 hr on ice in the presence of protease inhibitor (Roche Molecular Biochemicals). The cell lysates were immunoprecipitated (IP) using ANTI-FLAGS M2 beads Affinity Gel Freezer-Safe (SIGMA) and then resolved on a NuPAGE® 3-8% Tris-Acetate Gel (Invitrogen). The IP products were electro-blotted onto an Immobilon™ transfer membrane (MILLIPORE) and probed with α-Leucine-rich-repeat (LRR) and α-C-terminus (CT) antibodies for PC1. These antibodies have been previously described (Boletta A. et al., Mol Cell 6:1267-1273, 2000; Qian F. et al., Proc Natl Acad Sci USA 24:99(26):16981-16986, 2002).

Results

DNA sequence variance analysis identified three categories of variants. Class I variants were defined as those having definitive pathogenic sequence variants, including stop codons, frameshift and splice site alterations, that are diagnostic without additional information (Tables 3, 4). Class II variants included those demonstrating in-frame deletions or amino acid substitutions determined likely to be pathogenic based on various algorithms, as described in detail below. Class III variants included those where no pathogenic changes were confirmed.

Class I Variants

Forty-two percent (N=34) of the study population had stop codons, frameshift or splice site alterations (Tables 3, 4). Twenty-four of these alterations occurred in PKD1 (29% of total sample) and 10 in PKD2 (12% of total sample).

The mutations found in Class I variants were expected to result in premature truncation of a PKD1 or PKD2 protein and therefore segregate with ADPKD.

Class II Variants

Thirty participants had either an in-frame deletion or at least one amino acid substitution deemed likely to be pathogenic (Tables 5 and 6). A total of 8 unique in-frame deletions (6 in the PKD1 gene and 2 in PKD2 gene) were detected (Table 5). In each case, the deletion affected one or more residues fully or highly conserved between *Fugu rubripes* (Fugu fish) and *Mus musculus* (mouse) polycystin proteins.

There were 10 individuals with no other truncating PKD mutations who had unique intronic variants. Two of the predicted splice site mutations did not directly affect a consensus splice donor/acceptor site; JHU573 and JHU595 had an intronic change at the 5$^{th}$ base pair from the intron 24 splice donor site (IVS24+5 G>C) that affected a residue that is highly conserved as a guanine in 84% of donor splice sites. Both the Neural Network Splice Site prediction program (SSPN) and Automated Splice Site Analyses (ASSA) predicted that these variants resulted in improper splicing, as such an alteration would severely disrupt the architecture of the splice donor site at the exon 24/intron 24 boundary. JHU105 had a similar alteration (IVS8+5,G>A) at the 5$^{th}$ basepair from the end of PKD2 exon 8 splice donor site (i.e., the 5$^{th}$ nucleotide base counted from left to right after nucleotide residue 1964 of SEQ ID NO:5 into the following intron (intron 8)), in which the highly conserved guanine residue was replaced by an adenine. In addition, IVS37-10C>A (JHU 604), was previously reported to segregate with ADPKD in a European family (Bogdanova, M. et al., Hum Mutat 16(2): 166-174, 2000). JHU562 also had a PKD2 pathogenic mutation that affected a splice site, IVS7-1 G>A (i.e., a change from a guanine to an adenine at the 1$^{st}$ nucleotide residue counted right to left from the beginning of exon 8 (e.g., nucleotide residue 1783 of SEQ ID NO:5) into the previous intron (intron 7)), which resulted in the loss of the acceptor site for exon 7.

Most of the remaining participants had a combination of amino acid substitutions, primarily in PKD1. Three major criteria were used to judge the pathogenicity of each missense variant. Conservation of the altered residue between human polycystin-1 and Fugu fish and mouse proteins was examined. Amino acids that were considered "fully conserved" were those that were identical in all three species, while amino acids with similar properties (i.e. belonging to the same class) were deemed to be "highly conserved" residues. In addition, a pathogenicity score for each missense variant was assigned using the matrix of Miller and Kumar (Miller M. P. and Kumar S., Hum Mol Genet. 12(21):2319-2328, 2001), which defines the relative likelihood that a missense change represents a pathogenic alteration versus a polymorphism. This algorithm was developed by using interspecies sequence comparisons coupled with Grantham's chemical difference matrix to determine the common attributes of amino acid replacement mutations across 7 disease genes (including tuberous sclerosis and cystic fibrosis). Other investigators have used this strategy to assist in characterizing amino acid substitutions (Sharp A. M. et al., J Med Genet. 42(4):336-349, 2005). Finally, literature was reviewed to determine whether any of the variants had been reported by others to occur in unaffected individuals. Several amino acid substitutions (N=13, Table 9), detected in homozygosity in one or more individuals, were classified as polymorphisms. Since germ line ADPKD mutations are heterozygous, one of these changes would have to be associated with a wild type allele, presumably inherited from an unaffected parent.

Analysis of individual amino acid substitutions, grouped by patient, is summarized in Table 6. An amino acid substitution was deemed to be pathogenic, if it occurred at a fully or highly conserved amino acid residue and if it was also predicted to have a higher pathogenic potential using the matrix of Miller and Kumar (Table 6, shaded in Gray). Using these strict criteria, 24 of 30 patients had one or more pathogenic amino acid substitutions. Six of these missense changes were predicted to disrupt structural determinants of either the C-type lectin (Y420C, Y528C) or one of the PKD repeats (S1047L, R1340W, R1351W, T1861I) (FIGS. 5A and 5B). Three of the missense changes (Q3016R, E2771K, F2853S) were previously shown to disrupt polycystin-1 cleavage, a property that is critical for normal polycystin-1 function (see FIG. 6) (Qian F. et al., Proc Natl Acad Sci USA 24:99(26): 16981-16986, 2002).

Recurrent PKD1 variants (R2200c, Q739R, G2814R, Q2182R, G2309R, R1340W) that met the criteria for pathogenicity were observed in 7 individuals and were also present in other individuals who harbored either chain terminating mutations or other predicted pathogenic amino acid substitutions (Tables 4, 6 and 7). For example, R2200c was present in 4 patients, JHU584, JHU606, JHU111 and JHU573. The latter two individuals had a PKD1 frame shift mutation and a splice site mutation, respectively. This association suggested that these changes represented polymorphisms. To further characterize the missense mutations, 342 normal chromosomes were sequenced to identify polymorphisms and the R2200C sequence alteration was seen in a small (1.4%) fraction but greater than the polymorphism threshold of 1%. Likewise Q739R (this study 6.4%) and G2814R (Rossetti et al., 0.9%) have also been reported in a small percentage of the unaffected population and are or may be polymorphisms, respectively (Thomas T. et al., *Am J Hum Genet.* 65(1):39-49, 1999 and Rossetti S. et al., *Kidney Int* 61(5):1588-1599, 2002).

If patients with only these pathogenic recurrent variants (without additional chain terminating mutations or other pathogenic amino acid substitution) were eliminated, then approximately 21% of the sample (N=17/82 patients) would be predicted to harbor a pathogenic PKD1 missense mutation.

Five participants JHU 602 (N=2), JHU100 (N=3), JHU588 (N=2), JHU411 (N=2), JHU114 (N=2) had more than one PKD1 amino acid variant that met the criteria for pathogenicity. This observation raises the possibility that a combination of missense changes in cis might cooperatively result in a diminished level of functional PKD1 protein (Reiterova J. et al., *Hum Mutat* 19(5):573, 2002).

In contrast with PKD1, only two PKD2 amino acid substitutions were detected among the 37 patients lacking chain-terminating mutations. One change (M800L in JHU559, Table 6), was not considered pathogenic by the criteria of the present system and did not segrate with disease in a PKD2 family. A second PKD2 substitution, A190T, was found in 3 patients and, likewise, did not meet the criteria for pathogenicity as it was identified in 3.2% of normal chromosomes (Table 6).

In assessing Class II variants, detection of in-frame deletions was a useful predictor of pathogenicity. Also amino acid substitutions resulting in loss of polycystin-1 cleavage were predictive of pathogenicity.

Figure 8B:
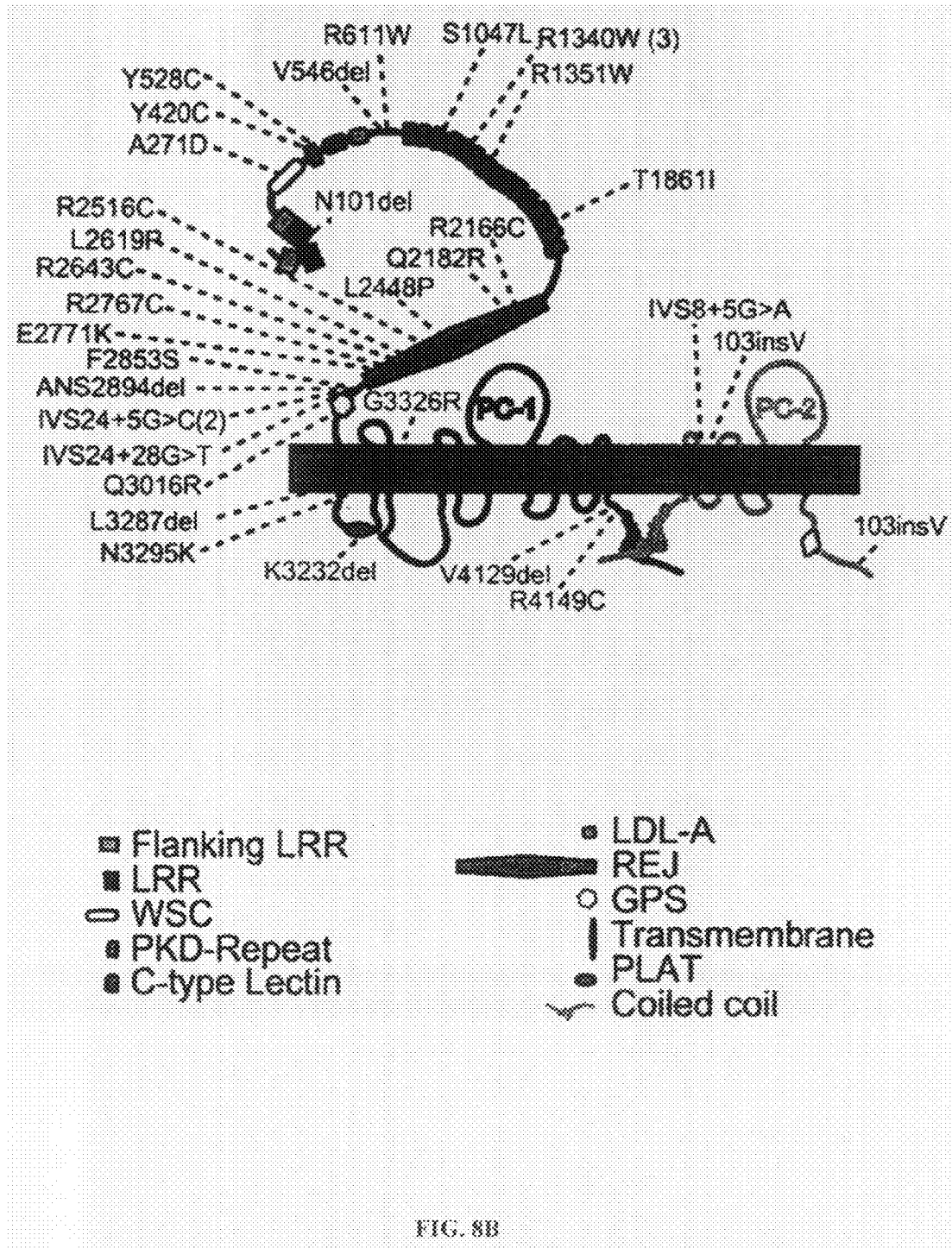

Class I and Class II amino acid changes in the PKD-1 protein (polycystin-1) and PKD-2 protein (polycystin-2) are depicted in a schematic in FIG. 8.

Class III Variants

Eighteen subjects in the study lacked definitive pathogenic sequence alterations (Tables 6 and 9). Of these, 9 had clear and extensive family history of polycystic kidney disease (Table 9). The other 9 had enlarged kidneys with cysts, with 4 of these individuals suffering from significant renal dysfunction (GFR<40) at the time of DNA testing.

Failure to detect pathogenic or potentially pathogenic changes in a subset of individuals with polycystic kidney disease may be due to several reasons. Mutational events in individuals with Class III tests could involve introns or other regulatory regions that were not assayed by the methodology that was used. Direct sequencing might also miss deletions or duplications, which would appear as an area of homozygous normal sequence. Alternatively, the stringent criteria used may have identified some missense changes as benign when they are in fact pathogenic. For example, JHU617, with an extensive family history of ADPKD, was found to have a unique leucine to valine change in PKD repeat 4 that was judged more likely to be a polymorphism by the matrix of Miller/Kumar. Nevertheless, this change does disrupt the structure of PKD repeat 4 and could be pathogenic (see FIGS. 5A and 5B). In addition, as reported by Reynolds, missense variants may unexpectedly activate cryptic splice sites, thereby reducing the level of normal transcript (Reynolds D. M. et al., *J Am Soc Nephrol* 10(11):2342-2351, 1999).

Functional Analysis of Missense Changes

Figure 6:
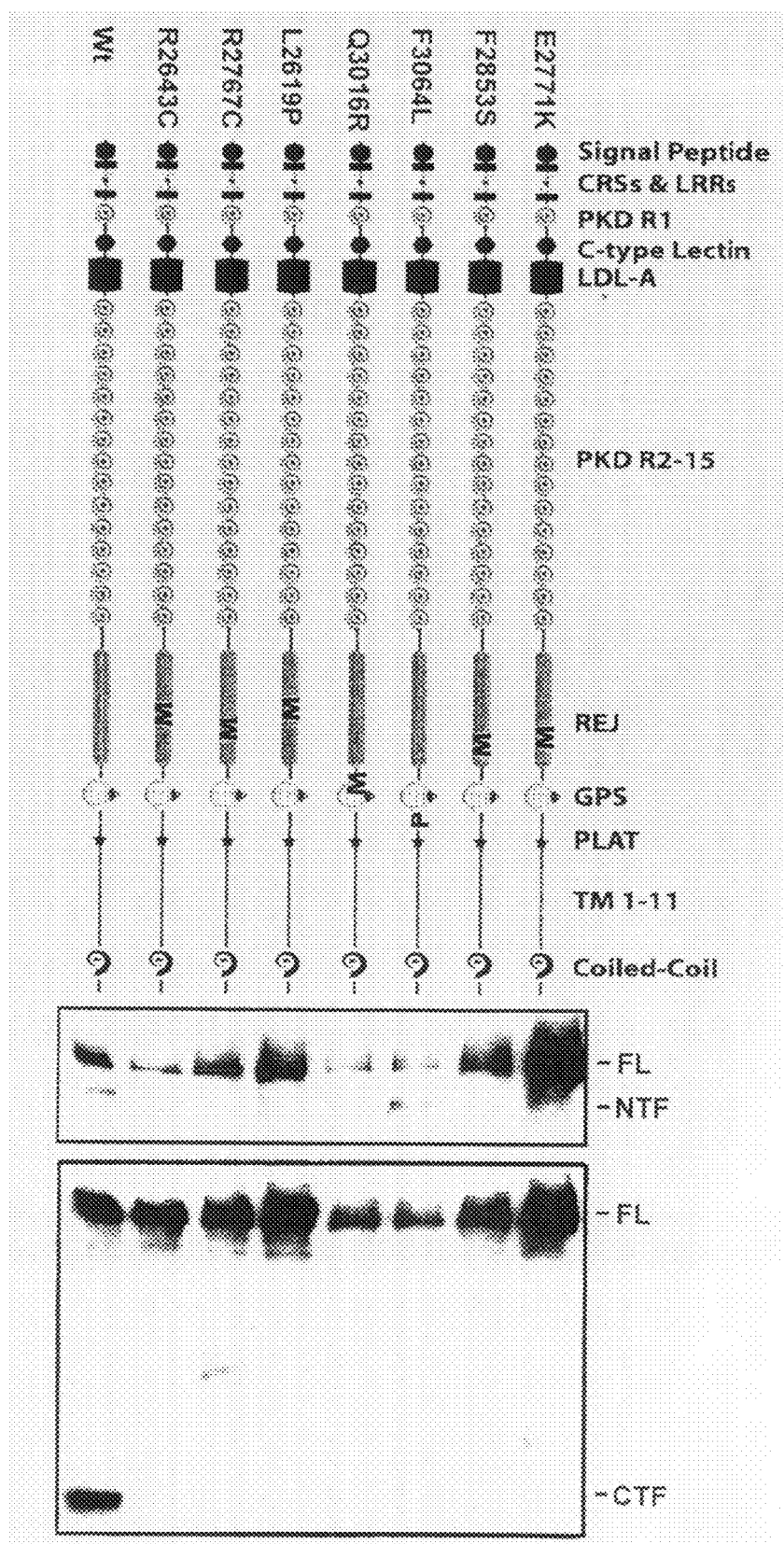
FIG. 6 illustrates a schematic of PKD1 mutant polypeptides with the location of each amino acid substitution indicated, M (missense) or P (polymorphism) and a photograph of a western blot of the full-length, flagged-tagged PKD1 constructs for each mutant protein and any cleavage products. FL: full-length, NTF: PKD1 N-terminal cleavage fragment, CTF; PKD1 C-terminal cleavage fragment.

To confirm that a subset of PKD1 amino acid substitutions predicted to be pathogenic disrupted the functional properties of the protein, full-length mutant constructs were generated and transiently expressed in HEK293 cells. FIG. 6 demonstrates that E2771K, Q3016R and F2853S disrupt cleavage, as do three additional missense changes, R2643c, R2767c and L2619P.

Polymorphism and Variability in PKD Genes

Figure 7A:
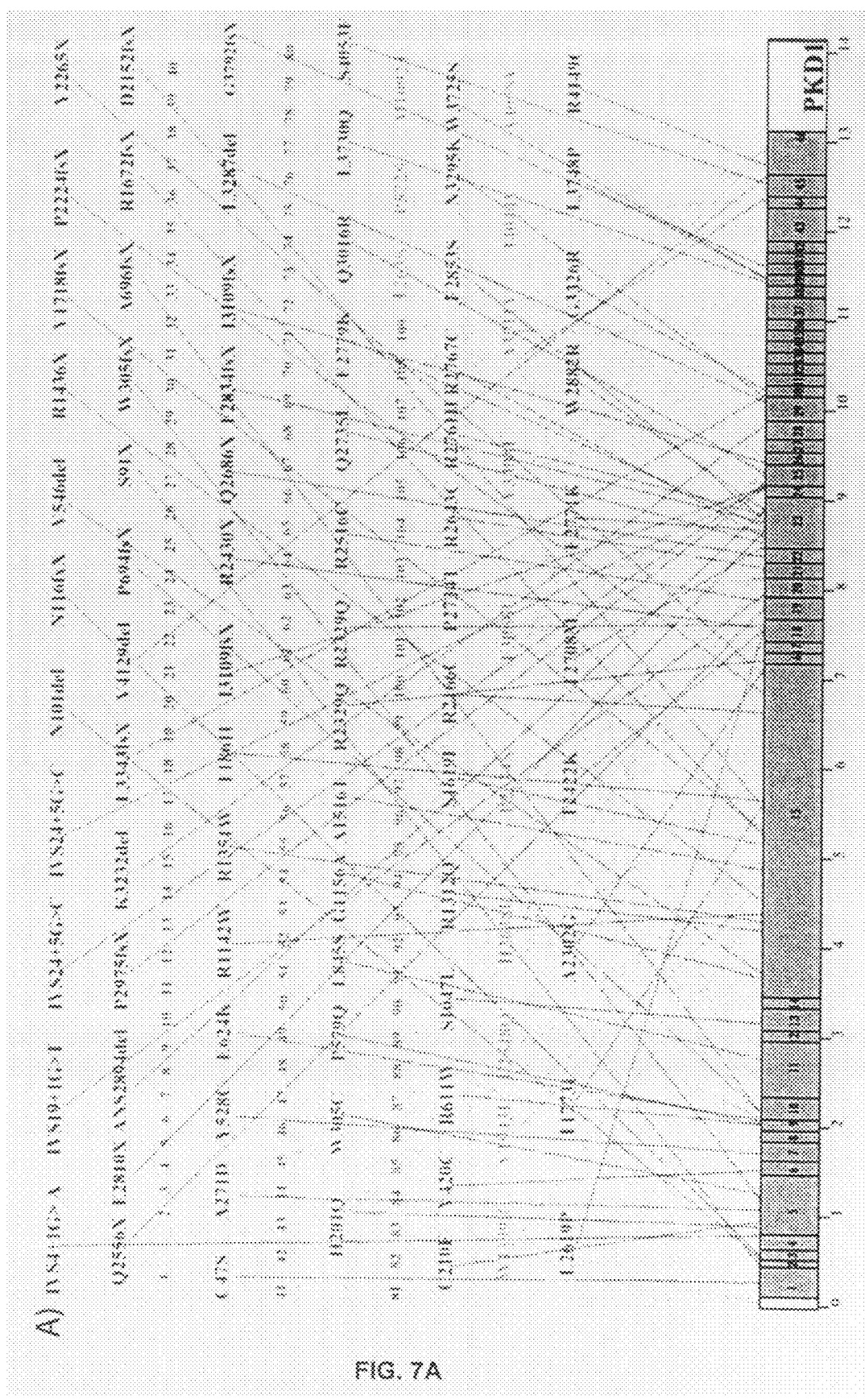
FIGS. 7A-7B are schematics illustrating all the PKD1 (5A) and PKD2 (5B) mutations identified. Numbers 1-113 refer to identifiers of the mutations in Table 8.
Figure 7B:
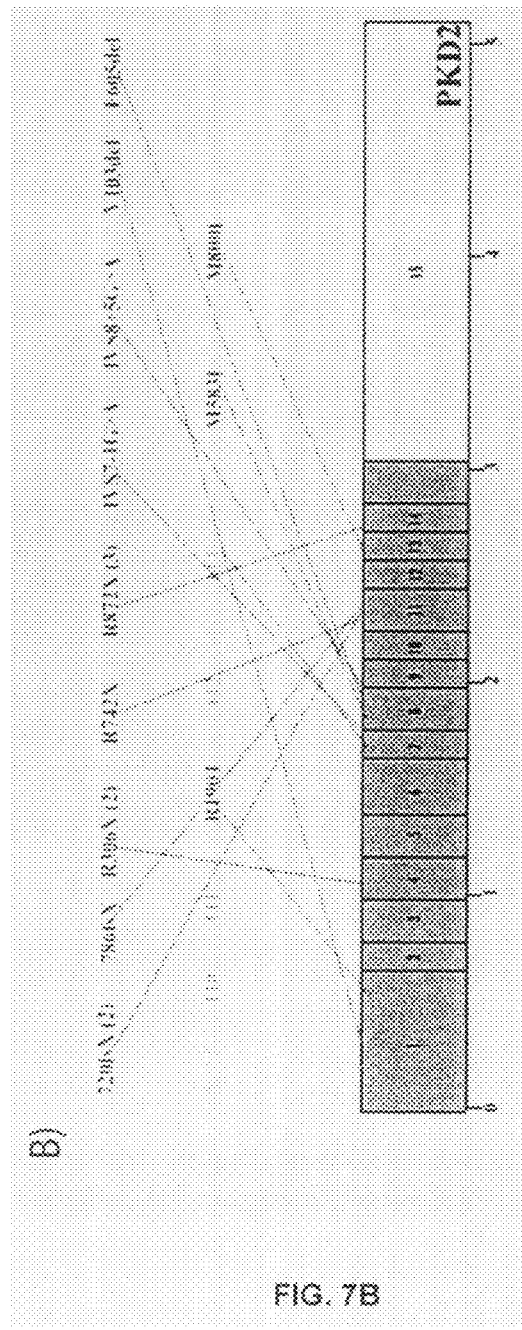

In addition to the sequence alterations described in Tables 4-7, a large number of polymorphisms were detected (Table 9) (see also FIGS. 7A and 7B). Polymorphisms are defined as: (i) sequence variants not predicted to alter an amino acid; (ii) missense changes found in homozygosity in at least one patient; (iii) intronic sequences of unknown significance; or (iv) changes in the 3' UTR of unknown significance.

Further discussion of the above example can be found in M. A. Garcia-Gonzalez et al., Evaluating the clinical utility of a molecular genetic test for polycystic kidney disease, *Mol. Genet. Metab* (2007) in press, doi:10.1016/j.ymgme.2007.05.004, which is herein incorporated by reference.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

TABLE 2

Cohort characteristics.

| | |
|---|---|
| % Female* | 50% |
| Average Age at time of Test* | 46.5 (range 1-73y) |
| % ESRD[€, *] | 20.7% |
| Average GFR (ml/min)[¥] | 68.7 (range 14-126) |
| % Liver cysts* | 74.3% |
| % Vascular complications* | 9.8% |
| % Unknown or no Family history* | 30.5% |

*N = 82 subjects.
[€]ESRD defined as transplant, dialysis or MDRD GFR <10 ml/minute.
[¥]N = 80 patients.

TABLE 3

PKD mutations definitively pathogenic.

| | Truncation and Splicing | | | |
|---|---|---|---|---|
| Gene | Stop Codon | Frameshift | Splicing | Total % |
| PKD1 | 8 (9.8%) | 14 (17.1%) | 4 (4.9%) | 31.7% |
| PKD2 | 6 (7.3%) | 3 (3.7%) | 2 (2.4%) | 13.4% |
| Total % | 17.1% | 20.8% | 7.3% | 45.1% |

TABLE 4

Truncating and Splice site mutations. Leucine Rich Repeat (LRR), Polycystic Kidney Disease Repeat (PKD-R), Receptor for Egg Jelly domain (REJ), Transmembrane (TM), Coiled Coil (CC), Novel change (N). See Full Reference List for mutation references.

| | Mutation | | Mutation Effect | | | | | |
|---|---|---|---|---|---|---|---|---|
| ID | cDNA | Protein | Stop Codon | Splice Site | Exon | Domain | Rate | Ref. |
| | | | PKD1 gene | | | | | |
| Frameshift: | | | | | | | | |
| JHU111 | 559delTTTAA | N116fsX | 117 | | 3 | LRR2 | 1/164 | N. |
| JHU568 | 1124insCT | W305 fsX | 334 | | 5 | PKDR1 | 1/164 | N. |
| JHU582 | 2291ins1 | P694 fsX | 713 | | 10 | | 1/164 | N. |
| JHU585 | 2297ins1 | A696 fsX | 713 | | 10 | | 1/164 | N. |
| JHU15 | 5225delAG | R1672 fsX | 1721 | | 15 | PKDR11 | 1/164 | 1, 8, 23 |
| JHU508 | 5365insT | V1718 fsX | 1770 | | 15 | PKDR12 | 1/164 | N. |
| JHU613 | 6666insG | D2152 fsX | 2174 | | 15 | REJ | 1/164 | N. |
| JHU611 | 6881insA | P2224 fsX | 2261 | | 15 | REJ | 1/164 | N. |
| JHU577 | 8713delT | F2834 fsX | 2874 | | 23 | | 1/164 | N. |
| JHU600 | 9134ins1 | P2975 fsX | 3068 | | 24 | | 1/164 | N. |
| JHU579 | 9536ins5 | I3109 fsX | 3317 | | 26 | | 2/164 | N. |
| JHU609 | 9536ins5 | I3109 fsX | 3317 | | 26 | | 2/164 | N. |
| JHU599 | 10239delT | L3343 fsX | 3395 | | 30 | TM3 | 1/164 | N. |
| JHU104 | 11587delG | G3792 fsX | 3824 | | 40 | | 1/164 | 26 |
| Nonsense: | | | | | | | | |
| JHU605 | 483 C > A | S91X | 91 | | 2 | LRR1 | 1/164 | N. |
| JHU567 | 4517 C > T | R1436X | 1436 | | 15 | PKDR8 | 1/164 | N. |
| JHU108 | 7006 C > A | Y2265X | 2265 | | 15 | REJ | 1/164 | N. |
| JHU563 | 7499 C > T | R2430X | 2430 | | 18 | REJ | 1/164 | 2, 3 |
| JHU593 | 7877 C > T | Q2556X | 2556 | | 19 | REJ | 1/164 | N. |
| JHU083 | 8267 C > T | Q2686X | 2686 | | 22 | REJ | 1/164 | N. |
| JHU574 | 8639 G > T | E2810X | 2810 | | 23 | REJ | 1/164 | N. |
| JHU620 | 12243 G > A | W4011X | 4011 | | 44 | TM9 | 1/164 | N. |
| Splicing: | | | | | | | | |
| JHU572 | | IVS4 + 1G > A. | | Loss of donor site | 4 | | 1/164 | N. |
| JHU580 | | IVS19 + 1G > T. | | Loss of donor site | 19 | REJ | 1/164 | N. |
| JHU573 | | IVS24 + 5G > C. | | Loss of donor site | 24 | | 2/164 | N. |
| JHU595 | | IVS24 + 5G > C. | | Loss of donor site | 24 | | 2/164 | N. |
| | | | PKD2 gene | | | | | |
| Frameshift: | | | | | | | | |
| JHU586 | 2226insA | 720fsX | | | 11 | | 2/164 | N. |
| JHU116 | 2226insA | 720fsX | | | 11 | | 2/164 | N. |
| JHU591 | 2422delAG | 786fsX | | | 12 | CC | 1/164 | N. |
| Nonsense: | | | | | | | | |
| JHU578 | 982 C > T | R306X | | | 4 | TM1 | 2/164 | 5 |
| JHU583 | 982 C > T | R306X | | | 4 | TM1 | 2/164 | 5 |
| JHU607 | 2224 C > T | R742X | | | 11 | | 1/164 | 6 |
| JHU594 | 2680 C > T | R872X | | | 14 | | 3/164 | N. |
| JHU566 | 2680C > T | R872X | | | 14 | | 3/164 | N. |
| JHU608 | 2680C > T | R872X | | | 14 | | 3/164 | N. |
| Splicing: | | | | | | | | |
| JHU562 | | IVS7 − 1G > A | | Loss of acceptor site | 7 | | 1/164 | N. |
| JHU105[L2] | | IVS8 + 5G > A | | Loss of donor site | 8 | | 1/164 | N. |

TABLE 5

In-Frame Deletions. Leucine rich repeat-2 (LRR2), polycystic kidney disease repeat (PKD-R), receptor for egg jelly domain (REJ), Transmembrane (TM), coiled coil (CC), Novel change (N),
* Disrupts the Consensus sequence for the Domain.

| | Mutation | | | | Conservation | | | | |
|---|---|---|---|---|---|---|---|---|---|
| ID | cDNA | Protein | Exon | Domain | Fugu | Mouse | Level | Variant | Ref. |
| | PKD1 gene | | | | | | | | |
| JHU115 | 514-551delCAA | N101del | 3 | LRR2 | N | N | Fully | 1/164 | N. |
| JHU107[L1] | 1848-1851delTGG | V546del | 8 | | V | V | Fully | 1/164 | N. |

TABLE 5-continued

In-Frame Deletions. Leucine rich repeat-2 (LRR2), polycystic kidney disease repeat (PKD-R), receptor for egg jelly domain (REJ), Transmembrane (TM), coiled coil (CC), Novel change (N), * Disrupts the Consensus sequence for the Domain.

| ID | Mutation | | | | Conservation | | | | |
|---|---|---|---|---|---|---|---|---|---|
| | cDNA | Protein | Exon | Domain | Fugu | Mouse | Level | Variant | Ref. |
| JHU560 | 8892-8898delCCAACTCCG | ANS2894del | 23 | | AGA | VGS | Highly | 1/164 | N. |
| JHU592 | 9905-9909delAAG | K3232del | 28 | PLAT | I | K | Highly | 1/164 | N. |
| JHU571 | 10070-10074delCTC | L3287del | 29 | TM2 | L | L | Fully | 1/164 | N. |
| JHU112 | 12597-12600delTGG PKD2 gene | V4129del | 45 | | V | V | Fully | 1/164 | N. |
| JHU 596 | 374-378delTGG | V103del | 1 | Poly-Glu | — | V | Highly | 1/164 | N. |
| JHU416[L2] | 1879-1882delTTC | F605del | 8 | TM5 | — | F | Highly | 1/164 | N. |

TABLE 6

Families with One or More Amino Acid Changes. Families underlined are those with one or more amino acid change that meets criteria of pathogenicity (grey shadow) and not found in patients with definitive pathogenic sequence variants. Fp = do not disrupt cleavage; Fm = disrupt cleavege. See Full Reference List for mutation references.

| ID | Mutation | | | Exon | Domain | Graham | Conservation | | | Rate | Ref. | Total # of variants. | |
|---|---|---|---|---|---|---|---|---|---|---|---|---|---|
| | Gene | cDNA | Protein | | | | Fugu | Mouse | Level | | | PKD1 | PKD2 |
| JHU612 | PKD1 | 1023C>A | A271D | 5 | WSC | Path.H. | A | A | Fully | 1/164 | N. | 4 | 0 |
| | PKD1 | 385G>A | A92T | 2 | | Equal | F | A | Highly | 1/164 | N. | | |
| JHU602 | PKD1 | 1470A>G | Y420C | 6 | C-LECT* | Path.H. | F | Y | Highly | 1/164 | N. | 25 | 1 |
| | PKD1 | 4262C>T | R1351W | 15 | PKDR7* | Path.H. | R | R | Fully | 1/164 | N. | | |
| | PKD1 | 8855T>A | W2882R | 23 | | Path.H. | G | Q | No | 1/164 | N. | | |
| | PKD1 | 9109G>C | E2966D[Fp] | 24 | | Poly. H. | G | E | Highly | 1/164 | 10, 3, 24, 27 | | |
| JHU103 | PKD1 | 1794A>G | Y528C | 7 | C-LECT* | Path.H. | Y | Y | Fully | 1/164 | N. | 28 | 1 |
| | PKD1 | 6036G>A | R1942H | 15 | PKDR14 | Equal | R | R | Fully | 1/164 | N. | | |
| JHU001 | PKD1 | 2042C>T | R611W | 9 | | Path.H. | R | R | Fully | 1/164 | N. | 6 | 0 |
| | PKD1 | 8651G>A | G2814R | 23 | REJ | Path.H. | A | G | Highly | 6/164 | 8, 9 | | |
| JHU411 | PKD1 | 3351C>T | S1047L | 13 | PKDR4* | Path.H. | M | S | Highly | 1/164 | N. | 60 | 1 |
| | PKD1 | 6756A>G | Q2182R | 15 | REJ | Path.H. | G | Q | Highly | 2/164 | N. | | |
| | PKD2 | 634G>A | A190T | 1 | | Equal | - | A | Highly | 3/164 | N. | | |
| JHU100 | PKD1 | 5793C>T | T1861I | 15 | PKDR13* | Path.H. | L | S | Highly | 1/164 | N. | 8 | 1 |
| | PKD1 | 6707C>T | R2166C | 15 | REJ | Path.H. | P | R | Highly | 3/164 | N. | | |
| | PKD1 | 4229C>T | R1340W | 15 | PKDR6* | Path.H. | H | H | Fully | 1/164 | 8 | | |

TABLE 6-continued

Families with One or More Amino Acid Changes. Families underlined are those with one or more amino acid change that meets criteria of pathogenicity (grey shadow) and not found in patients with definitive pathogenic sequence variants. Fp = do not disrupt cleavage; Fm = disrupt cleavege. See Full Reference List for mutation references.

| ID | Mutation | | | Exon | Domain | Graham | Conservation | | | Rate | Ref. | Total # of variants. | |
|---|---|---|---|---|---|---|---|---|---|---|---|---|---|
| | Gene | cDNA | Protein | | | | Fugu | Mouse | Level | | | PKD1 | PKD2 |
| JHU564 | PKD1 | 10187G>C | G3326R | 30 | TM3 | Path.H. | G | G | Fully | 1/164 | N. | 4 | 1 |
| | PKD1 | 7116C>G | A2302G | 15 | REJ | Equal | S | A | Highly | 1/164 | N. | | |
| | PKD1 | 10311A>G | I3367V | 31 | | Poly.H. | I | V | Highly | 1/164 | N. | | |
| JHU588 | PKD1 | 7554T>C | L2448P | 18 | REJ | Path.H. | L | L | Fully | 1/164 | N. | 39 | 0 |
| | PKD1 | 4229C>T | R1340W | 15 | PKDR6* | Path.H. | H | H | Highly | 3/164 | 8 | | |
| JHU603 | PKD1 | 7757C>T | R2516C | 19 | REJ | Path.H. | R | R | Fully | 1/164 | N. | 4 | 0 |
| JHU569 | PKD1 | 8067T>C | L2619P | 20 | REJ | Path.H. | L | L | Fully | 1/164 | N. | 22 | 2 |
| | PKD1 | 8411C>A | P2734T | 23 | REJ | Equal | P | P | Fully | 1/164 | 3 | | |
| | PKD1 | 8415A>T | Q2735L | 23 | REJ | Equal | S | Q | Highly | 1/164 | 3 | | |
| JHU597 | PKD1 | 8138C>T | R2643C | 21 | REJ | Path.H. | R | R | Fully | 1/164 | N. | 3 | 1 |
| JHU101 | PKD1 | 8509C>T | R2767C | 23 | REJ | Path.H. | R | R | Fully | 1/164 | N. | 4 | 2 |
| JHU109 | PKD1 | 8522G>A | E2771K$^{Fm}$ | 23 | REJ | Path.H. | E | E | Fully | 1/164 | 3, 24, 23 | 3 | 0 |
| JHU589 | PKD1 | 8769T>C | F2853S$^{Fm}$ | 23 | | Path.H. | F | F | Fully | 1/164 | 4, 24 | 22 | 2 |
| JHU576 | PKD1 | 10096C>A | N3295K | 29 | TM2 | Path.H. | N | N | Fully | 1/164 | N. | 3 | 0 |
| JHU114 | PKD1 | 12658C>T | R4149C | 46 | | Path.H. | R | R | Fully | 1/164 | N. | 22 | 1 |
| | PKD1 | 4229C>T | R1340W | 15 | PKDR6* | Path.H. | H | H | Highly | 3/164 | 8 | | |
| JHU 601B | PKD1 | 9258A>G | Q3016R$^{Fm}$ | 25 | GPS | Path.H. | Q | Q | Fully | 1/164 | 4, 3, 27, 24 | 43 | 1 |
| | PKD1 | 2427A>G | Q739R | 11 | | Path.H. | R | Q | Highly | 11/164 | 21 | | |
| JHU565 | PKD1 | 7476C>A | T2422K | 18 | REJ | Equal | T | T | Fully | 1/164 | N. | 24 | 0 |
| | PKD1 | 3527C>G | L1106V | 15 | PKDR4 | Poly.H. | S | V | No | 1/164 | N. | | |
| | PKD1 | 3713C>T | P1168S | 15 | PKDR5 | Equal | - | P | Highly | 2/164 | 8 | | |
| JHU570 | PKD1 | 1947C>A | P579Q | 9 | | Equal | P | P | Fully | 1/164 | N. | 5 | 1 |
| | PKD1 | 2427A>G | Q739R | 11 | | Path.H. | R | Q | Highly | 11/164 | 21 | | |
| JHU575 | PKD1 | 3312A>G | N1034S | 13 | PKD R4 | Poly.H. | G | S | No | 1/164 | N. | 17 | 1 |
| JHU178 | PKD1 | 3717C>T | P1168S | 15 | PKDR5 | Equal | - | P | Highly | 2/164 | 8 | 2 | 1 |
| | PKD2 | 634G>A | A190T | 1 | | Equal | - | A | Highly | 3/164 | N. | | |
| JHU610 | PKD2 | 634G>A | A190T | 1 | | Equal | - | A | Highly | 3/164 | N. | 40 | 2 |
| JHU617 | PKD1 | 4391C>G | L1394V | 15 | PKDR8* | Poly.H. | V | L | Highly | 1/164 | N. | 5 | 1 |
| | PKD1 | 11040T>A | L3730Q | 39 | | Equal | F | L | Highly | 1/164 | N. | | |

TABLE 6-continued

Families with One or More Amino Acid Changes. Families underlined are those with one or more amino acid change that meets criteria of pathogenicity (grey shadow) and not found in patients with definitive pathogenic sequence variants. Fp = do not disrupt cleavage; Fm = disrupt cleavege. See Full Reference List for mutation references.

| ID | Mutation | | | Exon | Domain | Graham | Conservation | | | Rate | Ref. | Total # of variants. | |
|---|---|---|---|---|---|---|---|---|---|---|---|---|---|
| | Gene | cDNA | Protein | | | | Fugu | Mouse | Level | | | PKD1 | PKD2 |
| JHU587 | PKD1 | 840G>T | C210F | 5 | | Equal | C | C | Fully | 1/164 | N. | 6 | 2 |
| | PKD1 | 7197G>A | R2329Q | 16 | REJ | Equal | E | R | Highly | 1/164 | N. | | |
| | PKD1 | 2427A>G | Q739R | 11 | | Path.H. | R | Q | Highly | 11/164 | 21 | | |
| JHU559 | PKD1 | 351G>C | C47S | 1 | LRR-N | Poly.H. | W | C | Highly | 1/164 | N. | 24 | 3 |
| | PKD2 | 2464A>C | M800L | 13 | | Poly.H. | - | M | Highly | 1/164 | 11 | | |
| JHU606 | PKD1 | 6809C>T | R2200C | 15 | REJ | Path.H. | R | R | Fully | 4/164 | 23 | 5 | 2 |
| JHU584 | PKD1 | 6809C>T | R2200C | 15 | REJ | Path.H. | R | R | Fully | 4/164 | 23 | 20 | 1 |
| JHU106 | PKD1 | 8651G>A | G2814R | 23 | REJ | Path.H. | A | G | Highly | 6/164 | 3, 8 | 4 | 1 |
| JHU614 | PKD1 | 4757G>A | A1516T | 15 | PKDR9 | Equal | T | I | No | 2/164 | N. | 10 | 0 |
| | PKD1 | 1973A>C | E586D | 9 | | Equal | A | E | Highly | 1/164 | N. | | |
| | PKD1 | 2427A>G | Q739R | 11 | | Path.H. | R | Q | Highly | 11/164 | 21 | | |

TABLE 7

Families with multiple PKD mutations associated with ADPKD. Occasionally, families with a mutation associated to the disease had other change that could be classified also as associated to the disease by meeting our criteria or disrupting the consensus sequence of the Domain*.

| Pedigree | Mutations Disease Associated | | Amino acid changes highly pathogenic | | # of Changes per patient | |
|---|---|---|---|---|---|---|
| | PKD1 | PKD2 | PKD1 | PKD2 | PKD1 | PKD2 |
| JHU605 | S91X | | | | 4 | 0 |
| JHU 567 | R1436X | | | | 24 | 0 |
| JHU108 | Y2265X | | Q739R | | 5 | 1 |
| JHU563 | R2430X | | Q739R | R807Q | 19 | 1 |
| JHU593 | Q2556X | | | | 3 | 2 |
| JHU083 | Q2686X | | | | 5 | 0 |
| JHU574 | E2810X | | G2814R | | 4 | 0 |
| JHU620 | W4011X | | | | 22 | 0 |
| JHU568 | W305 fsX | | W305C* | | 4 | 1 |
| JHU582 | P694 fsX | | | | 1 | 0 |
| JHU585 | A696 fsX | | | | 6 | 2 |
| JHU508 | V1718 fsX | | | | 5 | 2 |
| JHU613 | D2152 fsX | | E624K | | 21 | 0 |
| JHU611 | P2224 fsX | | | | 29 | 1 |
| JHU600 | P2975 fsX | | Q739R | | 25 | 2 |
| JHU609 | I3109 fsX | | | | 41 | 1 |
| JHU579 | I3109 fsX | | G2814R | | 23 | 2 |
| JHU577 | F2834fsX | | Q739R | | 4 | 1 |
| JHU111 | N116 fsX | | R2200C S1619F | | 7 | 1 |
| JHU15 | R1672 fsX | | | | 5 | 1 |
| JHU599 | L3343 fsX | | R1312Q | | 20 | 1 |
| JHU104 | G3792 fsX | | | | 4 | 2 |
| JHU115 | N101del | | | | 20 | 0 |
| JHU107 | V546del | | R1142W | | 25 | 1 |
| JHU560 | ANS2894del | | | | 21 | 1 |
| JHU592 | K3232del | | | | 3 | 1 |
| JHU571 | L3287del | | | | 10 | 0 |
| JHU112 | V4129del | | S4053F | | 19 | 2 |

TABLE 7-continued

Families with multiple PKD mutations associated with ADPKD.
Occasionally, families with a mutation associated to the disease had other
change that could be classified also as associated to the disease by
meeting our criteria or disrupting the consensus sequence of the Domain*.

| Pedigree | Mutations Disease Associated | | Amino acid changes highly pathogenic | | # of Changes per patient | |
|---|---|---|---|---|---|---|
| | PKD1 | PKD2 | PKD1 | PKD2 | PKD1 | PKD2 |
| JHU580 | IVS19 + 1G > T. | | G2814R | | 5 | 1 |
| JHU573 | IVS24 + 5G > C | | R2200C | | 5 | 0 |
| JHU595 | IVS24 + 5G > C | | | | 16 | 2 |
| JHU572 | IVS4 + 1G > A | | | | 17 | 1 |
| JHU578 | | R306X | | | 3 | 3 |
| JHU583 | | R306X | | | 5 | 1 |
| JHU607 | | R742X | | | 21 | 1 |
| JHU594 | | R872X | | | 22 | 3 |
| JHU566 | | R872X | | | 1 | 3 |
| JHU608 | | R872X | | G2814R | 4 | 2 |
| JHU596 | | V103del | | Q2182R | 35 | 1 |
| JHU416 | | F605del | | | 2 | 3 |
| JHU591 | | 786fsX | | | 4 | 2 |
| JHU562 | | IVS7 − 1G > A | | | 3 | 2 |
| JHU105 | | IVS8 + 5G > A | | T1773I* | 3 | 2 |
| JHU116 | | 720 fsX | | Q739R | 3 | 2 |
| JHU586 | | 720 fsX | | T1773I* | 22 | 1 |

TABLE 8

Families without disease-associated PKD mutations.

| ID | Non-pathogenic missense | | Intronic Changes | | Family history | # of Changes | |
|---|---|---|---|---|---|---|---|
| | PKD1 | PKD2 | PKD1 | PKD2 | | PKD1 | PKD2 |
| JHU565 | L1106V P1168S T2422K | | | | Yes | 24 | 0 |
| JHU570 | Q739R P579Q | | | | Yes | 5 | 1 |
| JHU575 | N1034S | | | | No | 17 | 1 |
| JHU178 | P1168S | A190T | | | Yes | 2 | 1 |
| JHU610 | | A190T | | | No | 40 | 2 |
| JHU617 | L1394V* L3730Q | | | | Yes | 5 | 1 |
| JHU587 | C210F Q739R R2329Q | | | | No | 6 | 2 |
| JHU559 | C47S | M800L | | | Yes | 24 | 3 |
| JHU604 | Q739R | | IVS37 − 10C > A^^ | | Yes | 2 | 0 |
| JHU606 | R2200C | | | | No | 5 | 2 |
| JHU584 | R2200C | | | | No | 20 | 1 |
| JHU590 | | | IVS24 + 28G > T^^ | | Yes | 3 | 1 |
| JHU106 | G2814R | | | | Yes | 4 | 1 |
| JHU614 | E586D Q739R A1516T | | | | No | 10 | 0 |
| JHU102[L1] | | | | | Yes | 21 | 0 |
| JHU616 | | | | | Yes | 17 | 0 |
| JHU615 | | | | | No | 0 | 1 |
| JHU110[L3] | | | | | Yes | 3 | 0 |
| JHU113 | | | | | No | 2 | 1 |
| JHU598 | | | | | No | 19 | 0 |

*disrupts the consensus sequence.
^^predicted to generate a new splice site.

TABLE 9

Polymorphisms Identified. See Full Reference List for mutation references.

| ID# | Designation | cDNA Change(s) | Location | Domain | Frequency | Ref. |
|---|---|---|---|---|---|---|
| | | | PKD1 Polymorphisms. | | | |
| — | T263S(H) | 1004C > T | Exon 5 | | 2/164 | N. |
| — | P572S(H) | 1925C > T | Exon 8 | | 4/164 | 8. |
| — | M1092T(H) | 3486T > C | Exon 14 | PKD R4 | 30/164 | 8 |
| — | W1399R(H) | 4406T > G | Exon 15 | PKD R8 | 22/164 | 1, 8, 16 |
| — | V1943I(H) | 6038G > A | Exon 15 | PKD R14 | 5/164 | 8 |
| — | E2548Q(H) | 7853G > C | Exon 19 | REJ | 4/164 | 1 |
| — | H2638R(H) | 8124A > G | Exon 21 | REJ | 32/164 | 1 |
| — | P2674S(H) | 8231C > T | Exon 21 | REJ | 2/164 | 3, 8 |
| — | F3066L (H) | 9407T > C | Exon 25 | | 38/164 | 3, 17, 34 |
| — | V3408L(H) | 10433G > C | Exon 33 | | 5/164 | N. |
| — | A3511V(H) | 10743C > T | Exon 35 | | 13/164 | 3, 8 |
| — | I4044V(H) | 12341A > G | Exon 44 | TM10 | 42/164 | 3, 8, 17, 18, 14, 10 |
| — | A4058V(H) | 12386C > T | Exon 45 | | 12/164 | 8, 10 |
| 1 | | 104C > T | Exon 1 | 5'UTR | 1/164 | N. |
| 2 | | 145C > T | Exon 1 | 5'UTR | 2/164 | N. |
| 3 | | 160C > T | Exon 1 | 5'UTR | 1/164 | N. |
| 4 | | 210C > T | Exon 1 | 5'UTR | 1/164 | N. |
| 5 | L72L | 425C > T | Exon 1 | LRR1 | 2/164 | N. |
| 6 | G109G | 538A > T | Exon 3 | LRR2 | 1/164 | N. |
| 7 | IVS4 + 1G > A(H) | | Intron 4 | | 1/164 | N. |
| 8 | S196S | 799C > T | Exon 5 | | 2/164 | N. |
| 9 | A341A | 1234C > T | Exon 5 | PKD R1 | 5/164 | 3 |
| 10 | L373L(H) | 1330T > C | Exon 5 | | 36/164 | 3, 8, 15 |
| 11 | G441G | 1534G > A | Exon 6 | C-LECT | 1/164 | N. |
| 12 | H570H | 1921C > T | Exon 8 | | 1/164 | 3, 8 |
| 13 | IVS9 + 2del7 | | Intron 9 | | 12/164 | N. |
| 14 | IVS9 + 2 T > A | | Intron 9 | | 1/164 | N. |
| 15 | IVS9 + 28del7 (H) | | Intron 9 | | 4/164 | 8 |
| 16 | ISV9 – 44G > C | | Intron 9 | | 1/164 | 8 |
| 17 | IVS9 – 4A > G | | Intron 9 | | 42/164 | 8 |
| 18 | IVS10 – 4 G > A | | Intron10 | | 1/164 | N. |
| 19 | P738P(H) | 2425C > G | Exon 11 | | 4/164 | N. |
| 20 | A745A | 2448C > G | Exon 11 | | 1/164 | N. |
| 21 | A898A | 2905A > C | Exon 11 | PKD R2 | 4/164 | 8, 9 |
| 22 | P900P | 2911G > A | Exon 11 | PKD R2 | 10/164 | 8, 16, 9 |
| 23 | D910D | 2941C > T | Exon 11 | PKD R2 | 10/164 | 8, 16, 9 |
| 24 | IVS11 – 5C > T | | Intron 11 | | 2/164 | 8 |
| 25 | IVS11 + 23C > T(H) | | Intron 11 | | 4/164 | N. |
| 26 | IVS12 – 15C > T | | Intron 12 | | 5/164 | N. |
| 27 | G1021G(H) | 3274T > C | Exon 13 | PKD R4 | 30/164 | 8, 16, 9 |
| 28 | L1037L | 3392A > G | Exon 13 | PKD R4 | 15/164 | 9 |
| 29 | E1061E | 3394G > A | Exon 14 | PKD R4 | 1/164 | N. |
| 30 | P1076P | 3439G > A | Exon 14 | PKD R4 | 1/164 | N. |
| 31 | A1124A | 3583C > T | Exon 15 | PKD R4 | 25/164 | 8, 9 |
| 32 | S1125S | 3586C > T | Exon 15 | PKD R5 | 25/164 | 8, 9 |
| 33 | F1163F | 3700C > T | Exon 15 | PKD R5 | 1/164 | N. |
| 34 | T1171T | 3724C > G | Exon 15 | PKD R5 | 1/164 | N. |
| 35 | D1310D | 4141C > T | Exon 15 | PKD R7 | 1/164 | N. |
| 36 | L1357L | 4282G > T | Exon 15 | PKD R7 | 1/164 | N. |
| 37 | S1373S | 4330C > T | Exon 15 | PKD R7 | 1/164 | N. |
| 38 | S1452S | 4567T > C | Exon 15 | PKD R8 | 1/164 | N. |
| 39 | P1511P | 4744G > A | Exon 15 | PKD R9 | 1/164 | N. |
| 40 | A1555A(H) | 4876A > C | Exon 15 | Extracellular | 42/164 | 16, 1, 9 |
| 41 | T1558T | 4885G > A | Exon 15 | Extracellular | 9/164 | 2 |
| 42 | S1603S | 5020C > T | Exon 15 | Extracellular | 1/164 | N. |
| 43 | T1724T(H) | 5383C > T | Exon 15 | PKD R12 | 40/164 | 8, 9, 21 |
| 44 | A1818A(H) | 5665A > A | Exon 15 | PKD R13 | 5/164 | 8, 9 |
| 45 | G1860G | 5791G > A | Exon 15 | PKD R13 | 1/164 | N. |
| 46 | A1894A | 5893C > T | Exon 15 | PKD R14 | 1/164 | 8, 9 |
| 47 | L1921L | 5974G > A | Exon 15 | PKD R14 | 2/164 | 8, 9 |
| 48 | V2026V | 6289C > T | Exon 15 | PKD R15 | 1/164 | N. |
| 49 | R2121R | 6574C > T | Exon 15 | PKD R16 | 1/164 | N. |
| 50 | T2180T | 6751C > T | Exon 15 | REJ | 1/164 | N. |
| 51 | A2202A | 6817G > A | Exon 15 | REJ | 1/164 | N. |
| 52 | V2257V | 6982G > A | Exon 15 | REJ | 1/164 | N. |
| 53 | G2309G | 7138C > T | Exon 16 | REJ | 4/164 | 8, 9 |
| 54 | IVS16 + 10 G > A | | Intron 16 | REJ | 1/164 | N. |
| 55 | R2359R | 7289G > C | Exon 17 | REJ | 3/164 | N. |
| 56 | L2389L(H) | 7376T > C | Exon 17 | REJ | 46/164 | 1, 2, 8, 9 |
| 57 | G2425G | 7486G > T | Exon 18 | REJ | 1/164 | N. |
| 58 | L2481L(H) | 7652C > T | Exon 18 | REJ | 39/164 | 1, 8 |
| 59 | IVS19 + 24 C > A | | Intron 19 | REJ | 2/164 | N. |
| 60 | L2570L(H) | 7919T > C | Exon 20 | REJ | 31/164 | 1, 9 |
| 61 | IVS20 + C > A | | Intron20 | REJ | 1/164 | N. |

TABLE 9-continued

Polymorphisms Identified. See Full Reference List for mutation references.

| ID# | Designation | cDNA Change(s) | Location | Domain | Frequency | Ref. |
|---|---|---|---|---|---|---|
| 62 | ISV20 − 16C > G | | Intron20 | REJ | 2/164 | N. |
| 63 | T2708M | 8334C > T | Exon 22 | REJ | 1/164 | 3, 8 |
| 64 | IVS22 + 8G > A (H) | | Intron 22 | REJ | 1/164 | 1, 8 |
| 65 | S2729S | 8398G > A | Exon 23 | REJ | 2/164 | N. |
| 66 | A2749A | 8458G > A | Exon 23 | REJ | 1/164 | N. |
| 67 | S2766S | 8509C > T | Exon 23 | REJ | 1/164 | 13 |
| 68 | D2789D | 8578C > T | Exon 23 | REJ | 2/164 | N. |
| 69 | S2813S | 8650C > T | Exon 23 | REJ | 2/164 | 3, 8, 24 |
| 70 | S2893S | 8890C > G | Exon 23 | | 2/164 | 3 |
| 71 | A2971A(H) | 9124T > C | Exon 24 | | 2/164 | N. |
| 72 | IVS24 − 20G > A (H) | | Intron 24 | | 3/164 | N. |
| 73 | IVS24 − 17A > G(H) | | Intron 24 | | 6/164 | N. |
| 74 | IVS24 + 17A > G | | Intron 24 | | 32/164 | N. |
| 75 | S3007S | 9232C > T | Exon 25 | | 1/164 | N. |
| 76 | V3065V(H) | 9406G > C | Exon 25 | | 38/164 | 24 |
| 77 | V3090V | 9481C > T | Exon 26 | TM1 | 3/164 | N. |
| 78 | P3110P(H) | 9543T > C | Exon 26 | | 37/164 | 6 |
| 79 | IVS26 + 76C > A | | Intron26 | | 1/164 | N. |
| 80 | IVS27 − 13T > C(H) | | Intron27 | | 15/164 | 8 |
| 81 | T3223T | 9880G > A | Exon 28 | PLAT | 2/164 | 6, 3, 8 |
| 82 | S3265S | 10006C > T | Exon 29 | | 1/164 | N. |
| 83 | IVS29 − 4 C > T | | Intron29 | | 1/164 | N. |
| 84 | A3455A | 10576C > T | Exon 34 | | 1/164 | N. |
| 85 | L3589L | 10976C > T | Exon 36 | TM5 | 5/164 | N. |
| 86 | IVS37 − 4C > T | | Intron 37 | | 1/164 | N. |
| 87 | IVS38 + 11G > A | | Intron 38 | | 4/164 | N. |
| 88 | R3752R | 11385C > A | Exon 39 | Polycystin motif | 1/164 | N. |
| 89 | L3753L | 11465G > C | Exon 39 | Polycystin motif | 1/164 | N. |
| 90 | IVS39 − 25del72bp | | Intron 39 | | 1/164 | 7, 3 |
| 91 | IVS41 + C > T | | Intron 41 | | 1/164 | N. |
| 92 | IVS41 + 5insGGG | | Intron 41 | | 2/164 | 8 |
| 93 | IVS41 − 11C > T | C > T | Intron 41 | | 2/164 | N. |
| 94 | S3893S(H) | 11890C > T | Exon 42 | | 3/164 | 8 |
| 95 | IVS43 + 42C > A | | Intron 43 | | 6/164 | N. |
| 96 | R3971R | 12124C > T | Exon 43 | | 3/164 | N. |
| 97 | L4025L | 12286C > T | Exon 44 | | 1/164 | N. |
| 98 | L4035L | 12316C > T | Exon 44 | TM10 | 1/164 | N. |
| 99 | IVS44 + 22delG | | Intron44 | | 4/164 | N. |
| 100 | L4089L | 12478C > G | Exon 45 | TM11 | 1/164 | N. |
| 101 | A4091A(H) | 12484A > G | Exon 45 | TM11 | 43/164 | 8, 3, 17, 18, 7 |
| 102 | L4136L(H) | 12617C > T | Exon 45 | | 13/164 | 8, 14 |
| 103 | V4152V | 12667C > T | Exon 46 | | 2/164 | N. |
| 104 | P4161P | 12696C > A | Exon 46 | | 1/164 | N. |
| 105 | S4189S | 12778C > T | Exon 46 | | 1/164 | 6 |
| 106 | P4209P(H) | 12838T > C | Exon 46 | | 40/164 | 8, 6, 3 |
| 107 | L4221L | 12874C > T | Exon 46 | COILED COIL | 1/164 | N. |
| 108 | A4255A | 12978C > T | Exon 46 | | 1/164 | N. |
| 109 | | 13135G > A | 3'UTR | | 2/164 | 8 |
| PKD2 Polymorphisms. | | | | | | |
| — | R28P(H) | 149C > T | Exon 1 | | 50/164 | 8, 10, 22 |
| 110 | R60R | 246G > A | Exon 1 | | 1/164 | N. |
| 111 | G140G(H) | 486G > A | Exon 1 | | 22/164 | N. |
| 112 | IVS6 − 4C > T | | Intron 6 | | 1/164 | N. |
| 113 | L539L | 1683G > C | Exon 7 | | 1/164 | N. |

FULL REFERENCE LIST

1. Watnick T, Phakdeekitcharoen B, Johnson A, et al. Mutation detection of PKD1 identifies a novel mutation common to three families with aneurysms and/or very-early-onset disease. *Am J Hum Genet* 65(6):1561-71, 1999.
2. Phakdeekitcharoen B, Watnick T J, Ahn C, et al. Thirteen novel mutations of the replicated region of PKD1 in an Asian population. *Kidney Int* 58(4):1400-12, 2000.
3. Rossetti S, Strmecki L, Gamble V, et al. Mutation analysis of the entire PKD1 gene: genetic and diagnostic implications. *Am J Hum Genet.* 68(1):46-63, 2001.
4. Peral B, Gamble V, Strong C, et al. Identification of mutations in the duplicated region of the polycystic kidney disease 1 gene (PKD1) by a novel approach. *Am J Hum Genet.* 60(6):1399-410, 1997.
5. Veldhuisen B, Saris J J, de Haij S, et al. A spectrum of mutations in the second gene for autosomal dominant polycystic kidney disease (PKD2). *Am J Hum Genet.* 61(3): 547-55, 1997.
6. Peral B, Ong A C, San Millan J L, et al. A stable, nonsense mutation associated with a case of infantile onset polycystic kidney disease 1 (PKD1). *Hum Mol Genet.* 5(4):539-42, 1996.
7. Peral B, San Millan J L, Ong A, et al. Screening the 3' region of the polycystic kidney disease 1 (PKD1) gene reveals six novel mutations. *Am J Hum Genet.* 58(1):86-96, 1996.
8. Rossetti S, Chauveau D, Walker D, et al. A complete mutation screen of the ADPKD genes by DHPLC. *Kidney Int* 61, 1588-1599, 2002.

9. Thomas R, McConnell R, Whittacker J, et al. Identification of mutations in the repeated part of the autosomal dominant polycystic kidney disease type 1 gene, PKD1, by long-range PCR. *Am J Hum Genet.* 65(1):39-49, 1999.
10. Rossetti S, Bresin E, Restagno G, et al. Autosomal dominant polycystic kidney disease (ADPKD) in an Italian family carrying a novel nonsense mutation and two missense changes in exons 44 and 45 of the PKD1 Gene. *Am J Med Genet.* 16; 65(2):155-9, 1996.
11. Reiterova J, Stekrova J, Peters D J, et al. Four novel mutations of the PKD2 gene in Czech families with autosomal dominant polycystic kidney disease. *Hum Mutat* 19(5):573, 2002.
12. Hanaoka K, Qian F, Boletta A, et al. Co-assembly of polycystin-1 and -2 produces unique cation-permeable currents. *Nature* 408, 990-994, 2000.
13. Inoue S, Inoue K, Utsunomiya M, et al. Mutation analysis in PKD1 of Japanese autosomal dominant polycystic kidney disease patients. *Hum Mutat* 19(6):622-8, 2002.
14. Perrichot R A, Mercier B, Simon P M, et al. DGGE screening of PKD1 gene reveals novel mutations in a large cohort of 146 unrelated patients. *Hum Genet.* 105(3):231-9, 1999.
15. Bogdanova N, McCluskey M, Sikmann K, et al. Screening the 3' region of the polycystic kidney disease 1 (PKD1) gene in 41 Bulgarian and Australian kindreds reveals a prevalence of protein truncating mutations. *Hum Mutat* 16(2):166-74, 2000.
16. Watnick T J, Torres V E, Gandolph M A, et al. Somatic mutation in individual liver cysts supports a two-hit model of cystogenesis in autosomal dominant polycystic kidney disease. *Mol Cell* 2(2):247-51, 1998.
17. Perrichot R, Mercier B, Quere I, et al. Novel mutations in the duplicated region of PKD1 gene. *Eur J Hum Genet.* 8(5):353-9, 2000.
18. Boletta, A., Qian, F., Onuchic, L. F., et al. Polycystin-1, the gene product of PKD1, induces resistance to apoptosis and spontaneous tubulogenesis in MDCK cells. *Mol. Cell.* 6, 1267-1273, 2000.
19. Aguiari G, Savelli S, Garbo M, et al. Novel splicing and missense mutations in autosomal dominant polycystic kidney disease 1 (PKD1) gene: expression of mutated genes. *Hum Mutat* 16(5):444-5, 2000.
20. Bycroft M, Bateman A, Clarke J, et al. The structure of a PKD domain from polycystin-1: implications for polycystic kidney disease. *EMBO J.* 15; 18(2):297-305, 1999.
21. Torra R, Viribay M, Telleria D, et al. Seven novel mutations of the PKD2 gene in families with autosomal dominant polycystic kidney disease. *Kidney Int* 56(1):28-33, 1999.
22. Rossetti S, Chauveau D, Kubly V, et al. Association of mutation position in polycystic kidney disease 1 (PKD1) gene and development of a vascular phenotype. *Lancet* 28; 361(9376):2196-201, 2003.
23. Afzal A R, Florencio R N, Taylor R, et al. Novel mutations in the duplicated region of the polycystic kidney disease 1 (PKD1) gene provides supporting evidence for gene conversion. *Genet.* 4(4):365-70, 2000.
24. Roelfsema J H, Spruit L, Saris J J, et al. Mutation detection in the repeated part of the PKD1 gene. *Am J Hum Genet.* 61(5):1044-52, 1997.
25. Bogdanova N, McCluskey M, Sikmann K, et al. Screening the 3' region of the polycystic kidney disease 1 (PKD1) gene in 41 Bulgarian and Australian kindreds reveals a prevalence of protein truncating mutations. *Hum Mutat* 16(2):166-74, 2000.
26. Qian F, Boletta A, Bhunia A K, Xu H, et al. Cleavage of polycystin-1 requires the receptor for egg jelly domain and is disrupted by human autosomal-dominant polycystic kidney disease 1-associated mutations. *Proc Natl Acad Sci USA* 24; 99(26):16981-6, 2002.
27. Gabow P A. Autosomal dominant polycystic kidney disease. *N Engl J Med* 29; 329(5):332-42, 1993.

SEQUENCE LISTING

```
<160> NUMBER OF SEQ ID NOS: 23

<210> SEQ ID NO 1
<211> LENGTH: 14136
<212> TYPE: DNA
<213> ORGANISM: Homo sapiens

<400> SEQUENCE: 1
gcactgcagc gccagcgtcc gagcgggcgg ccgagctccc ggagcggcct ggccccgagc      60
cccgagcggg cgtcgctcag cagcaggtcg cggccgcgca gccccatcca gccccgcgcc     120
cgccatgccg tccgcgggcc ccgcctgagc tgcggtctcc gcgcgcgggc gggcctgggg     180
acggcggggc catgcgcgcg ctgccctaac gatgccgccc gccgcgcccg cccgcctggc     240
gctggccctg ggcctgggcc tgtggctcgg ggcgctggcg ggggccccg ggcgcggctg      300 cgggccctgc gagccccct gcctctgcgg cccagcgccc ggcgccgcct gccgcgtcaa      360
ctgctcgggc cgcgggctgc ggacgctcgg tcccgcgctg cgcatccccg cggacgccac      420
agcgctagac gtctcccaca acctgctccg ggcgctggac gttgggctcc tggcgaacct      480
ctcggcgctg gcagagctgg atataagcaa caacaagatt tctacgttag aagaaggaat      540
atttgctaat ttatttaatt taagtgaaat aaacctgagt gggaacccgt ttgagtgtga      600
ctgtggcctg gcgtggctgc cgcgatgggc ggaggagcag caggtgcggg tggtgcagcc      660
```

-continued

```
cgaggcagcc acgtgtgctg ggcctggctc cctggctggc cagcctctgc ttggcatccc      720
cttgctggac agtggctgtg gtgaggagta tgtcgcctgc ctccctgaca acagctcagg      780
caccgtggca gcagtgtcct tttcagctgc ccacgaaggc ctgcttcagc cagaggcctg      840
cagcgccttc tgcttctcca ccggccaggg cctcgcagcc ctctcggagc agggctggtg      900
cctgtgtggg gcggcccagc cctccagtgc ctcctttgcc tgcctgtccc tctgctccgg      960 cccccccgcca cctcctgccc ccacctgtag ggccccacc ctcctccagc acgtcttccc     1020
tgcctcccca ggggccaccc tggtggggcc ccacggacct ctggcctctg ccagctagc      1080 agccttccac atcgctgccc cgctcccgt cactgccaca cgctgggact tcggagacgg      1140
ctccgccgag gtggatgccg ctgggccggc tgcctcgcat cgctatgtgc tgcctgggcg      1200
ctatcacgtg acggccgtgc tggccctggg ggccggctca gccctgctgg ggacagacgt      1260
gcaggtggaa gcggcacctg ccgccctgga gctcgtgtgc ccgtcctcgg tgcagagtga      1320
cgagagcctt gacctcagca tccagaaccg cggtggttca ggcctggagg ccgcctacag      1380
catcgtggcc ctgggcgagg agccggcccg agcggtgcac ccgctctgcc cctcggacac      1440
ggagatcttc cctggcaacg ggcactgcta ccgcctggtg gtggagaagg cggcctggct      1500
gcaggcgcag gagcagtgtc aggcctgggc cggggccgcc ctggcaatgg tggacagtcc      1560
cgccgtgcag cgcttcctgg tctcccgggt caccaggagc ctagacgtgt ggatcggctt      1620
ctcgactgtg caggggggtgg aggtgggccc agcgccgcag ggcgaggcct tcagcctgga      1680
gagctgccag aactggctgc cggggagcc acacccagcc acagccgagc actgcgtccg      1740
gctcgggccc accgggtggt gtaacaccga cctgtgctca cgccgcaca gctacgtctg      1800 cgagctgcag cccggaggcc cagtgcagga tgccgagaac ctcctcgtgg gagcgcccag      1860
tggggacctg cagggacccc tgacgcctct ggcacagcag gacggcctct cagcccgca      1920 cgagcccgtg gaggtcatgg tattcccggg cctgcgtctg agccgtgaag ccttcctcac      1980
cacggccgaa tttgggaccc aggagctccg gcggcccgcc cagctgcggc tgcaggtgta      2040
ccggctcctc agcacagcag ggaccccgga gaacggcagc gagcctgaga gcaggtcccc      2100
ggacaacagg acccagctgg ccccccgcgtg catgccaggg ggacgctggt gccctggagc      2160
caacatctgc ttgccgctgg acgcctcttg ccaccccag gcctgcgcca atggctgcac      2220
gtcagggcca gggctacccg ggccccccta tgcgctatgg agagagttcc tcttctccgt      2280
tgccgcgggg cccccgcgc agtactcggt caccctccac ggccaggatg tcctcatgct      2340
ccctggtgac ctcgttggct tgcagcacga cgctggccct ggcgccctcc tgcactgctc      2400
gccggctccc ggccacccctg gtccccaggc cccgtacctc tccgccaacg cctcgtcatg      2460
gctgccccac ttgccagccc agctggaggg cacttgggcc tgccctgcct gtgccctgcg      2520
gctgcttgca gccacggaac agctccaccgt gctgctgggc ttgaggccca accctggact      2580
gcggatgcct gggcgctatg aggtccgggc agaggtgggc aatggcgtgt ccaggcacaa      2640
cctctcctgc agctttgacg tggtctcccc agtggctggg ctgcgggtca tctaccctgc      2700
cccccgcgac ggccgcctct acgtgcccac caacggctca gccttggtgc tccaggtgga      2760
ctctggtgcc aacgccacgg ccacggcctcg ctggcctggg gcagtgtca cgcccgctt      2820 tgagaatgtc tgccctgccc tggtggccac cttcgtgccc ggctgccct gggagaccaa      2880 cgataccctg ttctcagtgg tagcactgcc gtggctcagt gagggggagc acgtggtgga      2940
cgtggtggtg gaaaacagcg ccagccgggc caacctcagc ctgcgggtga cggcggagga      3000
gcccatctgt ggcctccgcg ccacgcccag ccccgaggcc cgtgtactgc agggagtcct      3060
```

```
agtgaggtac agccccgtgg tggaggccgg ctcggacatg gtcttccggt ggaccatcaa    3120
cgacaagcag tccctgacct tccagaacgt ggtcttcaat gtcatttatc agagcgcggc    3180
ggtcttcaag ctctcactga cggcctccaa ccacgtgagc aacgtcaccg tgaactacaa    3240
cgtaaccgtg gagcggatga acaggatgca gggtctgcag gtctccacag tgccggccgt    3300
gctgtccccc aatgccacgc tagcactgac ggcgggcgtg ctggtggact cggccgtgga    3360
ggtggccttc ctgtggaact ttggggatgg ggagcaggcc ctccaccagt tccagcctcc    3420
gtacaacgag tccttcccgg ttccagaccc ctcggtggcc caggtgctgg tggagcacaa    3480
tgtcatgcac acctacgctg ccccaggtga gtacctcctg accgtgctgg catctaatgc    3540
cttcgagaac ctgacgcagc aggtgcctgt gagcgtgcgc gcctccctgc cctccgtggc    3600
tgtgggtgtg agtgacggcg tcctggtggc cggccggccc gtcaccttct acccgcaccc    3660
gctgccctcg cctggggggtg ttctttacac gtgggacttc ggggacggct cccctgtcct    3720
gacccagagc cagccggctg ccaaccacac ctatgcctcg aggggcacct accacgtgcg    3780
cctggaggtc aacaacacgg tgagcggtgc ggcggcccag gcggatgtgc gcgtctttga    3840
ggagctccgc ggactcagcg tggacatgag cctggccgtg gagcagggcg ccccgtggt    3900 ggtcagcgcc gcggtgcaga cgggcgacaa catcacgtgg accttcgaca tggggacgg    3960 caccgtgctg tcgggcccgg aggcaacagt ggagcatgtg tacctgcggg cacagaactg    4020
cacagtgacc gtgggtgcgg ccagccccgc cggccacctg gcccggagcc tgcacgtgct    4080
ggtcttcgtc ctggaggtgc tgcgcgttga accgccgcc tgcatcccca cgcagcctga    4140
cgcgcggctc acggcctacg tcaccgggaa cccggcccac tacctcttcg actggacctt    4200
cggggatggc tcctccaaca cgaccgtgcg ggggtgcccg acggtgacac acaacttcac    4260
gcggagcggc acgttccccc tggcgctggt gctgtccagc cgcgtgaaca gggcgcatta    4320
cttcaccagc atctgcgtgg agccagaggt gggcaacgtc accctgcagc cagagaggca    4380
gtttgtgcag ctcggggacg aggcctggct ggtggcatgt gcctggcccc gttcccta    4440 ccgctacacc tgggactttg gcaccgagga agccgcccc acccgtgcca ggggccctga    4500
ggtgacgttc atctaccgag acccaggctc ctatcttgtg acagtcaccg cgtccaacaa    4560
catctctgct gccaatgact cagccctggt ggaggtgcag gagcccgtgc tggtcaccag    4620
catcaaggtc aatggctccc ttgggctgga gctgcagcag ccgtacctgt tctctgctgt    4680
gggccgtggg cgccccgcca gctacctgtg ggatctgggg gacggtgggt ggctcgaggg    4740
tccgagagtc acccacgctt acaacagcac aggtgacttc accgttaggg tggccggctg    4800
gaatgaggtg agccgcagcg aggcctggct caatgtgacg gtgaagcggc gcgtgcgggg    4860
gctcgtcgtc aatgcaagcc gcacggtggt gcccctgaat gggagcgtga gcttcagcac    4920
gtcgctggag gccggcagtg atgtgcgcta ttcctgggtg ctctgtgacc gctgcacgcc    4980
catccctggg ggtcctacca tctcttacac cttccgctcc gtgggcacct tcaatatcat    5040
cgtcacggct gagaacgagg tgggctccgc ccaggacagc atcttcgtct atgtcctgca    5100
gctcatagag gggctgcagg tggtgggcgg tggccgctac ttccccacca accacacggt    5160
acagctgcag gccgtggtta gggatggcac caacgtctcc tacagctgga ctgcctggag    5220
ggacaggggc ccggccctgg ccggcagcgg caaaggcttc tcgctcaccg tgctcgaggc    5280
cggcacctac catgtgcagc tgcgggccac caacatgctg ggcagcgcct gggcgactg    5340 caccatggac ttcgtggagc ctgtggggtg gctgatggtg accgcctccc cgaacccagc    5400
```

-continued

```
tgccgtcaac acaagcgtca ccctcagtgc cgagctggct ggtggcagtg gtgtcgtata    5460
cacttggtcc ttggaggagg ggctgagctg ggagacctcc gagccattta ccacccatag    5520
cttccccaca cccggcctgc acttggtcac catgacggca gggaacccgc tgggctcagc    5580
caacgccacc gtggaagtgg atgtgcaggt gcctgtgagt ggcctcagca tcagggccag    5640
cgagcccgga ggcagcttcg tgcggccgg gtcctctgtg cccttttggg ggcagctggc    5700
cacgggcacc aatgtgagct ggtgctgggc tgtgcccggc ggcagcagca agcgtggccc    5760
tcatgtcacc atggtcttcc cggatgctgg caccttctcc atccggctca atgcctccaa    5820
cgcagtcagc tgggtctcag ccacgtacaa cctcacggcg gaggagccca tcgtgggcct    5880
ggtgctgtgg gccagcagca aggtggtggc gcccgggcag ctggtccatt ttcagatcct    5940
gctggctgcc ggctcagctg tcaccttccg cctgcaggtc ggcggggcca accccgaggt    6000
gctccccggg ccccgtttct cccacagctt ccccgcgtc ggagaccacg tggtgagcgt    6060
gcggggcaaa aaccacgtga gctgggccca ggcgcaggtg cgcatcgtgg tgctggaggc    6120
cgtgagtggg ctgcagatgc ccaactgctg cgagcctggc atcgccacgg gcactgagag    6180
gaacttcaca gcccgcgtgc agcgcggctc tcgggtcgcc tacgcctggt acttctcgct    6240
gcagaaggtc cagggcgact cgctggtcat cctgtcgggc cgcgacgtca cctacacgcc    6300
cgtggccgcg ggctgttgg agatccaggt gcgcgccttc aacgccctgg gcagtgagaa    6360
ccgcacgctg gtgctggagg ttcaggacgc cgtccagtat gtgggccctgc agagcggccc    6420 ctgcttcacc aaccgctcgg cgcagtttga ggccgccacc agcccagcc cccggcgtgt    6480 ggcctaccac tgggactttg gggatgggtc gccagggcag gacacagatg agcccagggc    6540
cgagcactcc tacctgaggc ctggggacta ccgcgtgcag gtgaacgcct ccaacctggt    6600
gagcttcttc gtgcgcagg ccacggtgac cgtccaggtg ctggcctgcc gggagccgga    6660
ggtggacgtg gtcctgcccc tgcaggtgct gatgcggcga tcacagcgca actacttgga    6720
ggcccacgtt gacctgcgcg actgcgtcac ctaccagact gagtaccgct gggaggtgta    6780
tcgcaccgcc agctgccagc ggccggggcg cccagcgcgt gtggccctgc ccggcgtgga    6840
cgtgagccgg cctcggctgg tgctgccgcg gctggcgctg cctgtggggc actactgctt    6900
tgtgtttgtc gtgtcatttg gggacacgcc actgacacag agcatccagg ccaatgtgac    6960
ggtggccccc gagcgcctgg tgcccatcat tgagggtggc tcataccgcg tgtggtcaga    7020
cacacgggac ctggtgctgg atgggagcga gtcctacgac cccaacctgg aggacggcga    7080
ccagacgccg ctcagtttcc actgggcctg tgtggcttcg acacagaggg aggctggcgg    7140
gtgtgcgctg aactttgggc cccgcgggag cagcacggtc accattccac gggagcggct    7200
ggcggctggc gtgagtaca ccttcagcct gaccgtgtgg aaggccggcc gcaaggagga    7260
ggccaccaac cagacggtgc tgatccggag tggccgggtg cccattgtgt ccttggagtg    7320
tgtgtcctgc aaggcacagg ccgtgtacga agtgagccgc agctcctacg tgtacttgga    7380
gggccgctgc ctcaattgca gcagcggctc caagcgaggg cggtgggctg cacgtacgtt    7440
cagcaacaag acgctggtgc tggatgagac caccacatcc acgggcagtg caggcatgcg    7500
actggtgctg cggcggggcg tgctgcggga cggcgaggga tacaccttca cgctcacggt    7560
gctgggccgc tctggcgagg aggagggctg cgcctccatc cgcctgtccc caaccgccc    7620 gccgctgggg ggctcttgcc gcctcttccc actgggcgct gtgcacgccc tcaccaccaa    7680
ggtgcacttc gaatgcacgg gctggcatga cgcgaggat gctggcgccc cgctggtgta    7740
cgccctgctg ctgcggcgct gtcgccaggg ccactgcgag gagttctgtg tctacaaggg    7800
```

```
cagcctctcc agctacggag ccgtgctgcc cccgggtttc aggccacact tcgaggtggg    7860
cctggccgtg gtggtgcagg accagctggg agccgctgtg gtcgccctca acaggtcttt    7920
ggccatcacc ctcccagagc ccaacggcag cgcaacgggg ctcacagtct ggctgcacgg    7980
gctcaccgct agtgtgctcc cagggctgct gcggcaggcc gatccccagc acgtcatcga    8040
gtactcgttg gccctggtca ccgtgctgaa cgagtacgag cgggccctgg acgtggcggc    8100
agagcccaag cacgagcggc agcaccgagc ccagatacgc aagaacatca cggagactct    8160
ggtgtccctg agggtccaca ctgtggatga catccagcag atcgctgctg cgctggccca    8220
gtgcatgggg cccagcaggg agctcgtatg ccgctcgtgc ctgaagcaga cgctgcacaa    8280
gctggaggcc atgatgctca tcctgcaggc agagaccacc gcgggcaccg tgacgcccac    8340
cgccatcgga gacagcatcc tcaacatcac aggagacctc atccacctgg ccagctcgga    8400
cgtgcgggca ccacagccct cagagctggg agccgagtca ccatctcgga tggtggcgtc    8460
ccaggcctac aacctgacct ctgccctcat gcgcatcctc atgcgctccc gcgtgctcaa    8520
cgaggagccc ctgacgctgg cgggcgagga gatcgtggcc cagggcaagc gctcggaccc    8580
gcggagcctg ctgtgctatg gcggcgcccc agggcctggc tgccacttct ccatccccga    8640
ggctttcagc ggggccctgg ccaacctcag tgacgtggtg cagctcatct ttctggtgga    8700
ctccaatccc tttcccttg gctatatcag caactacacc gtctccacca aggtggcctc    8760
gatggcattc cagacacagg ccggcgccca gatccccatc gagcggctgg cctcagagcg    8820
cgccatcacc gtgaaggtgc ccaacaactc ggactgggct gccgggggcc accgcagctc    8880
cgccaactcc gccaactccg ttgtggtcca gccccaggcc tccgtcggtg ctgtggtcac    8940
cctggacagc agcaacctg cggcggggct gcatctgcag ctcaactata cgctgctgga    9000
cggccactac ctgtctgagg aacctgagcc ctacctggca gtctacctac actcggagcc    9060
ccggcccaat gagcacaact gctcggctag caggaggatc cgcccagagt cactccaggg    9120
tgctgaccac cggccctaca ccttcttcat ttccccgggg agcagagacc cagcggggag    9180
ttaccatctg aacctctcca gccacttccg ctggtcggcg ctgcaggtgt ccgtgggcct    9240
gtacacgtcc ctgtgccagt acttcagcga ggaggacatg gtgtggcgga cagaggggct    9300
gctgcccctg gaggagacct cgccccgcca ggccgtctgc ctcacccgcc acctcaccgc    9360
cttcggcgcc agcctcttcg tgcccccaag ccatgtccgc tttgtgtttc ctgagccgac    9420
agcggatgta aactacatcg tcatgctgac atgtgctgtg tgcctggtga cctacatggt    9480 catgccgcc atcctgcaca agctggacca gttggatgcc agccggggcc gcgccatccc    9540
tttctgtggg cagcggggcc gcttcaagta cgagatcctc gtcaagacag gctggggccg    9600
gggctcaggt accacggccc acgtgggcat catgctgtat ggggtggaca gccggagcgg    9660
ccaccggcac ctggacggcg acagagcctt ccaccgcaac agcctggaca tcttccggat    9720
cgccaccccg cacagcctgg gtagcgtgtg gaagatccga gtgtggcacg acaacaaagg    9780
gctcagccct gcctggttcc tgcagcacgt catcgtcagg gacctgcaga cggcacgcag    9840
cgccttcttc ctggtcaatg actggctttc ggtggagacg gaggccaacg ggggcctggt    9900
ggagaaggag gtgctggccg cgagcgacgc agccctttg cgcttccggc gctgctggt    9960 ggctgagctg cagcgtggct tctttgacaa gcacatctgg ctctccatat gggaccggcc    10020
gcctcgtagc cgtttcactc gcatccagag ggccacctgc tgcgttctcc tcatctgcct    10080
cttcctgggc gccaacgccg tgtggtacgg ggctgttggc gactctgcct acagcacggg    10140
```

```
gcatgtgtcc aggctgagcc cgctgagcgt cgacacagtc gctgttggcc tggtgtccag   10200
cgtggttgtc tatcccgtct acctggccat ccttttctc ttccggatgt cccggagcaa   10260
ggtggctggg agcccgagcc ccacacctgc cgggcagcag gtgctggaca tcgacagctg   10320
cctggactcg tccgtgctgg acagctcctt cctcacgttc tcaggcctcc acgctgaggc   10380
ctttgttgga cagatgaaga gtgacttgtt tctggatgat tctaagagtc tggtgtgctg   10440
gccctccggc gagggaacgc tcagttggcc ggacctgctc agtgacccgt ccattgtggg   10500
tagcaatctg cggcagctgg cacggggcca ggcgggccat gggctgggcc cagaggagga   10560
cggcttctcc ctggccagcc cctactcgcc tgccaaatcc ttctcagcat cagatgaaga   10620
cctgatccag caggtccttg ccgagggggt cagcagccca gcccctaccc aagacaccca   10680 catgaaacg gacctgctca gcagcctgtc cagcactcct ggggagaaga cagagacgct   10740
ggcgctgcag aggctggggg agctggggcc acccagccca ggcctgaact gggaacagcc   10800
ccaggcagcg aggctgtcca ggacaggact ggtggagggt ctgcggaagc gcctgctgcc   10860
ggcctggtgt gcctccctgg cccacgggct cagcctgctc ctggtggctg tggctgtggc   10920
tgtctcaggg tgggtgggtg cgagcttccc cccgggcgtg agtgttgcgt ggctcctgtc   10980
cagcagcgcc agcttcctgg cctcattcct cggctgggag ccactgaagg tcttgctgga   11040
agccctgtac ttctcactgg tggccaagcg gctgcacccg gatgaagatg acaccctggt   11100
agagagcccg gctgtgacgc ctgtgagcgc acgtgtgccc cgcgtacggc caccccacgg   11160
ctttgcactc ttcctggcca aggaagaagc ccgcaaggtc aagaggctac atggcatgct   11220
gcggagcctc ctggtgtaca tgcttttct gctggtgacc ctgctggcca gctatgggga   11280
tgcctcatgc catgggcacg cctaccgtct gcaaagcgcc atcaagcagg agctgcacag   11340
ccgggccttc ctgccatca cgcggtctga ggagctctgg ccatggatgg cccacgtgct   11400
gctgccctac gtccacggga accagtccag cccagagctg ggccccacg gctgcggca   11460 ggtgcggctg caggaagcac tctacccaga ccctcccggc cccagggtcc acacgtgctc   11520
ggccgcagga ggcttcagca ccagcgatta cgacgttggc tgggagagtc ctcacaatgg   11580
ctcggggacg tgggcctatt cagcgccgga tctgctgggg gcatggtcct ggggctcctg   11640
tgccgtgtat gacagcgggg gctacgtgca ggagctgggc ctgagcctgg aggagagccg   11700
cgaccggctg cgcttcctgc agctgcacaa ctggctggac aacaggagcc gcgctgtgtt   11760
cctggagctc acgcgctaca gcccggccgt ggggctgcac gccgccgtca cgctgcgcct   11820
cgagttcccg gcggccggcc gcgccctggc cgccctcagc gtccgcccct ttgcgctgcg   11880
ccgcctcagc gcgggcctct cgctgcctct gctcacctcg gtgtgcctgc tgctgttcgc   11940
cgtgcacttc gccgtggccg aggcccgtac ttggcacagg gaagggcgct ggcgcgtgct   12000
gcggctcgga gctgggcgc ggtggctgct ggtggcgctg acggcggcca cggcactggt   12060
acgcctcgcc cagctgggtg ccgctgaccg ccagtggacc cgtttcgtgc gcggccgccc   12120
gcgccgcttc actagcttcg accaggtggc gcagctgagc tccgcagccc gtggcctggc   12180
ggcctcgctg ctcttcctgc ttttggtcaa ggctgcccag cagctacgct tcgtgcgcca   12240
gtggtccgtc tttggcaaga cattatgccg agctctgcca gagctcctgg gggtcacctt   12300
gggcctggtg gtgctcgggg tagcctacgc ccagctggcc atcctgctcg tgtcttcctg   12360
tgtggactcc ctctggagcg tggcccaggc cctgttggtg ctgtgccctg ggactgggct   12420
ctctaccctg tgtcctgccg agtcctgcca cctgtcaccc ctgctgtgtg tggggctctg   12480
ggcactgcgg ctgtggggcg ccctacggct gggggctgtt attctccgct ggcgctacca   12540
```

-continued

```
cgccttgcgt ggagagctgt accggccggc ctgggagccc caggactacg agatggtgga   12600
gttgttcctg cgcaggctgc gcctctggat gggcctcagc aaggtcaagg agttccgcca   12660
caaagtccgc tttgaaggga tggagccgct gccctctcgc tcctccaggg gctccaaggt   12720
atccccggat gtgcccccac ccagcgctgg ctccgatgcc tcgcacccct ccacctcctc   12780
cagccagctg gatgggctga gcgtgagcct gggccggctg gggacaaggt gtgagcctga   12840
gccctcccgc ctccaagccg tgttcgaggc cctgctcacc cagtttgacc gactcaacca   12900
ggccacagag gacgtctacc agctggagca gcagctgcac agcctgcaag gccgcaggag   12960
cagccgggcg cccgccggat cttcccgtgg cccatccccg ggcctgcggc cagcactgcc   13020
cagccgcctt gcccgggcca gtcggggtgt ggacctggcc actggcccca gcaggacacc   13080
ccttcgggcc aagaacaagg tccaccccag cagcacttag tcctccttcc tggcgggggt   13140
gggccgtgga gtcggagtgg acaccgctca gtattacttt ctgccgctgt caaggccgag   13200
ggccaggcag aatggctgca cgtaggttcc ccagagagca ggcagggggca tctgtctgtc   13260
tgtgggcttc agcactttaa agaggctgtg tggccaacca ggacccaggg tcccctcccc   13320
agctcccttg ggaaggacac agcagtattg gacggtttct agcctctgag atgctaattt   13380
atttccccga gtcctcaggt acagcgggct gtgcccggcc ccaccccctg ggcagatgtc   13440
ccccactgct aaggctgctg gcttcaggga gggttagcct gcaccgccgc caccctgccc   13500
ctaagttatt acctctccag ttcctaccgt actccctgca ccgtctcact gtgtgtctcg   13560
tgtcagtaat ttatatggtg ttaaaatgtg tatattttg tatgtcacta ttttcactag   13620
ggctgagggg cctgcgccca gagctggcct ccccaacac ctgctgcgct tggtaggtgt   13680
ggtggcgtta tggcagcccg gctgctgctt ggatgcgagc ttggccttgg gccggtgctg   13740
ggggcacagc tgtctgccag gcactctcat caccccagag gccttgtcat cctcccttgc   13800
cccaggccag gtagcaagag agcagcgccc aggcctgctg gcatcaggtc tgggcaagta   13860
gcaggactag gcatgtcaga ggaccccagg gtggttagag gaaaagactc ctcctggggg   13920
ctggctccca gggtggagga aggtgactgt gtgtgtgtgt gtgtgcgcgc gcgacgcgcg   13980
agtgtgctgt atgcccagg cagcctcaag gccctcggaa ctggctgtgc ctgcttctgt   14040
gtaccacttc tgtgggcatg gccgcttcta gagcctcgac accccccaa ccccccgcacc   14100
aagcagacaa agtcaataaa agagctgtct gactgc                             14136
```

<210> SEQ ID NO 2
<211> LENGTH: 12909
<212> TYPE: DNA
<213> ORGANISM: Homo sapiens

<400> SEQUENCE: 2

```
atgccgcccg ccgcgcccgc ccgcctggcg ctggccctgg gcctgggcct gtggctcggg   60
gcgctggcgg ggggccccgg gcgcggctgc gggccctgcg agcccccctg cctctgcggc   120
ccagcgcccg gcgccgcctg ccgcgtcaac tgctcgggcc gcgggctgcg gacgctcggt   180
cccgcgctgc gcatccccgc ggacgccaca gcgctagacg tctcccacaa cctgctccgg   240
gcgctggacg ttgggctcct ggcgaacctc tcggcgctgg cagagctgga tataagcaac   300
aacaagattt ctacgttaga agaaggaata tttgctaatt tatttaattt aagtgaaata   360
aacctgagtg gaacccgtt tgagtgtgac tgtggcctgg cgtggctgcc gcgatgggcg   420
gaggagcagc aggtgcgggt ggtgcagccc gaggcagcca cgtgtgctgg gcctggctcc   480
```

```
ctggctggcc agcctctgct tggcatcccc ttgctggaca gtggctgtgg tgaggagtat      540
gtcgcctgcc tccctgacaa cagctcaggc accgtggcag cagtgtcctt ttcagctgcc      600
cacgaaggcc tgcttcagcc agaggcctgc agcgccttct gcttctccac cggccagggc      660
ctcgcagccc tctcggagca gggctggtgc ctgtgtgggg cggcccagcc ctccagtgcc      720
tcctttgcct gcctgtccct ctgctccggc ccccgccac ctcctgcccc cacctgtagg       780
ggccccaccc tcctccagca cgtcttccct gcctccccag gggccaccct ggtgggccc       840 cacggacctc tggcctctgg ccagctagca gccttccaca tcgctgcccc gctccctgtc      900
actgccacac gctgggactt cggagacggc tccgccgagg tggatgccgc tgggccggct      960
gcctcgcatc gctatgtgct gcctgggcgc tatcacgtga cggccgtgct ggccctgggg     1020
gccggctcag ccctgctggg acagacgtg caggtggaag cggcacctgc cgccctggag     1080
ctcgtgtgcc cgtcctcggt gcagagtgac gagagccttg acctcagcat ccagaaccgc     1140
ggtggttcag gcctggaggc cgcctacagc atcgtggccc tgggcgagga gccggcccga     1200
gcggtgcacc cgctctgccc ctcggacacg gagatcttcc ctggcaacgg gcactgctac     1260
cgcctggtgg tggagaaggc ggcctggctg caggcgcagg agcagtgtca ggcctgggcc     1320
ggggccgccc tggcaatggt ggacagtccc gccgtgcagc gcttcctggt ctcccgggtc     1380
accaggagcc tagacgtgtg gatcggcttc tcgactgtgc aggggtgga ggtgggccca      1440 gcgccgcagg gcgaggcctt cagcctggag agctgccaga actggctgcc cggggagcca     1500
cacccagcca cagccgagca ctgcgtccgg ctcgggccca ccgggtggtg taacaccgac     1560
ctgtgctcag cgccgcacag ctacgtctgc gagctgcagc ccgaggcccc agtgcaggat     1620
gccgagaacc tcctcgtggg agcgcccagt ggggacctgc agggacccct gacgcctctg     1680
gcacagcagg acgcctctc agcccgcac gagcccgtgg aggtcatggt attcccgggc      1740
ctgcgtctga gccgtgaagc cttcctcacc acggccgaat ttgggaccca ggagctccgg     1800
cggcccgccc agctgcggct gcaggtgtac cggctcctca gcacagcagg gaccccggag     1860
aacggcagcg agcctgagag caggtccccg gacaacagga cccagctggc ccccgcgtgc     1920
atgccagggg gacgctggtg ccctggagcc aacatctgct gccgctgga cgcctcttgc     1980 cacccccagg cctgcgccaa tggctgcacg tcagggccag ggctacccgg ggcccctat      2040 gcgctatgga gagagttcct cttctccgtt gccgcgggc ccccgcgca gtactcggtc       2100 accctccacg gccaggatgt cctcatgctc cctggtgacc tcgttggctt gcagcacgac     2160
gctggccctg gcgccctcct gcactgctcg ccggctcccg gccaccctgg tccccaggcc     2220
ccgtacctct ccgccaacgc ctcgtcatgg ctgccccact gccagcccca gctggagggc     2280
acttgggcct gccctgcctg tgccctgcgg ctgcttgcag ccacggaaca gctcaccgtg     2340
ctgctgggct tgaggcccaa ccctggactg cggatgcctg ggcgctatga ggtccgggca     2400
gaggtgggca atggcgtgtc caggcacaac ctctcctgca gctttgacgt ggtctcccca     2460
gtggctgggc tgcgggtcat ctaccctgcc ccccgcgacg gccgcctcta cgtgcccacc     2520
aacggctcag ccttggtgct ccaggtggac tctggtgcca acgccacggc cacggctcgc     2580
tggcctgggg gcagtgtcag cgcccgcttt gagaatgtct gccctgccct ggtggccacc     2640
ttcgtgcccg gctgccccctg ggagaccaac gatacccctg tctcagtggt agcactgccg     2700
tggctcagtg agggggagca cgtggtggac gtggtggtgg aaaacagcgc cagccgggcc     2760
aacctcagcc tgcgggtgac ggcggaggag cccatctgtg gcctccgcgc cacgcccagc     2820
cccgaggccc gtgtactgca gggagtccta gtgaggtaca gccccgtggt ggaggccggc     2880
```

```
tcggacatgg tcttccggtg gaccatcaac gacaagcagt ccctgacctt ccagaacgtg    2940
gtcttcaatg tcatttatca gagcgcggcg gtcttcaagc tctcactgac ggcctccaac    3000
cacgtgagca acgtcaccgt gaactacaac gtaaccgtgg agcggatgaa caggatgcag    3060
ggtctgcagg tctccacagt gccggccgtg ctgtccccca atgccacgct agcactgacg    3120
gcgggcgtgc tggtggactc ggccgtggag gtggccttcc tgtggaactt tggggatggg    3180
gagcaggccc tccaccagtt ccagcctccg tacaacgagt ccttcccggt tccagacccc    3240
tcggtggccc aggtgctggt ggagcacaat gtcatgcaca cctacgctgc cccaggtgag    3300
tacctcctga ccgtgctggc atctaatgcc ttcgagaacc tgacgcagca ggtgcctgtg    3360
agcgtgcgcg cctccctgcc ctccgtggct gtgggtgtga gtgacggcgt cctggtggcc    3420
ggccggcccc tcaccttcta cccgcacccg ctgccctcgc tgggggtgt tctttacacg    3480 tgggacttcg gggacggctc ccctgtcctg acccagagcc agccggctgc caaccacacc    3540
tatgcctcga ggggcaccta ccacgtgcgc ctggaggtca caacacggt gagcggtgcg    3600 gcggcccagg cggatgtgcg cgtctttgag gagctccgcg gactcagcgt ggacatgagc    3660
ctggccgtgg agcagggcgc ccccgtggtg gtcagcgccg cggtgcagac gggcgacaac    3720
atcacgtgga ccttcgacat gggggacggc accgtgctgt cgggcccgga ggcaacagtg    3780
gagcatgtgt acctgcgggc acagaactgc acagtgaccg tgggtgcggc cagccccgcc    3840
ggccacctgg cccggagcct gcacgtgctg gtcttcgtcc tggaggtgct gcgcgttgaa    3900
cccgccgcct gcatccccac gcagcctgac gcgcggctca cggcctacgt caccgggaac    3960
ccggcccact acctcttcga ctggaccttc ggggatggct cctccaacac gaccgtgcgg    4020
gggtgcccga cggtgacaca caacttcacg cggagcggca cgttcccccct ggcgctggtg    4080 ctgtccagcc gcgtgaacag ggcgcattac ttcaccagca tctgcgtgga gccagaggtg    4140
ggcaacgtca ccctgcagcc agagaggcag tttgtgcagc tcggggacga ggcctggctg    4200
gtggcatgtg cctggccccc gttcccctac cgctacacct gggactttgg caccgaggaa    4260
gccgccccca cccgtgccag gggccctgag gtgacgttca tctaccgaga cccaggctcc    4320
tatcttgtga cagtcaccgc gtccaacaac atctctgctg ccaatgactc agccctggtg    4380
gaggtgcagg agcccgtgct ggtcaccagc atcaaggtca atggctccct tgggctggag    4440
ctgcagcagc cgtacctgtt ctctgctgtg ggccgtgggc gccccgccag ctacctgtgg    4500
gatctggggg acggtgggtg gctcgagggt ccggaggtca cccacgctta caacagcaca    4560
ggtgacttca ccgttagggt ggccggctgg aatgaggtga gccgcagcga ggcctggctc    4620
aatgtgacgg tgaagcggcg cgtgcggggg ctcgtcgtca atgcaagccg cacggtggtg    4680
cccctgaatg ggagcgtgag cttcagcacg tcgctggagg ccggcagtga tgtgcgctat    4740
tcctgggtgc tctgtgaccg ctgcacgccc atccctgggg tcctaccat ctcttacacc    4800 ttccgctccg tgggcacctt caatatcatc gtcacggctg agaacgaggt gggctccgcc    4860
caggacagca tcttcgtcta tgtcctgcag ctcatagagg ggctgcaggt ggtgggcggt    4920
ggccgctact tccccaccaa ccacacggta cagctgcagg ccgtggttag ggatggcacc    4980
aacgtctcct acagctggac tgcctggagg gacaggggcc cggccctggc cggcagcggc    5040
aaaggcttct cgctcaccgt gctcgaggcc ggcacctacc atgtgcagct gcgggccacc    5100
aacatgctgg gcagcgcctg ggcgactgc accatggact cgtggagcc tgtggggtgg    5160 ctgatggtga ccgcctcccc gaacccagct gccgtcaaca caagcgtcac cctcagtgcc    5220
```

```
gagctggctg gtggcagtgg tgtcgtatac acttggtcct tgaggagggg gctgagctgg    5280
gagacctccg agccatttac cacccatagc ttccccacac ccggcctgca cttggtcacc    5340
atgacggcag ggaacccgct gggctcagcc aacgccaccg tggaagtgga tgtgcaggtg    5400
cctgtgagtg gcctcagcat cagggccagc gagcccggag gcagcttcgt ggcggccggg    5460
tcctctgtgc cctttgggg gcagctggcc acgggcacca atgtgagctg gtgctgggct    5520
gtgcccggcg gcagcagcaa gcgtggccct catgtcacca tggtcttccc ggatgctggc    5580
accttctcca tccggctcaa tgcctccaac gcagtcagct gggtctcagc cacgtacaac    5640
ctcacggcgg aggagcccat cgtgggcctg tgtctgtggg ccagcagcaa ggtggtggcg    5700
cccgggcagc tggtccattt tcagatcctg ctggctgccg gctcagctgt caccttccgc    5760
ctgcaggtcg gcggggccaa ccccgaggtg ctccccgggc cccgtttctc ccacagcttc    5820
ccccgcgtcg agaccacgt ggtgagcgtg cggggcaaaa accacgtgag ctgggcccag    5880
gcgcaggtgc gcatcgtggt gctggaggcc gtgagtgggc tgcagatgcc caactgctgc    5940
gagcctggca tcgccacggg cactgagagg aacttcacag cccgcgtgca gcgcggctct    6000
cgggtcgcct acgcctggta cttctcgctg cagaaggtcc agggcgactc gctggtcatc    6060
ctgtcgggcc gcgacgtcac ctacacgccc gtggccgcgg ggctgttgga gatccaggtg    6120
cgcgccttca acgccctggg cagtgagaac cgcacgctgg tgctggaggt tcaggacgcc    6180
gtccagtatg tggccctgca gagcggcccc tgcttcacca accgctcggc gcagtttgag    6240
gccgccacca gccccagccc cggcgtgtg gcctaccact gggactttgg ggatgggtcg    6300
ccagggcagg acacagatga gcccagggcc gagcactcct acctgaggcc tggggactac    6360
cgcgtgcagg tgaacgcctc caacctggtg agcttcttcg tggcgcaggc cacggtgacc    6420
gtccaggtgc tggcctgccg ggagccggag gtggacgtgg tcctgcccct gcaggtgctg    6480
atgcggcgat cacagcgcaa ctacttggag gcccacgttg acctgcgcga ctgcgtcacc    6540
taccagactg agtaccgctg ggaggtgtat cgcaccgcca gctgccagcg gccggggcgc    6600
ccagcgcgtg tggccctgcc cggcgtggac gtgagccggc ctcggctggt gctgccgcgg    6660
ctggcgctgc ctgtggggca ctactgcttt gtgtttgtcg tgtcatttgg ggacacgcca    6720
ctgacacaga gcatccaggc caatgtgacg gtggcccccg agcgcctggt gcccatcatt    6780
gagggtggct cataccgcgt gtggtcgac acacggacc tggtgctgga tgggagcgag    6840
tcctacgacc ccaacctgga ggacggcgac cagacgccgc tcagttccca ctgggcctgt    6900
gtggcttcga cacagaggga ggctggcggg tgtgcgctga actttgggcc ccgcgggagc    6960
agcacggtca ccattccacg ggagcggctg gcggctggcg tggagtacac cttcagcctg    7020
accgtgtgga aggccggccg caaggaggag gccaccaacc agacggtgct gatccggagt    7080
ggccgggtgc ccattgtgtc cttggagtgt gtgtcctgca aggcacaggc cgtgtacgaa    7140
gtgagccgca gctcctacgt gtacttggag ggccgctgcc tcaattgcag cagcggctcc    7200
aagcgagggc ggtgggctgc acgtacgttc agcaacaaga cgctggtgct ggatgagacc    7260
accacatcca cggggcagtgc aggcatgcga ctggtgctgc ggcggggcgt gctgcgggac    7320
ggcgagggat acaccttcac gctcacggtg ctggccgct ctggcgagga ggagggctgc    7380
gcctccatcc gcctgtcccc caaccgcccg ccgctggggg gctcttgccg cctcttccca    7440
ctgggcgctg tgcacgccct caccaccaag gtgcacttcg aatgcacggg ctggcatgac    7500
gcggaggatg ctgcgccccc gctggtgtac gccctgctgc tgcggcgctg tcgccagggc    7560
cactgcgagg agttctgtgt ctacaagggc agcctctcca gctacggagc cgtgctgccc    7620
```

```
ccgggtttca ggccacactt cgaggtgggc ctggccgtgg tggtgcagga ccagctggga    7680
gccgctgtgg tcgccctcaa caggtctttg gccatcaccc tcccagagcc caacggcagc    7740
gcaacggggc tcacagtctg gctgcacggg ctcaccgcta gtgtgctccc agggctgctg    7800
cggcaggccg atcccagca cgtcatcgag tactcgttgg ccctggtcac cgtgctgaac    7860
gagtacgagc gggccctgga cgtggcggca gagcccaagc acgagcggca gcaccgagcc    7920
cagatacgca agaacatcac ggagactctg gtgtccctga gggtccacac tgtggatgac    7980
atccagcaga tcgctgctgc gctggcccag tgcatggggc ccagcaggga gctcgtatgc    8040
cgctcgtgcc tgaagcagac gctgcacaag ctggaggcca tgatgctcat cctgcaggca    8100
gagaccaccg cgggcaccgt gacgcccacc gccatcggag acagcatcct caacatcaca    8160
ggagacctca tccacctggc cagctcggac gtgcgggcac cacagccctc agagctggga    8220
gccgagtcac catctcggat ggtggcgtcc caggcctaca acctgacctc tgccctcatg    8280
cgcatcctca tgcgctcccg cgtgctcaac gaggagcccc tgacgctggc gggcgaggag    8340
atcgtggccc agggcaagcg ctcggacccg cggagcctgc tgtgctatgg cggcgcccca    8400
gggcctggct gccacttctc catccccgag gctttcagcg gggccctggc caacctcagt    8460
gacgtggtgc agctcatctt tctggtggac tccaatccct ttcccttagg ctatatcagc    8520
aactacaccg tctccaccaa ggtggcctcg atggcattcc agacacaggc cggcgcccag    8580
atccccatcg agcggctggc ctcagagcgc gccatcaccg tgaaggtgcc caacaactcg    8640
gactgggctg cccggggcca ccgcagctcc gccaactccg ccaactccgt tgtggtccag    8700
ccccaggcct ccgtcggtgc tgtggtcacc ctggacagca gcaaccctgc ggccgggctg    8760
catctgcagc tcaactatac gctgctggac ggccactacc tgtctgagga acctgagccc    8820
tacctggcag tctacctaca ctcggagccc cggcccaatg agcacaactg ctcggctagc    8880
aggaggatcc gcccagagtc actccagggt gctgaccacc ggcccctacac cttcttcatt    8940
tccccgggga gcagagaccc agcggggagt taccatctga acctctccag ccacttccgc    9000
tggtcggcgc tgcaggtgtc cgtgggcctg tacacgtccc tgtgccagta cttcagcgag    9060
gaggacatgg tgtggcggac agaggggctg ctgcccctgg aggagacctc gccccgccag    9120
gccgtctgcc tcacccgcca cctcaccgcc ttcggcgcca gcctcttcgt gcccccaagc    9180
catgtccgct ttgtgtttcc tgagccgaca gcggatgtaa actacatcgt catgctgaca    9240
tgtgctgtgt gcctggtgac ctacatggtc atggccgcca tcctgcacaa gctggaccag    9300
ttggatgcca gccggggccg cgccatccct ttctgtgggc agcggggccg cttcaagtac    9360
gagatcctcg tcaagacagg ctggggccgg ggctcaggta ccacggccca cgtgggcatc    9420
atgctgtatg gggtggacag ccggagcggc caccggcacc tggacggcga cagagccttc    9480
caccgcaaca gcctggacat cttccggatc gccaccccgc acagcctggg tagcgtgtgg    9540
aagatccgag tgtggcacga caacaaaggg ctcagccctg cctggttcct gcagcacgtc    9600
atcgtcaggg acctgcagac ggcacgcagc gccttcttcc tggtcaatga ctggctttcg    9660
gtggagacgg aggccaacgg gggcctggtg gagaaggagg tgctggccgc gagcgacgca    9720
gccccttttgc gcttccggcg cctgctggtg gctgagctgc agcgtggctt ctttgacaag    9780
cacatctggc tctccatatg ggaccggccg cctcgtagcc gtttcactcg catccagagg    9840
gccacctgct gcgttctcct catctgcctc ttcctgggcg ccaacgccgt gtggtacggg    9900
gctgttggcg actctgccta cagcacgggg catgtgtcca ggctgagccc gctgagcgtc    9960
```

```
gacacagtcg ctgttggcct ggtgtccagc gtggttgtct atcccgtcta cctggccatc    10020 cttttctct tccggatgtc ccggagcaag gtggctggga gcccgagccc cacacctgcc    10080
gggcagcagg tgctggacat cgacagctgc ctggactcgt ccgtgctgga cagctccttc    10140
ctcacgttct caggcctcca cgctgaggcc tttgttggac agatgaagag tgacttgttt    10200
ctggatgatt ctaagagtct ggtgtgctgg ccctccggcg agggaacgct cagttggccg    10260
gacctgctca gtgacccgtc cattgtgggt agcaatctgc ggcagctggc acggggccag    10320
gcgggccatg ggctgggccc agaggaggac ggcttctccc tggccagccc ctactcgcct    10380
gccaaatcct tctcagcatc agatgaagac ctgatccagc aggtccttgc cgagggggtc    10440
agcagcccag cccctaccca agacacccac atggaaacgg acctgctcag cagcctgtcc    10500
agcactcctg gggagaagac agagacgctg gcgctgcaga ggctgggggga gctggggcca    10560 cccagcccag gcctgaactg ggaacagccc caggcagcga ggctgtccag gacaggactg    10620
gtggagggtc tgcggaagcg cctgctgccg gcctggtgtg cctccctggc ccacgggctc    10680
agcctgctcc tggtggctgt ggctgtgtgct gtctcagggt gggtgggtgc gagcttcccc    10740
ccgggcgtga gtgttgcgtg gctcctgtcc agcagcgcca gcttcctggc ctcattcctc    10800
ggctgggagc cactgaaggt cttgctggaa gccctgtact tctcactggt ggccaagcgg    10860
ctgcacccgg atgaagatga caccctggta gagagcccgg ctgtgacgcc tgtgagcgca    10920
cgtgtgcccc gcgtacggcc accccacggc tttgcactct tcctggccaa ggaagaagcc    10980
cgcaaggtca gaggctaca tggcatgctg cggagcctcc tggtgtacat gcttttctg    11040 ctggtgaccc tgctggccag ctatgggat gcctcatgcc atgggcacgc ctaccgtctg    11100
caaagcgcca tcaagcagga gctgcacagc cgggccttcc tggccatcac gcggtctgag    11160
gagctctggc catggatggc ccacgtgctg ctgccctacg tccacgggaa ccagtccagc    11220
ccagagctgg ggcccccacg gctgcggcag gtgcggctgc aggaagcact ctacccagac    11280
cctcccggcc ccagggtcca cacgtgctcg gccgcaggag gcttcagcac cagcgattac    11340
gacgttggct gggagagtcc tcacaatggc tcggggacgt gggcctattc agcgccggat    11400
ctgctggggg catggtcctg gggctcctgt gccgtgtatg acagcggggg ctacgtgcag    11460
gagctgggcc tgagcctgga ggagagccgc gaccggctgc gcttcctgca gctgcacaac    11520
tggctggaca acaggagccg cgctgtgttc ctggagctca cgcgctacag cccggccgtg    11580
gggctgcacg ccgccgtcac gctgcgcctc gagttcccgg cggccggccg cgccctggcc    11640
gccctcagcg tccgccccctt tgcgctgcgc gcctcagcg cgggcctctc gctgcctctg    11700
ctcacctcgg tgtgcctgct gctgttcgcc gtgcacttcg ccgtggccga ggcccgtact    11760
tggcacaggg aagggcgctg gcgcgtgctg cggctcggag cctggcgcg gtggctgctg    11820 gtggcgctga cggcggccac ggcactggta cgcctcgccc agctgggtgc cgctgaccgc    11880
cagtggaccc gtttcgtgcg cggccgcccg cgccgcttca ctagcttcga ccaggtggcg    11940
cagctgagct ccgcagcccg tggcctggcg gcctcgctgc tcttcctgct tttggtcaag    12000
gctgcccagc agctacgctt cgtgcgccag tggtccgtct ttggcaagac attatgccga    12060
gctctgccag agctcctggg ggtcaccttg gcctggtgg tgctcggggt agcctacgcc    12120
cagctggcca tcctgctcgt gtcttcctgt gtggactccc tctggagcgt ggcccaggcc    12180
ctgttggtgc tgtgccctgg gactgggctc tctaccctgt gtcctgccga gtcctggcac    12240
ctgtcacccc tgctgtgtgt ggggctctgg gcactgcggc tgtggggcgc cctacgctgg    12300
ggggctgtta ttctccgctg gcgctaccac gccttgcgtg gagagctgta ccggccggcc    12360
```

-continued

```
tgggagcccc aggactacga gatggtggag ttgttcctgc gcaggctgcg cctctggatg    12420
ggcctcagca aggtcaagga gttccgccac aaagtccgct ttgaagggat ggagccgctg    12480
ccctctcgct cctccagggg ctccaaggta tccccggatg tgcccccacc cagcgctggc    12540
tccgatgcct cgcaccccte cacctcctcc agccagctgg atgggctgag cgtgagcctg    12600
ggccggctgg ggacaaggtg tgagcctgag ccctcccgcc tccaagccgt gttcgaggcc    12660
ctgctcaccc agtttgaccg actcaaccag gccacagagg acgtctacca gctggagcag    12720
cagctgcaca gcctgcaagg ccgcaggagc agccgggcgc ccgccggatc ttcccgtggc    12780
ccatccccgg gcctgcggcc agcactgccc agccgccttg cccgggccag tcggggtgtg    12840
gacctggcca ctggccccag caggacaccc cttcgggcca agaacaaggt ccaccccagc    12900
agcacttag                                                             12909
```

<210> SEQ ID NO 3
<211> LENGTH: 4302
<212> TYPE: PRT
<213> ORGANISM: Homo sapiens
<400> SEQUENCE: 3

```
Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
            20                  25                  30

Cys Glu Pro Pro Cys Leu Cys Gly Pro Ala Pro Gly Ala Ala Cys Arg
        35                  40                  45

Val Asn Cys Ser Gly Arg Gly Leu Arg Thr Leu Gly Pro Ala Leu Arg
    50                  55                  60

Ile Pro Ala Asp Ala Thr Ala Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Arg Trp Ala Glu Glu Gln Gln
    130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270
```

-continued

```
Pro Gly Ala Thr Leu Val Gly Pro His Gly Pro Leu Ala Ser Gly Gln
            275                 280                 285

Leu Ala Ala Phe His Ile Ala Ala Pro Leu Pro Val Thr Ala Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
            355                 360                 365

Ser Asp Glu Ser Leu Asp Leu Ser Ile Gln Asn Arg Gly Gly Ser Gly
            370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
            435                 440                 445

Ser Pro Ala Val Gln Arg Phe Leu Val Ser Arg Val Thr Arg Ser Leu
    450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
    515                 520                 525

Val Cys Glu Leu Gln Pro Gly Gly Pro Val Gln Asp Ala Glu Asn Leu
530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
            580                 585                 590

Glu Phe Gly Thr Gln Glu Leu Arg Arg Pro Ala Gln Leu Arg Leu Gln
            595                 600                 605

Val Tyr Arg Leu Leu Ser Thr Ala Gly Thr Pro Glu Asn Gly Ser Glu
    610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
            660                 665                 670

Pro Gly Leu Pro Gly Ala Pro Tyr Ala Leu Trp Arg Glu Phe Leu Phe
    675                 680                 685
```

-continued

```
Ser Val Ala Ala Gly Pro Pro Ala Gln Tyr Ser Val Thr Leu His Gly
690                 695                 700
Gln Asp Val Leu Met Leu Pro Gly Asp Leu Val Gly Leu Gln His Asp
705                 710                 715                 720
Ala Gly Pro Gly Ala Leu Leu His Cys Ser Pro Ala Pro Gly His Pro
                725                 730                 735
Gly Pro Gln Ala Pro Tyr Leu Ser Ala Asn Ala Ser Ser Trp Leu Pro
            740                 745                 750
His Leu Pro Ala Gln Leu Glu Gly Thr Trp Ala Cys Pro Ala Cys Ala
        755                 760                 765
Leu Arg Leu Leu Ala Ala Thr Glu Gln Leu Thr Val Leu Leu Gly Leu
770                 775                 780
Arg Pro Asn Pro Gly Leu Arg Met Pro Gly Arg Tyr Glu Val Arg Ala
785                 790                 795                 800
Glu Val Gly Asn Gly Val Ser Arg His Asn Leu Ser Cys Ser Phe Asp
                805                 810                 815
Val Val Ser Pro Val Ala Gly Leu Arg Val Ile Tyr Pro Ala Pro Arg
            820                 825                 830
Asp Gly Arg Leu Tyr Val Pro Thr Asn Gly Ser Ala Leu Val Leu Gln
        835                 840                 845
Val Asp Ser Gly Ala Asn Ala Thr Ala Thr Ala Arg Trp Pro Gly Gly
850                 855                 860
Ser Val Ser Ala Arg Phe Glu Asn Val Cys Pro Ala Leu Val Ala Thr
865                 870                 875                 880
Phe Val Pro Gly Cys Pro Trp Glu Thr Asn Asp Thr Leu Phe Ser Val
                885                 890                 895
Val Ala Leu Pro Trp Leu Ser Glu Gly Glu His Val Val Asp Val Val
            900                 905                 910
Val Glu Asn Ser Ala Ser Arg Ala Asn Leu Ser Leu Arg Val Thr Ala
        915                 920                 925
Glu Glu Pro Ile Cys Gly Leu Arg Ala Thr Pro Ser Pro Glu Ala Arg
930                 935                 940
Val Leu Gln Gly Val Leu Val Arg Tyr Ser Pro Val Val Glu Ala Gly
945                 950                 955                 960
Ser Asp Met Val Phe Arg Trp Thr Ile Asn Asp Lys Gln Ser Leu Thr
                965                 970                 975
Phe Gln Asn Val Val Phe Asn Val Ile Tyr Gln Ser Ala Ala Val Phe
            980                 985                 990
Lys Leu Ser Leu Thr Ala Ser Asn His Val Ser Asn Val Thr Val Asn
        995                 1000                1005
Tyr Asn Val Thr Val Glu Arg Met Asn Arg Met Gln Gly Leu Gln
        1010                1015                1020
Val Ser Thr Val Pro Ala Val Leu Ser Pro Asn Ala Thr Leu Ala
        1025                1030                1035
Leu Thr Ala Gly Val Leu Val Asp Ser Ala Val Glu Val Ala Phe
        1040                1045                1050
Leu Trp Asn Phe Gly Asp Gly Glu Gln Ala Leu His Gln Phe Gln
        1055                1060                1065
Pro Pro Tyr Asn Glu Ser Phe Pro Val Pro Asp Pro Ser Val Ala
        1070                1075                1080
Gln Val Leu Val Glu His Asn Val Met His Thr Tyr Ala Ala Pro
        1085                1090                1095
Gly Glu Tyr Leu Leu Thr Val Leu Ala Ser Asn Ala Phe Glu Asn
```

```
                1100                1105                1110
Leu Thr Gln Gln Val Pro Val Ser Val Arg Ala Ser Leu Pro Ser
    1115                1120                1125

Val Ala Val Gly Val Ser Asp Gly Val Leu Val Ala Gly Arg Pro
    1130                1135                1140

Val Thr Phe Tyr Pro His Pro Leu Pro Ser Pro Gly Gly Val Leu
    1145                1150                1155

Tyr Thr Trp Asp Phe Gly Asp Gly Ser Pro Val Leu Thr Gln Ser
    1160                1165                1170

Gln Pro Ala Ala Asn His Thr Tyr Ala Ser Arg Gly Thr Tyr His
    1175                1180                1185

Val Arg Leu Glu Val Asn Asn Thr Val Ser Gly Ala Ala Ala Gln
    1190                1195                1200

Ala Asp Val Arg Val Phe Glu Glu Leu Arg Gly Leu Ser Val Asp
    1205                1210                1215

Met Ser Leu Ala Val Glu Gln Gly Ala Pro Val Val Val Ser Ala
    1220                1225                1230

Ala Val Gln Thr Gly Asp Asn Ile Thr Trp Thr Phe Asp Met Gly
    1235                1240                1245

Asp Gly Thr Val Leu Ser Gly Pro Glu Ala Thr Val Glu His Val
    1250                1255                1260

Tyr Leu Arg Ala Gln Asn Cys Thr Val Thr Val Gly Ala Ala Ser
    1265                1270                1275

Pro Ala Gly His Leu Ala Arg Ser Leu His Val Leu Val Phe Val
    1280                1285                1290

Leu Glu Val Leu Arg Val Glu Pro Ala Ala Cys Ile Pro Thr Gln
    1295                1300                1305

Pro Asp Ala Arg Leu Thr Ala Tyr Val Thr Gly Asn Pro Ala His
    1310                1315                1320

Tyr Leu Phe Asp Trp Thr Phe Gly Asp Gly Ser Ser Asn Thr Thr
    1325                1330                1335

Val Arg Gly Cys Pro Thr Val Thr His Asn Phe Thr Arg Ser Gly
    1340                1345                1350

Thr Phe Pro Leu Ala Leu Val Leu Ser Ser Arg Val Asn Arg Ala
    1355                1360                1365

His Tyr Phe Thr Ser Ile Cys Val Glu Pro Glu Val Gly Asn Val
    1370                1375                1380

Thr Leu Gln Pro Glu Arg Gln Phe Val Gln Leu Gly Asp Glu Ala
    1385                1390                1395

Trp Leu Val Ala Cys Ala Trp Pro Pro Phe Pro Tyr Arg Tyr Thr
    1400                1405                1410

Trp Asp Phe Gly Thr Glu Glu Ala Ala Pro Thr Arg Ala Arg Gly
    1415                1420                1425

Pro Glu Val Thr Phe Ile Tyr Arg Asp Pro Gly Ser Tyr Leu Val
    1430                1435                1440

Thr Val Thr Ala Ser Asn Asn Ile Ser Ala Ala Asn Asp Ser Ala
    1445                1450                1455

Leu Val Glu Val Gln Glu Pro Val Leu Val Thr Ser Ile Lys Val
    1460                1465                1470

Asn Gly Ser Leu Gly Leu Glu Leu Gln Gln Pro Tyr Leu Phe Ser
    1475                1480                1485

Ala Val Gly Arg Gly Arg Pro Ala Ser Tyr Leu Trp Asp Leu Gly
    1490                1495                1500
```

```
Asp Gly Gly Trp Leu Glu Gly Pro Glu Val Thr His Ala Tyr Asn
1505                1510                1515

Ser Thr Gly Asp Phe Thr Val Arg Val Ala Gly Trp Asn Glu Val
1520                1525                1530

Ser Arg Ser Glu Ala Trp Leu Asn Val Thr Val Lys Arg Arg Val
1535                1540                1545

Arg Gly Leu Val Val Asn Ala Ser Arg Thr Val Val Pro Leu Asn
1550                1555                1560

Gly Ser Val Ser Phe Ser Thr Ser Leu Glu Ala Gly Ser Asp Val
1565                1570                1575

Arg Tyr Ser Trp Val Leu Cys Asp Arg Cys Thr Pro Ile Pro Gly
1580                1585                1590

Gly Pro Thr Ile Ser Tyr Thr Phe Arg Ser Val Gly Thr Phe Asn
1595                1600                1605

Ile Ile Val Thr Ala Glu Asn Glu Val Gly Ser Ala Gln Asp Ser
1610                1615                1620

Ile Phe Val Tyr Val Leu Gln Leu Ile Glu Gly Leu Gln Val Val
1625                1630                1635

Gly Gly Gly Arg Tyr Phe Pro Thr Asn His Thr Val Gln Leu Gln
1640                1645                1650

Ala Val Val Arg Asp Gly Thr Asn Val Ser Tyr Ser Trp Thr Ala
1655                1660                1665

Trp Arg Asp Arg Gly Pro Ala Leu Ala Gly Ser Gly Lys Gly Phe
1670                1675                1680

Ser Leu Thr Val Leu Glu Ala Gly Thr Tyr His Val Gln Leu Arg
1685                1690                1695

Ala Thr Asn Met Leu Gly Ser Ala Trp Ala Asp Cys Thr Met Asp
1700                1705                1710

Phe Val Glu Pro Val Gly Trp Leu Met Val Thr Ala Ser Pro Asn
1715                1720                1725

Pro Ala Ala Val Asn Thr Ser Val Thr Leu Ser Ala Glu Leu Ala
1730                1735                1740

Gly Gly Ser Gly Val Val Tyr Thr Trp Ser Leu Glu Glu Gly Leu
1745                1750                1755

Ser Trp Glu Thr Ser Glu Pro Phe Thr Thr His Ser Phe Pro Thr
1760                1765                1770

Pro Gly Leu His Leu Val Thr Met Thr Ala Gly Asn Pro Leu Gly
1775                1780                1785

Ser Ala Asn Ala Thr Val Glu Val Asp Val Gln Val Pro Val Ser
1790                1795                1800

Gly Leu Ser Ile Arg Ala Ser Glu Pro Gly Gly Ser Phe Val Ala
1805                1810                1815

Ala Gly Ser Ser Val Pro Phe Trp Gly Gln Leu Ala Thr Gly Thr
1820                1825                1830

Asn Val Ser Trp Cys Trp Ala Val Pro Gly Gly Ser Ser Lys Arg
1835                1840                1845

Gly Pro His Val Thr Met Val Phe Pro Asp Ala Gly Thr Phe Ser
1850                1855                1860

Ile Arg Leu Asn Ala Ser Asn Ala Val Ser Trp Val Ser Ala Thr
1865                1870                1875

Tyr Asn Leu Thr Ala Glu Glu Pro Ile Val Gly Leu Val Leu Trp
1880                1885                1890
```

```
Ala Ser  Ser Lys Val Val Ala  Pro Gly Gln Leu Val  His Phe Gln
    1895             1900              1905

Ile Leu  Leu Ala Ala Gly Ser  Ala Val Thr Phe Arg  Leu Gln Val
    1910             1915              1920

Gly Gly  Ala Asn Pro Glu Val  Leu Pro Gly Pro Arg  Phe Ser His
    1925             1930              1935

Ser Phe  Pro Arg Val Gly Asp  His Val Val Ser Val  Arg Gly Lys
    1940             1945              1950

Asn His  Val Ser Trp Ala Gln  Ala Gln Val Arg Ile  Val Val Leu
    1955             1960              1965

Glu Ala  Val Ser Gly Leu Gln  Met Pro Asn Cys Cys  Glu Pro Gly
    1970             1975              1980

Ile Ala  Thr Gly Thr Glu Arg  Asn Phe Thr Ala Arg  Val Gln Arg
    1985             1990              1995

Gly Ser  Arg Val Ala Tyr Ala  Trp Tyr Phe Ser Leu  Gln Lys Val
    2000             2005              2010

Gln Gly  Asp Ser Leu Val Ile  Leu Ser Gly Arg Asp  Val Thr Tyr
    2015             2020              2025

Thr Pro  Val Ala Ala Gly Leu  Leu Glu Ile Gln Val  Arg Ala Phe
    2030             2035              2040

Asn Ala  Leu Gly Ser Glu Asn  Arg Thr Leu Val Leu  Glu Val Gln
    2045             2050              2055

Asp Ala  Val Gln Tyr Val Ala  Leu Gln Ser Gly Pro  Cys Phe Thr
    2060             2065              2070

Asn Arg  Ser Ala Gln Phe Glu  Ala Ala Thr Ser Pro  Ser Pro Arg
    2075             2080              2085

Arg Val  Ala Tyr His Trp Asp  Phe Gly Asp Gly Ser  Pro Gly Gln
    2090             2095              2100

Asp Thr  Asp Glu Pro Arg Ala  Glu His Ser Tyr Leu  Arg Pro Gly
    2105             2110              2115

Asp Tyr  Arg Val Gln Val Asn  Ala Ser Asn Leu Val  Ser Phe Phe
    2120             2125              2130

Val Ala  Gln Ala Thr Val Thr  Val Gln Val Leu Ala  Cys Arg Glu
    2135             2140              2145

Pro Glu  Val Asp Val Val Leu  Pro Leu Gln Val Leu  Met Arg Arg
    2150             2155              2160

Ser Gln  Arg Asn Tyr Leu Glu  Ala His Val Asp Leu  Arg Asp Cys
    2165             2170              2175

Val Thr  Tyr Gln Thr Glu Tyr  Arg Trp Glu Val Tyr  Arg Thr Ala
    2180             2185              2190

Ser Cys  Gln Arg Pro Gly Arg  Pro Ala Arg Val Ala  Leu Pro Gly
    2195             2200              2205

Val Asp  Val Ser Arg Pro Arg  Leu Val Leu Pro Arg  Leu Ala Leu
    2210             2215              2220

Pro Val  Gly His Tyr Cys Phe  Val Phe Val Val Ser  Phe Gly Asp
    2225             2230              2235

Thr Pro  Leu Thr Gln Ser Ile  Gln Ala Asn Val Thr  Val Ala Pro
    2240             2245              2250

Glu Arg  Leu Val Pro Ile Ile  Glu Gly Gly Ser Tyr  Arg Val Trp
    2255             2260              2265

Ser Asp  Thr Arg Asp Leu Val  Leu Asp Gly Ser Glu  Ser Tyr Asp
    2270             2275              2280

Pro Asn  Leu Glu Asp Gly Asp  Gln Thr Pro Leu Ser  Phe His Trp
```

```
                  2285                2290                2295
Ala Cys Val Ala Ser Thr Gln Arg Glu Ala Gly Gly Cys Ala Leu
    2300                2305                2310
Asn Phe Gly Pro Arg Gly Ser Ser Thr Val Thr Ile Pro Arg Glu
    2315                2320                2325
Arg Leu Ala Ala Gly Val Glu Tyr Thr Phe Ser Leu Thr Val Trp
    2330                2335                2340
Lys Ala Gly Arg Lys Glu Ala Thr Asn Gln Thr Val Leu Ile
    2345                2350                2355
Arg Ser Gly Arg Val Pro Ile Val Ser Leu Glu Cys Val Ser Cys
    2360                2365                2370
Lys Ala Gln Ala Val Tyr Glu Val Ser Arg Ser Tyr Val Tyr
    2375                2380                2385
Leu Glu Gly Arg Cys Leu Asn Cys Ser Ser Gly Ser Lys Arg Gly
    2390                2395                2400
Arg Trp Ala Ala Arg Thr Phe Ser Asn Lys Thr Leu Val Leu Asp
    2405                2410                2415
Glu Thr Thr Thr Ser Thr Gly Ser Ala Gly Met Arg Leu Val Leu
    2420                2425                2430
Arg Arg Gly Val Leu Arg Asp Gly Glu Gly Tyr Thr Phe Thr Leu
    2435                2440                2445
Thr Val Leu Gly Arg Ser Gly Glu Glu Glu Gly Cys Ala Ser Ile
    2450                2455                2460
Arg Leu Ser Pro Asn Arg Pro Pro Leu Gly Gly Ser Cys Arg Leu
    2465                2470                2475
Phe Pro Leu Gly Ala Val His Ala Leu Thr Thr Lys Val His Phe
    2480                2485                2490
Glu Cys Thr Gly Trp His Asp Ala Glu Asp Ala Gly Ala Pro Leu
    2495                2500                2505
Val Tyr Ala Leu Leu Leu Arg Arg Cys Arg Gln Gly His Cys Glu
    2510                2515                2520
Glu Phe Cys Val Tyr Lys Gly Ser Leu Ser Ser Tyr Gly Ala Val
    2525                2530                2535
Leu Pro Pro Gly Phe Arg Pro His Phe Glu Val Gly Leu Ala Val
    2540                2545                2550
Val Val Gln Asp Gln Leu Gly Ala Ala Val Val Ala Leu Asn Arg
    2555                2560                2565
Ser Leu Ala Ile Thr Leu Pro Glu Pro Asn Gly Ser Ala Thr Gly
    2570                2575                2580
Leu Thr Val Trp Leu His Gly Leu Thr Ala Ser Val Leu Pro Gly
    2585                2590                2595
Leu Leu Arg Gln Ala Asp Pro Gln His Val Ile Glu Tyr Ser Leu
    2600                2605                2610
Ala Leu Val Thr Val Leu Asn Glu Tyr Glu Arg Ala Leu Asp Val
    2615                2620                2625
Ala Ala Glu Pro Lys His Glu Arg Gln His Arg Ala Gln Ile Arg
    2630                2635                2640
Lys Asn Ile Thr Glu Thr Leu Val Ser Leu Arg Val His Thr Val
    2645                2650                2655
Asp Asp Ile Gln Gln Ile Ala Ala Ala Leu Ala Gln Cys Met Gly
    2660                2665                2670
Pro Ser Arg Glu Leu Val Cys Arg Ser Cys Leu Lys Gln Thr Leu
    2675                2680                2685
```

-continued

His Lys Leu Glu Ala Met Met Leu Ile Leu Gln Ala Glu Thr Thr
2690                2695                2700

Ala Gly Thr Val Thr Pro Thr Ala Ile Gly Asp Ser Ile Leu Asn
2705                2710                2715

Ile Thr Gly Asp Leu Ile His Leu Ala Ser Ser Asp Val Arg Ala
2720                2725                2730

Pro Gln Pro Ser Glu Leu Gly Ala Glu Ser Pro Ser Arg Met Val
2735                2740                2745

Ala Ser Gln Ala Tyr Asn Leu Thr Ser Ala Leu Met Arg Ile Leu
2750                2755                2760

Met Arg Ser Arg Val Leu Asn Glu Glu Pro Leu Thr Leu Ala Gly
2765                2770                2775

Glu Glu Ile Val Ala Gln Gly Lys Arg Ser Asp Pro Arg Ser Leu
2780                2785                2790

Leu Cys Tyr Gly Gly Ala Pro Gly Pro Gly Cys His Phe Ser Ile
2795                2800                2805

Pro Glu Ala Phe Ser Gly Ala Leu Ala Asn Leu Ser Asp Val Val
2810                2815                2820

Gln Leu Ile Phe Leu Val Asp Ser Asn Pro Phe Pro Phe Gly Tyr
2825                2830                2835

Ile Ser Asn Tyr Thr Val Ser Thr Lys Val Ala Ser Met Ala Phe
2840                2845                2850

Gln Thr Gln Ala Gly Ala Gln Ile Pro Ile Glu Arg Leu Ala Ser
2855                2860                2865

Glu Arg Ala Ile Thr Val Lys Val Pro Asn Asn Ser Asp Trp Ala
2870                2875                2880

Ala Arg Gly His Arg Ser Ser Ala Asn Ser Ala Asn Ser Val Val
2885                2890                2895

Val Gln Pro Gln Ala Ser Val Gly Ala Val Val Thr Leu Asp Ser
2900                2905                2910

Ser Asn Pro Ala Ala Gly Leu His Leu Gln Leu Asn Tyr Thr Leu
2915                2920                2925

Leu Asp Gly His Tyr Leu Ser Glu Glu Pro Glu Pro Tyr Leu Ala
2930                2935                2940

Val Tyr Leu His Ser Glu Pro Arg Pro Asn Glu His Asn Cys Ser
2945                2950                2955

Ala Ser Arg Arg Ile Arg Pro Glu Ser Leu Gln Gly Ala Asp His
2960                2965                2970

Arg Pro Tyr Thr Phe Phe Ile Ser Pro Gly Ser Arg Asp Pro Ala
2975                2980                2985

Gly Ser Tyr His Leu Asn Leu Ser Ser His Phe Arg Trp Ser Ala
2990                2995                3000

Leu Gln Val Ser Val Gly Leu Tyr Thr Ser Leu Cys Gln Tyr Phe
3005                3010                3015

Ser Glu Glu Asp Met Val Trp Arg Thr Glu Gly Leu Leu Pro Leu
3020                3025                3030

Glu Glu Thr Ser Pro Arg Gln Ala Val Cys Leu Thr Arg His Leu
3035                3040                3045

Thr Ala Phe Gly Ala Ser Leu Phe Val Pro Pro Ser His Val Arg
3050                3055                3060

Phe Val Phe Pro Glu Pro Thr Ala Asp Val Asn Tyr Ile Val Met
3065                3070                3075

```
Leu Thr Cys Ala Val Cys Leu Val Thr Tyr Met Val Met Ala Ala
3080            3085            3090

Ile Leu His Lys Leu Asp Gln Leu Asp Ala Ser Arg Gly Arg Ala
3095            3100            3105

Ile Pro Phe Cys Gly Gln Arg Gly Arg Phe Lys Tyr Glu Ile Leu
3110            3115            3120

Val Lys Thr Gly Trp Gly Arg Gly Ser Gly Thr Thr Ala His Val
3125            3130            3135

Gly Ile Met Leu Tyr Gly Val Asp Ser Arg Ser Gly His Arg His
3140            3145            3150

Leu Asp Gly Asp Arg Ala Phe His Arg Asn Ser Leu Asp Ile Phe
3155            3160            3165

Arg Ile Ala Thr Pro His Ser Leu Gly Ser Val Trp Lys Ile Arg
3170            3175            3180

Val Trp His Asp Asn Lys Gly Leu Ser Pro Ala Trp Phe Leu Gln
3185            3190            3195

His Val Ile Val Arg Asp Leu Gln Thr Ala Arg Ser Ala Phe Phe
3200            3205            3210

Leu Val Asn Asp Trp Leu Ser Val Glu Thr Glu Ala Asn Gly Gly
3215            3220            3225

Leu Val Glu Lys Glu Val Leu Ala Ala Ser Asp Ala Ala Leu Leu
3230            3235            3240

Arg Phe Arg Arg Leu Leu Val Ala Glu Leu Gln Arg Gly Phe Phe
3245            3250            3255

Asp Lys His Ile Trp Leu Ser Ile Trp Asp Arg Pro Pro Arg Ser
3260            3265            3270

Arg Phe Thr Arg Ile Gln Arg Ala Thr Cys Cys Val Leu Leu Ile
3275            3280            3285

Cys Leu Phe Leu Gly Ala Asn Ala Val Trp Tyr Gly Ala Val Gly
3290            3295            3300

Asp Ser Ala Tyr Ser Thr Gly His Val Ser Arg Leu Ser Pro Leu
3305            3310            3315

Ser Val Asp Thr Val Ala Val Gly Leu Val Ser Ser Val Val Val
3320            3325            3330

Tyr Pro Val Tyr Leu Ala Ile Leu Phe Leu Phe Arg Met Ser Arg
3335            3340            3345

Ser Lys Val Ala Gly Ser Pro Ser Pro Thr Pro Ala Gly Gln Gln
3350            3355            3360

Val Leu Asp Ile Asp Ser Cys Leu Asp Ser Ser Val Leu Asp Ser
3365            3370            3375

Ser Phe Leu Thr Phe Ser Gly Leu His Ala Glu Ala Phe Val Gly
3380            3385            3390

Gln Met Lys Ser Asp Leu Phe Leu Asp Asp Ser Lys Ser Leu Val
3395            3400            3405

Cys Trp Pro Ser Gly Glu Gly Thr Leu Ser Trp Pro Asp Leu Leu
3410            3415            3420

Ser Asp Pro Ser Ile Val Gly Ser Asn Leu Arg Gln Leu Ala Arg
3425            3430            3435

Gly Gln Ala Gly His Gly Leu Gly Pro Glu Glu Asp Gly Phe Ser
3440            3445            3450

Leu Ala Ser Pro Tyr Ser Pro Ala Lys Ser Phe Ser Ala Ser Asp
3455            3460            3465

Glu Asp Leu Ile Gln Gln Val Leu Ala Glu Gly Val Ser Ser Pro
```

```
                3470               3475               3480
Ala Pro Thr Gln Asp Thr His Met Glu Thr Asp Leu Leu Ser Ser
    3485               3490               3495

Leu Ser Ser Thr Pro Gly Glu Lys Thr Glu Thr Leu Ala Leu Gln
    3500               3505               3510

Arg Leu Gly Glu Leu Gly Pro Pro Ser Pro Gly Leu Asn Trp Glu
    3515               3520               3525

Gln Pro Gln Ala Ala Arg Leu Ser Arg Thr Gly Leu Val Glu Gly
    3530               3535               3540

Leu Arg Lys Arg Leu Leu Pro Ala Trp Cys Ala Ser Leu Ala His
    3545               3550               3555

Gly Leu Ser Leu Leu Leu Val Ala Val Ala Val Ala Val Ser Gly
    3560               3565               3570

Trp Val Gly Ala Ser Phe Pro Pro Gly Val Ser Val Ala Trp Leu
    3575               3580               3585

Leu Ser Ser Ser Ala Ser Phe Leu Ala Ser Phe Leu Gly Trp Glu
    3590               3595               3600

Pro Leu Lys Val Leu Leu Glu Ala Leu Tyr Phe Ser Leu Val Ala
    3605               3610               3615

Lys Arg Leu His Pro Asp Glu Asp Asp Thr Leu Val Glu Ser Pro
    3620               3625               3630

Ala Val Thr Pro Val Ser Ala Arg Val Pro Arg Val Arg Pro Pro
    3635               3640               3645

His Gly Phe Ala Leu Phe Leu Ala Lys Glu Glu Ala Arg Lys Val
    3650               3655               3660

Lys Arg Leu His Gly Met Leu Arg Ser Leu Leu Val Tyr Met Leu
    3665               3670               3675

Phe Leu Leu Val Thr Leu Leu Ala Ser Tyr Gly Asp Ala Ser Cys
    3680               3685               3690

His Gly His Ala Tyr Arg Leu Gln Ser Ala Ile Lys Gln Glu Leu
    3695               3700               3705

His Ser Arg Ala Phe Leu Ala Ile Thr Arg Ser Glu Glu Leu Trp
    3710               3715               3720

Pro Trp Met Ala His Val Leu Leu Pro Tyr Val His Gly Asn Gln
    3725               3730               3735

Ser Ser Pro Glu Leu Gly Pro Pro Arg Leu Arg Gln Val Arg Leu
    3740               3745               3750

Gln Glu Ala Leu Tyr Pro Asp Pro Pro Gly Pro Arg Val His Thr
    3755               3760               3765

Cys Ser Ala Ala Gly Gly Phe Ser Thr Ser Asp Tyr Asp Val Gly
    3770               3775               3780

Trp Glu Ser Pro His Asn Gly Ser Gly Thr Trp Ala Tyr Ser Ala
    3785               3790               3795

Pro Asp Leu Leu Gly Ala Trp Ser Trp Gly Ser Cys Ala Val Tyr
    3800               3805               3810

Asp Ser Gly Gly Tyr Val Gln Glu Leu Gly Leu Ser Leu Glu Glu
    3815               3820               3825

Ser Arg Asp Arg Leu Arg Phe Leu Gln Leu His Asn Trp Leu Asp
    3830               3835               3840

Asn Arg Ser Arg Ala Val Phe Leu Glu Leu Thr Arg Tyr Ser Pro
    3845               3850               3855

Ala Val Gly Leu His Ala Ala Val Thr Leu Arg Leu Glu Phe Pro
    3860               3865               3870
```

-continued

```
Ala Ala Gly Arg Ala Leu Ala  Leu Ser Val Arg  Pro Phe Ala
3875         3880             3885
Leu Arg Arg Leu Ser Ala Gly  Leu Ser Leu Pro  Leu Thr Ser
3890         3895             3900
Val Cys Leu Leu Leu Phe Ala  Val His Phe Ala  Val Ala Glu Ala
3905         3910             3915
Arg Thr Trp His Arg Glu Gly  Arg Trp Arg Val  Leu Arg Leu Gly
3920         3925             3930
Ala Trp Ala Arg Trp Leu Leu  Val Ala Leu Thr  Ala Ala Thr Ala
3935         3940             3945
Leu Val Arg Leu Ala Gln Leu  Gly Ala Ala Asp  Arg Gln Trp Thr
3950         3955             3960
Arg Phe Val Arg Gly Arg Pro  Arg Arg Phe Thr  Ser Phe Asp Gln
3965         3970             3975
Val Ala Gln Leu Ser Ser Ala  Ala Arg Gly Leu  Ala Ala Ser Leu
3980         3985             3990
Leu Phe Leu Leu Leu Val Lys  Ala Ala Gln Gln  Leu Arg Phe Val
3995         4000             4005
Arg Gln Trp Ser Val Phe Gly  Lys Thr Leu Cys  Arg Ala Leu Pro
4010         4015             4020
Glu Leu Leu Gly Val Thr Leu  Gly Leu Val Val  Leu Gly Val Ala
4025         4030             4035
Tyr Ala Gln Leu Ala Ile Leu  Leu Val Ser Ser  Cys Val Asp Ser
4040         4045             4050
Leu Trp Ser Val Ala Gln Ala  Leu Leu Val Leu  Cys Pro Gly Thr
4055         4060             4065
Gly Leu Ser Thr Leu Cys Pro  Ala Glu Ser Trp  His Leu Ser Pro
4070         4075             4080
Leu Leu Cys Val Gly Leu Trp  Ala Leu Arg Leu  Trp Gly Ala Leu
4085         4090             4095
Arg Leu Gly Ala Val Ile Leu  Arg Trp Arg Tyr  His Ala Leu Arg
4100         4105             4110
Gly Glu Leu Tyr Arg Pro Ala  Trp Glu Pro Gln  Asp Tyr Glu Met
4115         4120             4125
Val Glu Leu Phe Leu Arg Arg  Leu Arg Leu Trp  Met Gly Leu Ser
4130         4135             4140
Lys Val Lys Glu Phe Arg His  Lys Val Arg Phe  Glu Gly Met Glu
4145         4150             4155
Pro Leu Pro Ser Arg Ser Ser  Arg Gly Ser Lys  Val Ser Pro Asp
4160         4165             4170
Val Pro Pro Pro Ser Ala Gly  Ser Asp Ala Ser  His Pro Ser Thr
4175         4180             4185
Ser Ser Ser Gln Leu Asp Gly  Leu Ser Val Ser  Leu Gly Arg Leu
4190         4195             4200
Gly Thr Arg Cys Glu Pro Glu  Pro Ser Arg Leu  Gln Ala Val Phe
4205         4210             4215
Glu Ala Leu Leu Thr Gln Phe  Asp Arg Leu Asn  Gln Ala Thr Glu
4220         4225             4230
Asp Val Tyr Gln Leu Glu Gln  Gln Leu His Ser  Leu Gln Gly Arg
4235         4240             4245
Arg Ser Ser Arg Ala Pro Ala  Gly Ser Ser Arg  Gly Pro Ser Pro
4250         4255             4260
```

```
Gly Leu Arg Pro Ala Leu Pro Ser Arg Leu Ala Arg Ala Ser Arg
    4265                4270                4275

Gly Val Asp Leu Ala Thr Gly Pro Ser Arg Thr Pro Leu Arg Ala
    4280                4285                4290

Lys Asn Lys Val His Pro Ser Ser Thr
    4295                4300

<210> SEQ ID NO 4
<211> LENGTH: 6749
<212> TYPE: DNA
<213> ORGANISM: Homo sapiens
<220> FEATURE:
<221> NAME/KEY: modified_base
<222> LOCATION: (719)..(1277)
<223> OTHER INFORMATION: a, c, t or g
<220> FEATURE:
<221> NAME/KEY: modified_base
<222> LOCATION: (1278)..(1280)
<223> OTHER INFORMATION: a, c, t or g
<220> FEATURE:
<221> NAME/KEY: modified_base
<222> LOCATION: (1288)..(1289)
<223> OTHER INFORMATION: a, c, t or g
<220> FEATURE:
<221> NAME/KEY: modified_base
<222> LOCATION: (1638)..(1638)
<223> OTHER INFORMATION: a, c, t or g
<220> FEATURE:
<221> NAME/KEY: modified_base
<222> LOCATION: (1967)..(1967)
<223> OTHER INFORMATION: a, c, t or g
<220> FEATURE:
<221> NAME/KEY: modified_base
<222> LOCATION: (2248)..(2248)
<223> OTHER INFORMATION: a, c, t or g
<220> FEATURE:
<221> NAME/KEY: modified_base
<222> LOCATION: (2251)..(2251)
<223> OTHER INFORMATION: a, c, t or g
<220> FEATURE:
<221> NAME/KEY: modified_base
<222> LOCATION: (2254)..(2254)
<223> OTHER INFORMATION: a, c, t or g
<220> FEATURE:
<221> NAME/KEY: modified_base
<222> LOCATION: (2283)..(2283)
<223> OTHER INFORMATION: a, c, t or g
<220> FEATURE:
<221> NAME/KEY: modified_base
<222> LOCATION: (2585)..(2586)
<223> OTHER INFORMATION: a, c, t or g
<220> FEATURE:
<221> NAME/KEY: modified_base
<222> LOCATION: (2625)..(2625)
<223> OTHER INFORMATION: a, c, t or g
<220> FEATURE:
<221> NAME/KEY: modified_base
<222> LOCATION: (2932)..(2932)
<223> OTHER INFORMATION: a, c, t or g
<220> FEATURE:
<221> NAME/KEY: modified_base
<222> LOCATION: (2949)..(2949)
<223> OTHER INFORMATION: a, c, t or g
<220> FEATURE:
<221> NAME/KEY: modified_base
<222> LOCATION: (2972)..(2972)
<223> OTHER INFORMATION: a, c, t or g
<220> FEATURE:
<221> NAME/KEY: modified_base
<222> LOCATION: (2978)..(3406)
<223> OTHER INFORMATION: a, c, t or g
<220> FEATURE:
<221> NAME/KEY: modified_base
<222> LOCATION: (3419)..(3419)
<223> OTHER INFORMATION: a, c, t or g
<220> FEATURE:
```

```
<221> NAME/KEY: modified_base
<222> LOCATION: (3604)..(3604)
<223> OTHER INFORMATION: a, c, t or g
<220> FEATURE:
<221> NAME/KEY: modified_base
<222> LOCATION: (3675)..(3675)
<223> OTHER INFORMATION: a, c, t or g
<220> FEATURE:
<221> NAME/KEY: modified_base
<222> LOCATION: (3849)..(3849)
<223> OTHER INFORMATION: a, c, t or g
<220> FEATURE:
<221> NAME/KEY: modified_base
<222> LOCATION: (4132)..(4132)
<223> OTHER INFORMATION: a, c, t or g
<220> FEATURE:
<221> NAME/KEY: modified_base
<222> LOCATION: (4337)..(4337)
<223> OTHER INFORMATION: a, c, t or g
<220> FEATURE:
<221> NAME/KEY: modified_base
<222> LOCATION: (4367)..(4369)
<223> OTHER INFORMATION: a, c, t or g
<220> FEATURE:
<221> NAME/KEY: modified_base
<222> LOCATION: (4396)..(4396)
<223> OTHER INFORMATION: a, c, t or g
<220> FEATURE:
<221> NAME/KEY: modified_base
<222> LOCATION: (4404)..(4404)
<223> OTHER INFORMATION: a, c, t or g
<220> FEATURE:
<221> NAME/KEY: modified_base
<222> LOCATION: (5700)..(5702)
<223> OTHER INFORMATION: a, c, t or g
<220> FEATURE:
<221> NAME/KEY: modified_base
<222> LOCATION: (6611)..(6611)
<223> OTHER INFORMATION: a, c, t or g
<220> FEATURE:
<221> NAME/KEY: modified_base
<222> LOCATION: (6628)..(6628)
<223> OTHER INFORMATION: a, c, t or g
<220> FEATURE:
<221> NAME/KEY: modified_base
<222> LOCATION: (6637)..(6637)
<223> OTHER INFORMATION: a, c, t or g
<220> FEATURE:
<221> NAME/KEY: modified_base
<222> LOCATION: (6700)..(6733)
<223> OTHER INFORMATION: a, c, t or g

<400> SEQUENCE: 4
ggctcctgag gcgcacagcg ccgagcgcgg cgccgcgcac ccgcgcgccg gacgccagtg      60
accgcgatgg tgaactccag tcgcgtgcag cctcagcagc ccggggacgc caagcggccg     120
cccgcgcccc gcgcgccgga cccgggccgg ctgatggctg gctgcgcggc cgtgggcgcc     180
agcctcgccg ccccgggccg cctctgcgag cagcggggcc tggagatcga gatgcagcgc     240
atccggcagg cggccgcgcg ggaccccccg gccggagccg cggcctcccc ttctcctccg     300
ctctcgtcgt gctcccggca ggcgtggagc cgcgataacc ccggcttcga ggccgaggag     360
gaggaggagg aggtggaagg ggaagaaggc ggaatggtgg tggagatgga cgtagagtgg     420
cgcccgggca gccggaggtc ggccgcctcc tcggccgtga gctccgtggg cgcgcggagc     480
cgggggcttg ggggctacca cggcgcggc cacccgagcg ggaggcggcg ccggcgagag     540
gaccagggcc cgccgtgccc cagcccagtc ggcggcgggg accgctgca tcgccacctc     600 cccctggaag ggcagccgcc ccgagtggcc tgggcggaga ggctggttcg cgggctgcga     660
ggtgtaagag cgcgcgaccc gcagcggcag atgcacgaac cagaacgcc ggcgccggng     720 gcttcttaaa taaaatgata tcttttcttt tcttcattat tatttaaag gtctctgggg     780
```

```
aacaagactc atggaggaaa gcagcactaa ccgagagaaa taccttaaaa gtgttttacg    840
ggaactggtc acatacctcc tttttctcat agtcttgtgc atctgtaagt agaatatttc    900
cttgcactaa tgggaaagtt ttgaaacgat gtgaatttgt ccaaaatgtt tatccacagg    960
aacaatccct ttgtgaaggc tgctggtatg tggatgtgtg ccggttccct tggggcgttc   1020
atttggatct ttctgtgttc cagtgaccta cggcatgatg agctccaatg tgtactacta   1080
cacccggatg atgtcacagc tcttcctaga caccccgtg tccaaaacgg agaaaactaa    1140 cttttaaaact ctgtcttcca tggaagactt ctggaaggta tttggaaata actttgaaag  1200
tacctctcta tcacaagcca atgcttggtt atgcaacgat gcaggcaggg caaagcagcg   1260
gcatgagctt gaacttnnnn agatgttnnc tttcttttag ttcacagaag gctccttatt   1320
ggatgggctg tactgaaaga tgcagcccag caaccagact gaagctgaca accgaagttt   1380
catcttctat gagaacctgc tgttagggt tccacgaata cggcaactcc gagtcagaaa    1440
tggatcctgc tctatccccc aggacttgag agatgaaatt aaagagtgct atgatgtcta   1500
ctctgtcagt agtgaagata gggctccctt tgggccccga aatggaaccg cgtaagtgtc   1560
tgtgactcat tggcactcgg tgatattcat ccttgtaatt gcctcaagtg ttccactgat   1620
tgtaactgtt tgtttttngg ttttgttttt aatcagttgg atctacacaa gtgaaaaga    1680 cttgaatggt agtagccact ggggaatcat tgcaacttat agtggagctg gctattatct   1740
ggatttgtca agaacaagag aggaaacagc tgcacaagtt gctagcctca agaaaaatgt   1800
ctggctggac cgaggaacca gggcaacttt tattgacttc tcagtgtaca acgccaacat   1860
taacctgttc tgtgtggtca ggtgtgtgac tgaggacatg catccctcct atttctgtgt   1920
ggttgtacat acatcctatt ctagggttac ccagaaaaac cttttntgc aggttgttat    1980 tgttttaatt gttcttattt acatgcaggt tattggttga attcccagca acaggtggtg   2040
tgattccatc ttggcaattt cagcctttaa agctgatccg atatgtcaca acttttgatt   2100
tcttcctggc agcctgtgag attatctttt gtttctttat cttttactat gtggtggaag   2160
agatattgga aattcgcatt cacaaactac actatttcag gagtttctgg aattgtctgg   2220
atgttgtgat cgttgtggta ggtccganca ncancaccaa atttcctatt ctattctaca   2280
agnatgttaa caattaatac attggtgaag aaaaatatac tagtcatatt aaggtaagtt   2340
tcatatttct aaaacactgt aataaaatat aaatattttg cttttcagct gtcagtggta   2400
gctataggaa ttaacatata cagaacatca aatgtggagg tgctactaca gtttctggaa   2460
gatcaaaata cttcccccaa ctttgagcat ctggcatatt ggcagataca gttcaacaat   2520
atagctgctg tcacagtatt ttttgtctgg attaaggtaa tttataaatt tcatgttcta   2580
cattnnaaat aatattttct ttaaaaaaaa tgagttccac aaaancatgc gaaacaatgt   2640
tttattatac acagtcacac catttggttt atccattcat ctattgatgt cttctctctc   2700
ttacagctct tcaaattcat caattttaac aggaccatga gccagctctc gacaaccatg   2760
tctcgatgtg ccaaagacct gtttggcttt gctattatgt tcttcattat tttcctagcg   2820
tatgctcagt tggcatacct tgtctttggc actcaggtcg atgacttcag tactttccaa   2880
gagtgtatgt aagtatatat gaaattaaga agaaaaattg agtcagagta gncactgttg   2940
cgtggacant ctttggtttt gtattgtggt gntttgtntt atttttatag cttcactcaa   3000
ttccgtatca ttttgggcga tatcaacttt gcagagattg aggaagctaa tcgagttttg   3060
ggaccaattt atttcactac atttgtgttc tttatgttct tcattctttt ggtatgtaca   3120
```

```
tttatattta tagtggaggt tcaatttaaa cttcgtaaat ccttgtcttc tcttttttga    3180
ttgataattc caaattatgt ttcttccttt aattttttgcc ctccttttcat ttacaaacag  3240 aatatgtttt tggctatcat caatgatact tactctgaag tgaaatctga cttggcacag   3300
cagaaagctg aaatggaact ctcagatctt atcagaaagg taggaaaaac cttaattctc   3360
aaaaattctt ctgtttctga cataaaatga gcattgtttc acccanattt tagaatacnc   3420
taaaccaagt ctttattttt ttctctctct gatagggcta ccataaagct ttggtcaaac   3480
taaaactgaa aaaaaatacc gtggatgaca tttcagagag tctgcggcaa ggaggaggca   3540
agttaaactt tgacgaactt cgacaagatc tcaagggtg agaatcatgc ttcctgaggt    3600
tctnaaaaat tcctgcttct aaagataaat tcctggtgat aagagtattt ctagcccaag   3660
ggctcatggg aacanaggat gaatgttatc tgtatcctct ctctaatttc aggaagggcc   3720
atactgatgc agagattgag gcaatattca caaagtacga ccaagatgga gaccaagaac   3780
tgaccgaaca tgaacatcag cagatgagag acgacttgga gaaagagagg gtgggtctgg   3840
tttaggagna accggatttg atttggtacc tacaacacca cacttctgtg gggtctcagt   3900
gttctgctcc tcactcagtg accccttgtt cttcaggagg acctggatttt ggatcacagt  3960 tctttaccac gtcccatgag cagccgaagt ttccctcgaa gcctgatga ctctgaggag    4020 gatgacgatg aagatagcgg acatagctcc agaaggaggg gaagcatttc tagtggcgtt   4080
tcttacgaag agttttcaagt gtaagtataa aggaattggc agaatttgcg tngacaattt   4140
gtccctctgt actgtgtttt ccttgcagcc tggtgagacg agtggaccgg atggagcatt   4200
ccatcggcag catagtgtcc aagattacg ccgtgatcgt gaagctagag attatggagc    4260
gagccaaact gaagaggagg gaggtgctgg gaaggctgtt ggatggggtg gccgaggtca   4320
gtagtcatga gctgaanaca ccgctgctga gcatggtgtt attaatnnna atatatgttg   4380
ctgacagttg tatttnaagt attnactgac ccccaacacc agtttctttt tccctttta    4440 ggatgaaagg ctgggtcgtg acagtgaaat ccataggaa cagatggaac ggctagtacg    4500
tgaagagttg gaacgctggg aatccgatga tgcagcttcc cagatcagtc atggtttagg   4560
cacgccagtg ggactaaatg gtcaacctcg ccccagaagc tcccgcccat cttcctccca   4620
atctacagaa ggcatggaag gtgcaggtgg aaatgggagt tctaatgtcc acgtatgata   4680
tgtgtgtttc agtatgtgtg tttctaataa gtgaggaagt ggctgtcctg aattgctgta   4740
acaagcacac tatttatatg ccctgaccac cataggatgc tagtctttgt gaccgattgc   4800
taatcttctg cactttaatt tattttatat aaacttacc catggttcaa agatttttt    4860 ttctttttct catataagaa atctaggtgt aaatattgag tacagaaaaa aaatcttcat   4920
gatgtgtatt gagcggtacg cccagttgcc accatgactg agtcttctca gttgacaatg   4980
aagtagcctt ttaaagctag aaaactgtca aagggcttct gagtttcatt tccagtcaca   5040
aaaatcagta ttgttatttt tttccaagag tgtgaaggaa atggggcaa ttccttcca    5100 ctctggcata gttcatgagc ttaatacata gctttctttt aagaaaggag cctttttttt   5160
caactagctt cctggggtaa acttttctaa aagataaaat gggaaggaac tccaaactat   5220
gatagaatct gtgtgaatgg ttaagatgaa tgttaaatac tatgcttttt tgtaagttga   5280
tcgtatctga tgtctgtggg actaactgta tcacttaatt tttaccttat tttggctcta   5340
atttgaataa gctgagtaaa accaccaaag atcagttata ggataaaatg gcatctctaa   5400
ccataacaca ggagaattgg aaggagccct aagttgtcac tcagtttaat ttcttttaat   5460
ggttagttta gcctaaagat ttatctgcat attcttttc ccatgtggct ctactcattt    5520
```

| | |
|---|---:|
| gcaactgaat ttaatgttat aactcatcta gtgagaccaa cttactaaat ttttagtatg | 5580 |
| cactgaaagt ttttatccaa caattatgtt cattttaagc aaaatttaa gaaagttttg | 5640 |
| aaattcataa agcatttggt tttaaactat tttaagaata tagtactcgg tcaggtatgn | 5700 |
| nncacgcctg taatcccagc actttgggag gccgaaacag gcgaatcact tgagcccagg | 5760 |
| agttcaagac caacatgggc aatgtggcga aactccatct ctacaaaaaa tgcaaaaata | 5820 |
| aaaaatatag tactcaagta ttcttgatcc tgtgtttcaa aactagaatt tgtaatgcaa | 5880 |
| atggagctca gtctaataaa aaagaggttt tggtattaaa agttcataca ttagacagta | 5940 |
| tcagccaaaa tttgagttag caacactgtt ttctttacga gagggtctca cccaaattta | 6000 |
| tggggagaaa tctatttctc aaaaaaaaaa aatcttcttt tacagaaatg ttgagtaagg | 6060 |
| tgacattttg agcgctaata agcaaaagag catgcagtgc tgttaataa ccctcacttg | 6120 |
| gagaaccaag agaatcctgt cgtttaatgc tatattttaa tttcacaagt tgttcattta | 6180 |
| actggtagaa tgtcagtcca atctccaatg agaacatgag caaatagacc tttccaggtt | 6240 |
| gaaagtgaaa catactgggt ttctgtaagt ttttcctcat ggcttcatct ctatctttac | 6300 |
| tttctcttga atatgctaca caaagttctt tattactaca tactaaagtt tgcattccag | 6360 |
| ggatattgac tgtacatatt tatgtatatg taccatgttg ttacatgtaa acaaacttca | 6420 |
| atttgaagtg cagctattat gtggtatcca tgtgtatcga ccatgtgcca tatatcaatt | 6480 |
| atggtcacta gaaagtctct ttatgatact ttttattgta ctgttttca tttcacttgc | 6540 |
| aaaattttgc agaattcctc ctttctaccc ataaattaca tataattttt cttctttagt | 6600 |
| catggagaac nccccccat catctcancc ctattanctt tcccatgtgt actggtatta | 6660 |
| ttaaaaagac atttacatac gcaagttttt cactgacaan caagaatgtt attaatgtgt | 6720 |
| aatactgagc acntttactt cttaataaa | 6749 |

<210> SEQ ID NO 5
<211> LENGTH: 2907
<212> TYPE: DNA
<213> ORGANISM: Homo sapiens

<400> SEQUENCE: 5

| | |
|---|---:|
| atggtgaact ccagtcgcgt gcagcctcag cagcccgggg acgccaagcg gccgcccgcg | 60 |
| ccccgcgcgc cggaccccgg gccggctgatg gctggctgcg cggccgtggg cgccagcctc | 120 |
| gccgccccgg gcggcctctg cgagcagcgg ggcctggaga tcgagatgca gcgcatccgg | 180 |
| caggcggccg cgcgggaccc ccggccggga gccgcggcct ccccttctcc tccgctctcg | 240 |
| tcgtgctccc ggcaggcgtg gagccgcgat aaccccggct tcgaggccga ggaggaggag | 300 |
| gaggaggtgg aagggaaga aggcggaatg gtggtggaga tggacgtaga gtggcgcccg | 360 |
| ggcagccgga ggtcggccgc ctcctcggcc gtgagctccg tgggcgcgcg gagccggggg | 420 |
| cttgggggct accacggcgc gggccacccg agcggggagc ggcgccggcg agaggaccag | 480 |
| ggcccgccgt gccccagccc agtcggcggc ggggacccgc tgcatcgcca cctcccctg | 540 |
| gaagggcagc cgccccgagt ggcctgggcg gagaggctgg ttcgcgggct gcgaggtctc | 600 |
| tggggaacaa gactcatgga ggaaagcagc actaaccgag agaaataccct taaaagtgtt | 660 |
| ttacgggaac tggtcacata cctccttttt ctcatagtct tgtgcatctt gacctacggc | 720 |
| atgatgagct ccaatgtgta ctactacacc cggatgatgt cacagctctt cctagacacc | 780 |
| cccgtgtcca aaacgcgagaa aactaacttt aaaactctgt cttccatgga agacttctgg | 840 |

```
aagttcacag aaggctcctt attggatggg ctgtactgga agatgcagcc cagcaaccag    900
actgaagctg acaaccgaag tttcatcttc tatgagaacc tgctgttagg ggttccacga    960
atacggcaac tccgagtcag aaatggatcc tgctctatcc cccaggactt gagagatgaa   1020
attaaagagt gctatgatgt ctactctgtc agtagtgaag atagggctcc ctttgggccc   1080
cgaaatggaa ccgcttggat ctacacaagt gaaaaagact tgaatggtag tagccactgg   1140
ggaatcattg caacttatag tggagctggc tattatctgg atttgtcaag aacaagagag   1200
gaaacagctg cacaagttgc tagcctcaag aaaaatgtct ggctggaccg aggaaccagg   1260
gcaactttta ttgacttctc agtgtacaac gccaacatta acctgttctg tgtggtcagg   1320
ttattggttg aattcccagc aacaggtggt gtgattccat cttggcaatt tcagccttta   1380
aagctgatcc gatatgtcac aactttgat ttcttcctgg cagcctgtga gattatcttt   1440
tgtttcttta tcttttacta tgtggtggaa gagatattgg aaattcgcat tcacaaacta   1500
cactatttca ggagtttctg gaattgtctg gatgttgtga tcgttgtgct gtcagtggta   1560
gctataggaa ttaacatata cagaacatca aatgtggagg tgctactaca gtttctggaa   1620
gatcaaaata ctttcccaa ctttgagcat ctggcatatt ggcagataca gttcaacaat   1680
atagctgctg tcacagtatt ttttgtctgg attaagctct tcaaattcat caattttaac   1740
aggaccatga gccagctctc gacaaccatg tctcgatgtg ccaaagacct gtttggcttt   1800
gctattatgt tcttcattat tttcctagcg tatgctcagt tggcatacct tgtctttggc   1860
actcaggtcg atgacttcag tactttccaa gagtgtatct tcactcaatt ccgtatcatt   1920
ttgggcgata tcaactttgc agagattgag gaagctaatc gagttttggg accaatttat   1980
ttcactacat ttgtgttctt tatgttcttc attcttttga atatgttttt ggctatcatc   2040
aatgatactt actctgaagt gaatctgac ttggcacagc agaaagctga atggaactc   2100
tcagatctta tcagaaaggg ctaccataaa gctttggtca aactaaaact gaaaaaaat   2160
accgtggatc acatttcaga gagtctgcgg caaggaggag gcaagttaaa ctttgacgaa   2220
cttcgacaag atctcaaagg gaagggccat actgatgcag agattgaggc aatattcaca   2280
aagtacgacc aagatggaga ccaagaactg accgaacatg aacatcagca gatgagagac   2340
gacttggaga aagagaggga ggacctggat ttggatcaca gttctttacc acgtcccatg   2400
agcagccgaa gtttccctcg aagcctggat gactctgagg aggatgacga tgaagatagc   2460
ggacatagct ccagaaggag gggaagcatt tctagtggcg tttcttacga agagtttcaa   2520
gtcctggtga cgagtggga ccggatggag cattccatcg gcagcatagt gtccaagatt   2580
gacgccgtga tcgtgaagct agagattatg gagcgagcca aactgaagag gagggaggtg   2640
ctgggaaggc tgttggatgg ggtggccgag gatgaaaggc tgggtcgtga cagtgaaatc   2700
catagggaac agatggaacg gctagtacgt gaagagttgg aacgctggga atccgatgat   2760
gcagcttccc agatcagtca tggtttaggc acgccagtgg gactaaatgg tcaacctcgc   2820
cccagaagct cccgcccatc ttcctcccaa tctacagaag gcatggaagg tgcaggtgga   2880
aatgggagtt ctaatgtcca cgtatga                                      2907
```

<210> SEQ ID NO 6
<211> LENGTH: 968
<212> TYPE: PRT
<213> ORGANISM: Homo sapiens

<400> SEQUENCE: 6

Met Val Asn Ser Ser Arg Val Gln Pro Gln Gln Pro Gly Asp Ala Lys

-continued

```
  1               5                  10                 15
Arg Pro Pro Ala Pro Arg Ala Pro Asp Pro Gly Arg Leu Met Ala Gly
             20                  25                 30

Cys Ala Ala Val Gly Ala Ser Leu Ala Ala Pro Gly Gly Leu Cys Glu
             35                  40                 45

Gln Arg Gly Leu Glu Ile Glu Met Gln Arg Ile Arg Gln Ala Ala Ala
             50                  55                 60

Arg Asp Pro Pro Ala Gly Ala Ala Ser Pro Ser Pro Pro Leu Ser
65                   70                 75                 80

Ser Cys Ser Arg Gln Ala Trp Ser Arg Asp Asn Pro Gly Phe Glu Ala
                 85                  90                 95

Glu Glu Glu Glu Glu Val Glu Gly Glu Gly Gly Met Val Val
                100                 105                110

Glu Met Asp Val Glu Trp Arg Pro Gly Ser Arg Ser Ala Ala Ser
            115                 120                125

Ser Ala Val Ser Ser Val Gly Ala Arg Ser Arg Gly Leu Gly Gly Tyr
            130                 135                 140

His Gly Ala Gly His Pro Ser Gly Arg Arg Arg Arg Glu Asp Gln
145                 150                 155                160

Gly Pro Pro Cys Pro Ser Pro Val Gly Gly Asp Pro Leu His Arg
                165                 170                 175

His Leu Pro Leu Glu Gly Gln Pro Pro Arg Val Ala Trp Ala Glu Arg
            180                 185                 190

Leu Val Arg Gly Leu Arg Gly Leu Trp Gly Thr Arg Leu Met Glu Glu
            195                 200                 205

Ser Ser Thr Asn Arg Glu Lys Tyr Leu Lys Ser Val Leu Arg Glu Leu
210                 215                 220

Val Thr Tyr Leu Leu Phe Leu Ile Val Leu Cys Ile Leu Thr Tyr Gly
225                 230                 235                 240

Met Met Ser Ser Asn Val Tyr Tyr Tyr Thr Arg Met Met Ser Gln Leu
                245                 250                 255

Phe Leu Asp Thr Pro Val Ser Lys Thr Glu Lys Thr Asn Phe Lys Thr
            260                 265                 270

Leu Ser Ser Met Glu Asp Phe Trp Lys Phe Thr Glu Gly Ser Leu Leu
            275                 280                 285

Asp Gly Leu Tyr Trp Lys Met Gln Pro Ser Asn Gln Thr Glu Ala Asp
290                 295                 300

Asn Arg Ser Phe Ile Phe Tyr Glu Asn Leu Leu Leu Gly Val Pro Arg
305                 310                 315                 320

Ile Arg Gln Leu Arg Val Arg Asn Gly Ser Cys Ser Ile Pro Gln Asp
                325                 330                 335

Leu Arg Asp Glu Ile Lys Glu Cys Tyr Asp Val Tyr Ser Val Ser Ser
            340                 345                 350

Glu Asp Arg Ala Pro Phe Gly Pro Arg Asn Gly Thr Ala Trp Ile Tyr
            355                 360                 365

Thr Ser Glu Lys Asp Leu Asn Gly Ser Ser His Trp Gly Ile Ile Ala
370                 375                 380

Thr Tyr Ser Gly Ala Gly Tyr Tyr Leu Asp Leu Ser Arg Thr Arg Glu
385                 390                 395                 400

Glu Thr Ala Ala Gln Val Ala Ser Leu Lys Lys Asn Val Trp Leu Asp
                405                 410                 415

Arg Gly Thr Arg Ala Thr Phe Ile Asp Phe Ser Val Tyr Asn Ala Asn
            420                 425                 430
```

```
Ile Asn Leu Phe Cys Val Val Arg Leu Leu Glu Phe Pro Ala Thr
            435                 440                 445

Gly Gly Val Ile Pro Ser Trp Gln Phe Gln Pro Leu Lys Leu Ile Arg
        450                 455                 460

Tyr Val Thr Thr Phe Asp Phe Leu Ala Ala Cys Glu Ile Ile Phe
465                 470                 475                 480

Cys Phe Phe Ile Phe Tyr Tyr Val Glu Glu Ile Leu Glu Ile Arg
                485                 490                 495

Ile His Lys Leu His Tyr Phe Arg Ser Phe Trp Asn Cys Leu Asp Val
                500                 505                 510

Val Ile Val Val Leu Ser Val Val Ala Ile Gly Ile Asn Ile Tyr Arg
            515                 520                 525

Thr Ser Asn Val Glu Val Leu Leu Gln Phe Leu Glu Asp Gln Asn Thr
        530                 535                 540

Phe Pro Asn Phe Glu His Leu Ala Tyr Trp Gln Ile Gln Phe Asn Asn
545                 550                 555                 560

Ile Ala Ala Val Thr Val Phe Phe Val Trp Ile Lys Leu Phe Lys Phe
                565                 570                 575

Ile Asn Phe Asn Arg Thr Met Ser Gln Leu Ser Thr Thr Met Ser Arg
                580                 585                 590

Cys Ala Lys Asp Leu Phe Gly Phe Ala Ile Met Phe Phe Ile Ile Phe
                595                 600                 605

Leu Ala Tyr Ala Gln Leu Ala Tyr Leu Val Phe Gly Thr Gln Val Asp
        610                 615                 620

Asp Phe Ser Thr Phe Gln Glu Cys Ile Phe Thr Gln Phe Arg Ile Ile
625                 630                 635                 640

Leu Gly Asp Ile Asn Phe Ala Glu Ile Glu Glu Ala Asn Arg Val Leu
                645                 650                 655

Gly Pro Ile Tyr Phe Thr Thr Phe Val Phe Phe Met Phe Phe Ile Leu
        660                 665                 670

Leu Asn Met Phe Leu Ala Ile Ile Asn Asp Thr Tyr Ser Glu Val Lys
        675                 680                 685

Ser Asp Leu Ala Gln Gln Lys Ala Glu Met Glu Leu Ser Asp Leu Ile
    690                 695                 700

Arg Lys Gly Tyr His Lys Ala Leu Val Lys Leu Lys Leu Lys Lys Asn
705                 710                 715                 720

Thr Val Asp Asp Ile Ser Glu Ser Leu Arg Gln Gly Gly Gly Lys Leu
                725                 730                 735

Asn Phe Asp Glu Leu Arg Gln Asp Leu Lys Gly Lys Gly His Thr Asp
                740                 745                 750

Ala Glu Ile Glu Ala Ile Phe Thr Lys Tyr Asp Gln Asp Gly Asp Gln
            755                 760                 765

Glu Leu Thr Glu His Glu His Gln Gln Met Arg Asp Asp Leu Glu Lys
        770                 775                 780

Glu Arg Glu Asp Leu Asp Leu Asp His Ser Ser Leu Pro Arg Pro Met
785                 790                 795                 800

Ser Ser Arg Ser Phe Pro Arg Ser Leu Asp Asp Ser Glu Glu Asp Asp
                805                 810                 815

Asp Glu Asp Ser Gly His Ser Ser Arg Arg Arg Gly Ser Ile Ser Ser
                820                 825                 830

Gly Val Ser Tyr Glu Glu Phe Gln Val Leu Val Arg Arg Val Asp Arg
                835                 840                 845
```

-continued

```
Met Glu His Ser Ile Gly Ser Ile Val Ser Lys Ile Asp Ala Val Ile
    850                 855                 860

Val Lys Leu Glu Ile Met Glu Arg Ala Lys Leu Lys Arg Arg Glu Val
865                 870                 875                 880

Leu Gly Arg Leu Leu Asp Gly Val Ala Glu Asp Glu Arg Leu Gly Arg
                885                 890                 895

Asp Ser Glu Ile His Arg Glu Gln Met Glu Arg Leu Val Arg Glu Glu
                900                 905                 910

Leu Glu Arg Trp Glu Ser Asp Asp Ala Ala Ser Gln Ile Ser His Gly
            915                 920                 925

Leu Gly Thr Pro Val Gly Leu Asn Gly Gln Pro Arg Pro Arg Ser Ser
    930                 935                 940

Arg Pro Ser Ser Ser Gln Ser Thr Glu Gly Met Glu Gly Ala Gly Gly
945                 950                 955                 960

Asn Gly Ser Ser Asn Val His Val
                965
```

<210> SEQ ID NO 7
<211> LENGTH: 53522
<212> TYPE: DNA
<213> ORGANISM: Homo sapiens

<400> SEQUENCE: 7

| | | | | | |
|---|---|---|---|---|---|
| tgtaaacttt | ttgagacagc | atctcaccct | gttccccagg | ctggagtgca | gtggtgtgat | 60 |
| catggctcac | tgcagcgtca | acctcctggg | tctacttgat | ctgtaaactt | cgagggaagg | 120 |
| tgtaataaac | cctcctgcaa | tgtctttgtt | tttcaaaatc | tttgtatttc | acagtttagc | 180 |
| ttcgtgggtt | gatgttctat | tttgtttttg | tgtgtgtgtg | tgtgtgtttt | gtgttttttt | 240 |
| ttgagacaca | gtcttgctct | tgttgcccag | gctggagtgc | aatggtgtga | tcttggctca | 300 |
| ctgcaacttc | cacctcttgg | gttcaagaga | ttctcctgcc | tcagccttcc | gagtagctag | 360 |
| gattacaggc | gccgccacca | caccccgcta | attttgtatt | tttagtagag | atggggtttc | 420 |
| tccatattgg | tcaggctggt | ctcaaactcc | cgacctcagg | tgatccgccc | acctcagcct | 480 |
| cccaaaatgc | tgggattaca | ggcgtgagtc | accgcacctg | gccaatgttc | tattttttgag | 540 |
| aacacaacag | ttcataatat | attctacata | gaccatacct | gttatgtgta | gataaacaga | 600 |
| ctctttttccc | atttaacacc | ttttgcctta | ggtttatttt | tctggtatca | atactggcac | 660 |
| acttactttg | tttgcagttt | cctgtctttt | tttttttttt | tttttttttt | gagacagagt | 720 |
| ctcactctgt | cacccaggct | ggagtgaagt | ggcgggatct | cggctcactg | caacctctac | 780 |
| ctcctgggtt | catgcgattc | tcctgcctca | gcttcccgaa | tagctgagac | acaactgtg | 840 |
| tgccaccatg | cccagccaat | ttttgtattt | tagtagaca | cggggtttca | ccatactggc | 900 |
| caggatggct | caatctcttg | acctcgtgat | ccacctgcct | ccgcctccca | aagtgctggg | 960 |
| attacaggca | tgagccactg | tgcctggcct | ttttttttct | ttttgagatg | gagtctcact | 1020 |
| ctgtcaccca | ggctggagtg | cagtggggta | acctcaggtc | actgcgacct | ccgcctcccg | 1080 |
| ggttccagtg | attctcctgc | ctcagcctcc | cgagtagctg | ggattacagg | cacccaccac | 1140 |
| catgcctggc | taattttgt | attttagta | gagacgggt | tttgccacgt | tggccaggtt | 1200 |
| ggtctcgaac | tcttggcctc | atgtgacccg | cctgccttgg | cctcccaaag | tgctgggatt | 1260 |
| acaggtgtga | gccactgtgc | ctggcctggc | tttcttgttt | cttttctcct | cttctagttt | 1320 |
| cccccttttta | ggctaacaat | tattcactgt | taataaaaac | cctcaggtct | gtattttatc | 1380 |
| aagaaacatt | tccctcacgt | cttcttccct | gaaccaaaca | agatctctgg | cacattttat | 1440 |

```
ttgctctgtc tcaccacatg gattttgttt ttttgtttct ttgttttttg agatggagtc    1500
tcactcttgt tgcccaggct ggagtgccat ggcacaatct cagctcactg caacctccac    1560
ctcctgggtt caagcgattc tcctgtctca gcctcctgag tagctgggat tacaggcgcg    1620
tggcaccacc cccagctaat ttttgtattt ttagtagaga cggggtttca ccatgttggt    1680
caggctggtc tcgaactcct gaccttgtga tctgcccacc ttggcctccc aaagtgctgg    1740
gattacagga tgagccacc acgcccggcc cccatggttt ttcaaatagt ttagaatttc    1800
atttccaggt aactaatttg cttctttaaa catatgtctt ttctatttaa gaaatccttt    1860
ctaaacaatt gcattttatt ccacaaccgc cttcaaacaa tcattgagac ttggttaatc    1920
tgttttgctc atttggcagc agtttcttgt ggctgtttct tccctccact ggagtccttg    1980
aatcttaagt ctgtcatttg actgcaatta aaagctgggt ttggaataca atcgcagcct    2040
taccatccac ctgctgtgtg acctggtaaa tttctttttt ttttttttgag acggagtctt    2100 gctctgttgc ccaggctgga gtgcagtggc acaacctctg cctcccaggt tcaagcgatt    2160
ctactgcctc aggctcccta gtagctggga ttataggtgc ctgccaccat gcccagctga    2220
tttttgtatt tttagtagag atgaggtttc accatgttgg ctaggctggt ctcgaacttc    2280
tgatcttgtg atctgcccgc ctcggcctcc caaagtgctg ggattacagg catgagccac    2340
cactcccagc cagttctttt tttcttttt ccattttttt ttttttcgag acaggatctt    2400
actcttttgc ccaggcggga gtgcagtggc acaatcacgg ctcagcgcag ccactgccta    2460
ctgggctcac acgctcctcc ggcctcagcc tctcgagtac ctgggactac aagcgtgagc    2520
cagtttggct aattttggct aattttttgta gaaacggggt ctcgccatgt tggccaggct    2580
ggtctccaac tcctggactc aagggatcca ccttcctccc cctctcaaag ttctgggatt    2640
accggagtga gccactgtgc cctgctggca aatttcttaa actgtctgtg cctcagtgac    2700
ctcatttaat aaagggaata attgtagcac actttttcta gagctgtgaa gattcaatgg    2760
aataaataag gcaataaatg aatggatggg gaatgaagga tgtgggtttc ctccctcttg    2820
tctttcaata agctctcacc atcaacctcc cattgcctgt tctctctctt ccccctctct    2880
ccctctgtct ctctctcagc caggaaacct ggggtaggga ggcttggagc cagcgggtgc    2940
gtcgggaggc tgcgggtact gactcgggcc gcgcacggag atcgcgggag aaggatccac    3000
aaccgcggaa gaaggatcag ggtggagcct gtggctgctg caggaggagg aacccgccgc    3060
ctggcccaca ccacaggaga agggcggagc agatggcacc ctgcccaccg cttcccgccc    3120 acgcactttta gcctgcagcg gggcggagcg tgaaaaatag ctcgtgctcc tcggccgact    3180
ctgcagtgcg acggcggtgc ttccagacgc tccgccccac gtcgcatgcg ccccgggaac    3240 gcgtggggc gagcttccgg aggccccgcc ctgctgccga ccctgtggag cggagggtga    3300
agcctccgga tgccagtccc tcatcgctgg cccggtcgcg ctgtggcgaa ggggcggag    3360 cctgcacccg ccccgccccc cctcgccccg tccgccccgc gccgcgcggg gaggaggagg    3420
aggagccgcg gcgggcccg cactgcagcg ccagcgtccg agcgggcggc cgagctcccg    3480
gagcggcctg gccccgagcc ccgagcgggc gtcgctcagc agcaggtcgc ggccgcagcc    3540
ccatccagcc cgcgcccgcc atgccgtccg cgggccccgc ctgagctgcg gcctccgcgc    3600
gcgggcgggc ctgggacgg cggggccatg cgcgcgctgc cctaacgatg ccgcccgccg    3660
cgcccgcccg cctggcgctg gcctgggcc tgggcctgtg gctcggggcg ctggcggggg    3720 gccccggggcg cggctgcggg ccctgcgagc ccccctgcct ctgcggccca gcgcccggcg    3780
```

```
ccgcctgccg cgtcaactgc tcgggccgcg ggctgcggac gctcggtccc gcgctgcgca    3840
tccccgcgga cgccacagcg ctgtgagtag cgggcccagc ggcacccggg agaggccgcg    3900
ggacgggcgg gcgtgggcgg gttccctggc ccgggacggg aagcaggacg cgggccagga    3960
cgctcccagg ggcgaggctc cggcgcggca cggcgggccc tgctaaataa ggaacgcctg    4020
gagccgcggt tggcacggcc ccggggagcc gaaaaacccc gggtctggag acagacgtcc    4080
cacccggggg ctctgcagac gccagcgggg cggggcgcg gaggccgcgc tcagctggga     4140
ggacaaacag tcgctaattg gagaggaatt gggatgcggc ctggggctgc ggggtacccg    4200
gagaggtggg gatggctgta gggggcggca gggaagagtt ccaggaggtg tctggaaaag    4260
gatttgatgg atgtgcaaga attgggctga tgcttaggaa ggggcgatga ggtgggtcca    4320
gaagaagggg ggtgaacggt gtgagcaaag accgtgaggc tggaggctgg ccacgggagg    4380
tgtgaggggt aggggcaggg tgggaggtgg gctcgcgggt gggctggggt catgaagggc    4440
ctcaggcgct ctgctattgg gttccaaggc tatcctgaga acaggggtga gggggattg     4500 ccgtgggggg ttaaagcctt gtcatgttcg ctttcgggag ataaaaacaa caggtggcct    4560
ttatggagac gctgcccaga gccaggtctg tgccaggctc ctgttggggg tcgtcatgcg    4620
gaatcctgac tctgaccatc cgaggcatag ggaccgtgga gatttgcatt tcacagatga    4680
ggaaacaggt ttggagaggt gacacgacct gtcccaggca tcacagccgg gatgtgcata    4740
gcaggggttt ggaactatga ggtgcccagg acccagggtt ggattgaaaa gggcggaggg    4800
gactaagata agcagacagt tgtccccagc gctggggaga gtcttgggac cagtctgatg    4860
ccttgtattt cccaggctcc aggctcctcg ccgggacagt gtctccttgg gtgcgtgctg    4920
gatccctggg ggacgtggca catccccagg cttgctaaac attgggtggg ttctggcatt    4980
tggttttgta acgtttctgg gtcactcccg cctgtggcca cccttcctta ggggagccgt    5040
gtgtccttgg ggctttgctg ggtggtctcg agggtgggag aagaatgggt tctcctggac    5100
caatggagcc cgtgccctc ggggccacat tgctcctgcg ctccctgact gcggacgcgt     5160
gtgtctcgcg gctgtctctg tggagatggc ctcctcctgc ctggcaacag cacccacaga    5220
attgcatcag acctacccca cccgttgttt gtgatgctgt agctgagggc tcctctgtct    5280
gccaggccgg tcactgggga ctctgtccag ggcctggtgg ttcctgcttc ccagcacctg    5340
atggtgtcca tgagagcagc ccctcaggag cgtccggga gagaagggcg ctggtggctg     5400
ctgagcggag agcaaggccc gtgttctcca ggcccttggc acagcagtgg agcccccgcc    5460
cctgccttgt gttgtcctct taggctctgg tcctggggtt tggaggaggg ggaccctggg    5520
agttggtggc ctgtcccagc ctgagctggc aagattccga atgccaggcc ccccaagtgt    5580
gcaacagggc acagggtgac ctcatgtggg caggtgggtg ctgttctgta cacacctggg    5640
gccgccgctg ggagagttct ggaaggtggg gtgagggac ccatggcaaa ctagggcctt     5700
aggaaggatg tgaaggccct ggctggcccc ccaggccacc ctctgtgctg tgggcagcc     5760 cagccatttt gctgtctacc ctgcaaactc ctcctcgggg agacggctgg gttttcccca    5820
gggaagaggg gtcaagctgg gagaggtgaa ggacacagat cacagctgct ggcaggtgtt    5880
caagggtcca agagcgttgc tgtctgggtg tcaccagtag ccttcctggg gggctcacgc    5940
aggtgcctct ccacttgtgg ctccctggct gctgaagctc agcagggaca gctgtgtcca    6000
gttccaggtg gaggacagcc ggggcttctg aggccacagc ctgccttggg ttaatgatgc    6060
tgccgagagg tggtggcttt tggaaaagat ggcgtactgc aaaacgtgct gctctgcgtg    6120
gctcgaagct tcgtggggag acgtgggcag agccgtggct gactcacaga ccccccaccc    6180
```

```
cagagcctgc cctgccctcc ctgccccgac ccttctccct cctgacccat gtgttttttt    6240
tttttttttt ttttttgag acagagttca ctcttgttgc caaggctgga gtgcaatggc     6300
acgatctcgg ctcatggcaa cctccgcctc ctgggttcaa gcgcttttc ctgcctcagc     6360 ctcccgagta gctgggatta caggcgtgca ccaccatgcc tggctaattt tgtattttta    6420
gtagagacag ggtttctcca tattggtcag gctggtcttg aactcctgac ctcagatgat    6480
ccgcccgcct cggcctccca agtgctggg attacaggca tgagccacca cgcccagccc    6540
tgacccatgt tttgaaccaa attccagcca ccctttatc tgcaagcatt ttggagggca    6600
tcgcaatact gcagacccac ctaacacaac agacagttcc ttcatgccac cgaaggcctg    6660
gtgtgttcac attttggtt taatagtttg aattaagagc caaataaggt ccacacactg     6720
caattagttg atgtcttttt tttttctttt tttttttttt ttttgagacg gagtcttgct    6780
cttgtctcca ggccgcagtg cagtggcatg atctcagctc accgcaacct ccgactccct    6840
ggttcaagcg attctcctgc ctcagcctcc gagtacctg gtagctgggt ttacaggcat     6900
gcaccaccgt gcccagctaa ttttgtatt tttagtagag acggggtttt actgtgttgg     6960
ccaggatggt ctcgatctcc tgacctcgtg atctgcccac ctcggcctcc caaagtgctg    7020
ggattacagg cgtgagccac cgcacccggc caatgtcttt taaaaatata ctttttttt    7080 tttttttga cggagtttt cgctcttgtt gcccaggctg gagtgcagtg gcgcgatctc      7140
acctcacggc aacctccgcc tcccgggttc aagtgattct cctgcctcag cctctccagt    7200
agctgggatt acaggcatgt gccaccatgc ctggctaatt ttgtattttt aggagagacg    7260
gggtttctcc acgttggtca ggctggtctc aaactcctga cctcaggtga tccgcctgcc    7320
ttggcctccc aaagtgttgg gattacaggt gtgagccaac gcgccagac aaaaatatat     7380 gtgtgtcttt aaggctggtc aagcaaagca gtaggactgg agaaagaatg aagaattcta    7440
cctggctgtg atcaattcgt tgtgaacacc actgtgcttg gaccagctag ctgatgtctt    7500 ttgtttttgtt ttgtttgaga cggagtctgg ctctgtcacc caggctggag acaatggtg    7560 tgatctcggc tcactgcagc ctccatctcc cgggttcaag cgattctcct gcctcagcct    7620
cctgagtagc tgggattaga ggcgcgcgcc accacgcccg gctaattttt aaaaatattt    7680
ttagtagaga tggggtttca ccatgttggt caggctggtc ttgaactctt ggccttaggt    7740
gatctgcttg cctcggcctc ccaaagtgct gggattacag gtgtgagtga tgtattttat    7800
ttatttattt atttatttat tttattatt tgagatggag tctcactctg ttgcccaggc     7860
tggagtgcag cagtgccatc tcagctcact gcaagctccg cctcctgggt tcacgccatt    7920
ctcctgcctc agcctcctga gtagcctgga ctggtgcccg ccaccatgcc cagctaattt    7980
tttgtatttt tagtagagac ggggtttcac cgtgttagcc aggatggtct ggatctcctg    8040
acctcgtgat cctcccgcct cagcctccca agtgctggg attacaggct gagccaccg     8100 cctgtctttt aaatgtccga tgatgtctag gagcttccct tcctctcttt ttccttgtgc    8160
aatttgttga agaaactggc tcctgcagcc tggatttctc gctgtgtctt gggggtgcca    8220
cctccatggt gtcacctccg tggtgctgtg agtgtgtgct ttgtgtttct tgtaaattgg    8280
tcgttggagc cgacatccca ttgtcccaga ggttgtcctg gctggactg gcctaggtgt     8340 agatgtcatc agctcagggc ccctgctct aaaggccact tctggtgctg gttgccactc     8400
accctggctg ggggtcacct gggtctgctg ctgtctcgca aatgctgggg tccaggactg    8460
ggcacatcga gggacttggt aggtgcttgg ttcactgatg taaaatatag gagcacccgg    8520
```

```
ggccttgccc tttcccacct gcatccctga atgacaggag agtgtgggag agtgtaggga   8580
cagcaggcgc agaccccggg gcccctgcct gggattggcg tcggggaaga caggcattct   8640
ggagcgaccc ctaggcctga tgccttagag cgcaactgcc agagacacag cttccttggg   8700
gggctggcca ggccacggag gggccctggc tcccatttct ggtccctgga tcctgagagc   8760
gaggactagg gattgtcacc aaggcctcca tgagccctca gcagaaggag gccacccctc   8820
gagggctccg ttatcactgg agcccgcgtt caaccaacac gcagatgatt ctccaaggac   8880
agagatggat gatgggagg gggctggcct ggaaggaccc ccagtgcagg tgacattgaa    8940
gccaggtttc aaagctccca cagggagctg cccagagaga gtccccaagg ggcaaggtga   9000
ctcggggggca ggggtagggc ctctgtcagg agagcctagg agaggcctgt gtcttctagg  9060
aagagccctg gcagccgagc ggaggcagtg gtgaggacct gcatcctgca tgtccagctg   9120
gcctcacccg gggtccctga gccgggtctt acgtggctcc cgcactcggg cgttcagaac   9180
gtgcctgcgt gagaaacggt agtttctta ttagacgcgg atgcaaactc gccaaacttg   9240
tggacaaaaa tgtggacaag aagtcacacg ctcactcctg tacgcgattg ccggcagggg   9300
tgggggaagg gatggggagg ctttggttgt gtctgcagca gttgggaatg tggggcaccc   9360
gagctcccac tgcagaggcg actgtggaga cagagagcac ctgcaggtca tccatgcagt   9420
atcggcttgc atccagatca tacagggaac actatgattc aacaacagac agggaccccg   9480
tttaaacatg gacaagggt cactcacgcc tggaatccca gcagtttggg aggccagggt   9540
gggtggatcg cttgagccca ggagtttgac accagcctgg gcaacagggt gagaccccgg   9600
tctctaaaaa ataaaagaac attggccggg cgtggtggta tgcatctgtg gtcccagcta   9660
ttcaggagac tgaggtggga catcacttga gccgaggagg tcaaggctgc agtgagctgt   9720
gatcacacca ctgcactcca ggctgggtca cagagcaaga ccctgtctca aaaaaaaaa    9780
aaaaaaaaa aaaaaatcac aggatctgaa cagagatttc tccaaagaag acgcacagat   9840
ggccaacagc gtgtgagaag atggtcggcc tcattagtca tgagggaaac gtaaatcaaa   9900
accactgtcc agccgggcgc ggtgcctcac gcctgtaatc ccagcacttt aggagagcag   9960
atggcttgag gccaggagtt tgaggccagc ctggcaaca tagcgagacc aataaataga   10020
tattagtggt ggcgcctgta gtcccagcta gttgggaggc tgaggggga ggattccctg    10080
agtctatgag gttgagactg cagttagctg tgatggtgcc actgcactcc agcctgggcg   10140
actaggaaac ggtcttttaaa aaaaaaaaaa aaaacaggg tgggcgcggt ggttcacgcc    10200
tgtaatctca gcactttggg aggccaaggt ggggggatca caaggtcagg agtttgtgac   10260
cagcctgacc aacatggtga aaccccgttc tactaaaaat acaaaaatta gcgaggtgtg   10320
gtcgtgggcg cctgtaatcc cagctaatta ggaggctgag gcaggagaat cacttgaacc   10380
cgggaggcgg aggttgcagt gagccaatat cacaccactg cactctagcc tggtcaacag   10440
agcgagactc tgtctcaaaa aaaaaaaatg ctgagcgtgg tggcgcatgc ctgtagtctc   10500
agctactttg ggggctgagg caggagatc gcttgaacct gggaggcaga ggtcgcagtg   10560
aggcaagatt gcaccattgc actccagcct gggagacaga gtgaaactct gtctcaaaaa   10620
gaaaaggtct aggaagagtc cgcacccctct ccccgcggtg gccacgccgg gctccgcgct   10680
gagccctctg tgttcttgtc tctccatacc tcatcacggc accgcagggt tgcagccact   10740
cctggtctca ttttacacac caggaaattg aggctctttg agaagccgtg gtgatgattt   10800
catcagcatg ctctggggca gacccctgca gccgcacagg gtgcctgggg cccacactag   10860
tgccctggtt tatagacaga cagaggtggc agtggcgcctt ccgagtcggg ctgcgatgtg   10920
```

```
cttgcactcc ccgaggggct gagggccct gcgcccaggt gcagctgctt gggtgctgcc    10980
agcccctccc acctctccct ccctgccagc cctcccacc tctccctccc tgccagcccc    11040
tcccacctct ccctccctgc cagcccctcc cacctctccc tcctgccag ccctcccac     11100 ctctccctcc ctgccagccc ctcccacctc tccctccctg ccagcccctc ccacctctcc   11160
ctccctgcca gcccctccca cctctccctc cctccagccc ctcccacctc tccctccctg   11220
ccagcccctc ccacctctcc ctccctgcca gcccctccca cctctccctc cctgccagcc   11280
cctcccacct ctccctccct gccagcccct cccacctctc cctccctgcc agcccctccc   11340
acctctccct cctgccagc ccctcccacc tctccctccc tggctcatcc ctgctgtgtc    11400
ccttctctct agtttcctgt tcagtttcag gaaggaggct gggaacccag atgtagggaa   11460
tttgcgcccc ggagtcagac ctgggttcac gtcccagcgc ctccacctct ggtgtgacct   11520
tggtccagtc tctcagcctc agtttcctca cctgtaaagt gggctccatg attagatgca   11580
ccctgcaggg cagtgtagca gtgacctggc tcagccactg gcagcccaa caatcatacc    11640 ttgttaaagt agctctgtcg gttccctcag gggttccggg ggcccattcc cctgtcctcc   11700
atgcactgtg agacctgccc tgccacagag cagagtgtaa cagcctgagg gtgagagcca   11760
gacactgtgc ctgtgcttag accagacact ggacgacggg agccagtgca gcctgggcgg   11820
gtggactcct atggacccct cagcacccag cctcggtgcc ttcagcgcag gccgcgtgg    11880 ctgtggggggc tcacaagacc cggcccactc ctgcttgtgc ctacatctgg gtgtttgccc   11940
attggtgcct tttgacgcgt tctggtgtgt gtgagacgtg cggggctggg aagtgttggc   12000
agagccgcga gtaccgtcct cactcctttt gttcttttga cgtaagctgg cgagtggcac   12060
tgcctgagtt ccgctcagtg cccgccctga tgtgcggacc ccgctgcatt cttgctgtta   12120
ggtggtggcg gtgtgcgctg tcgctggtgg gcaccgagag tctttgggag cttgggag     12180 gttgtgccaa gcctgagcct cgacgtcccc cttcccggct ttctgttggc tcttctgagg   12240
ccagggcatc tctatgaggg cctcctgctg gagccgtctc tgtggatctc ctctgccatc   12300
ctggcccatg agtgggtgat gcgctggcca ccatctggtg acagtggccg ggcaccgctg   12360
ccaaatgtgg gtcccgcatc tgcaagcccc tccctgggtc ccctagggta tggggtggtt   12420
ctgccactgc cctcgctccc ccaccttggg gtgcctctcc ccctgctcgt ggggagacc    12480 ctgcctggga tctgctttcc agcaaggaat atactttgga gggagacaca catgttcttt   12540
tctggagctc tgcagtggcc acggcagccc agcccgccaa gcaccctgga atgaaaacat   12600
cccgctgctg tctgggcctg gcctgcactc tgctgcctgc gctccagctg ctgaggccg    12660 ggcacgtctg cgggcacagc agcggggcg ccacagtctc cctgcagagt gagcgcagct    12720
ggaaaatgca gctcacgccc tttcccagaa cacctcgctc ttcatggctt ggcagctgtc   12780
cttgcctagg ggccagggtg cccaggcact ggtggcagga aagggctac atctgggggct   12840 gaggcgggct gggtccttttt ctccctgcag ctcccgaggc cagccctgg cccagcctgg    12900 cattcctgac cttagcagcg ccatgatctg aagacaggct ggcttctgtg aggccacctc   12960
agaaagggct ttgtgcccag gcagaggcgg aagccagctc ttccttctgg ttgaggcagg   13020
aatgaggcca gcgctgggca agcccatgcc cagggaacgt cacagctgtg ggagtacagg   13080
ggctccgggt tctgagcccg tccactgtgc atcgtggccc tggcctcagg atggctcgta   13140
ccatcattgg ctgtgcccac agccgagtgg gtgatgggat tccggctgcc ccgctggatc   13200
tgtgctgctg ccctctccag ggcactgctg tgcccgcaca gccgggcgca gatggccagt   13260
```

```
ttgcttgccc ccccccccac catcctcttc ctaccttggc ttcctccatt gacacactgg   13320
accctgctgg ctgcccgggg aggtgtttgg gggatggtgt tgggggagga ggagggcccc   13380
ttgagcctca gtgtgcccat caggagcgta aggtcagtgc agcacctgcc cacacaggct   13440
gtgaagggtg ggagtggaga gggatgcaag ggggtcacaa cgcctggctc catgtcagct   13500
gcgtgcaggg gcaccaggag ccggccctca ttctccccdtt gaactggaag ggtggccccg   13560
accccagcgg caggtagcat acgtatgaag cgctctcctt cctacacccc acaggtgggc   13620
tcgtctccag acggccctt ttgagctggc tgtgtttttc catctgtgta ggcaaggaca   13680
tcgcagactc ccctttctca tctccctcgt tcagcctccg aggccggagt ctccatccct   13740
gtgcctgcct gtgggtcccg ggaggacctg aggctgccca tgtcacccccc ggcatctcat   13800
cctggggaca gttcagccgt gggagggatc tgtaaggaca gaatgccgct gagcctgggg   13860
ctcccccagct agtctcacac cccgtgtctg ggacccagag accctcgtgc agggctctgt   13920
tgcttggggc ctggcagcct cgtcctgtat cagaggctgc cacccccacc cctcgtgggg   13980
ccagggttgt ggccggcctc cctggccctc cccatggaag tggtaggcgg agccagcagc   14040
catctgccca gcccggggct gcactgtttt ttttcaaatg agcaccgtcc caaactgcag   14100
cccgttaatt taaacaggat catttccggc cctggaagcc gcctcactct ccttaaaatag  14160
aaaggagcac agcgcagagg gaaacagatg aggtcatggc tcggctggcc cagcgaggaa   14220
ggggccgcag tggggtggc actgccgcct gtccctgtc ctctccagcg cccacactgc   14280
agcccatttc ctcaccctgg gcctgctctc gggagggacg ggcctggggg tcctcttgct   14340
gggcggaggg gaaccagctc ctccaggaga ggacggggcc tggcagggg catgggcct   14400
ccctgggtct ggcgtcctgt cctgcccctg ccgagggagg agcggttaca taagctccgc   14460
aggcggcccc tccgagccgg tccccccagc ccagtttcca gtgaggcggc cagcgcgggc   14520
gggggtgccg ggcctggcgc acacccgctg ctgaccacac gtgtctggaa tgtgcagatg   14580
tttctttggg ggctccgtcc ggccccaga ccccactcag catctggtct ggggagtggg   14640
cgcctggggc actcagctct gagtgtgaga ctctgaggca ggtctggttt gtctggggcc   14700
attccctctg ctgtggattg ggagggcccc gggagctgcc ccacacccag ggaagttctc   14760
ctcagtccca ctgttgcatt ccccgacccc ggctcccccg gcccaggagc gcctgtgggg   14820
cagaaggccc agcccccaaga cttcccggcc ctgccagcct caggcttcac ccaccctcgc   14880
gccaactgtg ggcagagccc aggggagggg caggagagcc agcgcctggc tgggaacacc   14940
cctgagggc cgaggctcca gggcgagggg gcccgacctg gggttcacac gcccgggtgg   15000
cgggcagacc cgctgcagca tgagacacgt gtcagctacc tcgggccggc aggctggccc   15060
tgctgcccac agcccctgga cgtggcccca cctgtgacgg gtgtggaggg gcagcctcca   15120
ggcctggcca caccctctgc tgttgctgct cctgctccag gattggcaag ggtgctggga   15180
aggggtgaag accgtactg tggccacaca cctgggactt ccttctccac ccagtggtgc   15240
cccagcagcc gctaaggagc ccgctgggtc ccacgctagg atggtcctaa ctcctcccgc   15300
cttccagatc ggacgctcgg cgctggggac cccttgtgtc ccggggctgg ggcaccgtcc   15360
tgcccccatg ggggtgtact cctcccgaca agcttggctt cagcttccct gggagcacat   15420
cctggccctc gggcacccat caggctgtcc ctgtgcacct ggctcccacc cttccagctc   15480
atagcaggaa ctggggtgag gagtgcgtgg ggcagcaagg gcctgggacc ccagaggacc   15540
ctgcactctg ctctgtgctc ttgcctgggc ttagggccgc tcgtggtcc tgctgccaga   15600
tgcctgggcc ctgctgtgtc ccccatcctt gcagggaacc agaacgtggg ggcagggcat   15660
```

```
cagacagcgg cgatgatgtc acctggcggg tgcagaggaa gcccgagggg cggggtgggg    15720
gggctggcgc gaggctgcct ggctaggcct tggcgttccc ccagaacggc gatggcaaaa    15780
gcagatggag acgtgaaaaa gtacgggagc aagcgaggtg aggactccac ggggacccct    15840
gtgctgttcc ctgtccctga agcccacacc tgagtcctgc ccagggcaga tgcttccaca    15900 cccaggggc acctgagtcc tacccagggc agacgcttcc acaccctggg ggctggggga     15960
ctgcacctgc ctcctgtctg ggcccagct tcattccact gccctgggcc ctggggagctc    16020 ggccgagcgg ggtccccaag accttgctgc atttctgggc cttgggctgg ggtgagggcc    16080
gggagaagga gccagcctgg agcctggcac gcagggagtg catggccaga accggtgaca    16140
ggcagggctg cctgctggcg tggaagaagt gtccatggca cccccaggcc tggttcacag    16200
tgggatgggc ggggagccgg ggggctctgg ggtcctcggc tgacctgccc ccaccctgc     16260 cctggcttgt cagctcccag cagcagccac tcttgatgga ttttccagaa aatgaggtgt    16320
ggccaaacat cttcaggctt ttccttcttt cctttctccc gtggcctggg tgggagctgc    16380
tccccatgcc tgggggcagg tgcgagagcc tgtgcccctc cctgggcag tttcacagct     16440 gtgtcccttc caggggggcct gcctgtgttc accgtggcct ctgcagcacc tctcgcccct    16500
tagggctcct gcgcctcggg tcccggtgcc tcatttctcc ctaaagcatt ggttctgctg    16560
ccgccgcagc cgctggaaag tccctcctca ggtctaactg cagttcctca cggcacagtg    16620
ttccccctcg ggcatggtgc ttgggcagtg ggtgtgagtc cagctgcctc accctgtctc    16680
gagaatggcc tcttgctggt ctcccagcca ccacctgtc ccaccccacg gcggggatgg     16740
tgtggatgcc tagcagcgcg gctgtgggcc cacccatcct tatgggcagt ggggagcacc    16800
tcagcccgtg tccctacctt ggtgtagagg aggggacggc agagaagcag ggttcagtta    16860
ggggggaagt ggtggccctg ccggaggggc cgttccctgt gtgcctggcc cccagatcct    16920
ctcccctccc ggagcccagg gcacaggcat aggctctctg agtgtcccac agccctgggg    16980
ggaagggaac tgcaccccca accgtgccct ccatccgcag atggaacgag aagctccggg    17040
agccagtgcc cagcgtctca tctgtctggg cacccagccc aggtgagggc ctggctccac    17100
cgtccgtggc tggtgctgct tcctggcacg gagaaggcct cggctgctct gtcccctcag    17160
ctggggtggc ctctggtccc cttctttgtt ggttcccttc tcaagctctt gccctggccc    17220
cgggccccac cgggcagcct gtgtgtgcgt ctctcctgcg ccgggtaggc tcctgtggga    17280
gcggagctcc ggtgggagga gcagggctgg aggctggcag gggctgggcg ggtgttcagg    17340
gatgcaggcc gccccggctt ggggctggct gccgggtggt cattgctggg aagagcaagt    17400
ctaggcggag gcacctgctg ggtcactcgt ggggagggtg acacctgggg aagtagaggc    17460
ccgtggcagg aggtgaggcc tcgggtcct ggggagcagg gggtggtgt gcagacctgc      17520 ggagccatag tcctgtgcca ggagcactac tgggagtgcg tgggaccagg aggggtgccc    17580
agggtgggcg gcagagtgac ccccgaggtg cttgaggccg aggggaggtg gagttctcgg    17640
tttgccccag ctctctgtct actcacctcc gcatcaccag ctccaggacc tggtttgtaa    17700
ctcgggcagc tctgaaaaga gagacatgct gccgccctgt ggtttctgtt gcttttctt    17760 cactgactac tgacatggga tgttttcct acggctgtga ccaattgtgc ttcttctaat    17820
tgcctggttt ttctttttt gtttttggag ttttctcttt cttcctcccc tccctctcac    17880
cctccatcct ttttttttt attttttatt tttgagatgg agcttcactc ttgcaggatg    17940
gggtgctgga gtgcagggggt gcgatctcag ctcactgcaa cctctgcctc gcgggttcaa    18000
```

```
gtgattctcc tgcctaagcc tcctgagtag ctggaattac aggtgcttgc caccacgccc    18060
gactaattct gtagttttgg tagagacagg gtgtctccgt gttggtcggt ctggtcttga    18120
actcctgacc tcaggtgatg cgcccgcctc agcctcccaa agtgctggga ttacaggcag    18180
gagccattgc acccggctct ttccccttct ccttttcttc tctctctcct cccttcttt     18240
cttttctttt ctttttttt tctttgaga tggagtctcg ctctgtcacc aggctggatt     18300
gcagtggcgt gatcttggct cactgcaacc ttcgcctccc gggttcacgt gattctcctg    18360
cctcagcctc ctgagtggct ggcactacag gctcccgccg ccatgcccgg ctaattttg     18420
cattttagt agagacaggg tttcaccctg ttggccagga tggtctcgat ctcttgatct     18480
catgatccac ccaccttggc ctcccaaagt tctggcatta caggagtgag ccaccgtgcc    18540
cggccatctt tctttccttg ctttctcttt gttttctttc gagaccgggt cttgctctgt    18600
cgcccaggct ggactgcagt ggcacaatca tagctcactg cagcctcgac ttccctggct    18660
caagcgatcc ttcctcctca gcccccgag tagctggaac tacagttaca cactaccatg     18720
cctggctgat tcttttttc cttgtagaga tggggtcttg ctatgctgtc catcctggtc     18780
tcaaactcct ggccttccca aagcactggg tttacaggca taagccacca cacccagttt    18840
ccttttcttc ttttttaactg gaatagttga cgttttcttt attagctgtg tgtcaggagg    18900
gtatttttgg cctttagtat gtcgtgtaag ttgctagtgc ttttctgaga ttgtagtttg    18960
ttttctaatt ttatttatat tttgcgtaga agttgtgtat tttagatgga gttaggtcgg    19020
ctggtctttg atgttttatt tattaattat gtatgtattt atttatttt gaggtagagt     19080
ctcgccgttt cacccaggct ggagtacagt gatgcgatct cagctccctg tagccttgac    19140
ctctctgggc tcaagtgatt tttctctcct ctacctcccg agtacttggg accccaggcg    19200
catgccgcca tgcctggcta atgtgtattt tttgtagata cggggtctca ctgtgttgcc    19260
cagggtggtt tcaaaatcct gggcccaggc gatccttccg tctcagctcc cacggtgctg    19320
tgttaccggc gtgtgcccag tgcctggccg tcttggaggt cttgtttctc tgggtttatg    19380
cctcgaggtg gcgcctgctc cctgtgctc cctggtagcc tggtagtgag cctgcttctc     19440
acacagtcat acctggttgt ggtcccacag tgggaccacc ctgttgggtt cagaacagga    19500
gatgggggcc cctcgagtct gtgtgggggc tgtggacagg gttgggagac cttggctctg    19560
tgggggactg tggacagggg atggggggcc ttggccctgc gtgggatggg ttggggtcc     19620
gtgcccttcc tggccctggg tggacaggtc catgtggcac tcggcatagg gctgagatgg    19680
gtgcagaggg ctgaggcccc caggcctctc ctggcttggt ttccccagat gagtgttcat    19740
ttgggtcttc catcagaaag tcccctcctg acctctggga gtggggagct caagggtggg    19800
aggccatagc ttgggatgc tggcaatgtg tgggatgggc caggaagg cctctggcct       19860
actagggct ctggccctga cccacggcca ctcactcctc agagacgtct cccacaacct     19920
gctccgggcg ctgacgttg ggctcctggc gaacctctcg cgctggcag agctgtgagt     19980
gtcccccagt cgtgccagca tgcggggctc actccgggtg ggctggcggc accgcctctt    20040
gctgctcagc tgtgggggct tccatcagct ttgccgaatc cccgtctct tccagggata    20100
taagcaacaa caagatttct acgttagaag aaggaatatt tgctaattta tttaatttaa   20160
gtgaaatgta agttgtggtt ctttgggtgg ggtcctggct ggaccccagg cccccaatat    20220
cccttctgcc ctcccagttg gtccgtgtcc ccttccaggc ttgagaccag atcctggggg    20280
cagttcactg cctgcttgga gcccccagt gccggcttgg ttggggcagg ggaggcggtg     20340
ctgtcagggt ggctccaggg cctggttgcc agtgggggc tggcatagac ccttcccacc    20400
```

```
agacctggtc cccaacacct gccctgccc tgcagaaacc tgagtgggaa cccgtttgag  20460
tgtgactgtg gcctggcgtg gctgccgcga tgggcggagg agcagcaggt gcgggtggtg  20520
cagcccgagg cagccacgtg tgctgggcct ggctccctgg ctggccagcc tctgcttggc  20580
atccccttgc tggacagtgg ctgtggtgag tgccggtggg tggggccagc tctgtccttc  20640
ccagccaggt gggacctggg ccctgcagac actgggcagg gctcaggaag gcctctctgg  20700
gggggggcctc cgggccaagg gaacagcatg ggagcctgtg agtgcggcgg gcggatgtgg  20760
gggcgtgggg tggagccagg aggagcagaa cccggggtcc agtggctgcc tcttctaggt  20820
gaggagtatg tcgcctgcct ccctgacaac agctcaggca ccgtggcagc agtgtccttt  20880
tcagctgccc acgaaggcct gcttcagcca gaggcctgca gcgccttctg cttctccacc  20940
ggccagggcc tcgcagccct ctcggagcag ggctggtgcc tgtgtggggc ggcccagccc  21000
tccagtgcct cctttgcctg cctgtccctc tgctccggcc cccgccacc tcctgccccc  21060
acctgtaggg gccccaccct cctccagcac gtcttccctg cctccccagg ggccaccctg  21120
gtggggcccc acggacctct ggcctctggc cagctagcag ccttccacat cgctgccccg  21180
ctccctgtca ctgccacacg ctgggacttc ggagacggct ccgccgaggt ggatgccgct  21240
gggccggctg cctcgcatcg ctatgtgctg cctgggcgct atcacgtgac ggccgtgctg  21300
gccctggggg ccggctcagc cctgctgggg acagacgtgc aggtggaagc ggcacctgcc  21360
gccctggagc tcgtgtgccc gtcctcggtg cagagtgacg agagcctcga cctcagcatc  21420
cagaaccgcg gtggttcagg cctggaggcc gcctacagca tcgtggccct gggcgaggag  21480
ccggcccgag gtgagtgtct gctgcccact ccccttcctc cccagggcca tccagatggg  21540
gcagagcctg gtaccccgt cttgggccca cactgaccgt tgacaccctc gttcccaccg  21600
gtctccagcg gtgcacccgc tctgcccctc ggacacggag atcttccctg gcaacgggca  21660
ctgctaccgc ctggtggtgg agaaggcggc ctggctgcag gcgcaggagc agtgtcaggc  21720
ctgggccggg gccgccctgg caatggtgga cagtcccgcc gtgcagcgct tcctggtctc  21780
ccgggtcacc aggtgcctgc ccccacccc cgagggcca taggttggga gatctctgaa  21840
gcactgggc agagactgcg gctggggagt ctcaggagga aggaggtggg agctgggccg  21900
gccctggtga gcaggtggcg ccggccggtg gggccgttcc tgtcagctct gcagatgcag  21960
aggtggacat gagctggggg cagcctccgg acactcctgg gcacgccata cgggaggtgg  22020
cctgcacggg gatccctgcc ggtacccaca ggccccgtgg gtgggtgctg ctgtgagcct  22080
gggctggtgg gccctggtct ccgggctctg agcctcagtt tccccatctg gaaaggggga  22140
cagtgatggg gctcccagcg ggctgctgtg agggtgggag gatggaggag tgccctgagc  22200
cccctgccat cccacacccg cccccaggag cctagacgtg tggatcggct tctcgactgt  22260
gcaggggtg gaggtgggcc cagcgccgca gggcgaggcc ttcagcctgg agagctgcca  22320
gaactggctg cccggggagc cacacccagc cacagccgag cactgcgtcc ggctcgggcc  22380
caccgggtgg tgtaacaccg acctgtgctc agcgccgcac agctacgtct gcgagctgca  22440
gcccggaggt gtgcgggggg ccaggcaggg gcctgagacg ctggctgtgg ttaggggcct  22500
gccgagcgcc cgcggtggag cctgggctga ggaggaggg ctggtggggg ggttttcggg  22560
cggctcggtc cccagtctgt tcgtcctggt gtcctgggcc ctggcccggc gcctcactgt  22620
gcactcgcca cccaggccc agtgcaggat gccgagaacc tcctcgtggg agcgcccagt  22680
ggggacctgc agggacccct gacgcctctg gcacagcagg acggcctctc agcccgcac  22740
```

```
gagcccgtgg aggtagtcgg cccccacgt tctacaacct gccctcctgc ctgcccctgg   22800
aggccttgcc tgccctgccc actgtgggtc tcgccaaaaa acttgggggc cttaatgttg   22860
cttgtgccca gtgaagatgg ttgggaaaat ccagagtgca gagaggaaag cgtttactca   22920
cattacctcc aggcctttc tctgagcgtg tgtgagttat tcctgaaagg caggtcaggg   22980
gtcctgcccc ccatggacag tttccaccgg agtcttcctc tcgagcgaca ggagccaggc   23040 ctgtggggt ctgatggctc gctctccttc cctcccctct tcctgggaag ttcgggtagg   23100
gggagtctgg gcttcaggct gggatggggt ctgtggagct gaggcggccc cctgcccacc   23160
aggtcatggt attcccgggc ctgcgtctga gccgtgaagc cttcctcacc acggccgaat   23220
ttgggaccca ggagctccgg cggcccgccc agctgcggct gcaggtgtac cggctcctca   23280
gcacagcagg tgggactctg ggtggtgggt ggtgggtggt gggcgccgca ggactcgggg   23340
tggcctctct gagctttcac gtctgctggt cctgtggcca ccagagtggt tcccagtctt   23400
aggtggacag agcaggggtt ccagagacac cagctcattc caggtgtcct gggggtggat   23460
tgggtggggc ctgcctgggg gccggcctgg gtcagtcggt tggccggaga cggacgcagc   23520
actgggctgg gagtgctgcc caggtgggga gacctgtcct cacagcaagg ccaggattgc   23580
tggtgcaggc agttgggcat ctctgacggt ggcctgtggg caaatcaggg ccccaacacc   23640
ctcccctcct cacagggacc ccggagaacg gcagcgagcc tgagagcagg tccccggaca   23700
acaggaccca gctggccccc gcgtgcatgc caggggacg ctggtgccct ggagccaaca   23760
tctgcttgcc gctggacgcc tcctgccacc cccaggcctg cgccaatggc tgcacgtcag   23820
ggccagggct acccggggcc ccctatgcgc tatggagaga gttcctcttc tccgttcccg   23880
cggggccccc cgcgcagtac tcggtgtgtg gccctgacct gggtctgttc cctgcatctc   23940
ctcaggccac cttcctgtct gctgcccagg gtctgggtct gtgcaccaga cacacccagc   24000
ctgcaggccc ctcccacgtc cttgccacct ctgacctccg acctctgcag tgccctcggc   24060
cctctcccag tgggagaagc tctcgcctgg gcccttggca cgagctgtgc ctcctcttcc   24120
tctctcccag cacagctgct ccttcctgtc tgccaggtct tggcctgtgt cctctccccg   24180
tgtgtccccc ggtctgcaac tgtcctgcct gtccttgtca cgagcactgt ggggaggctc   24240
cttgaggtgt ggctgacgaa gcggggagcc ctgcgtgtcc accctcatcc gtcgtgcggg   24300
ggtccacggg ccatgaccgt gaggacgtga tgcagcccctg cctccctctc acaggtcac   24360 cctccacggc caggatgtcc tcatgctccc tggtgacctc gttggcttgc agcacgacgc   24420
tggccctggc gccctcctgc actgctcgcc ggctcccggc cacccctggtc cccgggcccc   24480 gtacctctcc gccaacgcct cgtcatggct gccccacttg ccagcccagc tggagggcac   24540
ttgggcctgc cctgcctgtg ccctgcggct gcttgcagcc acggaacagc tcaccgtgct   24600
gctgggcttg aggcccaacc ctggactgcg gctgcctggg cgctatgagg tccgggcaga   24660
ggtgggcaat ggcgtgtcca ggcacaacct ctcctgcagc tttgacgtgg tctccccagt   24720
ggctgggctg cgggtcatct accctgcccc ccgcgacggc cgcctctacg tgcccaccaa   24780
cggctcagcc ttggtgctcc aggtggactc tggtgccaac gccacggcca cggctcgctg   24840 gcctggggc agtgtcagcg cccgctttga gaatgtctgc cctgccctgg tgccaccctt   24900
cgtgcccggc tgcccctggg agaccaacga taccctgttc tcagtggtag cactgccgtg   24960
gctcagtgag ggggagcacg tggtggacgt ggtggtggaa aacagcgcca gcgggccaa   25020 cctcagcctg cgggtgacgg cggaggagcc catctgtggc ctccgcgcca cgcccagccc   25080
cgaggcccgt gtactgcagg gagtcctagt ggtgagtatg gccgaggctc caccaccagc   25140
```

```
ccccaggcag gtgcctgcag acagggtgct cacacagggc gtgaggcctg gcttcccagt   25200
gagggcagca gcccagttac tggggacgtc ggccccgggc aggtcctgct ggctggctcc   25260
tcgggctacc tggtgggctt taaattcctg gaaagtcacg gctctgacag tggctccgct   25320
aactcattcc actgtctcat ttcacaaaat gaatttaaaa ctctgctccc tgacctcaca   25380 cgagccccg tgagtctctc acgccctctg ctgtgttctc gcctggctaa agcgagtggc   25440
ttttgaggtg gagtctgaac ccctgatggg aaactgcggg ctgcccgcgg tgccaccatg   25500
ctgggtacat gggggacagg gctgtctcca tcttgcgggt acctgcctct tcaccagggg   25560
ccttgggagg ggccatcaga aatggcgtga cctgtgcagc ctgtcctggg ttctgtaagc   25620
cagtgtaggt gcctcccctc actgctccga gctctctggg tgaggagctg gggcaagagc   25680
gccgggaggg tctgagaaga ctcagagaga ggtggactct ttgtagctgg tactaggttt   25740
gctttacaga tggggaaact gaggcacaga gaggttgagg cattagtagt actacatggc   25800
tggctggaga gccggacagt gagtgtccca gccgggctt ggctcccatg gcatgcagag   25860
ccccgggcac ctcctctcct ctgtgccccg cgtgggactc tccagcccga cgggaggtgt   25920
gtccaggagg cgacaggcta agggcagagt cctccacaga gcccaggctg acaccattcc   25980
ccccgcagag gtacagcccc gtggtggagg ccggctcgga catggtcttc cggtggacca   26040
tcaacgacaa gcagtccctg accttccaga acgtggtctt caatgtcatt tatcagagcg   26100
cggcggtctt caagctctca gtaggtgggc ggggtgggg aggggagggg atggggcggg   26160
gcagggcggg ggcgggctcc accttcacct ctgccttctg ctctgcttca tgctgcccga   26220
ggacgctgcc atggctgtgg gtgagtggag ggagggacgc caatcagggc caggcctctc   26280
acctgccacc tgggctcact gacgcctgtc cctgcagctg acggcctcca accacgtgag   26340
caacgtcacc gtgaactaca acgtaaccgt ggagcggatg aacaggatgc agggtctgca   26400
ggtctccaca gtgccggccg tgctgtcccc caatgccacg ctagcactga cggcgggcgt   26460
gctggtggac tcggccgtgg aggtggcctt cctgtgagtg actcggggc cggtttgggg   26520 tgggcaccag gctcttgtcc cagccccagc ctcagccgag ggaccccac atcacggggt   26580 tgcttttctg agcctcggtt tccctgtctg ttgggaggta actgggtgca caggagccct   26640
gaggctgcac gggagccggg agaggcctca gcacagccgg gtgggccctg aatggaggcc   26700
cggggcgtga ctgcagagtg gagcctcggc tgggtcccaa gcaccccctg ccccgccacc   26760
gcccacccct gtcccggttc actcactgcg tcccaccgcc ccggcaggtg gacctttggg   26820
gatggggagc aggccctcca ccagttccag cctccgtaca acgagtcctt cccggttcca   26880 gaccctcgg tggcccaggt gctggtggag cacaatgtca tgcacaccta cgctgcccca   26940
ggtgagggat gaggggtga gggggccact gcctttcagg ctctgagcac gggtccccc   27000 agctccccag tcaagctgcc ccccttcctc cccaacagcc ctcactgtga cctcacctgg   27060
gctgatggct taggccctac tggggtgagg gaggggccag gcgtgggggg agtggacagg   27120
gaagctgggc ccctgaactg cgcccccgc cctccgggg cctggctctt gctgctctgc   27180
tgccccgagt gcagctgcac ttggaggcgg tgcgtcctcg ccaggcagcc ctcagtgctg   27240
ctacacctgt gctccgtccc gcacgtgct tgggagcctg gacccttaa ggctgggccg   27300 caggtgcagc cgttcacccc gggctcctca ggcggggc ttctgccgag cgggtgggga   27360
gcaggtgggg gtgccgcggc tgccccactc gggcctgtcc ccacaggtga gtacctcctg   27420
accgtgctgg catctaatgc cttcgagaac cggacgcagc aggtgcctgt gagcgtgcgc   27480
```

```
gcctccctgc cctccgtggc tgtgggtgtg agtgacggcg tcctggtggc cggccggccc   27540
gtcaccttct acccgcaccc gctgccctcg cctggggtg ttctttacac gtgggacttc    27600
ggggacggct cccctgtcct gacccagagc cagccggctg ccaaccacac ctatgcctcg   27660
agggcacct accacgtgcg cctggaggtc aacaacacgg tgagcggtgc ggcggcccag    27720
gcggatgtgc gcgtctttga ggagctccgc ggactcagcg tggacatgag cctggccgtg   27780
gagcagggcg ccccgtggt ggtcagcgcc gcggtgcaga cgggcgacaa catcacgtgg    27840
accttcgaca tgggggacgg caccgtgctg tcgggcccgg aggcaacagt ggagcatgtg   27900
tacctgcggg cacagaactg cacagtgacc gtgggtgcgg ccagcccgc cggccacctg    27960
gcccggagcc tgcacgtgct ggtcttcgtc ctggaggtgc tgcgcgttga acccgccgcc   28020
tgcatcccca cgcagcctga cgcgcggctc acggcctacg tcaccgggaa cccgccccac   28080
tacctcttcg actggacctt cggggatggc tcctccaaca cgaccgtgcg ggggtgcccg   28140
acggtgacac acaacttcac gcggagcggc acgttccccc tggcgctggt gctgtccagc   28200
cgcgtgaaca gggcgcatta cttcaccagc atctgcgtgg agccagaggt gggcaacgtc   28260
accctgcagc cagagaggca gtttgtgcag ctcggggacg aggcctggct ggtggcatgt   28320
gcctggcccc cgttcccta ccgctacacc tgggactttg caccgagga agccgccccc    28380
acccgtgcca ggggcctga ggtgacgttc atctaccgag acccaggctc ctatcttgtg    28440
acagtcaccg cgtccaacaa catctctgct gccaatgact cagccctggt ggaggtgcag   28500
gagcccgtgc tggtcaccag catcaaggtc aatggctccc ttgggctgga gctgcagcag   28560
ccgtacctgt tctctgctgt gggccgtggg cgccccgcca gctacctgtg ggatctgggg   28620
gacggtgggt ggctcgaggg tccggaggtc acccacgctt acaacagcac aggtgacttc   28680
accgttaggt ggccggctgg aatgaggtga gccgcagcga ggcctggctc aatgtgacgg   28740
tgaagcggcg cgtgcggggg ctcgtcgtca atgcaagccc cacggtggtg cccctgaatg   28800
ggagcgtgag cttcagcacg tcgctggagg ccggcagtga tgtgcgctat tcctgggtgc   28860
tctgtgaccg ctgcacgccc atccctgggg gtcctaccat ctcttacacc ttccgctccg   28920
tgggcacctt caatatcatc gtcacggctg agaacgaggt gggctccgcc caggacagca   28980
tcttcgtcta tgtcctgcag ctcatagagg ggctgcaggt ggtgggcggt ggccgctact   29040
tccccaccaa ccacacggta cagctgcagg ccgtggttag ggatggcacc aacgtctcct   29100
acagctggac tgcctggagg gacaggggcc cggccctggc cggcagcggc aaaggcttct   29160
cgctcaccgt ctcgaggccg gcacctacca tgtgcagctg cgggccacca acatgctggg   29220
cagcgcctgg gccgactgca ccatggactt cgtggagcct gtggggtggc tgatggtggc   29280
cgcctccccg aacccagctg ccgtcaacaa aagcgtcacc ctcagtgccg agctggctgg   29340
tggcagtggt gtcgtataca cttggtcctt ggaggagggg ctgagctggg agacctccga   29400
gccatttacc acccatagct tccccacacc cggcctgcac ttggtcacca tgacggcagg   29460
gaacccgctg ggctcagcca acgccaccgt ggaagtggat gtgcaggtgc ctgtgagtgg   29520
cctcagcatc agggccagcg agccggagg cagcttcgtg gcggccgggt cctctgtgcc   29580
cttttggggg cagctggcca cgggcaccaa tgtgagctgg tgctggctg tgcccggcgg   29640
cagcagcaag cgtggccctc atgtcaccat ggtcttcccg gatgctggca ccttctccat   29700
ccggctcaat gcctccaacg cagtcagctg ggtctcagcc acgtacaacc tcacggcgga   29760
ggagcccatc gtgggcctgg tgctgtgggc cagcagcaag gtggtggcgc ccgggcagct   29820
ggtccatttt cagatcctgc tggctgccgg ctcagctgtc accttccgcc tgcaggtcgg   29880
```

```
cggggccaac cccgaggtgc tccccgggcc ccgtttctcc cacagcttcc cccgcgtcgg   29940
agaccacgtg gtgagcgtgc ggggcaaaaa ccacgtgagc tgggcccagg cgcaggtgcg   30000
catcgtggtg ctggaggccg tgagtgggct gcaggtgccc aactgctgcg agcctggcat   30060
cgccacgggc actgagagga acttcacagc ccgcgtgcag cgcggctctc gggtcgccta   30120
cgcctggtac ttctcgctgc agaaggtcca gggcgactcg ctggtcatcc tgtcgggccg   30180
cgacgtcacc tacacgcccg tggccgcggg gctgttggag atccaggtgc gcgccttcaa   30240
cgccctgggc agtgagaacc gcacgctggt gctggaggtt caggacgccg tccagtatgt   30300
ggccctgcag agcggcccct gcttcaccaa ccgctcggcg cagtttgagg ccgccaccag   30360
ccccagcccc cggcgtgtgg cctaccactg ggactttggg gatgggtcgc cagggcagga   30420
cacagatgag cccagggccg agcactccta cctgaggcct ggggactacc gcgtgcaggt   30480
gaacgcctcc aacctggtga gcttcttcgt ggcgcaggcc acggtgaccg tccaggtgct   30540
ggcctgccgg gagccggagg tggacgtggt cctgccccctg caggtgctga tgcggcgatc   30600
acagcgcaac tacttggagg cccacgttga cctgcgcgac tgcgtcacct accagactga   30660
gtaccgctgg gaggtgtatc gcaccgccag ctgccagcgg ccggggcgcc cagcgcgtgt   30720
ggccctgccc ggcgtggacg tgagccggcc tcggctggtg ctgccgcggc tggcgctgcc   30780
tgtggggcac tactgctttg tgtttgtcgt gtcatttggg gacacgccac tgacacagag   30840
catccaggcc aatgtgacgg tggcccccga gcgcctggtg cccatcattg agggtggctc   30900
ataccgcgtg tggtcagaca cacgggacct ggtgctggat gggagcgagt cctacgaccc   30960
caacctggag gacggcgacc agacgccgct cagtttccac tgggcctgtg tggcttcgac   31020
acaggtcagt gcgtggcagg gccgtcctcc atgcccctca cccgtccaca cccatgagcc   31080
cagagaacac ccagcttgcc accagggctg gcccgtcctc agtgcctggt gggccccgtc   31140
ccagcatggg gagggggtct cccgcgctgt ctcctgggcc gggctctgct ttaaaactgg   31200
atggggctct caggccacgt cgcccccttgt tctcggcctg cagagggagg ctggcgggtg   31260
tgcgctgaac tttgggcccc gcgggagcag cacggtcacc attccacggg agcggctggc   31320
ggctggcgtg gagtacacct tcagcctgac cgtgtggaag gccggccgca aggaggaggc   31380
caccaaccag acggtggggtg ccgcccgccc ctcggccact tgccttggac agcccagcct   31440
ccctggtcat ctactgtttt ccgtgtttta gtgctggtgg aggccgcacg ctctcccctc   31500
tctgtttctg atgcaaattc tatgtaacac gacagcctgc ttcagctttg cttccttcca   31560
aacctgccac agttccacgt acagtcttca agccacatat gctctagtgg caaaagctac   31620
acagtcccct agcaatacca acagtgagga agagcccctt cccacccag aggtagccac   31680 tgtccccagc ccatgtccct gttgctggat gtggtgggcc ggttctcacc ctcacgctcc   31740
cctctctgga ccggccagga ggcttggtga ccctgagccc gtggtggctg ctcctgctgc   31800
tgtcaggcgg ggcctgctgg tgccccagag tgggcgtctg ttccccagtc cctgctttcc   31860
tcagctggcc tgattggggg tcttcccaga ggggtcgtct gaggggaggg tgtgggagca   31920
ggttccatcc cagctcagcc tcctgaccca ggccctggct aagggctgca ggagtctgtg   31980
agtcaggcct acgtggcagc tgcggtcctc acacccacac atacgtctct tctcacacgc   32040 atcccccag gggccctcag tgagcattgc ctgcctcctg ctagggtcca gctgggtcca   32100
gtacaccaga acgcacactc cagtgtcctc tgccctgtgt atgcccttcc gccgtccaag   32160
ttggaaggtg gcaaaccgga tgagtatcct gggagggagt gagctcaccg gcagtggcca   32220
```

```
ggcccctggg aaacctggag tttgggagca gcatcctcca tgggtccccc agtccttcca    32280
gcaggccaaa tagacctgtg ttggaggtaa ccccactccc acgccaggtg ctgatccgga    32340
gtggccgggt gcccattgtg tccttggagt gtgtgtcctg caaggcacag gccgtgtacg    32400
aagtgagccg cagctcctac gtgtacttgg agggccgctg cctcaattgc agcagcggct    32460
ccaagcgagg ggtgagtgtt gagcggggtg tgggcgggct ggggatgggt cccatggccg    32520
aggggacggg gcctgcaggc agaagtgggg ctgacagggc agagggttgc gcccctcac     32580 caccccttct gcctgcagcg gtgggctgca cgtacgttca gcaacaagac gctggtgctg    32640
gatgagacca ccacatccac gggcagtgca ggcatgcgac tggtgctgcg gcggggcgtg    32700
ctgcgggacg gcgagggata caccttcacg ctcacggtgc tgggccgctc tggcgaggag    32760
gagggctgcg cctccatccg cctgtccccc aaccgcccgc cgctgggggg ctcttgccgc    32820
ctcttcccac tgggcgctgt gcacgccctc accaccaagg tgcacttcga atgcacgggt    32880
gagtgcaggc ctgcgtgggg ggagcagcgg gatcccccga ctctgtgacg tcacggagcc    32940
ctcccgtgat gccgtgggga ccgtcctca ggctggcatg acgcggagga tgctggcgcc     33000
ccgctggtgt acgccctgct gctgcggcgc tgtcgccagg gccactgcga ggagttctgt    33060
gtctacaagg gcagcctctc cagctacgga gccgtgctgc ccccgggttt caggccacac    33120
ttcgaggtgg gcctggccgt ggtggtgcag gaccagctgg gagccgctgt ggtcgccctc    33180
aacaggtgag ccaggccgtg ggaggggcgcc cccgagactg ccacctgctc accaccccct   33240
ctgctcgtag gtctttggcc atcaccctcc cagagcccaa cggcagcgca acggggctca    33300
cagtctggct gcacgggctc accgctagtg tgctcccagg gctgctgcgg caggccgatc    33360
cccagcacgt catcgagtac tcgttggccc tggtcaccgt gctgaacgag gtgagtgcag    33420
cctgggaggg gacgtcacat ctgctgcatg cgtgcttggg accaagacct gtaccctgc     33480 ctggagcttt gcagagggct catcccgggc ccagagata aatcccagtg accctgaagc      33540
agcaccccga ccttccgctc ccagcagcca caccaccgg gccctctccg gcgtctgctt      33600
tccacaatgc agccccgcc caggagggcc catgtgctta ccctgttttg cccatgaaga      33660
aacagctcag tgttgtgggt cagtgcccgc atcacacagc gtctagcacg taactgcacc    33720
ccgggagtcg tgggcatctg ctggcctcct gccggcctcc tgcgctgctg acagcttgct    33780 gtgcccctg cctgccccag tacgagcggg cctggacgt ggcgcagagc ccaagcacga       33840
gcggcagcac cgagcccaga tacgcaagaa catcacggag actctggtgt ccctgagggt    33900
ccacactgtg gatgacatcc agcagatcgc tgctgcgctg gcccagtgca tggtaggatg    33960
gccccacctg ctcaccctgc cccgcatgcc tgccaggca ctgggttcag cccccagggg      34020
cagacgggca gcttggccga ggagctgagc ctccagcctg ggctccttcc tgccatggcg    34080
ttcctcggtc tctgacctgc ttcagtagcc tcagccgttc tgtcctgtgt gaacgcaggg    34140
tgcctctcgg gggacccagg gtgtaaagag gggcccagat gtgggagggg actaagaaga    34200
tgctgctctg tgcctccac tctcccctcc cctccctcc ccttccctc cctagcccc        34260 tcccctcctc cccctcccta gcccttcccc tcctcccctc cctagccct ttcccttctt     34320 ccccccagc ccttcccctc ctccctccc ctagccttc cctcctccc ctccctacc         34380 ccttcccctc ctccctccc ctagaccttc cctcacctc ctcccgctga gcccctccac      34440
tcgtccccca gccctccct ccctagccc tcccctccc ccttcctccc tcctccccc        34500 tccctcctc cccctccctc ttcctccccc tccctcctc cccttcctc cctctcctc        34560 cccctcccct cctgtccccc ctcctcccct cctccctcct ccctcctcc ccctcctcc      34620
```

```
tccccctcct ccctcctccc tcctccccct cctcctcctc ccctcctccc tcctccccctc   34680
ctccctccc ctcctccccc tcccccctcc cttcctccc ctccccctc ccctcctccc        34740
cctctcctcc tcccatccct cctcccatcc ctcctcccg ttcccattct ctccctccc      34800
ccttccattt ctccctcctc cccctgccct cctctcctcc tcacctcccc ttctccgctc   34860
ctttcttctc ctccctccct ttctctcctc cctcccttc tccccttctc ctcttctccc   34920
cttctcctct cttttcatcc ttcccttctt ccctcctttc ctcctctttt ccctcttctc   34980
ccccctcctc ccctcctccc tcctcccatt cccctcctc ccccctccca ttcccctcc     35040
tccctcctt cctcctccca ttaccctccc tctcctccc tcctcccacc cccctctcct   35100
cccggctcct ctcctccct cctcatcccc ctcctctcct tcctcctaa cccccctcct   35160
ctcctcccct cctcatcccc ctcctctcct tccctcctcc tatcccccct cctctcctcc   35220
cctcctccta ttcccctcc tctcctccc tccttcctcc tcctctcctc ccatgccccc   35280
tcctccctc ctcccatccc cctctccc tcctccctcc tccatccca tcccctcct    35340
ctcctccct tctctcct cctctcctcc cctcctctcc tctcctcctc tcctcccctc    35400
ctcccatccc ccctcctccc atccccctc ctctcctcc cactcctctc ctccccactc   35460
ctctcctccc ctcatccccc tcctctctcc tcccctcccc ctcctctcct tccctcctcc   35520
tttcctcccc tccccctcct tccccctcct cccctcctt ctccccatcc ccttccct    35580
tctcctcctc tcccctccc cttctctttt tccctcctcc tccttcctc ctccctctt    35640
ctcccctttt ccctttctc ttcctctcct ccccttctcc cctcctgtcc tccctccctt   35700
tctctctttc tttcctcct ttccttctcc cctgttctcc tcccttccct tctccctt     35760
tcttccctcc tcctttcctc ccctcctcct tttctctgtt tctcttcctt tccccctccac 35820
tttcccttc ctttccctc tccttctcc ttcctttcct ctcccttct cttccttttc     35880
ctctctcccc ttcttttccc tcttcccctc ccctcctctt ccctcccct cctcttcccc   35940
tccctcctc ttcccctcc ctcctcttcc cctctcctcc tcttccctc ccctcctctt   36000
tccctccct cttctcctcc cctctctcc cctcttcccc tcccctcctc ttccctcccc   36060
ttccctccc ctcctcttcc ctcccttcc cctccctc tcttccctcc ccttccctc     36120
ctcttcttc ctctcttccc ctcccctcct cttccctccc ctcttccct ccccttctct   36180
tctcctcccc ttctcttccc ctcccttttt cttccctctc cttgtcttcc ctgccctcct   36240
cttccctccc ctcctcttcc cccctctt ccctctcct cctcttcct ccctcttcc     36300
tctttcctct tccctcccc tcctcctccc tcccttcc cctcttcccc tccctccgc     36360
ttccctcccc tttctcccc ttctctcccc tccctctcc ccctctctct ccctcccct   36420
ctccccttc tctcccctcc cctctcccc ttctctcccc tctcctctcc cccttctctc   36480
ccccttctct ccccttctc tctccctt tctccccctt ctctcccctc cccccttctc   36540
tcccctcccc tctcccctt ctccccctc ccctctcccc tgtcctctcc tctccaccct   36600
tctctccct cccctctcct ctccccttc cctctcctct cccccttctc tccctcccc   36660
tctcctctcc cccctttct ccactcccct ctcctctctc cctcctcct ccgctctcat   36720
gtgaagaggt gccttgtgtg gtcggtgggc tgcatcacgt ggtccccagg tggaggccct   36780
gggtcatgca gagccacaga aaatgcttag tgaggaggct gtggggtcc agtcaagtgg   36840
gctctccagc tgcagggctg ggggtgggag ccaggtgagg acccgtgtag agaggagggc   36900
gtgtgcaagg agtggggcca ggagcggggc tggacactgc tggctccaca caggggccca   36960
```

```
gcagggagct cgtatgccgc tcgtgcctga agcagacgct gcacaagctg gaggccatga    37020
tgctcatcct gcaggcagag accaccgcgg gcaccgtgac gcccaccgcc atcggagaca    37080
gcatcctcaa catcacaggt gccgcggccc gtgcccatg  ccacccgccc gccccgtgcg    37140
gccctttcct ctgcctccct cctcccccca accgcgtcgc ctttgcccca tcccatcttc    37200 gtcccctcc  cctccccca  attcccatcc tcatcccct  ccccaattc  ccattctcct    37260 cccctcccc  cttccctatt accatccctt ttctccatct ctctcccctt ttctccattt    37320 ccccccgt   cctccccgtc cttttgtcca ttccctcat  cttcctcatc ccctcatcc     37380 cccttcccct cccttatccc ccttccctc  ccttccccc  tgctcctctt cttctccctt    37440
ctcttttctc tacccttttc cttccttttt cctccctctc cccatcatcc ccctcatctt    37500
cgtcctcatc cccatcacct tcccctccc  cctccacca  ctctctctcc agcttccccc    37560
ttccttctgc ctgcacctcg ctctctgccc cctcaggttc cccctttctc ccagccccca    37620
ccctccggct ccccttttt  gcctgccccc accctccctc tacctccctg tctctgcact    37680
gacctcacgc atgtctgcag agacctcat  ccacctggcc agctcggacg tgcgggcacc    37740
acagccctca gagctgggag ccgagtcacc atctcggatg gtggcgtccc aggcctacaa    37800
cctgacctct gccctcatgc gcatcctcat gcgctcccgc gtgctcaacg aggagcccct    37860
gacgctggcg ggcgaggaga tcgtggccca gggcaagcgc tcggaccgc  ggagcctgct    37920 gtgctatggc ggcgccccag ggcctggctg ccacttctcc atccccgagg ctttcagcgg    37980
ggccctggcc aacctcagtg acgtggtgca gctcatcttt ctggtggact ccaatccctt    38040
tccctttggc tatatcagca actacaccgt ctccaccaag gtggcctcga tggcattcca    38100
gacacaggcc ggcgcccaga tccccatcga gcggctggcc tcagagcgcg ccatcaccgt    38160
gaaggtgccc aacaactcgg actgggctgc ccggggccac cgcagctccg ccaactccgc    38220
caactccgtt gtggtccagc cccaggcctc cgtcggtgct gtggtcaccc tggacagcag    38280
caaccctgcg gccgggctgc atctgcagct caactatacg ctgctggacg gtgcgtgcag    38340
cgggtggggc acacgcggcc ccctggcctt gttcttgggg ggaaggcgtt tctcgtaggg    38400
cttccatggg tgtctctggt gaaatttgct ttctgtttca tgggctgctg ggggcctggc    38460
cagagaggag ctgggggcca cggagaagca ggtgccagct ctggtgcaga ggctcctatg    38520
ctttcaggcc cgtggcagag ggtgggctca ggagggccat cgtgggtgtc ccccgggtgg    38580
ttgagcttcc cggcaggcgt gtgacctgcg cgttctgccc caggccacta cctgtctgag    38640
gaacctgagc cctacctggc agtctaccta cactcggagc cccggcccaa tgagcacaac    38700
tgctcggcta gcaggaggat ccgcccagag tcactccagg gtgctgacca ccggccctac    38760
accttcttca tttccccggg gtgagctctg cgggccagcc tggcagggca gggcaggca    38820 tcatgggtca gcattgcctg ggttactggc cccatgggga cggcaggcag cgagggact    38880 ggaccgggta tgggctctga gactgcgaca tccaacctgg cggagcctgg gctcacgtcc    38940
gctacccctt ccctgcccag gagcagagac ccagcgggga gttaccatct gaacctctcc    39000
agccacttcc gctggtcggc gctgcaggtg tccgtgggcc tgtacacgtc cctgtgccag    39060
tacttcagcg aggaggacat ggtgtggcgg acagagggc  tgctgcccct ggaggagacc    39120
tcgccccgcc aggccgtctg cctcacccgc cacctcaccg ccttcggcgc cagcctcttc    39180 gtgccccca  gccatgtccg cttttgtgttt cctgtgagtg acctgtgct  cctgggagcc    39240 tctgcagagt cgaggagggc ctgggtgggc tcggctctat cctgagaagg cacagcttgc    39300
acgtgacctc ctgggcccgg cggctgtgtc ctcacaggag ccgacagcgg atgtaaacta    39360
```

```
catcgtcatg ctgacatgtg ctgtgtgcct ggtgacctac atggtcatgg ccgccatcct    39420
gcacaagctg gaccagttgg atgccagccg gggccgcgcc atcccttcct gtgggcagcg    39480
gggccgcttc aagtacgaga tcctcgtcaa gacaggctgg ggccggggct caggtgaggg    39540
gcgcagcggg gtggcagggc ctcccctgct ctcactggct gtgctggttg caccctctgg    39600
gagtgagtct cgtcgcaggc gtcagaacaa ggcagttttt gcagtgctgt gtgaagggct    39660
cgtgtgttca tcctgggaat gacctcgtga gcactcactg tccctgagga ctaggacagc    39720
tcctagctgg aagtaggtgc cagtcagtca gggtgggcag cccacgttct gcacagtagc    39780
gtggccccac aagtgacgtg agcatcgcta ccactgtggg agactgtgca tccacccgcg    39840
atcctgactg catagctcgt ctctcagacg gaggcgccag caccctcccc gtggctgttt    39900
cttcagtacc tccattttcc tttcattgga attgcccttc tggcattccc ttttttgtttt   39960 cgttttttctt tttttagaga cggagtctca ctctgttgcc caggctggag tgcaatggca   40020
tgatcttggc tcacagcaac ttccagctcc cgggtttaag ccattcccct taagcgattc    40080
tcctgagtag ctgggagtac aggtgcacac caccacaccc agttaatttt tcaccatgtc    40140
agccaggcga actcctgacc tcaggtgatc cgcctgcctc ggcctgccag agtgctggga    40200
tgacaggtgt gagccaccac acctggctgt gttcccattt tttatctctg tgctgctttc    40260
ctcttcattg cccagttctt tcttttgatt acctactttt aaaaactgtc ggccgggcgc    40320
ggtggctcac acctgtaatc cgagcacttt gggaggccag gcaggcaaat cacggggtca   40380
ggagatcgag accatcctgg ctaacggtga acccctgtct ctaataaaaa gtacaaaaaa   40440
attagcccgg cgtagtggca ggcgcctgta gtcccagctc cttgggagac tgaggcagga    40500
gaatggcgtg aacccgggag gcggagcttg cagtgagctg agattgcgcc actgcactcc    40560
agcctgggtg acacagcaag actccatctc aaaaaaaaaa gaaaaaaaat actgtcacct    40620
gggtctgtca ctgggagagg aggtgacaca gcttcacgct ttgcagtctg tgcatgaact    40680
gagggacggg tgtgtggtgc gggtcaccgg ttgtggcatg actgaggcgt ggacaggtgt    40740
gcagtgcggg tcactggttg tggtgtggac tgaggcgtgt gcagccatgt ttgcatgtca    40800
caagttacag ttctttccat gtaacttaat catgtccttg aggtcctgct gttaattgga    40860
caaattgcag taaccgcagc tccttgtgta tggcagagcc gtgcaaagcc gggactgcct    40920
gtgtggctcc ttgagtgcgc acaggccaaa gctgagatga cttgcctggg atgccacacg    40980
tgttgggcag cagaccgagc ctcccacccc tccctcttgc ctcccaggta ccacggccca    41040
cgtgggcatc atgctgtatg gggtggacag ccggagcggc caccggcacc tggacggcga    41100
cagagccttc caccgcaaca gcctggacat cttccggatc gccacccgc acagcctggg    41160 tagcgtgtgg aagatccgag tgtggcacga caacaaaggt ttgtgcggac cctgccaagc    41220
tctgcccctc tgcccccgca ttggggcgcc ctgcgagcct gacctccctc ctgcgcctct    41280
gcagggctca gccctgcctg gttcctgcag cacgtcatcg tcaggacct gcagacggca    41340 cgcagcgcct tcttcctggt caatgactgg ctttcggtgg agacggaggc caacgggggc    41400
ctggtggaga aggaggtgct ggccgcgagt aaggcctcgt tccatggtcc cactccgtgg    41460
gaggttgggc agggtggtcc tgccccgtgg cctcctgcag tgcggccctc cctgccttct    41520
aggcgacgca gcccttttgc gcttccggcg cctgctggtg gctgagctgc agcgtggctt    41580 cttttgacaag cacatctggc tctccatatg ggaccggccg cctcgtagcc gtttcactcg    41640
catccagagg gccacctgct gcgttctcct catctgcctc ttcctgggcg ccaacgccgt    41700
```

```
gtggtacggg gctgttggcg actctgccta caggtgggtg ccgtagggt cggggcagcc   41760 tcttcctgcc cagcccttcc tgcccctcag cctcacctgt gtggcctcct ctcctccaca   41820
cagcacgggg catgtgtcca ggctgagccc gctgagcgtc gacacagtcg ctgttggcct   41880
ggtgtccagc gtggttgtct atcccgtcta cctggccatc cttttctct tccggatgtc     41940 ccggagcaag gtgggctggg gctggggacc cgggagtact gggaatggag cctgggcctc   42000
ggcaccatgc ctagggccgc cactttccag tgctgcagcc agagggaaag gcgtccacca   42060
aaggctgctc gggaagggtc aacacacttg agcagcctta gctagactga ccagggagaa   42120
agagagaaga ctcagaagcc agaatggtga agaacgagg gcactttgct aagcagacgc     42180
cacggacgac tgcacagcag cacgccagat aactcagaag aagcaagcac gcggctgtgc   42240
acgcttccga aatgcactcc agaagaaaat ctcagtacat ctataggaag tgaagaggct   42300
gagttagtcc cttagaaacg tcccagtggc cgggccgggt gtggtggctc acgcctgtaa   42360
tcccaacact tcaggtggcc gaggtgggcg gatctgagtc caggagtttg agaccagcct   42420
gggcaacata gcaagacccc atctatataa aacattaaaa agggccaggc gcggtggctc   42480
acgcctgtaa tcccagcact ttgggaggcc gaggcgggca gatcacttga ggtcaggagt   42540
tcgagaccag cctggccaac acaatgaaac cccgactcta ctacaaatac aaaaacttag   42600
ctgggcatgg tggcgggcgc ctgtagtccc agctactcga gaggctgagg caggagaatg   42660
gcatgaaccc aggaggcgga gcttgcagtg agccgagatt gcgccactgc actccatcct   42720
gggcaacgga gcaagactcc atctccaaaa aaaaaaaaa aaatcccac aaagaaaagc      42780 tcaggctcag agccttcacg atagaatttt tctaagcagt taaggaagaa ttaacaccaa   42840
tccttcacag actctttcca agaatacagc aggtgggaac gcttcccatt catacggaaa   42900
cgggaggccg cacccttag gaatgcacac gtggggtcct caagaggtta catgcaaact    42960
aaccccagca gcacacagag aaggcgcata agccgcgacc aggaggggtt gctcccgagt   43020
ccgtggcagg aaccagaggc cacatgtggc tgctcgtatt taagttaatt aaaatgaac    43080 gatggccggg tgtggtggct cacacctgta atcccagcac tttgggaggc ggaggcgggc   43140
agatcacttg aggtcaggag ttccaagacc agcctggcca acacagtgaa accccgtctc   43200
tactaaaaat acaaaaaatt agctgggcat ggtggcaggc acctgtaatc ccagctactc   43260
aggaggctga gccaggacaa tcgcctgaac gcgggaggtg gaggttgcag tgagctgaga   43320
ttgcgccatt gcactccagc ctgggtgaca gcgagactcc atctaaaaaa gaaaatatga   43380
aatttaaaac tctgttcctt agctgcacca gtctgctgtc aagtgttcag tggcacacgt   43440 cgcgagggggc tgccatcacg gacggtgcag atgtcccata tatccagcat tctaggacat   43500
tctgtcagat ggcaccgggc tctgtcctgt ctgctgagga ggtggcttct catccctgtc   43560
ctgagcaggt ctgagctgcc gcccgctgac cactgccctc gtcctgcagg tggctgggag   43620
cccgagcccc acacctgccg ggcagcaggt gctggacatc gacagctgcc tggactcgtc   43680
cgtgctggac agctccttcc tcacgttctc aggcctccac gctgaggtga ggactctact   43740
gggggtcctg ggctgggctg ggggtcctgc cgccttggcg cagcttggac tcaagacact   43800
gtgcacctct cagcaggcct tgttggaca gatgaagagt gacttgtttc tggatgattc     43860
taagaggtgg gttccctaga gaaacctcga gccctggtgc aggtcactgt gtctggggtg   43920
ccgggggtgt gcgggctgcg tgtccttgct gggtgtctgt ggctccatgt ggtcacacca   43980
cccgggagca ggtttgctcg gaagcccagg gtgtccgtgc gtgactggac gggggtgggc   44040
tgtgtgtgtg acacatcccc tggtaccttg ctgacccgcg ccacctgcag tctggtgtgc   44100
```

```
tggccctccg gcgagggaac gctcagttgg ccggacctgc tcagtgaccc gtccattgtg   44160
ggtagcaatc tgcggcagct ggcacggggc caggcgggcc atgggctggg cccagaggag   44220
gacggcttct ccctggccag ccoctactcg cctgccaaat ccttctcagc atcaggtgag   44280
ctggggtgag aggagggggc tctgaagctc acccttgcag ctgggcccac cctatgcctc   44340
ctgtacctct agatgaagac ctgatccagc aggtccttgc cgaggggtc agcagcccag    44400 cccctaccca agacacccac atggaaacgg acctgctcag cagcctgtga gtgtccggct   44460 ctcggggag gggggattgc cagaggaggg gccgggactc aggccaggca gccgtggttc    44520
ccgcctgggg tagggtgggg tggggtgcca gggcagggct gtggctgcac cacttcactt   44580
ctctgaacct ctgttgtctg tggaaagagc ctcatgggat ccccagggcc cagaaccttt  44640
ccctctaggg agggagcagg ctcatggggc tttgtaggag cagaaaggct cctgtgtgag   44700
gctggccggg gccacgttt tatcttggtc tcagagcagt gagaaattat gggcgggttt    44760
ttaaataccc catttttggc cgggcgcggt ggctcacacg tgtaatccca gcactttggg   44820
aggccgaggt gggcagatga cctgaggtca gcagttcgag accagcctgg ccaacatggc   44880 gaaacccgt ctctactaaa aatacaaaaa attagccggg catgctggca ggcgcctgta    44940
gtcccagtta ctcgggagac tgaggtagga gaatcgattg aacctggtag gtgaaggttg   45000
tagtgagccg agatcgcgcc actgcactcc agcctgggca acaagagcga aactccgtct   45060
caaaaacaaa aaaattcctc aatttcttgg ttgttttgta acttatcaac aaatggtcat   45120
atagaggtta ccttgtatgt agtcacgcac atagtcacgc acatggcagc cggcggcgga   45180
gcgcacccac ggcgtgttcc cacgcgtgtg accccgggct ctgccatgcc ctcctatgct   45240
caggtgtgct gaggtccaca cggccctgcc gttgcactgc agctgcctgc aggattcagt   45300
gcagtggcat gcagtgcagg tcggtgccc cggagccaca ggccacacca cagggcctgc    45360
atgcacaggg gctgcggtgt ctgggttttgg gtaactacgc cctgtgacat ttgcacagca   45420
acagaattac ctaatgacgc atttctcaga acacatccct ggcactaagt ggtgcgtgac   45480
tgctgctttt gcatccacat ctagtttgat ttgtgtgtta ttcctttgag tgcttctcat    45540
tgttaagcaa ccaagaacta agaggtatg aactgccct ggactcaaac aaaaaggaaa     45600
acttcctgat ttacaaaagg cagataacca tcacatgagg gcatctttat gaataaattg   45660
ctggttggtt ttaaaaatac agagtatggg gaaatccagg ggtagtcact acatgctgac   45720
cagccccagg tatctccggc ccaaagctct gtgaaatcca gattcagtgc ttccgcgggg   45780
atttctgacg gcagctcaga ctccgcatcc acacagagcg cgtggccctc accctcccgg   45840
cttcctcaac ccttggccgt cccttgctcg gacagtgctt cgggctgacc aggtcggagg   45900
cttgggtttg tcctggaccc ctctgcgtcc ttcctcactg cagcctccag cgcgtcccgt   45960
ggctcctttc ccaacgcaga gcacggcctt ccctgcgcct gagcctgcac cctccgtcct    46020
ggcggcgcct ctgccctggc attccctgcc actccatgcc tccctattgg ccattctccg    46080
tctctgccag cgagagcctg ctccctgagt cagaccctga gtcatttgtg ttgctataaa    46140
ggaatagttg aggctgggtt atttttatt tttatttatt tttttgagat ggagtctctg     46200
ttgcccagac tggagtgcag tcgcatgatc tcggctcact gcaaagtctg cctcccacgt    46260
tcaagcagtt atctgcctca gcctcccaag tagctaagat tacaggcgcc cgccgccaca    46320
gccggctaat ttttgtgtg tgtgttttag tagagaggag gtttcaccat cttagccagg     46380
ctggtcttga actcctgacc tcgtgatcca cccatctcag cctcccaaaa tgctgagatt    46440
```

```
acaggcgtga gccaccacgc ctgaccaagt tgaggctagg tcatttttta atttttgta    46500
aagacagggt ctcactgtct ccaactcctg agctcaagtg atcctcctgc ctcagcctcc    46560
tgaagtgctg ggattacagg cttgagacac tgcgcccagc caagagtgtc ttttatcctc    46620
cgagagacac caaaacagga agcattcagt gcagtgtgac cctgggtcag gccgttcttt    46680
cggtgatggg ctgacgaggg cgcaggtacg ggagagcgtc ctgagagccc gggactcggc    46740
gtctcgcagt tggtctcgtc ctcccccctca acgtgtcttc gctgcctctg tacctcttct    46800
ctagcagctc tgggaccggg catatcagca tggtggcccg atgcagtggc acagcctcgg    46860
tggtcactgg ctcctggaga cacaagcaga tctctggcct cagggagccc tacacactgt    46920
tgggatttga aaggcattca tatgtttcct tgtccagaag ttaattttag gccataaacc    46980
tgcatgggac agacacactg gcgtctctag attgtagaga tgcttgttgg atggttgaga    47040
cccaatcata gtttgcaggg ttgaaggggg gctcattgca ccctgagaga ctgtgcactg    47100
ctgtaagggc agctggtcag gctgtgggcg atgggtttat cagcagcaag cgggcgggag    47160
agggacgcag gcggacgcct gacttcggtg cctggagtgg ctcttggttc cctggctccc    47220
agcaccactc ccactctcgt ttggggtagg gtcttccggc tttttgtcgg ggggaccctg    47280
tgacccaaga ggctcaagaa actgcccgcc caggttaaca tgggcttggc tgcaactgcc    47340
tcctggaggc cgggatgaat tcacagccta ccatgtccct caggtccagc actcctgggg    47400
agaagacaga gacgctggcg ctgcagaggc tgggggagct ggggccaccc agcccaggcc    47460
tgaactggga acagcccag gcagcgaggc tgtccaggac aggtgtgctt gcgtagcccc    47520
gggatgccc tagcccctcc ctgtgagctg cctctcacag gtctgtctct gcttccccag    47580
gactggtgga gggtctgcgg aagcgcctgc tgccggcctg gtgtgcctcc ctggcccacg    47640
ggctcagcct gctcctggtg gctgtggctg tggctgtctc agggtgggtg ggtgcgagct    47700
tcccccgggg cgtgagtgtt gcgtggctcc tgtccagcag cgccagcttc ctggcctcat    47760
tcctcggctg ggagccactg aaggtgaggg ggctgccagg ggtaggctac aggcctccat    47820
cacgggggac ccctctgaag ccaccccctc cccaggtctt gctggaagcc ctgtacttct    47880
cactggtggc caagcggctg cacccggatg aagatgacac cctggtagag agcccggctg    47940
tgacgcctgt gagcgcacgt gtgccccgcg tacggccacc ccacggcttt gcactcttcc    48000
tggccaagga agaagcccgc aaggtcaaga ggctacatgg catgctgcgg gtgagcctgg    48060
gtgcggcctg tgcccctgcc acctccgtct cttgtctccc acctcccacc catgcacgca    48120
ggacactcct gtcccccttt cctcacctca gaaggccctt aggggttcaa tgctctgcag    48180
cctttgcccg gtctccctcc taccccacgc ccccacttg ctgccccagt ccctgccagg    48240
gcccagctcc aatgcccact cctgcctggc cctgaaggcc cctaagcacc actgcagtgg    48300
cctgtgtgtc tgcccccagg tggggttccg ggcagggtgt gtgctgccat taccctggcc    48360
aggtagagtc ttggggcgcc ccctgccagc tcaccttcct gcagccacac ctgccgcagc    48420
catggctcca gccgttgcca aagccctgct gtcactgtgg gctggggcca ggctgaccac    48480
agggccccc cgtccaccag agcctcctgg tgtacatgct ttttctgctg gtgaccctgc    48540
tggccagcta tggggatgcc tcatgccatg ggcacgccta ccgtctgcaa agcgccatca    48600
agcaggagct gcacagccgg gccttcctgg ccatcacgcg gtacgggcat ccggtgcact    48660
ggtctgtctt ctgggcttta gttttgcctt tagtccagcc agaccctagg ggacatgtgg    48720
acatgtgtag ataccttgt ggctgctaga actggaggta ggtgctgctg gcatcagtag    48780
gcagagggga gggacacagg tccgtgtctt gcagtgcaca ggacgggccc atgacagaca    48840
```

```
actgtctgcc ccagaacatc cccaggataa ggctgagaag cccaggtcta gccgtggcca   48900
gcagggcagt gggagccatg ttccctgggt ctctggtggc cgctcactcg aggcgggcat   48960
ggggcagtag gggctggagc gtgtgactga tgctgtggca ggtctgagga gctctggcca   49020
tggatggccc acgtgctgct gccctacgtc cacgggaacc agtccagccc agagctgggg   49080
cccccacggc tgcggcaggt gcggctgcag gaaggtgagc tggcagggcg tgccccaaga   49140
cttaaatcgt tcctcttgtt gagagagcag cctttagcgg agctctggca tcagccctgc   49200
tccctagctg tgtgaccttt gccctcttaa caccgccgtt tccttctctg tatatgagag   49260
atggtaacgt tgtctaattg atggctgctg ggagggttcc ctggggtggc gccgaaccag   49320
agctcaggcg agctggccag caggaaacac tcctgttggg ttttgatgag gccctggccc   49380
cggcctgggc tctgtgtgt ttcagcactc tacccagacc ctcccggccc cagggtccac   49440
acgtgctcgg ccgcaggagg cttcagcacc agcgattacg acgttggctg ggagagtcct   49500
cacaatggct cggggacgtg ggcctattca gcgccggatc tgctggggtg agcagagcga   49560
ggcccccggg cgtctacgcc aaggacaagg gagtagttct ccaggagtgc cgcggcctcc   49620
tgaccagcct ggctccgggg tgccggaagg gctgggtgc ggcacccacg ccaccccctct   49680 ccggcagggc atggtcctgg ggctcctgtg ccgtgtatga cagcgggggc tacgtgcagg   49740
agctgggcct gagcctggag gagagccgcg accggctgcg cttcctgcag ctgcacaact   49800
ggctggacaa caggtgggag ctccctcccc tgccctctcc ggggtggccg cagtcaccag   49860
ccaggagccc accctcactc ctccggcccc cgctggccta ggcggcttcc acagcccctc   49920
agccacgcct gcactgcgcg gtccccgcag ctcccgccct gccacccgct cctactgacc   49980
cgcaccctct gcgcaggagc cgcgctgtgt tcctggagct cacgcgctac agccggccg   50040 tggggctgca cgccgccgtc acgctgcgcc tcgagttccc ggcggccggc cgcgccctgg   50100 ccgcccctcag cgtccgcccc tttgcgctgc gccgcctcag cgcgggcctc tcgctgcctc   50160
tgctcacctc ggtacgcccg tccccggcca gaccccgcgc ctcccaccgg cagcgtcccg   50220 cccctcgcg gggccccgcc cggcagcgtc tcacccctcg cagcgccccg ccccctcgca   50280
gcgtcccgcc ccctcgcagg gccccgcccc ggcagcgtcc cgcccctcg tagggccccg   50340 ccccggcagc gtcccgcccc ctcgcagggc cccgccccgg cagcgtccct cccgccctcc   50400
tgaccgcgcc cccacaggt gtgcctgctg ctgttcgccg tgcacttcgc cgtggccgag   50460
gcccgtactt ggcacaggga agggcgctgg cgcgtgctgc ggctcggagc ctgggcgcgg   50520
tggctgctgg tggcgctgac ggcggccacg gcactggtac gcctcgccca gctgggtgcc   50580
gctgaccgcc agtggacccg tttcgtgcgc ggccgcccgc gccgcttcac tagcttcgac   50640
caggtggcgc agctgagctc cgcagcccgt ggcctggcgg cctcgctgct cttcctgctt   50700
ttggtcaagg tgagggctgg gccggtgggc gcggggctgg gcgcacaccc cagggctgca   50760
agcagacaga tttctcgtcc gcaggctgcc cagcagctac gcttcgtgcg ccagtggtcc   50820
gtctttggca agacattatg ccgagctctg ccagagctcc tgggggtcac cttgggcctg   50880
gtggtgctcg gggtagccta cgcccagctg gccatcctgg taggtgactg cgcggccggg   50940
gagggcgtct tagctcagct cagctcagct gtacgccctc actggtgtcg ccttcccgc   51000 agctcgtgtc ttcctgtgtg gactccctct ggagcgtggc ccaggccctg ttggtgctgt   51060
gccctgggac tgggctctct accctgtgtc ctgccgagtc ctggcacctg tcaccctgc   51120 tgtgtgtggg gctctgggca ctgcggctgt ggggcgccct acggctgggg gctgttattc   51180
```

```
tccgctggcg ctaccacgcc ttgcgtggag agctgtaccg gccggcctgg gagccccagg   51240
actacgagat ggtggagttg ttcctgcgca ggctgcgcct ctggatgggc ctcagcaagg   51300
tcaaggaggt gggtacggcc cagtgggggg gagagggaca cgccctgggc tctgcccagg   51360
gtgcagccgg actgactgag cccctgtgcc gcccccagtt ccgccacaaa gtccgctttg   51420
aagggatgga gccgctgccc tctcgctcct ccagggctc caaggtatcc ccggatgtgc    51480
ccccacccag cgctggctcc gatgcctcgc acccctccac ctcctccagc cagctggatg   51540
ggctgagcgt gagcctgggc cggctgggga caaggtgtga gcctgagccc tcccgcctcc   51600
aagccgtgtt cgaggccctg ctcacccagt ttgaccgact caaccaggcc acagaggacg   51660
tctaccagct ggagcagcag ctgcacagcc tgcaaggccg caggagcagc cgggcgcccg   51720
ccggatcttc ccgtggccca tccccggggc tgcggccagc actgcccagc cgccttgccc   51780
gggccagtcg gggtgtggac ctggccactg gccccagcag gacacccctt cgggccaaga   51840
acaaggtcca ccccagcagc acttagtcct ccttcctggc gggggtgggc cgtggagtcg   51900
gagtggacac cgctcagtat tactttctgc cgctgtcaag gccgagggcc aggcagaatg   51960
gctgcacgta ggttccccag agagcaggca ggggcatctg tctgtctgtg ggcttcagca   52020 cttttaaagag gctgtgtggc caaccaggac ccagggtccc ctccccagct cccttgggaa   52080
ggacacagca gtattggacg gtttctagcc tctgagatgc taatttattt ccccgagtcc   52140
tcaggtacag cgggctgtgc ccggcccac ccctgggca gatgtccccc actgctaagg    52200
ctgctggctt cagggagggt tagcctgcac cgccgccacc ctgcccctaa gttattacct   52260
ctccagttcc taccgtactc cctgcaccgt ctcactgtgt gtctcgtgtc agtaatttat   52320
atggtgttaa aatgtgtata tttttgtatg tcactatttt cactagggct gaggggcctg   52380
cgcccagagc tggcctcccc caacacctgc tgcgcttggt aggtgtggtg gcgttatggc   52440
agcccggctg ctgcttggat gcgagcttgg ccttgggccg gtgctggggg cacagctgtc   52500
tgccaggcac tctcatcacc ccagaggcct tgtcatcctc ccttgcccca ggccaggtag   52560
caagagagca gcgcccaggc ctgctggcat caggtctggg caagtagcag gactaggcat   52620
gtcagaggac cccagggtgg ttagaggaaa agactcctcc tggggctgg ctcccagggt    52680 ggaggaaggt gactgtgtgt gtgtgtgtgt gcgcgcgcgc acgcgcgagt gtgctgtatg   52740
gcccaggcag cctcaaggcc ctcggagctg gctgtgcctg cttctgtgta ccacttctgt   52800
gggcatggcc gcttctagag cctcgacacc cccccaaccc ccgcaccaag cagacaaagt   52860
caataaaaga gctgtctgac tgcaatctgt gcctctatgt ctgtgcactg gggtcaggac   52920
tttatttatt tcactgacag gcaataccgt ccaaggccag tgcaggaggg agggccccgg   52980
cctcacacaa actcggtgaa gtcctccacc gaggagatga ggcgcttccg ctggcccacc   53040
tcatagccag gtgtgggctc ggctggagtc tgtgcagggg cttttgctatg ggacggaggg   53100 tgcaccagag gtaggctggg gttggagtag gcggcttcct cgcagatctg aaggcagagg   53160
cggcttgggc agtaagtctg ggaggcgtgg caaccgctct gcccacacac ccgccccaca   53220
gcttgggcag ccagcacacc ccgctgaggg agccccatat tccctacccg ctggcggagc   53280
gcttgatgtg gcgagcggg caatccactt ggaggggtag atatcggtgg ggttggagcg    53340
gctatgatgc acctgtgagg ccatctgggg acgtaggcag ggggtgagct cactatcagg   53400
tggcacctgg gcctgtccca ccagctcacg cctggaccca cccccactca catttgcgtg   53460
cagggccatc tggcgggcca cgaagggcag gttgcggtca gacacgatct tggccacgct   53520
gg                                                                   53522
```

<210> SEQ ID NO 8
<211> LENGTH: 23
<212> TYPE: PRT
<213> ORGANISM: Homo sapiens

<400> SEQUENCE: 8

Leu Ser Pro Asn Ala Thr Leu Ala Leu Thr Ala Gly Val Leu Val Asp
1               5                   10                  15

Ser Ala Val Glu Val Ala Phe
            20

<210> SEQ ID NO 9
<211> LENGTH: 48
<212> TYPE: PRT
<213> ORGANISM: Homo sapiens
<220> FEATURE:
<221> NAME/KEY: MOD_RES
<222> LOCATION: (4)..(23)
<223> OTHER INFORMATION: Any amino acid

<400> SEQUENCE: 9

Asp Gly Glu Xaa Xaa Xaa Xaa Xaa Xaa Xaa Xaa Xaa Xaa Xaa Xaa
1               5                   10                  15

Xaa Xaa Xaa Xaa Xaa Xaa Xaa Val Ala Gln Val Leu Val Glu His Asn
            20                  25                  30

Val Met His Thr Tyr Ala Ala Pro Gly Glu Tyr Leu Leu Thr Val Leu
        35                  40                  45

<210> SEQ ID NO 10
<211> LENGTH: 22
<212> TYPE: PRT
<213> ORGANISM: Homo sapiens

<400> SEQUENCE: 10

Leu Val Ala Gly Arg Pro Val Thr Phe Tyr Pro His Pro Leu Pro Ser
1               5                   10                  15

Pro Gly Gly Val Leu Tyr
            20

<210> SEQ ID NO 11
<211> LENGTH: 28
<212> TYPE: PRT
<213> ORGANISM: Homo sapiens

<400> SEQUENCE: 11

Asp Gly Ser Pro Val Leu Thr Gln Ser Gln Pro Ala Ala Asn His Thr
1               5                   10                  15

Tyr Ala Ser Arg Gly Thr Tyr His Val Arg Leu Glu
            20                  25

<210> SEQ ID NO 12
<211> LENGTH: 21
<212> TYPE: PRT
<213> ORGANISM: Homo sapiens

<400> SEQUENCE: 12

Pro Thr Gln Pro Asp Ala Arg Leu Thr Ala Tyr Val Thr Gly Asn Pro
1               5                   10                  15

Ala His Tyr Leu Phe
            20

```
<210> SEQ ID NO 13
<211> LENGTH: 29
<212> TYPE: PRT
<213> ORGANISM: Homo sapiens

<400> SEQUENCE: 13

Asp Gly Ser Ser Asn Thr Thr Val Arg Gly Cys Pro Thr Val Thr His
1               5                   10                  15

Asn Phe Thr Arg Ser Gly Thr Phe Pro Leu Ala Leu Val
            20                  25

<210> SEQ ID NO 14
<211> LENGTH: 23
<212> TYPE: PRT
<213> ORGANISM: Homo sapiens

<400> SEQUENCE: 14

Gln Phe Val Gln Leu Gly Asp Glu Ala Trp Leu Val Ala Cys Ala Trp
1               5                   10                  15

Pro Pro Phe Pro Tyr Arg Tyr
            20

<210> SEQ ID NO 15
<211> LENGTH: 29
<212> TYPE: PRT
<213> ORGANISM: Homo sapiens

<400> SEQUENCE: 15

Thr Glu Glu Ala Ala Pro Thr Arg Ala Arg Gly Pro Glu Val Thr Phe
1               5                   10                  15

Ile Tyr Arg Asp Pro Gly Ser Tyr Leu Val Thr Val Thr
            20                  25

<210> SEQ ID NO 16
<211> LENGTH: 21
<212> TYPE: PRT
<213> ORGANISM: Homo sapiens

<400> SEQUENCE: 16

Gly Leu Glu Leu Gln Gln Pro Tyr Leu Phe Ser Ala Val Gly Arg Gly
1               5                   10                  15

Arg Pro Ala Ser Tyr
            20

<210> SEQ ID NO 17
<211> LENGTH: 25
<212> TYPE: PRT
<213> ORGANISM: Homo sapiens

<400> SEQUENCE: 17

Asp Gly Gly Trp Leu Glu Gly Pro Glu Val Thr His Ala Tyr Asn Ser
1               5                   10                  15

Thr Gly Asp Phe Thr Val Arg Val Ala
            20                  25

<210> SEQ ID NO 18
<211> LENGTH: 26
<212> TYPE: PRT
<213> ORGANISM: Homo sapiens
<220> FEATURE:
<221> NAME/KEY: MOD_RES
<222> LOCATION: (3)..(7)
<223> OTHER INFORMATION: Any amino acid
```

```
<400> SEQUENCE: 18

Pro Gly Xaa Xaa Xaa Xaa Xaa Ala Gly Ser Ser Val Pro Phe Trp Gly
1               5                   10                  15

Gln Leu Ala Thr Gly Thr Asn Val Ser Trp
            20                  25

<210> SEQ ID NO 19
<211> LENGTH: 25
<212> TYPE: PRT
<213> ORGANISM: Homo sapiens

<400> SEQUENCE: 19

Gly Gly Ser Ser Lys Arg Gly Pro His Val Thr Met Val Phe Pro Asp
1               5                   10                  15

Ala Gly Thr Phe Ser Ile Arg Leu Asn
            20                  25

<210> SEQ ID NO 20
<211> LENGTH: 22
<212> TYPE: PRT
<213> ORGANISM: Homo sapiens

<400> SEQUENCE: 20

Val Val Ala Pro Gly Gln Leu Val His Phe Gln Ile Leu Leu Ala Ala
1               5                   10                  15

Gly Ser Ala Val Thr Phe
            20

<210> SEQ ID NO 21
<211> LENGTH: 27
<212> TYPE: PRT
<213> ORGANISM: Homo sapiens

<400> SEQUENCE: 21

Gly Ala Asn Pro Glu Val Leu Pro Gly Pro Arg Phe Ser His Ser Phe
1               5                   10                  15

Pro Arg Val Gly Asp His Val Val Ser Val Arg
            20                  25

<210> SEQ ID NO 22
<211> LENGTH: 30
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Any amino acid

<400> SEQUENCE: 22

Cys Xaa Pro Ser Asp Thr Glu Ile Phe Pro Gly Asn Gly His Cys Tyr
1               5                   10                  15

Arg Leu Val Val Glu Lys Ala Ala Trp Leu Gln Ala Gln Glu
            20                  25                  30

<210> SEQ ID NO 23
<211> LENGTH: 16
<212> TYPE: PRT
<213> ORGANISM: Homo sapiens

<400> SEQUENCE: 23

Trp Cys Asn Thr Asp Leu Cys Ser Ala Pro His Ser Tyr Val Cys Glu
1               5                   10                  15
```

What is claimed is:

1. A method of diagnosing or predicting the occurrence of autosomal dominant polycystic kidney disease (ADPKD) in a human, comprising:
   a) assaying a sample comprising a nucleic acid encoding a PKD1 gene obtained from a human;
   b) detecting a mutation in the PKD1 gene, wherein the mutation is a deletion of TTTAA at nucleotide positions 559 to 563 of SEQ ID NO: 1; and
   c) diagnosing or predicting the occurrence of ADPKD in the human when the mutation in the PKD1 gene is detected.

2. The method of claim 1, wherein the assaying comprises a method selected from the group consisting of sequencing, polymerase chain reaction, denaturing high performance liquid chromatography, and combinations thereof.

3. A method for detecting a mutant PKD1 gene in a human, comprising:
   a) assaying a nucleic acid sample comprising a PKD1 gene obtained from a human; and
   b) detecting a mutation in the PKD1 gene, wherein the mutation is a deletion of TTTAA at nucleotide positions 559 to 563 of SEQ ID NO:1, and
   wherein the mutation indicates the human has a mutant PKD1 gene.

4. The method of claim 3, wherein the assaying comprises a method selected from the group consisting of sequencing, polymerase chain reaction, denaturing high performance liquid chromatography, and combinations thereof.

5. A method of diagnosing or predicting the occurrence of autosomal dominant polycystic kidney disease (ADPKD) in a human, comprising:
   a) sequencing all or a portion of a PKD1 gene isolated from a nucleic acid sample obtained from a human; and
   b) detecting a mutation in the PKD1 gene, wherein the mutation results in a N116fsX polymorphism of SEQ ID NO:3 in the polypeptide sequence encoded by the PKD1 gene;
   c) diagnosing or predicting the occurrence of ADPKD in the human when the polymorphism is detected.

* * * * *